US006417185B1

(12) United States Patent
Goff et al.

(10) Patent No.: US 6,417,185 B1
(45) Date of Patent: Jul. 9, 2002

(54) INHIBITORS OF GLYCOGEN SYNTHASE KINASE 3

(75) Inventors: Dane A. Goff, Redwood City; Stephen D. Harrison, Berkeley; John M. Nuss, Danville; David B. Ring, Palo Alto; Xiaohui A. Zhou, Berkeley, all of CA (US)

(73) Assignee: Chiron Corporation, Emeryville, CA (US)

(*) Notice: Subject to any disclaimer, the term of this patent is extended or adjusted under 35 U.S.C. 154(b) by 0 days.

(21) Appl. No.: 09/336,038

(22) Filed: Jun. 18, 1999

Related U.S. Application Data

(60) Provisional application No. 60/089,978, filed on Jun. 19, 1998.

(51) Int. Cl.[7] ............... C07D 413/14; C07D 401/12; A61K 31/535; A61K 31/506
(52) U.S. Cl. ............ 514/235.8; 544/330; 544/331; 544/122; 514/275
(58) Field of Search .................. 544/330, 331, 544/122; 514/275, 235.8

(56) References Cited

U.S. PATENT DOCUMENTS

| | | | |
|---|---|---|---|
| 4,006,149 A | 2/1977 | Bonnemann et al. ....... 260/290 |
| 4,334,912 A | 6/1982 | Yoshida et al. ................. 71/94 |
| 4,361,565 A | 11/1982 | Temple, Jr. et al. ........ 424/250 |
| 4,532,246 A | 7/1985 | Ife ............................. 514/275 |
| 4,547,506 A | 10/1985 | Ife ............................. 514/272 |
| 4,548,940 A | 10/1985 | Ife ............................. 514/272 |
| 4,554,276 A | 11/1985 | LaMattina ................. 514/272 |
| 4,594,421 A | 6/1986 | Bellani et al. ............... 546/121 |
| 4,607,106 A | 8/1986 | Ife ............................. 546/255 |
| 4,659,725 A | 4/1987 | Ife ............................. 514/352 |
| 4,661,501 A | 4/1987 | Nakatani et al. ........... 514/345 |
| 4,665,078 A | 5/1987 | Sach ......................... 514/272 |
| 4,673,677 A | 6/1987 | LaMattina ................. 514/272 |
| 4,685,961 A | * 8/1987 | Topfl et al. ..................... 71/92 |
| 4,711,888 A | 12/1987 | Walker et al. ............... 514/269 |
| 4,714,706 A | 12/1987 | Kisida et al. ............... 514/345 |
| 4,716,172 A | 12/1987 | Carmosin et al. .......... 514/306 |
| 4,745,652 A | 5/1988 | Rose et al. ..................... 8/409 |
| 4,751,225 A | 6/1988 | Nishida et al. ............. 514/275 |
| 4,757,073 A | 7/1988 | New et al. .................. 514/252 |
| 4,772,633 A | 9/1988 | Matsuo et al. .............. 514/717 |
| 4,791,139 A | 12/1988 | Bushell et al. .............. 514/721 |
| 4,814,340 A | 3/1989 | Nakatani et al. ........... 514/345 |
| 4,835,166 A | 5/1989 | Kitaura et al. .............. 514/339 |
| 4,847,259 A | 7/1989 | Kisida et al. ............... 514/274 |
| 4,855,286 A | 8/1989 | Wagner et al. ................ 514/19 |
| 4,876,256 A | 10/1989 | Coss et al. .................. 514/252 |
| 4,879,292 A | 11/1989 | Nishida et al. ............. 514/241 |
| 4,898,866 A | 2/1990 | Schonafinger et al. ...... 514/252 |
| 4,904,685 A | 2/1990 | Kitaura et al. .............. 514/418 |
| 4,906,643 A | 3/1990 | Van Daele et al. ......... 514/318 |
| 4,914,116 A | 4/1990 | Kisida et al. ............... 514/369 |
| 4,968,340 A | 11/1990 | Kaku et al. ..................... 71/92 |
| 4,970,222 A | 11/1990 | Nishida et al. ............. 514/369 |
| 4,971,982 A | 11/1990 | Attwood et al. ............ 514/337 |
| 4,985,560 A | 1/1991 | Sabb et al. .................. 544/115 |
| 4,988,700 A | 1/1991 | Traber et al. ............... 514/255 |
| 5,001,136 A | 3/1991 | Walker ....................... 514/336 |
| 5,002,953 A | 3/1991 | Hindley ...................... 514/275 |

(List continued on next page.)

FOREIGN PATENT DOCUMENTS

| | | |
|---|---|---|
| DE | 2410938 | 9/1974 |
| DE | 2615309 | 3/1977 |
| DE | 25 34 605 A1 | 2/1980 |
| DE | 28 34 605 A1 | 2/1980 |
| EP | 0 842 925 A1 | 8/1988 |
| EP | 0 419 035 B1 | 8/1990 |
| EP | 0 446 604 A2 | 2/1991 |
| EP | 0 519 211 A1 | 5/1992 |
| EP | 0 567 133 A1 | 4/1993 |
| EP | 0 576 906 A1 | 6/1993 |
| EP | 0 593 110 A1 | 9/1993 |
| EP | 593100 A1 | 4/1994 |
| EP | 593110 A1 | 4/1994 |
| EP | 0 711 757 A1 | 10/1995 |
| EP | 0 710 659 A1 | 11/1995 |
| EP | 0 919 232 A1 | 11/1998 |
| GB | 1384523 | 2/1975 |
| JP | 62051672 | 3/1987 |
| JP | 6041090 | 2/1991 |
| JP | 4078582 | 3/1992 |
| JP | 5-158195 | 6/1993 |
| JP | 6041118 | 2/1994 |
| JP | 9151184 | 6/1997 |
| JP | 10072371 | 3/1998 |
| WO | WO 88/08416 | 11/1988 |
| WO | WO 91/19702 | 12/1991 |
| WO | WO 92/18498 | 10/1992 |
| WO | WO 93/06118 | 4/1993 |
| WO | WO 93/10254 | 5/1993 |
| WO | WO 93/2166 | 10/1993 |
| WO | WO 93/21166 | 10/1993 |
| WO | WO 94/01420 | 1/1994 |

(List continued on next page.)

OTHER PUBLICATIONS

US 6,057,286, 05/2000, Harrison et al. (withdrawn)
Connor, S.C., et al., "Antidiabetic Efficacy of BRL 49653, a Potent Orally Active Insulin Sensitizing Agent, Assessed in the C57BL/KsJ db/db Diabetic Mouse by Non–invasive $^1$H NMR Studies of Urine," *J. Pharm. Pharmacol.* 49:336–344 (1997).

(List continued on next page.)

Primary Examiner—Mukund J. Shah
Assistant Examiner—Hong Liu
(74) Attorney, Agent, or Firm—Dennis K. Shelton; David P. Lentini; Robert P. Blackburn

(57) ABSTRACT

Novel pyridine and pyrimidine derivatives which selectively inhibit glycogen synthase kinase 3 are provided and methods of preparing these compounds are provided. These compounds are useful in treating certain conditions which may be mediated by glycogen synthase kinase 3.

13 Claims, 4 Drawing Sheets

U.S. PATENT DOCUMENTS

| | | | |
|---|---|---|---|
| 5,006,541 A | 4/1991 | Kitaura et al. | 514/367 |
| 5,010,100 A | 4/1991 | Biftu et al. | 514/461 |
| 5,036,088 A | 7/1991 | Kitaura et al. | 514/375 |
| 5,071,860 A | 12/1991 | Alig et al. | 514/332 |
| 5,075,308 A | 12/1991 | Ishikawa et al. | 514/252 |
| 5,082,851 A | 1/1992 | Appelbaum et al. | 514/332 |
| 5,084,456 A | 1/1992 | Guillaumet et al. | 514/252 |
| 5,086,000 A | 2/1992 | Pohlke et al. | 436/42 |
| 5,087,289 A | 2/1992 | Kaku et al. | 71/93 |
| 5,089,514 A | 2/1992 | Hulin | 514/374 |
| 5,118,694 A | 6/1992 | Attwood et al. | 514/337 |
| 5,130,312 A | 7/1992 | Van Daele et al. | 514/252 |
| 5,151,113 A * | 9/1992 | Smith et al. | 71/92 |
| 5,158,959 A | 10/1992 | Geiger et al. | 514/307 |
| 5,162,362 A | 11/1992 | Geiger et al. | 514/414 |
| 5,194,443 A | 3/1993 | Hindley | 514/367 |
| 5,202,316 A | 4/1993 | Claussner et al. | 514/176 |
| 5,202,321 A | 4/1993 | Hutchinson et al. | 514/727.5 |
| 5,232,925 A | 8/1993 | Hindley | 514/272 |
| 5,232,945 A | 8/1993 | Hulin | 514/456 |
| 5,250,401 A | 10/1993 | Okada et al. | 430/393 |
| 5,260,445 A | 11/1993 | Hindley | 548/183 |
| 5,302,719 A | 4/1994 | Claussner et al. | 544/360 |
| 5,306,726 A | 4/1994 | Hulin | 514/375 |
| 5,308,840 A | 5/1994 | Sugiyama et al. | 514/212 |
| 5,391,537 A | 2/1995 | Takabe et al. | 504/243 |
| 5,401,766 A | 3/1995 | Geiger et al. | 514/307 |
| 5,403,816 A | 4/1995 | Takabe et al. | 504/243 |
| 5,407,948 A | 4/1995 | Fey et al. | 514/333 |
| 5,411,934 A | 5/1995 | Yoshimura et al. | 504/239 |
| 5,413,999 A | 5/1995 | Vacca et al. | 514/234.5 |
| 5,418,212 A | 5/1995 | Yoshimura et al. | 504/227 |
| 5,438,074 A | 8/1995 | Hulin | 514/456 |
| 5,478,852 A | 12/1995 | Olefsky et al. | 514/369 |
| 5,527,796 A | 6/1996 | Binder et al. | 514/226.5 |
| 5,534,536 A | 7/1996 | Ohuchida et al. | 514/397 |
| 5,574,031 A | 11/1996 | Abramo et al. | 514/212 |
| 5,589,478 A | 12/1996 | Yamada et al. | 514/269 |
| 5,646,169 A | 7/1997 | Hindley et al. | 514/369 |
| 5,652,240 A | 7/1997 | Abramo et al. | 514/252 |
| 5,654,299 A | 8/1997 | Shenvi et al. | 514/222.5 |
| 5,658,910 A | 8/1997 | Bjork et al. | 514/252 |
| 5,665,748 A | 9/1997 | Sohda et al. | 514/365 |
| 5,668,140 A | 9/1997 | Schaper et al. | 514/269 |
| 5,688,795 A | 11/1997 | Pfister et al. | 514/252 |
| 5,703,095 A | 12/1997 | Galey et al. | 514/332 |
| 5,708,012 A | 1/1998 | Olefsky | 514/337 |
| 5,726,172 A | 3/1998 | Sparks et al. | 514/230.5 |
| 5,728,706 A | 3/1998 | Yamada et al. | 514/269 |
| 5,739,333 A | 4/1998 | Yamada et al. | 544/296 |
| 5,741,796 A | 4/1998 | Hartman et al. | 514/300 |
| 5,750,544 A | 5/1998 | Ohuchida et al. | 514/337 |
| 5,753,681 A | 5/1998 | Fujiwara et al. | 514/337 |
| 5,756,525 A | 5/1998 | Hindley et al. | 514/364 |
| 5,760,028 A | 6/1998 | Jadhav et al. | 514/211 |
| 5,760,037 A | 6/1998 | Galey et al. | 514/245 |
| 5,798,375 A | 8/1998 | Tsujita et al. | 514/369 |
| 5,830,896 A | 11/1998 | Perregaard et al. | 514/252 |
| 5,837,707 A | 11/1998 | Perragaard et al. | 514/255 |
| 5,849,914 A | 12/1998 | Dolling et al. | 546/14 |
| 5,859,037 A | 1/1999 | Whitcomb | 514/369 |
| 5,874,451 A | 2/1999 | Glombik et al. | 514/357 |
| 5,902,726 A | 5/1999 | Kliewer et al. | 435/7.1 |
| 5,916,889 A | 6/1999 | Hohlweg et al. | 514/253 |
| 5,939,439 A | 8/1999 | Anthony et al. | 514/333 |
| 5,942,525 A | 8/1999 | Pennington et al. | 514/345 |
| 5,945,436 A | 8/1999 | Lai et al. | 514/357 |
| 6,020,349 A | 2/2000 | Ankersen et al. | 514/341 |
| 6,024,937 A | 2/2000 | Kasina et al. | 424/1.65 |
| 6,077,855 A | 6/2000 | Bhatnagar et al. | 514/332 |

FOREIGN PATENT DOCUMENTS

| | | |
|---|---|---|
| WO | WO 94/05659 | 3/1994 |
| WO | WO 94/12169 | 6/1994 |
| WO | WO 94/13650 | 6/1994 |
| WO | WO 94/25026 | 11/1994 |
| WO | WO 95/03288 | 2/1995 |
| WO | WO 95/07694 | 3/1995 |
| WO | WO 95/07697 | 3/1995 |
| WO | WO 95/21608 | 8/1995 |
| WO | WO 95/30405 | 11/1995 |
| WO | WO 95/31438 | 11/1995 |
| WO | WO 95/32710 | 12/1995 |
| WO | WO 9604235 | 2/1996 |
| WO | WO 96/18616 | 6/1996 |
| WO | WO 96/29405 | 9/1996 |
| WO | WO 97/05785 A3 | 2/1997 |
| WO | WO 9705875 A2 | 2/1997 |
| WO | WO 97/06167 | 2/1997 |
| WO | WO 97/10819 | 3/1997 |
| WO | WO 97/14681 | 4/1997 |
| WO | WO 97/45141 | 4/1997 |
| WO | WO 97/18811 | 5/1997 |
| WO | WO 97/22589 | 6/1997 |
| WO | WO 97/22596 | 6/1997 |
| WO | WO 97/23480 | 7/1997 |
| WO | WO 97/24122 | 7/1997 |
| WO | WO 97/25992 | 7/1997 |
| WO | WO 97/36870 | 10/1997 |
| WO | WO 97/40017 A3 | 10/1997 |
| WO | WO 97/40017 A2 | 10/1997 |
| WO | WO 97/31907 | 12/1997 |
| WO | WO 98/02159 | 1/1998 |
| WO | WO 98/02183 | 2/1998 |
| WO | WO 98/05331 | 2/1998 |
| WO | WO 98/15537 | 4/1998 |
| WO | WO 98/15539 | 4/1998 |
| WO | WO 98/16528 | 4/1998 |
| WO | WO 98/16528 A1 | 4/1998 |
| WO | WO 98/17267 | 4/1998 |
| WO | WO 98/20871 | 5/1998 |
| WO | WO 98/24780 A2 | 6/1998 |
| WO | WO 98/24780 A3 | 6/1998 |
| WO | 98/24782 * | 6/1998 |
| WO | WO 98/24782 A2 | 6/1998 |
| WO | WO 98/24782 A3 | 6/1998 |
| WO | WO 98/25598 A2 | 6/1998 |
| WO | WO 98/25598 | 6/1998 |
| WO | WO 98/28319 | 7/1998 |
| WO | WO 98/29120 | 7/1998 |
| WO | WO 98/36755 | 8/1998 |
| WO | WO 98/37073 | 8/1998 |
| WO | WO 98/37877 | 9/1998 |
| WO | WO 98/38163 | 9/1998 |
| WO | WO 98/39006 | 9/1998 |
| WO | WO 98/42340 | 10/1998 |
| WO | WO 98/43081 | 10/1998 |
| WO | WO 98/44797 | 10/1998 |
| WO | WO 98/45267 | 10/1998 |
| WO | WO 98/51305 | 11/1998 |
| WO | WO 98/55122 | 12/1998 |
| WO | WO 98/57634 | 12/1998 |
| WO | WO 98/57635 | 12/1998 |
| WO | WO 98/57636 | 12/1998 |
| WO | WO 98/57649 | 12/1998 |
| WO | WO 99/00372 | 1/1999 |
| WO | WO 99/03476 | 1/1999 |
| WO | WO 99/03478 | 1/1999 |
| WO | WO 99/08660 | 2/1999 |
| WO | WO 99/18943 | 4/1999 |
| WO | WO 99/18944 | 4/1999 |
| WO | WO 99/25346 | 5/1999 |

| WO | WO 99/27365 | 6/1999 |
| WO | WO 99/27906 | 6/1999 |
| WO | WO 99/30739 | 6/1999 |
| WO | WO 99/41253 | 8/1999 |
| WO | WO 99/42436 | 8/1999 |
| WO | WO 99/48529 | 9/1999 |
| WO | WO 00/18758 | 4/2000 |
| WO | WO 00/21927 | 4/2000 |

OTHER PUBLICATIONS

CAS Printout for Marzinzik et al., Apr. 1998.*
CAS Printout for Hong et al., 1995.*
CAS Printout for Ogawa et al., Apr. 1994.*
CAS Printout for Renth et al., Sep. 1994.*
CAS Printout for Smith et al., Sep. 1992.*
CAS Printout for Diehr et al., Mar. 1986.*
CAS Printout for Forsyth et al., 1981.*
CAS Printout for Elslager et al., 1974.*
CAS Printout for WO 98/24782, Jun. 1998.*
Aplin et al., "Effect of increased glycogen synthase kinase–3 activity upon the maturation of the amyloid precursor protein in transfected cells", Molecular Neuroscience (1997) 8(3):639–643.
Aplin et al., "In Vitro phosphorylation of the cytoplasmic domain of the amyloid precursor protein by glycogen synthase kinase–3β", J Neurochem (1996) 67(2):699–707.
Avruch, "Insulin signal transduction through protein kinase cascades", Molecular and Cellular Biochemistry (1998) 182:31–48.
Baum et al., "Overexpressed tau protein in cultured cells in phosphorylated without formation of PHF implication of phosphoprotein phosphatase involvement", Brain Res Mol Brain Res (1995) 34:1–17.
Beals et al., "Nuclear export of NF–Atc enhanced by glycogen synthase kinase–3", Science (1997) 275:1930–1933.
Borthwick et al., "Inhibition of glycogen synthase kinase–3 insulin in cultured human skeletal muscle myoblasts", Biochem Biophys Res Commun (1995) 210(3):738–745.
Brady et al., "The activation of glycogen synthase by insulin switches from kinase inhibition to phosphatase activation during adipogenesis in 3T3–L1 cells", Journal of Biological Chemistry (1998) 273(23):14063–14066.
Brownlees et al., "Tau phosphorylation in transgenic mice expressing glycogen synthase kinase–3β transgenes", Molec Neuro (1997) 8(15):3251–3255.
Ciudad et al., "Control of glycogen synthase phosphorylation in isolated rat hepatocytes by epinephrine, vasopressin and glucagon", Eur J Biochem (1984) 142(3):511–520.
Cohen et al., "PDK1, one of the missing links in insulin signal transduction?", FEBS Letters (1997) 3–10.
Cross et al., "insulin activates protein kinase B, inhibits glycogen synthase kinase–3 and activates glycogen synthase by rapamycin–insensitive pathways in skeletal muscle and adipose tissue", FEBS Letters (1997) 211–215.
Cross et al., "Inhibition of glycogen synthase kinase–3 by insulin mediated by protein kinase B.", Nature (1995) 378:785–789.
Cross et al., "The inhibition of glycogen synthase kinase–3 by insulin or insulin–like growth factor 1 in the rat skeletal muscle cell line L6 is blocked by wortmannin, but not by rapamycin: evidence that wortmannin blocks activation of the mitogen–activated protein kinase pathway in L6 cells between Ras and Raf", Biochem J (1994) 303:21–26.

Elgar–Finkelman et al., "Phosphorylation of insulin receptor substrate 1 by glycogen synthase kinase 3 impairs insulin action", Proc Natl Acad Sci USA (1997) 94:9660–9664.
Elgar–Finkelman et al., "Expression and characterization of glycogen synthase kinase–3 mutants and their effect on glycogen synthase activity in intact cells", Proc Natl Acad Sci USA (1996) 93:10228–10233.
Fiol et al., "Ordered multisite protein phosphorylation. Analysis of glycogen synthase kinase 3 action using model peptide substrates", J. Biol. Chem (1990) 265(11):6061–6065.
Furnsinn et al., "More marked stimulation by lithium than insulin of the glycogenic pathway in rat skeletal muscle", American Physiological Society (1997) 514–520.
Garcia–Perez et al., "Implication of cyclin–dependent kinases and glycogen synthase kinase–3 in the phosphorylation of microtubule–associated protein 1B in developing neuronal cells", Journal of Neuroscience Research (1998) 52:445–452.
Hegazy et al., "Inhibitory effect of polycations on phosphorylation of glycogen synthase by glycogen synthase kinase 3.", Biochem Biophys Acta (1989) 198:204.
Hiken et al., "Rat skeletal muscle glycogen synthase: phosphorylation of the purified enzyme by cAMP–dependent and –independent protein kinases", Arch Biochem Biophys, 236(1):59–71.
Hong et al., "Lithium reduces tau phosphorylation by inhibition of glycogen synthase kinase–3", J Biol Chem (1997) 272(40):25326–25332.
Hoshi et al., "Notoxic amyloid β peptide $_{1-42}$ suppresses acetylcholine synthesis", J Biol Chem (1997) 272(4):2038–2041.
Hoshi et al., "Regulation of mitochondrial pyruvate dehydrogenase activity by tau protein kinase I/glycogen synthase kinase 3beta in brain", Proc Natl Acad Sci USA (1996) 93(7):2719–2723.
Hurel et al., Biochem J (1996) 871–877.
Imahori et al., "Physiology and pathology of tau protein kinases in relation to Alzheimer's disease", J Biochem (1997) 121:179–188.
Imazu et al., "Phosphorylation and inactivation of liver glycogen synthase by liver kinases", J Biol Chem (1984) 259(3):1813–1821.
Irving et al., "Tau phosphorylation in cells transfected with wild–type or an Alzheimer's disease mutant presenilin 1", Neuroscience Letters 222(1977) 71–74.
Ishiguro et al., "Glycogen synthase kinase 3 beta is identical to tau protein kinase I generating several epitopes of paired helical filaments", FEBS (1993) 167–172.
Klein et al., "A molecular mechanism for the effect of lithium on development", Proc Natl Acad Sci USA (1996) 93:8455–8459.
Lawrence et al., "New insights into the role and mechanism of glycogen synthase activation by insulin", Diabetes (1997) 46:541–547.
Lawrence et al., "Control of glycogen synthase by insulin and isoproterenol in rat adipocytes. Changes in the distribution of phosphate in the synthase subunit in response to insulin and beta–adrenergic receptor activation", J Biol Chem (1986) 669–677.
Liu et al., "The state of phosphorylation of normal adult brain tau, fetal tau, and tau from Alzheimer paired helical filaments at amino acid residue Ser262", J Neurochem (1996) 66(3):1131–1139.

Lovestone et al., "Phosphorylation of tau by glycogen synthase kinase–3β in intact mammalian cells: The effects on the organization and stability of microtubules", Neuroscience (1996) 73(4):1145–1157.

Lovestone et al., "Alzheimer's disease–like phosphorylation of the microtubule–associated protein tau by glycogen synthase kinase–3 in transfected mammalian cells", Curr Biol (1994) 4(12):1077–1086.

Lucas et al., "Inhibition of GSK–3β leading to the loss of phosphorylated MAP–1B is an early event in axonal remodelling induced by WNT–7a or lithium", Journal of Cell Science (1998) 111:1351–1361.

Lucas et al., "WNT–7a induces axonal remodeling and increases synapsin I levels in cerebellar neurons", Developmental biology (1997) 192:31–44.

Mandelkow et al., "Glycogen synthase kinase–3 and the Alzheimer–like state of microtubule–associated protein tau", FEBS (1992) 314(3):315–321.

Mandelkow et al., "Microtubule–associated protein tau, paired helical filaments, and phosphorylation", Ann NY Acad Sci (1993) 695:209–216.

Mandelkow et al., "Tau domains, phosphorylation, and interactions with microtubules" Neurobiol Aging (1995) 16(3):355–363.

Michel et al., "Characterization of tau phosphorylation in glycogen synthase kinase–3β and cyclin dependent kinase–5 activator (p23) tranfected cells", BBA (1998) 177–182.

Moreno et al., "Glycogen synthase kinase 3 phosphorylation of different residues in the presence of different factors: Analysis on tau protein", Molecular and Cellular Biochemistry (1996) 165:47–54.

Mulot et al., "PHF–tau from Alzheimer's brain comprises four species on SDS–PAGE which can be mimicked by in vitro phosphorylation of human brain tau by glycogen synthase kinase–3β", FEBS Letters (1994) 359–364.

Munoz–Montano et al., "Lithium inhibits Alzheimer's disease–like tau protein phosphorylation in neurons". FEBS Letters (1997) 183–188.

Pei et al., "Distribution, levels, and activity of glycogen synthase kinase–3 in the Alzheimer disease brain", Journal of Neuropathology and Experimental Neurology (1997) 56(1):70–78.

Shiurba et al., "Immmunocytochemistry of tau phosphoserine 413 and tau protein kinase I in Alzheimer pathology", Brain Research (1996) 119–132.

Singh et al., "Protein kinase C and calcium/calmodulin–dependent protein kinase II phosphorylate three–repeat and Four–repeat tau isoforms at different rates", Molecular and Cellular Biochemistry (1997) 168:141–148.

Singh et al., "Differential phosphorylation of human tau isoforms containing three repeats by several protein kinases", Arch Biochem Biophys (1996) 328(1):43–50.

Sivaramakrishnan et al., "Characterization of different forms of kinase FA from rabbit skeletal muscle", Adv Enzyme Regul (1983) 21:321–330.

Skurat et al., "Multiple mechanisms for the phosphorylation of C–terminal regulatory sites in rabbit muscle glycogen synthase expressed COS cells", Biochem J (1996) 313:45–50.

Song et al., "Tau protein kinase I/GSK–3 beta/kinase FA in heparin phosphorylates tau on Ser 199, Thr231, Ser 235, Ser262, Ser369, and Ser400 sites phosphorylated in Alzheimer disease brain", J Protein Chem (1995) 14(2):95–105.

Sperber et al., "Glycogen synthase kinase–3 beta phosphorylates tau protein at multiple sites in intact cells", Neurosci Lett (1995) 197(2):149–153.

Srivastava et al., "Potential mechanisms(s) involved in the regulation of glycogen synthesis by insulin", Molecular and Cellular Biochemistry (1998) 182:135–141.

Stambolic et al., "Lithium inhibits glycogen synthase kinase–3 activity and mimics wingless signalling in intact cells", Current Biology (1996) 6(12):1664–1668.

Sutherland et al., "Inactivation of glycogen synthase kinase–3 beta by phosphorylation: new kinase connections in insulin and growth–factor signalling", Biochem J (1993) 296:15–19.

Takahashi et al., "Localization and developmental changes of tau protein kinase I/glycogen synthase kinase–3 beta in rat brain", J Neurochem (1994) 63(1):245–255.

Takashima et al., "Amyloid beta peptide induces cytoplasmic accumulation of amyloid protein precursor via tau protein kinase I/glycogen synthase kinase–3 beta in rat hippocampal neurons", Neurosci Lett (1995) 198(2):83–86.

Takashima et al., "Exposure of rat hippocampal neurons to amyloid beta peptide (25–35) induces the inactivation of phosphatidyl inositol–3 kinase and the activation of tau protein kinase I/glycogen synthase kinase–3 beta", Neurosci Lett (1996) 203(1):33–36.

Ueki et al., "Potential role of protein kinase B in insulin–induced glucose transport, glycogen synthesis, and protein synthesis", J Biol Chem (1998) 273(9):5315–5322.

Utton et al., J Biol Chem (1997) 741–747.

Van Lint et al., "A specific immunoprecipitation assay for the protein kinase FA/glycogen synthase kinase 3", Anal Biochem (1993) 208(1):132–137.

Van Weeren et al., "Essential role for protein kinase B (PKB) in insulin–induced glycogen synthase kinase 3 inactivation", J Biol Chem (1998) 273(21):13150–13156.

Wagner et al., "Cellular phosphorylation of tau by GSK–3β influences tau binding to microtubules and microtubule organisation", Journal of Cell Science (1996) 109:1537–1543.

Wang et al., "Use of a synthetic peptide as a selective substrate for glycogen synthase kinase 3", Anal Biochem (1994) 220(2):397–402.

Wang et al., "Inactivation of rabbit muscle glycogen synthase by glycogen synthase kinase–3. Dominant role of the phosphorylation of Ser–640 (site–3a)", J Biol Chem (1993) 268(32):23876–23880.

Woodgett, "Molecular cloning and expression of glycogen synthase kinase–3/factor A", EMBO J (1990) 9(8):2431–2438.

Yamaguchi et al., "Preferential labeling of Alzheimer neurofibrillary tangles with antisera for tau protein kinase (TPK) I/glycogen synthase kinase–3β and cyclin–dependent kinase 5, a component of TPK II" Acta Neuropathol (1996) 92:232–241.

Yang et al., "Protein kinase $F_A$/GSK–3 Phosphorylates τ on $Ser^{235}$–pro and $Ser^{404}$–pro that are abnormally phosphorylated in Alzheimer's disease brain", J Neurochem (1993) 61(5):1742–1747.

Yang et al., "Synergistic control mechanism for abnormal site phosphorylation of Alzheimer's diseased brain tau by kinase FA/GSK–3 alpha", Biochem Biophys Res Commun (1993) 197(2):400–406.

Zhang et al., "Mechanisms of multisite phosphorylation and inactivation of rabbit muscle glycogen synthase", Arch Biochem Biophys (1993) 304(1):219–225.

Zheng–Fischhofer et al., "Sequential phosphorylation of tau by glycogen synthase kinase–3β and protein kinase A at Thr212 and Ser214 generates the Alzheimer–specific epitope of antibody AT100 and requires a paired–helical–filament–like conformation", Eur J Biochem (1998) 252:542–552.

Cantello et al., "[[ω–(Heterocyclylamino)alkoxy]benzyl]–2, 4–thiazolidinediones as Potent Antihyperglycemic Agents", J. Med. Chem., (1994) 37:3977–3985.

* cited by examiner

Ar = aryl
A1-and A2 = desired substituents

Step A. Knoevenagel Condensation

● ⁓ = attachment to the resin via a p-substituted carboxamide

B. Cyclization and Oxidation to the Pyrimidine Nucleus

C. Amine Displacement and Release from the Solid Support

$A_1$, $A_2$, $A_3$, and $A_4$ = desired substituents $A_1$, $A_2$, and $A_3$ = desired substituents $A_1$ and $A_2$ = desired substituents

SEQUENCE LISTING

<160> NUMBER OF SEQ ID NOS: 4

<210> SEQ ID NO 1
<211> LENGTH: 420
<212> TYPE: PRT
<213> ORGANISM: Homo sapiens

<400> SEQUENCE: 1

```
Met Ser Gly Arg Pro Arg Thr Thr Ser Phe Ala Glu Ser Cys Lys Pro
  1               5                  10                  15

Val Gln Gln Pro Ser Ala Phe Gly Ser Met Lys Val Ser Arg Asp Lys
             20                  25                  30

Asp Gly Ser Lys Val Thr Thr Val Val Ala Thr Pro Gly Gln Gly Pro
         35                  40                  45
```

-continued

```
Asp Arg Pro Gln Glu Val Ser Tyr Thr Asp Thr Lys Val Ile Gly Asn
         50                  55                  60

Gly Ser Phe Gly Val Val Tyr Gln Ala Lys Leu Cys Asp Ser Gly Glu
 65                  70                  75                  80

Leu Val Ala Ile Lys Lys Val Leu Gln Asp Lys Arg Phe Lys Asn Arg
                 85                  90                  95

Glu Leu Gln Ile Met Arg Lys Leu Asp His Cys Asn Ile Val Arg Leu
                100                 105                 110

Arg Tyr Phe Phe Tyr Ser Ser Gly Glu Lys Lys Asp Glu Val Tyr Leu
            115                 120                 125

Asn Leu Val Leu Asp Tyr Val Pro Glu Thr Val Tyr Arg Val Ala Arg
        130                 135                 140

His Tyr Ser Arg Ala Lys Gln Thr Leu Pro Val Ile Tyr Val Lys Leu
145                 150                 155                 160

Tyr Met Tyr Gln Leu Phe Arg Ser Leu Ala Tyr Ile His Ser Phe Gly
                165                 170                 175

Ile Cys His Arg Asp Ile Lys Pro Gln Asn Leu Leu Leu Asp Pro Asp
            180                 185                 190

Thr Ala Val Leu Lys Leu Cys Asp Phe Gly Ser Ala Lys Gln Leu Val
        195                 200                 205

Arg Gly Glu Pro Asn Val Ser Tyr Ile Cys Ser Arg Tyr Tyr Arg Ala
    210                 215                 220

Pro Glu Leu Ile Phe Gly Ala Thr Asp Tyr Thr Ser Ser Ile Asp Val
225                 230                 235                 240

Trp Ser Ala Gly Cys Val Leu Ala Glu Leu Leu Leu Gly Gln Pro Ile
                245                 250                 255

Phe Pro Gly Asp Ser Gly Val Asp Gln Leu Val Glu Ile Ile Lys Val
            260                 265                 270

Leu Gly Thr Pro Thr Arg Glu Gln Ile Arg Glu Met Asn Pro Asn Tyr
        275                 280                 285

Thr Glu Phe Lys Phe Pro Gln Ile Lys Ala His Pro Trp Thr Lys Val
    290                 295                 300

Phe Arg Pro Arg Thr Pro Pro Glu Ala Ile Ala Leu Cys Ser Arg Leu
305                 310                 315                 320

Leu Glu Tyr Thr Pro Thr Ala Arg Leu Thr Pro Leu Glu Ala Cys Ala
                325                 330                 335

His Ser Phe Phe Asp Glu Leu Arg Asp Pro Asn Val Lys His Pro Asn
            340                 345                 350

Gly Arg Asp Thr Pro Ala Leu Phe Asn Phe Thr Thr Gln Glu Leu Ser
        355                 360                 365

Ser Asn Pro Pro Leu Ala Thr Ile Leu Ile Pro Pro His Ala Arg Ile
    370                 375                 380

Gln Ala Ala Ala Ser Thr Pro Thr Asn Ala Thr Ala Ala Ser Asp Ala
385                 390                 395                 400

Asn Thr Gly Asp Arg Gly Gln Thr Asn Asn Ala Ala Ser Ala Ser Ala
                405                 410                 415

Ser Asn Ser Thr
            420

<210> SEQ ID NO 2
<211> LENGTH: 17
<212> TYPE: PRT
<213> ORGANISM: Artificial sequence
<220> FEATURE:
```

-continued

```
<223> OTHER INFORMATION: SGSG-linked CREB peptide; Ser in position 15
      must be phosphorlyated

<400> SEQUENCE: 2

Ser Gly Ser Gly Lys Arg Arg Glu Ile Leu Ser Arg Arg Pro Ser Tyr
 1               5                  10                  15

Arg

<210> SEQ ID NO 3
<211> LENGTH: 5
<212> TYPE: PRT
<213> ORGANISM: Artificial Sequence
<220> FEATURE:
<221> NAME/KEY: Variant
<222> LOCATION: Position 2, 3, and 4 can be any amino acid.
<223> OTHER INFORMATION: SXXXS motif of the CREB peptide

<400> SEQUENCE: 3

Ser Xaa Xaa Xaa Ser
 1               5

<210> SEQ ID NO 4
<211> LENGTH: 383
<212> TYPE: PRT
<213> ORGANISM: Homo sapiens

<400> SEQUENCE: 4

Met Ala Glu Pro Arg Gln Glu Phe Glu Val Met Glu Asp His Ala Gly
 1               5                  10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Ala Glu Glu Ala
            35                  40                  45

Gly Ile Gly Asp Thr Pro Ser Leu Glu Asp Glu Ala Ala Gly His Val
        50                  55                  60

Thr Gln Ala Arg Met Val Ser Lys Ser Lys Asp Gly Thr Gly Ser Asp
 65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
        130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Ile Asn Lys Lys Leu
    210                 215                 220

Asp Leu Ser Asn Val Gln Ser Lys Cys Gly Ser Lys Asp Asn Ile Lys
225                 230                 235                 240

His Val Pro Gly Gly Gly Ser Val Gln Ile Val Tyr Lys Pro Val Asp
```

|   |   | 245 |   |   | 250 |   |   |   | 255 |   |   |
|---|---|---|---|---|---|---|---|---|---|---|---|
| Leu | Ser | Lys | Val | Thr | Ser | Lys | Cys | Gly | Ser | Leu | Gly | Asn | Ile | His | His |
|   |   |   | 260 |   |   |   | 265 |   |   |   | 270 |

```
            245                 250                 255
Leu Ser Lys Val Thr Ser Lys Cys Gly Ser Leu Gly Asn Ile His His
            260                 265                 270

Lys Pro Gly Gly Gly Gln Val Glu Val Lys Ser Glu Lys Leu Asp Phe
            275                 280                 285

Lys Asp Arg Val Gln Ser Lys Ile Gly Ser Leu Asp Asn Ile Thr His
        290                 295                 300

Val Pro Gly Gly Gly Asn Lys Lys Ile Glu Thr His Lys Leu Thr Phe
305                 310                 315                 320

Arg Glu Asn Ala Lys Ala Lys Thr Asp His Gly Ala Glu Ile Val Tyr
                325                 330                 335

Lys Ser Pro Val Val Ser Gly Asp Thr Ser Pro Arg His Leu Ser Asn
                340                 345                 350

Val Ser Ser Thr Gly Ser Ile Asp Met Val Asp Ser Pro Gln Leu Ala
            355                 360                 365

Thr Leu Ala Asp Glu Val Ser Ala Ser Leu Ala Lys Gln Gly Leu
    370                 375                 380
```

INHIBITORS OF GLYCOGEN SYNTHASE KINASE 3

This application claims the benefit of U.S. Provisional Application No. 60/089,978, filed Jun. 19, 1998.

FIELD OF THE INVENTION

This invention relates generally to the field of medicinal chemistry and specifically, to compounds that inhibit the activity of glycogen synthase kinase 3 (GSK3).

BACKGROUND OF THE INVENTION

Protein kinases and phosphatases regulate a wide range of events such as cell division, cell signaling, differentiation and metabolism. Regulation of these events is achieved by changing the phosphorylation status of specific amino acid (mainly serine, threonine, or tyrosine) in target protein sequences, which in turn, alters the function of these target proteins. Precise control of protein phosphorylation is thus fundamental to normal cellular behaviors.

Glycogen synthase kinase 3 (GSK3) is a proline-directed serine/threonine kinase. Woodgett, *Trends Biochem Sci.* 16:177–81 (1991). GSK3 consists of two isoforms, α and β, and is constitutively active in resting cells, inhibiting glycogen synthase by direct phosphorylation. Upon insulin activation, GSK3 is inactivated, thereby allowing the activation of glycogen synthase and possibly other insulin-dependent events. Subsequently, it has been shown that GSK3 activity is inactivated by other growth factors or hormones, that, like insulin, signal through receptor tyrosine kinases (RTKs). Examples of such signaling molecules include IGF-1 and EGF. Saito et al., *Biochem J.,* 303:27–31 (1994); Welsh et al., *Biochem. J.* 294:625–29 (1993); and Cross et al., *Biochem. J.,* 303:21–26 (1994).

Inhibition of GSK3 will thus mimic the action of known growth factors and thus would be useful in the treatment of disorders in which signaling by these factors is inadequate. Accordingly, the identification of inhibitors of GSK3 would be highly desirable.

SUMMARY OF THE INVENTION

The present invention provides GSK3 inhibitors having the structure:

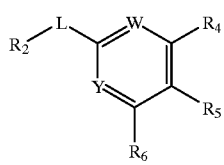

(I)

wherein:
W and Y are atoms each independently selected from the group consisting of a nitrogen atom and an optionally substituted carbon atom, wherein at least one of W and Y is a nitrogen atom;

L is a divalent aliphatic radical selected from the group consisting of a linear divalent radical having from about 2 to about 5 backbone atoms, acyclic divalent radical having from about 3 to about 7 backbone atoms, and a hybrid divalent having a linear component, which has from about 1 to about 3 backbone atoms, bonded to a cyclic component, which has from about 3 to about 7 backbone atoms, wherein each of said backbone atoms is selected from the group consisting of a carbon atom and a heteroatom, wherein at least 1 of said backbone atoms is a carbon atom, and wherein from 1 to about 3 of said backbone atoms is optionally a heteroatom, and wherein said divalent aliphatic radical is optionally substituted;

$R_2$ is an optionally substituted aryl;

$R_4$ and $R_6$ are each independently selected from the group consisting of hydrogen, a halo, and $R_7$, wherein $R_7$ is a monovalent radical selected from the group consisting of a lower alkyl, a cycloalkyl, an aryl, an aminoalkyl, an aminoarakyl, an aminocycloalkylaryl, an arylcarboxamidocycloalkylaralkyl, an arylcarboxamidocycloalkylaryl, an arylcarboxamidoalkylcycloalkyl, an arylcarboxamidoaryl, an arylcarboxamidoalkyl, an arylcarboxamidoaralkyl, an arylcarboxamidoalkoxyalkyl, an aminoalkoxyalkyl, and an arylsulfamidoaralkyl, and wherein $R_7$ is optionally substituted;

$R_5$ is selected from the group consisting of hydrogen, carboxyl, nitro, amino, cyano, an optionally substituted lower alkyl, an optionally substituted aryl, an optionally substituted aralkyl, an optionally substituted aminoalkyl, an optionally substituted aminoaryl, an optionally substituted aminoaralkyl, an optionally substituted aminoalkoxyalkyl, an optionally substituted arylaminoalkyl, an optionally substituted arylaminoaryl, an optionally substituted arylaminoaralkyl, an optionally substituted arylalkylamino, an optionally substituted arylalkylaminoalkyl, an optionally substituted arylalkylaminoaralkyl, an optionally substituted carboxcycloamido, an optionally substituted acyloxyalkyl, an optionally substituted acyloxyaryl, an optionally substituted acyloxyaralkyl, an optionally substituted acyloxyalkylcycloalkyl, an optionally substituted acyloxyalkylaminoalkyl, and an optionally substituted sulfonylalkyl, an optionally substituted carbamylallyl, an optionally substituted carbamylaryl, an optionally substituted carbamylarakyL, an optionally substituted carbamylalkylamino, an optionally substituted carbamylalkylaminoalkyl, an optionally substituted carbamylalkylaminoaryl and an optionally substituted carbamylalkylaminoaralkyl;

wherein, no more than two of $R_4$, $R_4$, and $R_6$ are hydrogen;

and salts thereof.

The present invention also provides GSK3 inhibitors having the structure:

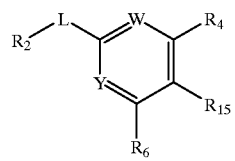

(II)

wherein:
W and Y are atoms each independently selected from the group consisting of a nitrogen atom and an optionally substituted carbon atom, wherein at least one of W and Y is a nitrogen atom;

L is a divalent aliphatic radical selected from the group consisting of a linear divalent radical having from 2 to about 5 backbone atoms, a cyclic divalent radical having from about 3 to about 7 backbone atoms, and a hybrid divalent radical having a linear component, which has from about 1 to about 3 backbone atoms, bonded to a cyclic component, which as from about 3 to about 7 backbone atoms,
  wherein each of said backbone atoms is selected from the group consisting of a carbon atom and a heteroatom,
  wherein at least 1 of said backbone atoms is a carbon atom,
  wherein 2 or 3 backbone atoms in said linear divalent radical are heteroatoms,
  wherein from 1 to about 3 of said backbone atoms in said cyclic divalent radical and said hybrid divalent radical are optionally heteroatoms, and
  wherein said divalent aliphatic radical is optionally substituted;

$R_2$ is an optionally substituted aryl;

$R_4$ and $R_6$ are each independently selected from the group consisting of hydrogen, a halo, and $R_7$,
  wherein $R_7$ is a monovalent radical selected the group consisting of a lower alkyl a cycloalkyl, an aryl, an aminoalkyl, an aminoaralkyl, an aminocycloalkylaryl, an arylcarboxamidocycloalkylarlkyl, an arylcarboxamidocycloalkylaryl, an arylcarboxamidoallylcycloalkyl an arylcarboxamidoaryl an arylcarboxamidoalkyl, an arylcarboxamidoaralkyl, an arylcarboxamidoalkoxyalkyl, an aminoalkoxyalkyl, and an arylsulfamidoaralkyl and
  wherein $R_7$ is optionally substituted;

$R_{15}$ is selected from the group consisting of carboxamido, an optionally substituted carboxamidoalkyl, an optionally substituted carboxamidoaryl, an optionally substituted carboxamidoaralkyl an optionally substituted carboxamidoalkylcarboxamido, an optionally substituted carboxamidoalkylcarboxamidoalkyl, an optionally substituted carboxamidoalkylcarboxamidoaryl, and an optionally substituted carboxamidoalkylcarboxamidoaralkyl;
  wherein no more than two of $R_4$, $R_{15}$, and $R_6$ are hydrogen; and salts thereof.

In yet another embodiment, the present invention provides a method for inhibiting GSK3 activity, said method comprising:
  (i) providing an effective amount of GSK3 inhibitor compound (I) or (II); then
  (ii) administering said effective amount of said GSK3 inhibitor compound to a subject.

In still a further embodiment, the present invention provides a method for treating a GSK3-mediated disorder, said method comprising:
  (i) providing therapeutically effective amount of GSK3 inhibitor compound (I) or (II); then
  (ii) administering to a subject said therapeutically effective amount of the GSK3 inhibitor compound, wherein said subject is afflicted with a GSK3-mediated disorder.

DETAILED DESCRIPTION

Figure 1:
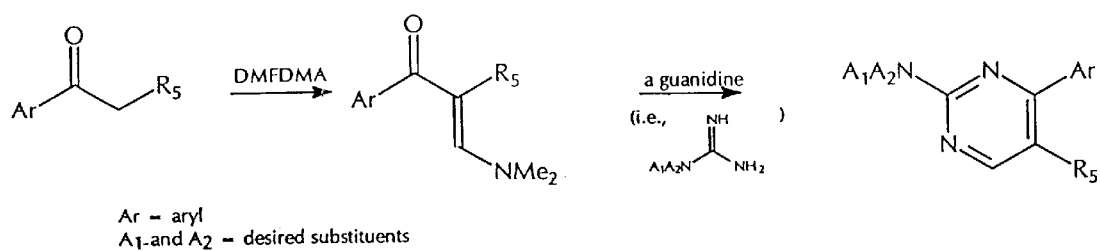
FIG. 1 illustrates the reaction scheme for the-synthesis of compounds of the present invention in accordance with Solution Phase Method A, described in Example 25.

In accordance with the present invention, there are provided pyridine- and pyrimidine-based compounds that are useful for inhibiting the activity of GSK3. The terms "glycogen synthase kinase 3" and "GSK3" are used interchangeably herein to refer to the protein originally identified by its phosphorylation of glycogen synthase as described in Woodgett et al., *Trends Biochem. S*, 16:177–81 (1991), incorporated herein by reference. By inhibiting GSK3 kinase activity, activities downstream of GSK3 activity are inhibited or alternatively, stimulated. For example, when GSK3 activity is inhibited, glycogen synthase may be activated, resulting in increased glycogen production. GSK3 is also known to act as a kinase in a variety of other contexts, including, for example, phosphorylation of c-jun, β-catenin, and tau protein. It is understood that inhibition of GSK3 kinase activity can lead to a variety of effects in a variety of biological contexts. The invention, however, is not limited by any theories of mechanism as to how the invention works.

The present invention provides GSK3 inhibitors having the structure:

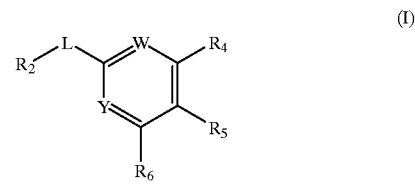

(I)

wherein:
  W and Y are atoms each independently selected from the group consisting of a nitrogen atom and an optionally substituted carbon atom, wherein at least one of W and Y is a nitrogen atom;
  L is a divalent aliphatic radical selected from the group consisting of a linear divalent radical having from about 2 to about 5 backbone atoms, a cyclic divalent radical having from about 3 to about 7 backbone atoms, and a hybrid divalent having a linear component, which has from about 1 to about 3 backbone atoms, bonded to a cyclic component, which has from about 3 to about 7 backbone atoms,
    wherein each of said backbone atoms is selected from the group consisting of a carbon atom and a heteroatom,
    wherein at least 1 of said backbone atoms is a carbon atom, and wherein from 1 to about 3 of said backbone atoms is optionally a heteroatom, and
    wherein said divalent aliphatic radical is optionally substituted;
  $R_2$ is an optionally substituted aryl;
  $R_4$ and $R_6$ are each independently selected from the group consisting of hydrogen, a halo, and $R_7$,
    wherein $R_7$ is a monovalent radical selected from the group consisting of a lower alkyl, a cycloalkyl, an aryl, an aminoalkyl, an aminoaralkyl, an aminocycloalkylaryl, an arylcarboxamidocycloalkylaralkyl, an arylcarboxamidocycloalkylaryl, an arylcarboxamidoalkylcycloalkyl, an arylcarboxamidoaryl, an arylcarboxamidoalkyl, an arylcarboxamidoaralkyl, an arylcarboxanudoalkoxyalkyl, an aminoalkoxyalkyl, and an arylsulfamidoaralkyl, and wherein R$_7$ is optionally substituted;

R$_5$ is selected from the group consisting of hydrogen, carboxyl, nitro, amino, cyano, an optionally substituted lower alkyl, an optionally substituted aryl, an optionally substituted aralkyl, an optionally substituted aminoalkyl, an optionally substituted aminoaryl, an optionally substituted aminoaralkyl, an optionally substituted aminoalkoxyalkyl, an optionally substituted arylaminoalkyl, an optionally substituted arylaminoaryl, an optionally substituted arylaminoaralkyl, an optionally substituted arylalkylamino, an optionally substituted arylalkylaminoalkyl, an optionally substituted arylalkylaminoaralkyl, an optionally substituted carboxcycloamido, an optionally substituted acyloxyalkyl, an optionally substituted acyloxyaryl, an optionally substituted acyloxyaralkyl, an optionally substituted acyloxyalkylcycloalkyl, an optionally substituted acyloxyalkylaminoalkyl, and an optionally substituted sulfonylalkyl, an optionally substituted carbamylalkyl, an optionally substituted carbamylaryl, an optionally substituted carbamylaralkyl, an optionally substituted carbamylalkylamino, an optionally substituted carbamylalkylaminoalkyl, an optionally substituted carbamylalkylaminoaryl, and an optionally substituted carbamylalkylaminoaralkyl;

wherein no more than two of R$_4$, R$_5$, and R$_6$ are hydrogen;

and salts thereof.

The present invention also provides GSK3 inhibitors having the structure:

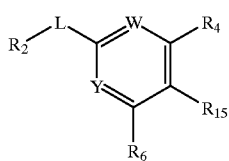

(II)

wherein:

W and Y are atoms each independently selected from the group consisting of a nitrogen atom and an optionally substituted carbon atom, wherein at least one of W and Y is a nitrogen atom;

L is a divalent aliphatic radical selected from the group consisting of a linear divalent radical having from 2 to about 5 backbone atoms, a cyclic divalent radical having from about 3 to about 7 backbone atoms, and a hybrid divalent radical having a linear component, which has from about 1 to about 3 backbone atoms, bonded to a cyclic component, which as from about 3 to about 7 backbone atoms, wherein each of said backbone atoms is selected from the group consisting of a carbon atom and a heteroatom, wherein at least 1 of said backbone atoms is a carbon atom, wherein 2 or 3 backbone atoms in said linear divalent radical are heteroatoms, wherein from 1 to about 3 of said backbone atoms in said cyclic divalent radical are optionally heteroatoms, and wherein said divalent aliphatic radical is optionally substituted;

R$_2$ is an optionally substituted aryl;

R$_4$ and R$_6$ are each independently selected from the group consisting of hydrogen, a halo, and R$_7$, wherein R$_7$ is a monovalent radical selected from the group consisting of a lower alkyl, a cycloalkyl, an aryl, an aminoalkyl, an aminoaralkyl, an aminocycloalkylaryl, an arylcarboxamidocycloalkylaralkyl, an arylcarboxamidocycloalkylaryl, an arylcarboxamidoalkylcycloalkyl, an arylcarboxamidoaryl, an arylcarboxamidoalkyl, an arylcarboxamidoaralkyl, an arylcarboxamidoalkoxyalkyl, an aminoalkoxyalkyl, and an arylsulfamidoaralkyl, and wherein R$_7$ is optionally substituted;

R$_{15}$ is selected from the group consisting of carboxamido, an optionally substituted carboxamidoalkyl, an optionally substituted carboxamidoaryl, an optionally substituted carboxamidoaralkyl, an optionally substituted carboxamidoalkylcarboxamido, an optionally substituted carboxamidoalkylcarboxamidoalkyl, an optionally substituted carboxamidoalkylcarboxamidoaryl, and an optionally substituted carboxamidoalkylcarboxamidoaralkyl;

wherein no more than two of R$_4$, R$_5$, and R$_6$ are hydrogen;

and salts thereof.

The phrases "compounds of the present invention" and "GSK3 inhibitor compounds of the present invention" are used interchangeably herein to refer to compounds having structures (I) and (II), including their salts. The terns "GSK3 inhibitor" and "GSK3 inhibitor compound" are used interchangeably herein to refer to a compound that, for example, typically exhibits an IC$_{50}$ (with respect to GSK3) of no more than about 100 $\mu$M and more typically not more than about 50 $\mu$M, as measured in a cell-fee assay for GSK3 inhibitory activity. As used herein, the phrase "cell-free assay for GSK3 inhibitory activity" refers to the cell-free GSK3 kinase assay described generally herein, and more specifically in Example 74, herein below. The term "IC$_{50}$" refers herein to that concentration of inhibitor which reduces the activity of a kinase (e.g., GSK3) to half-maximal level. Compounds of the present invention have been discovered to exhibit inhibitory activity against GSK3, as well as some other protein kinases (e.g., cdc2). The term "kinase inhibitory activity" refers herein to the capacity of a compound to inhibit the activity of a particular kinase.

Compounds of the present invention usually exhibit an IC$_{50}$ with respect to GSK3 of no more than about 10 $\mu$M, more typically, no more than about 5 $\mu$M, preferably not more than about 1 $\mu$M, and most desirably, not more than about 200 nM, as measured in a cell-free GSK3 kinase assay.

As used herein, the term "optionally substituted" refers to the replacement of hydrogen with a monovalent radical such as, for example, a halo, a lower haloalkyl, a lower haloalkoxy, carboxyl, amino, —SH, thioamido, carboxamido, sulfamido, a lower sulfonylalkyl, a sulfonylaryl, a sulfonylaralryl, nitro, —SO$_3$H, hydroxyl, cyano, a lower alkyl, a lower alkoxy, a hydroxyl-substituted lower alkyl, a cycloalkyl (i.e., a carbocyclic alkyl or a heterocyclic alkyl), a mono- or polycyclic (carbocyclic or heterocyclic) aryl, a lower aralkyl, an aminoalkyl, an aminoaryl, an aminoaralkyl, a lower alkylamino, a lower alkylaminoalkyl, a lower alkylaminoaryl, a lower alkylaminoaralkyl, an acyloxyalkyl, an acyloxyaryl, an acyloxyaralkyl, a lower alkylacyloxyalkyl, a lower alkylacyloxyaryl, a lower alkylacyloxyarlkyl, a lower alkoxyalkyl, a lower alkoxyaryl, a lower alkoxyaralkyl, an acyloxyalkylamino, an acyloxyalkylaminoalkyl, a lower acyloxyalkylaminoaryl, an acyloxyalkylaminoaralkyl, a lower alkylacyloxylalkylamino, a lower alkylacyloxyalkylaminoalkyl, a lower alkylacyloxyalkylaminoaryl, a lower alkylacyloxyalkylaminoaralyl, a carboxamidoalkyl, a carboxamidoaryl, a carboxamidoaralkyl, a carboxcycloamido, a carboxamidoalkylcarboxamido, a carboxamidoalkylcarboxamidoalkyl, a carboxamidoalkylcarboxamidoaryl, a carboxamidoalkylcarboxamidoaralkyl, a lower alkylcarboxamidoalkyl, a lower alkylcarboxamidoaryl, a lower alkylcarboxamidoaralkyl, an arylcarboxamidoalkyl, an arylcarboxamidoaryl, a arylcarboxamidoaralkyl, a thioamidoalkyl a thioamidoalkyl, a thioamidoaralkyl, a lower alkylthioamido, a lower alkylthioamidoalkyl, a lower alkylthioamidoaryl, a lower alkylthioamidoaralkyl, a lower alkylthiol, an arylthiol, an aralkylthiol, and the like.

Substitution groups employed in compounds of the present invention can themselves be substituted, e.g., substituted substition groups such as, amino-substituted phenyl, mono-, di-, and tri-halo substituted phenyl, and cyano-substituted phenyl, amino-substituted pyridyl, cyano-substituted lower alkyl, amino-substituted lower alkyl, carboxamido(hydroxyl-substituted)alkyl, carboxamido(cyano-substituted)alkyl, a carboxamidoalkylcarboxamido substituted with $R_\alpha$ (i.e. a carboxamidoalkylcarboxamido group that is derived from an amidated amino acid such that the resulting carboxamidoalkylcarboxamido is substituted with the a carbon substitution (i.e., $R_\alpha$) of the amino acid), and the like.

When the substitution group is substituted, the group substituted onto the substitution group is typically carboxyl, a halo; nitro, amino, cyano, hydroxyl, a lower alkyl having from 1 to about 6 carbon atoms in its backbone structure and optionally substituted with one or more halo or hydroxyl groups; a lower alkoxy having from 1 to about 6 carbon atoms in its backbone structure and optionally substituted with one or more halo or hydroxyl groups; —SH; thioamido; carboxamido; —SO$_3$H; a cycloalkyl; or $R_\alpha$ (i.e., the α-carbon substitution from an amino acid), an aryl carboxamidoalkyl, a lower alkyl or an aryl optionally substituted with carboxyl, a halo, nitro, amino cyano, hydroxyl, and/or a lower alkyl having from 1 to about 6 carbon atoms.

When the substituted substituent is a straight chain group, the substitution can occur either within the chain (e.g., 2-hydroxypropyl, 2-aminobutyl, and the like) or at the chain terminus (e.g., 2-hydroxyethyl, 3-cyanopropyl, and the like). As used herein, the term "backbone" refers to the scaffold structure of a substituent which is typically either a straight chain, branched or cyclic arrangement of covalently bonded carbon or heteroatoms (i.e., the scaffold structure does not include any of the hydrogen atoms, or alternatively, substitution groups bonded to it).

In the GSK3 inhibitors of the present invention, L, $R_2$, $R_4$, $R_5$, $R_6$, and $R_{15}$ can be substituted with more than one substitution group, e.g., they can be di-substituted, tri-substituted, etc. with two or more of the same or different substitution group.

As used herein, the term "alkyl" refers to straight chain, branched, or cyclic saturated radicals having from 1 to about 20 carbon atoms. The term "lower" refers herein to organic radicals having up to about 10 carbon atoms, and more typically up to about 6 carbon atoms in a straight chain or branched configuration. Thus, for example, the term "lower alkyl" includes methyl, ethyl, propyl, isopropyl, butyl, t-butyl, and the like.

The term "alkylenyl" refers to a divalent straight chain or branched chain saturated aliphatic radical having from 1 to about 20 carbon atoms. Typical alkylenyl groups employed in compounds of the present invention have from 1 to about 6 carbon atoms in their backbone.

The terms "cycloalkyl" and "cyclic alkyl" are used interchangeably herein to refer to a mono- or polycyclic, heterocyclic or carbocyclic alkyl substituent. Typical cycloalkyl substituents have from about 3 to about 8 backbone (i.e., ring) atoms in which each backbone atom is either carbon or a heteroatom. The term "heterocyclic alkyl" refers herein to cycloalkyl substituents which have from 1 to about 5, and more typically from 1 to about 4 heteroatoms in the ring structure. Carbocyclicoalkyl groups are cycloalkyl groups in which all ring atoms are carbon. When used in connection with cycloalkyl substituents, the term "polycyclic" refers herein to fused and non-fused alkyl cyclic structures. Suitable heteroatoms employed in compounds of the present invention are nitrogen, oxygen, and sulfur.

As used herein, the term "alkoxy" refers to the moiety, —OR, where R is an alkyl. The term "lower alkoxy" refers herein to an alkoxy moiety in which R is a lower alkyl. The term "alkenyl" refers to straight chain, branched, or cyclic radicals having one or more double bonds and from 2 to about 20 carbon atoms. The term "alkynyl" refers herein to straight chain, branched, or cyclic radicals having one or more triple bonds and from 2 to about 20 carbon atoms.

The term "halo" refers herein to a halogen radical, such as fluorine, chlorine, bromine, or iodine. The term "haloalkyl" refers to an alkyl radical substituted with one or more halogen atoms. The term "lower haloalkyl" refers to a lower alkyl radical substituted with one or more halogen atoms. The term "haloalkoxy" refers to an alkoxy radical substituted with one or more halogen atoms. The term "lower haloalkoxy" refers to a lower alkoxy radical substituted with one or more halogen atoms.

As used herein, the term "aryl" refers to monocyclic and polycyclic aromatic groups having from 3 to about 14 backbone (carbon or hetero) atoms, and includes both carbocyclic aryl groups and heterocyclic aryl groups. Carbocyclic aryl groups are aryl groups in which all ring atoms in the aromatic ring are carbon. The term "heterocyclic aryl" refers herein to aryl groups having from 1 to about 4 heteroatoms as ring atoms in an aromatic ring with the remainder of the ring atoms being carbon atoms. When used in connection with aryl substituents, the term "polycyclic" refers herein to fused and non-fused cyclic structures in which at least one cyclic structure is aromatic, such as for example, benzodioxozolo (which has a heterocyclic structure fused to a phenyl group, i.e.

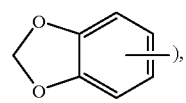

), naphthyl, and the like. Exemplary aryl moieties employed as substituents in compounds of the present invention include phenyl, pyridyl, pyrimidinyl, imidazolo, oxadiazolo (e.g., 1,2,4-oxadiazolo, 1,3,4-oxadiazolo, 1,2,3-oxadiazolo, and the like), tetrazolo, pyrazinyl, triazolo, thiophenyl, furanyl, quinolino, purinyl, naphthyl, benzothiazolo, benzopyridyl, benzimidazolo, benzodioxolo, thiazolo, oxazolo, and the like.

The term "aralkyl" refers to an alkyl group substituted with an aryl group. The term "lower aralkyl" refers to an aralkyl group in which the alkyl component of the aralkyl group is a lower alkyl. Typically, aralkyl groups employed in compounds of the present invention have from 1 to about 6 carbon atoms incorporated within the alkyl portion of the aralkyl group. Suitable aralkyl groups employed in compounds of the present invention include, for example, benzyl, picolyl, and the like.

The term "amino" refers herein to the group —NH$_2$. The term "aminoalkyl" refers herein to the group —NPP' where R and R' are each independently selected from hydrogen or a lower alkyl The term "aminoaryl" refers herein to the group —NRR' where R is aryl and R' is hydrogen, a lower alkyl, or an aryl. The term "aminoaralkyl" refers herein to the group —RR' where R is a lower aralkyl and R' is hydrogen, a lower alkyl, an aryl, or a lower aralkyl.

The term "aminocycloalkylaryl" refers herein to the group, —NH-cycloalk$_1$-aryl, where cycloalk$_1$ is a divalent cycloalkyl group. Typically, cycloalk$_1$ has from 3 to about 6 backbone atoms, of which, optionally 1 to about 4 are heteroatoms. Preferably, cycloalk$_1$ is cyclopropyl.

The term "alkylamino" refers to an alkyl group that is terminally substituted with an amino group, i.e., —NH$_2$. The terms (1) "alkylaminoalkyl," (2) "alkylaminoaryl," and (3) "alkylaminoaralkyl" refer herein to the groups, (1)-alk$_1$-(aminoalkyl), (2)-alk$_1$(aminoaryl), and (3)-aklk$_1$-(aminoaralkyl), where alk$_1$ is an alkylenyl. The terms "lower alkylaminoalkyl," "lower alkylaminoaryl," and "lower alkylaminoaralkyl" refer to alkylaminoalkyl, alkylaminoaryl, and alkylaminoaralkyl groups in which alk$_1$ is a lower alkylenyl group. Typically, alk$_1$ is an alkylenyl having from 1 to about 6 carbon atoms in its backbone.

The terms (1) "arylaminoalkyl," (2) "arylaminoaryl," and (3) "arylaminoaralkyl" refer herein to the groups, (1)-aryl-(aminoalkyl), (2)-aryl-(aminoaryl), and (3)-aryl-(aminoaralkyl).

The terms (1) "arylalkylamino, (2) "arylalkylaminoalkyl," (3) "arylalkylaminoaryl," and (4) "arylalkylaminoaralkyl" refer herein to the groups, (1)-aryl-alk$_2$-(amino), (2)-aryl-alk$_2$-(aminoalkyl), (3)-aryl-alk$_2$-(aminoaryl), and (4)-aryl-alk$_2$-(aminoaralkyl), where -aryl- is a divalent aryl, and alk$_2$ is an alkylenyl. The terms "lower arylalkyamino," "lower arylalkylaminoalkyl," "lower arylalkylaminoaryl," and lower "arylalkylaminoaralkyl" refer herein to arylalkylamino, arylalkylaminoalkyl, arylalkylaminoaryl, and arylalkylaminoaralkyl groups in which alk$_2$ is a lower alkylenyl group. More typically, alk$_2$ has from 1 to about 6 carbon atoms in its backbone.

The term "alkoxyalkyl" refers to the group -alk$_3$-O-alk$_4$ where alk$_3$ is an alkylenyl and alk$_4$ is an alkyl. The term "lower alkoxyalkyl" refers to an alkoxyalkyl where alk$_3$ and alk$_4$ are a lower alkylenyl and lower alkyl respectively. Typically, alk$_3$ and alk$_4$ have from 1 to about 6 carbon atoms in their backbone structures. The term "alkoxyaryl" refers to the group -alk$_3$-O-aryl, where alk$_3$ is an alkylenyl. The term "alkoxyaralkyl" refers to the group -alk$_3$-O-aralkyl, where alk$_3$ is an alkylenyl and the aralkyl is a lower aralkyl. The terms "lower alkoxyaryl" and "lower alkoxyaralkyl" refer to alkoxyaryl and alkoxyaralkyl groups in which alk$_3$ is a lower alkylenyl group. Typically, alk$_3$ has from 1 to about 6 carbon atoms in its backbone.

The term "aminoalkoxyalkyl" refers herein to the group —NH-(alkoxylalkyl). The term "lower aminoalkoxyalkyl" refers herein to an aminoalkoxyalkyl in which the alkoxyalkyl is a lower alkoxyalkyl.

The term "carboxamido" refers herein to the group —C(O)—NH$_2$. The term "carboxidoalkyl" refers herein to the group —C(O)—NRR' where R is a lower alkyl and R' is hydrogen or a lower alkyl. The term "carboxamidoaryl" refers herein to the group —C(O)—NRR' where R is an aryl and R' is hydrogen, a lower alkyl, or an aryl. The term "carboxamidoaralkyl" refers herein to the group —C(O)—NRR' where R is a lower aralkyl and R' is hydrogen, a lower alkyl, an aryl, or a lower alkyl.

The terms, (1) "carboxamidoalkylcarboxamido," (2) "carboxamidoalkylcarboxamidoalkyl," (3) "carboxamidoalkylcarboxamidoaryl," and (4) "carboxamidoalkylcarboxamidoaralkyl," refer herein to a carboxamidoalkyl, that is terminally substituted through the alkyl group with (1) a carboxamido, (2) a carboxamidoalkyl, (3) a carboxamidoaryl, and (4) a carboxamidoaralkyl. Exemplary carboxamidoalkylcarboxamido groups employed in compounds of the present invention are substituted carboxamidoalkylcarboxamido groups that are derived from an amidated amino acid, i.e., —C(O)—NH—(CHR$_\alpha$)—C(O)—NH$_2$, where R$_\alpha$ is the carbon substitution of an α-amino acid (i.e., the carboxamidoalkylcarboxamido group is substituted with R$_\alpha$). The term "amino acid" refers herein to both naturally and non-naturally occuring amino acids.

The term "carboxcycloamido" refers herein to the group —C(O)-cycloalk$_2$, where cycloalk$_2$ is a heterocyclic alkyl having at least one nitrogen atom incorporated in its ring structure which is bonded directly to the carbonyl carbon. The group, cycloalk$_2$, typically has from 3 to about 6 carbon atoms, and at least one heteroatom that is nitrogen. Suitable cycloalk$_2$ substituents include, for example, morpholino, piperazinyl, piperidinyl, and the like.

The terms (1) "alkylboxamidoalkyl," (2) "alkylcarboxamidoaryl," and (3) "alkylcarboxamidoaralkyl" refer herein to the groups, (1)-alk$_5$-(carboxamidoalkyl), (2)-alk$_5$-(carboxamidoaryl), and (3)-alk$_5$-(carboxamidoaralkyl), where alk$_5$ is an alkylenyl. The term "lower" when used in conjuction with the terms "alkylcarboxamidoalkyl," alkylcarboxamidoaryl," and "alkylcarboxamidoaralkyl" refers to alkylcarboxamidoalkyl, alkylcarboxamidoaryl, and alkylcarboxamidoalkyl groups in which alk$_5$ is a lower alkylenyl group. More typically, alk$_5$ has from 1 to about 6 carbon atoms in its backbone structure.

Similarly, the terms (1) "arylcarboxamidoalkyl," (2) "arylcarboxamidoaryl," and (3) "arylcarboxamidoaralkyl" refer herein to the groups, (1)-aryl-(carboxamidoalkyl), (2)-aryl-(carboxamidoaryl), and (3)-aryl-(carboxamidoaralkyl), where -aryl- is a divalent aryl.

The terms "arylcarboxamidocycloalkylaralkyl" and "arylcarboxamidocycloalkylaralkyl" refer herein to the groups -aryl-C(O)—NH-cycloalk$_3$-aralkyl and -aryl-C(O)—NH-cycloalk$_3$-aryl, respectively, in which cycloalk$_3$ is a divalent cycloalkyl radical and the aralkyl is a lower aralkyl. Typically, cycloalk$_3$ has from 3 to about 6 carbon atoms, and optionally from 1 to about 4 heteroatoms as ring atoms. Preferably, cycloalk$_3$ is a divalent cyclopropyl radical. Preferably, the lower alkyl has from 1 to about 6 carbon atoms in its backbone structure.

The term "arylcarboxamidoalkylcycloalkyl" refers herein to the group -aryl-C(O)—NH-alk$_6$-cycloalk$_4$, in which alk$_6$ is a lower alkylenyl and cycloalk$_4$ is a cycloalkyl radical having from 3 to about 6 ring atoms, of which, optionally from 1 to about 4 are heteroatoms. Typically, $alk_6$ has from 1 to about 6 carbon atoms in its backbone structure and $cycloalk_3$ is a cyclopropyl radical.

The term "arylcarboxamidoalkoxyalkyl" refers herein to the group aryl-C(O)—NH-$alk_3$-O-$alk_4$, where $alk_3$ and $alk_4$ are defined above.

The term "sulfamido" refers herein to the group —S(O)$_2$—NH$_2$. The term "arylsulfamidoaralkyl" refers herein to the group -aryl-S(O)$_2$—NH-aralkyl, where the aralkyl is a lower aralkyl.

The term "acyloxy" refers generally to the ester group —C(O)—O—R, where R is a lower alkyl, a cycloalkyl, an aryl, or a lower aralkyl. The tern "acyloxyalkyl" refers herein to the ester group —C(O)—O—R where R is a lower alkyl. The term "acyloxycycloalkyl" refers generally herein to both an "acyloxycarbocyclic alkyl" and an "acyloxyheterocyclic alkyl", i.e., where R is a carbocyclic alkyl or heterocyclic alkyl, respectively. The term "acyloxyaryl" refers herein to the group —C(O)—O-aryl, where aryl is a mono- or polycyclic, carbocyclic or heterocyclic aryl. The term "acyloxyaralkyl" refers herein to the group —C(O)—O-aralkyl, where the aralkyl is a lower aralkyl.

The term "alkylacyloxy" refers generally to the group, $alk_7$-(acyloxy), where $alk_7$ is an alkylenyl. Typically, $alk_7$ is a lower alkylenyl, and mose typically, $alk_7$ has from 1 to about 6 carbon atoms in its backbone structure. The terms, (1) "alkylacyloxyarlkyl," (2) "alkylacyloxyaryl," and (3) "alkylacyloxyaralkyl," referred the groups, (1) $alk_7$-(acyloxyalkyl), (2) $alk_7$-(acyloxyaryl), and (3) $alk_7$-(acyloxyaralkyl), where $alk_7$ is as defined above. The terms "lower alkylacyloxyarlkyl," "lower alkylacyloxyaryl," and "lower alkylacyloxyaralkyl" refer to alkylacyloxyarlkyl, alkylacyloxyaryl, and alkylacyloxyaralkyl groups in which $alk_7$ is a lower alkylenyl.

The term "alkylacyloxyalkylamino" refers to an alkylacyloxyarlkyl that is terminally substituted with an amino group (i.e., —NH$_2$). The term "alkylacyloxyalkylaminoalkyl" refers to an alkylacyloxyarlkyl that is terminally substituted with an aminoalkyl. The term "alkylacyloxyalkylaminoaryl" refers to an alkylacyloxyarlkyl that is terminally substituted with an aminoaryl. The term "alkylacyloxyalkylaminoaralkyl" refers to an alkylacyloxyarlkyl that is terminally substituted with an aminoaralkyl.

The term "acyloxyalkylcycloalkyl" refers herein to the ester group —C(O)—O-$alk_8$-$cycloalk_4$, where $alk_8$ is an alkylenyl and $cycloalk_4$ is a carbocyclic alkyl or heterocyclic alkyl. Typically, $alk_8$ is a lower alkylenyl. More typically, $alk_8$ has from 1 to about 6 carbon atoms in its backbone structure. The term "acyloxyalkylcarbocyclic alkyl" refers herein to an acyloxyalkylcycloalkyl in which $cycloalk_4$ is a carbocyclic alkyl, such as, for example, cyclopropyl, cyclobutyl, cyclopentyl, cyclohexyl, and the like. The term "acyloxyalkylheterocyclic alkyl" refers herein to an acyloxyalkylcycloalkyl in which $cycloalk_4$ is a heterocyclic alkyl, such as, for example, morpholino, piperazinyl, piperadinyl, and the like.

The terms, (1) "acyloxyalkylamino," (2) "acyloxyalkylaminoaralkyl," (3) "acyloxyalkylaminoaryl," and (4) "acyloxyalkylaminoaralkyl" refer herein to an acyloxyalkyl group that is terminally substituted with (1) an amino group, (2) an aminoalkyl group, (3) an aminoaryl group, and (4) an aminoaralkyl group.

The term "sulfonyl" refers herein to the group —SO$_2$-R, where R is a straight chain, branched or cyclic alkyl, an aryl, or an aralkyl. The term "sulfonylalkyl" refers to a sulfonyl in which R is an alkyl. Sulfonylalkyl groups employed in compounds of the present invention are typically lower sulfonylalkyl groups. More typically, the alkyl component of the sulfonylalkyl group has from 1 to about 6 carbon atoms in its backbone structure. Thus, typical sulfonylalkyl groups employed in compounds of the present invention include, for example, methyl sulfonyl (i.e., where R is methyl), ethyl sulfonyl (i.e., where R is ethyl), propyl sulfonyl (i.e., where R is propyl), and the like. The term "sulfonylaryl" refers herein to the group —SO$_2$-aryl. The term "sulfonylaralkyl" refers herein to the group —SO$_2$-aralkyl, in which the aralkyl is a lower aralkyl.

As used herein, the term "carbamyl" refers to the group —NH—C(O)—O—R, where R is a straight chain, branched or cyclic alkyl, an aryl, or a lower aralkyl. The term "carbamylalkyl" refers to a carbamyl where R is a lower alkyl. More typically, the alkyl component of the carbamylalkyl has from 1 to about 6 carbon atoms in its backbone structure. The team "carbamylaryl" refers to a carbamyl where R is an aryl. The term "carbamylaralkyl" refers to a carbamyl where R is a lower aralkyl.

As used herein, the terms (1) "carbamylalkylamino," (2) "carbamylalkylaminoalkyl," (3) "carbamylalklylaminoaryl," and (4) "carbamylalkylaminoaralkyl refer to a carbamylalkyl group that is terminally substituted with (1) an amino group, (2) an aminoalkyl group, (3) an aminoaryl group, and (4) an aminoaralkyl group.

The term "thioamido" refers herein to the group —CS)—NH$_2$. The term "thioamidoalkyl" refers herein to the group —C(S)—NRR' where R is a lower alkyl and R' is hydrogen or a lower alkyl. The term "thioamidoaryl" refers herein to the group —C(S)—NRR' where R is an aryl and R' is hydrogen, a lower alkyl, or an aryl. The term "thioamidoaralkyl" refers herein to the group —C(S)—NRR' where R is a lower aralkyl and R' is hydrogen, a lower alkyl, an aryl, or a lower alkyl.

The terns (1) "alkylthioamido," (2) "alkylthioamidoaralkyl," (3) "alkylthioamidoaryl," and (4) "alkylthioamidoaralkyl" refer herein to the groups, (1)-$alk_9$-(thioamido), (2)-$alk_9$-(thioamidoalkyl), (3)-$alk_9$-(thioamidoaryl), and (4)-$alk_9$-(thioamidoaralkyl), where $alk_9$ is an alkylenyl. The term "lower" when used in conjuction with the terms "alkylthioamidoaralkyl," "alkylthioamidoaryl," and "alkylthioamidoaralkyl" refers to the $alk_9$ alkylenyl group.

The terms "alkylthiol" and "lower alkylthiol" refer to the group -$alk_{10}$-SH, in which $alk_{10}$ is an alkylenyl and lower alkylenyl respectively. The term "arylthiol" refers to the group -aryl-SH. The term "aralkylthiol" refers to the group -aralkyl-SH, where the aralkyl is a lower aralkyl group.

Salts of compounds of the present invention are typically acid addition salts with an inorganic or organic acid or salts with an inorganic or organic base. Pharmaceutically acceptable salts of compounds of the present invention are preferred. Illustrative examples of such salts include: an acid addition salt with a mineral acid such as hydrochloric acid, hydrobromic acid, hydriodic acid, sulfuric acid, nitric acid, phosphoric acid and the like, or an organic acid such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid and the like, or with an acidic amino acid such as aspartic acid, glutamic acid and the like; and a salt with an inorganic base such as sodium, potassium, magnesium, calcium, aluminum and the like, or with an organic base such as methylamine, ethylamine, ethanolamine and the like, or with a basic amino acid such as lysine, ornithine and the like.

As used herein, the term "linker" and symbol "L" are used interchangeably herein to refer to an optionally substituted, divalent aliphatic radical that is covalently bonded to both $R_2$ and the 2-position carbon of the central pyridinelpyrimidine ring. The numbering convention employed herein, which refers to positions and/or atoms on the central pyridinelpyrimidine ring is as follows:

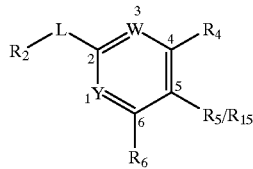

When only one of Y and W is nitrogen, the central ring structure is a pyridine. When both Y and W are nitrogen, the central ring structure is a pyrimidine.

In compounds (I) and (II), L is either a linear aliphatic divalent radical having from about 2 to about 5 carbon atoms, a cyclic aliphatic divalent radical having from about 3 to about 7 backbone atoms, or a hybrid aliphatic divalent radical having a linear component, which has from about 1 to about 3 backbone atoms, bonded to a cyclic component, which has from about 3 to about 7 backbone atoms. Each backbone atom incorporated in L is either a carbon atom or a heteroatom. At least one of the backbone atoms in L is a carbon atom. Typically, L in compounds (I) and (II) has incorporated within it at least 2 carbon atoms.

In compound (I), from 1 to about 3 of the backbone atoms in L are optionally heteroatoms. Typically 1 to 2 of the linker backbone atoms in compound (I) is a heteroatom. In compound (II), when L is a cyclic divalent radical, from 1 to about 3 of the backbone atoms are optionally heteroatoms. When L in compound (II) is a linear divalent radical, from 2 to 3 of the backbone atoms are heteroatoms.

Typically, when L in compounds (I) and (II) is a linear aliphatic divalent radical, it has 4 to 5 backbone atoms incorporated within it. When L in compounds (I) and (II) is a cyclic aliphatic divalent radical, it typically has incorporated within it from about 5 to about 6 backbone atoms (i.e., ring atoms). Usually, at least one of the backbone atoms in the cyclic aliphatic divalent linker in compound (I) is a heteroatom. Suitable cyclic aliphatic divalent linker moieties include the divalent forms of piperazine, homopiperazine, piperidine, and the like. When L in compounds (I) and (II) is a hybrid divalent radical, typically the backbone atoms in the linear component of the hybrid radical are carbon atoms, and the cyclic component is a heterocyclic alkyl moiety. Typical hybrid divalent radicals include divalent forms of, for example, N-methyl-piperazine, N-methyl piperidine, and the like.

Typically, the linker moiety is a linear divalent mono or di-amino radical. Suitable mono- and di-amino divalent radicals include, for example, —$(CH_2)_n$NH— and isomers thereof (including, for example, —HN$(CH_2)_n$—, and the like), where n is an integer from 1 to about 4. When the linker moiety is —$CH_2)_n$NH— or —HN$(CH_2)_n$— n is typically an integer from about 2 to about 4. Typically, n is 2 or 3.

When the linker moiety has incorporated within it both oxygen and nitrogen, it typically has the structure (i) —O—$(CH_2)_m$NH—, —HN$(CH_2)_m$NH—, or an isomer thereof, where m is an integer from 1 to 3; or alternatively, (ii) —O—(CO)$(CH_2)_p$NH—, where p is an integer from 1 to about 2. Typically, m is either 2 or 3. L is preferably a divalent diamino aliphatic radical such as, for example, —NH$(CH_2)_m$NH— or isomer thereof.

When L is substituted, it is usually substituted with not more than about 2 substitution groups. Typically substitution groups are aryl (e.g., phenyl) and lower alkyls. Preferred lower alkyl substitution groups for L are methyl and ethyl.

$R_2$ is an optionally substituted mono- or polycyclic, carbocyclic or heterocyclic aryl group that has from about 3 to about 14 ring atoms, of which, optionally 1 or more ring atoms are heteroatoms. Typically $R_2$ has from about 3 to about 10 ring atoms, and most typically $R_2$ has from about 3 to about 6 ring atoms. Usually, $R_2$ has no more than 2 hetero ring atoms. Suitable $R_2$ cyclic aryl moieties include, optionally-substituted monocyclic and polycyclic moieties, such as, for example, an optionally substituted phenyl, an optionally substituted naphthyl, an optionally substituted pyridyl, an optionally substituted pyrimidinyl, an optionally substituted imidazolo, an optionally substituted oxadiazolo, a tetrazolo, an optionally substituted pyrazinyl, an optionally substituted triazolo, an optionally substituted thiophenyl, an optionally substituted furanyl, an optionally substituted quinolino, an optionally substituted purinyl, an optionally substituted naphthyl, an optionally substituted benzothiazolo, an optionally substituted benzopyridyl, an optionally substituted benzimidazolo, an optionally substituted benzodioxozolo, and the like.

Typically, $R_2$ is an optionally substituted pyridinyl, an optionally substituted pyrimidinyl, an optionally substituted imidazolo, an optionally substituted oxadiazolo, an optionally substituted pyrazinyl, an optionally substituted triazolo, tetrazolo, an optionally substituted thiophenyl, an optionally substituted furanyl, an optionally substituted quinolino, an optionally substituted purinyl, an optionally substituted naphthyl, an optionally substituted benzothiazolo, an optionally substituted benzopyridyl, an optionally substituted benzoimidazolo, or an optionally substituted benzodioxolo.

Preferably, $R_2$ is an optionally substituted pyridinyl, an optionally substituted pyrimidinyl, an optionally substituted imidazolo, an optionally substituted oxadiazolo, an optionally substituted pyrazinyl, an optionally substituted quinolino, an optionally substituted naphthyl, an optionally substituted benzothiazolo, an optionally substituted benimidazolo, or an optionally substituted benzodioxolo.

$R_2$ is typically substituted with not more than about 3 substitution groups, and more typically not more than about 2 substitution groups. Typical substitution groups on $R_2$ include, for example, nitro, amino, cyano, halo (e.g., bromine chlorine, fluorine, and iodine), thioamido, carboxyl, a lower alkyl (more typically having from 1 to about 6 carbon atoms in its backbone structure, and preferably, methyl), a lower alkoxy (more typically having from 1 to about 6 carbon atoms in its backbone structure, and preferably, methoxy), a lower alkoxyalkyl (more typically having from 1 to about 6 carbon atoms in each of the backbone structures of the alkoxy and alkyl components, and preferably, methylmethoxy), a lower alkylhalo (more typically, an alkylhalo having from 1 to about 6 carbon atoms in its backbone structure, and preferably, a trihalo-substituted methyl group such as, for example, trifluoromethyl), an aminoalkyl (more typically, an aminoalkyl in which the alkyl component(s) have from 1 to about 6 carbon atoms in each backbone structure), an aminoaralkyl (preferably, —N-benzyl), a lower alkylaminoalkyl (e.g., —$(CH_2)_{1-6}$—NH$(CH_3)$, and preferably, —$CH_2$—NH$(CH_3)$), a carboxamidoalkyl, a carboxycloamido (preferably, —C(O)—N$(C_4H_8)$O, —C(O)—N$(C_4H_8)$N, and —C(O)—N$(C_5H_{10})$), an aryl optionally having up to about 4 hetero ring atoms, an aralkyl having up to 4 hetero ring atoms, a carboxamidoalkyl (more typically, a carboxamidoalkyl in which the alkyl component has from 1 to about 6 carbon atoms in its backbone structure, and preferably, methyl or ethyl), a carboxamidoaralkyl, an acyloxyalkyl (more typically, an acyloxyalkyl in which the alkyl component has from 1 to about 6 carbon atoms in its backbone structure, and preferably t-butyl), and the like, and substituted variants thereof.

Typically, when the substitution group on $R_2$ is itself substituted, the substitution group (i.e., the group substituted onto $R_2$) is a substituted aryl group, such as, for example, a mono-, di-, or tri-substituted halophenyl, a mono-, di-, or tri-substituted aminophenyl, a lower alkylaminoalkyl-substituted phenyl, and the like.

Typical combinations of two or more substitution groups on $R_2$, include, for example, two or more of the same or different halo groups, nitro in combination with amino, cyano in combination with amino, nitro in combination with a lower alkyl, two or more of the same or different lower alkoxy groups, two or more of the same or different alkyl-halo groups, two or more of the same or different lower alkyl groups, a lower alkyl group in combination with a lower alkoxy, and the like.

Typically, at least one of $R_4$ and $R_6$ is an optionally substituted $R_7$. When W and Y are both nitrogen, $R_4$ is typically an optionally substituted $R_7$.

Typical $R_7$ groups are aryl, arylcarboxamidocycloalkylaralkyl, arylcarboxamidoalkylcycloalkyl, arylcarboxamidoaryl, arylcarboxamidoalkyl, arylcarboxamidoaralkyl, arylcarboxamidoalkoxyalkyl, arylsulfamidoaralkyl, and substituted variants thereof.

Suitable aryl substituents employed as $R_7$ aryl substituents and $R_7$ aryl containing substituents include both carboyclic aryl or heterocyclic aryl substituents, such as, for example, phenyl, naphtyl, pyridyl, pyrimidinyl, imidazolo, oxadiazolo, tetrazolo, pyrazinyl, triazolo, thiophenyl, furanyl, quinolino, purinyl, benzothiazolo, benzopyridyl, benzimidazolo, and benzodioxolo.

When $R_7$ is an aryl group, it is typically a phenyl or a substituted (e.g., benzimidazolo-substituted, piperazinyl-substituted, mono, di-, or tri-halo-substituted, imidizolo-substituted, triazolo-substituted, morpholino-substituted, oxazolo-substituted, hydroxy-substituted, amino-substituted, aminoalkyl-substituted, nitro-substituted, haloalkyl-substituted, carboxamido-substituted, haloalkoxy-substituted, cyano-substituted, furanyl-substituted, lower alkyl-substituted, lower alkylaminoalkyl-substituted, naphthyl-substituted, and the like) phenyl, an optionally substituted furanyl, an optionally substituted pyridyl, an optionally substituted benzopyridyl, an optionally substituted thiazolo, an optionally substituted imidazolo and the like. When $R_7$ is an arylcarboxamidocycloalkylaralkyl, the cycloalkyl component typically has about 3 to about 6 ring atoms.

When $R_7$ is an arylcarboxamidoalkylcycloalkyl, an arylcarboxamidoaryl, an arylcarboxamidoalkyl an arylcarboxamidoaralkyl, an arylcarboxamido(lower) alkoxyalkyl, or an arylsulfamidoaralkyl, the aryl component is typically an optionally substituted phenyl, an optionally substituted pyridyl, an optionally substituted thiophenyl, an optionally substituted oxazolo, an optionally substituted thiazolo, and the like. When $R_7$ is an arylcarboxamidoalkylcycloalkyl, the alkyl component typically has from 1 to about 6 carbon atoms in a backbone, and the cycloalkyl component is typically a heterocyclic alkyl, such as, for example, tetrahydrofuranyl, morpholino, piperadinyl, piperazinyl, and the like.

Typically, when $R_7$ is substituted, the substitution group is an aryl (a mono- or polycyclic, carbocyclic or heterocyclic aryl, optionally substituted with, for example, one or more halos, one or more amino groups, one or more alkylaminoalkyl groups, etc.), a lower alkyl, a lower alkoxy, a cycloalkyl (either a carbocyclic alkyl or a heterocyclic alkyl), a halo, a lower haloalkyl, a lower haloalkoxy, a carboxamido, nitro, carboxyl, a sulfonylalkyl, cyano, hydroxyl, —SH, an alkylthiol, sulfamido, an aminoalkyl, and the like.

Suitable substitutions onto $R_7$ include, for example, chloro, fluoro, bromo, iodo, cyano, imidazolo, oxazolo, triazolo, morpholino, methyl, ethyl, isopropyl, t-butyl, bromo, fluoro, trifluoromethyl, carboxamide, nitro, carboxylic acid, methyl sulfone, methoxy, dimethylamino, trifluoromethoxy, furanyl, methyl thiol, hydroxyl, tetrazolo, acyloxyethyl, phenyl, diethylamino, dichloroimidazolo, naphthyl, sulfonamido, benzimidazolo, n-butoxy, benzylsulfanamido, bromobenzylsulfonamido, an amidated amino acids (i.e., a carboxyamidoalkylamido that is substituted with the a carbon substituent (i.e., $R_\alpha$) of an amino acid (i.e., —C(O)—NH—(CHR$_\alpha$)—C(O)—NH$_2$), and methylpiperazino.

When both W and Y are nitrogen atoms, $R_6$ is typically hydrogen, a halo, a lower alkyl, a lower haloalkyl, an optionally substituted aryl group having from 3 to about 14 ring atoms, of which, optionally 1 to about 3 ring atoms are heteroatoms, or an optionally substituted aralkyl group having from 4 to about 25 backbone atoms of which, optionally 1 to about 5 backbone or (i.e., ring) atoms are heteroatoms. Preferably $R_6$ is hydrogen, a halo, a lower alkyl having from 1 to about 6 carbon atoms, or a lower haloalkyl having from 1 to about 6 carbon atoms.

Preferably $R_4$ is an optionally substituted aryl and $R_6$ is hydrogen, a lower alkyl, or an optionally substituted cyclic aryl.

Typically, when $R_5$ is an optionally substituted lower alkyl, it has from 1 to about 6 atoms in its backbone structure, and more typically, from 1 to about 4 atoms in its backbone structure. Similarly, when $R_5$ is an optionally substituted aralkyl, an optionally substituted aminoalkyl, an optionally substituted aminoaralkyl, an optionally substituted aminoalkoxyalkyl, an optionally substituted arylaminoalkyl, an optionally substituted arylaminoaralkyl, an optionally substituted arylalkylamino, an optionally substituted arylalkylaminoalkyl, an optionally substituted arylalkylaminoaralkyl, an optionally substituted acyloxyalkyl, an optionally substituted acyloxyaralkyl, an optionally substituted acyloxyalkylcycloalkyl, an optionally substituted acyloxyalkylaminoaralkyl, an optionally substituted sulfonylalkyl, optionally substituted carbamylalkyl, an optionally substituted carbamylaralkyl, an optionally substituted carbamylalkylamino, an optionally substituted carbamylalkylaminoalkyl, an optionally substituted carbamylalklylaminoaryl, or an optionally substituted carbamylalkylaminoaralkyl, the alkyl and alkylenyl portions of these groups typically have from 1 to about 6 carbon atoms in their backbone structure, and more typically from 1 to about 4 carbon atoms in their backbone structure.

More typically, $R_5$ is hydrogen, carboxyl, nitro, an optionally substituted lower alkyl having from 1 to about 4 atoms in its backbone structure, an optionally substituted aryl, an optionally substituted aminoaralkyl, an optionally substituted carboxcycloamido, an optionally substituted acyloxyalkyl, an optionally substituted acyloxyaralkyl, an optionally substituted acyloxyalkylcycloalkyl, an optionally substituted acyloxyalkylaminoaralkyl, an optionally substituted sulfonylalkyl, or an optionally substituted carbamylalkylaminoalkyl.

When $R_5$ is an aryl or when $R_5$ or $R_{15}$ is an aryl-containing moiety, the aryl group is typically optionally substituted phenyl, or an optionally substituted heterocyclic aryl. Optionally substituted heterocyclic aryl groups that are typically employed either alone as $R_5$ or as part of an $R_5$ or $R_{15}$ substituent include pyridyl, pyrimidinyl, imidazolo, oxadiazolo, tetrazolo, pyrazinyl, triazolo, thiophenyl, furanyl, quinolino, purinyl, naphthyl, benzothiazolo, benzopyridyl, benzimidazolo, benzodioxolo, and the like. Heterocyclic aryl groups employed as $R_5$ typically have 2 or more heteroatoms incorporated in their ring structures, such as, for example, oxadiazolo, imidazolo, and the like.

Typically, when $R_{15}$ is an optionally substituted carboxamidoalkyl, an optionally substituted an optionally substituted carboxamidoaralkyl or an optionally substituted carboxamidoalkylcarboxamido, the alkyl and alkylenyl portions of these groups typically have from 1 to about 6 carbon atoms in their backbone structure, and more typically from 1 to about 4 atoms in their backbone structure.

Preferred substitution groups on $R_5$ and $R_{15}$ substituents are halo, hydroxy, cyano, a hydroxy-substituted lower alkyl, cyano, a cyano-substituted lower alkyl, and an amino-substituted lower alkyl.

Preferably, no more than one of $R_4$, $R_5$, and $R_6$ in compound (I), and no more than one of $R_4$, $R_{15}$, and $R_6$ in compound (II) is hydrogen.

Preferred compounds of the present invention are those in which $R_2$ is an optionally substituted pyridyl, $R_6$ is hydrogen or a lower alkyl, and $R_4$ is a phenyl substituted with one or more substitution groups, in which each substitution group has a molecular weight from about 15 to about 300 g/mole, and usually from 15 to about 150 g/mole.

Preferably, $R_5$ is a lower alkyl, an optionally substituted phenyl, nitro, a carboxcycloalkylamido, a acyloxyaralkyl, a acyloxyalkyl, a carboxamidoalkyl, an aminoaralkyl, hydrogen, a heterocyclic aryl, cyano, a lower sulfonylalkyl, an arylalkylaminoalkyl, carboxyl, an acyloxylalkyl, an acyloxyalkylaminoaralkyl, an acyloxyalkylheterocycloalkyl, an acyloxyalkylamino(hydroxy-substituted alkyl), an acyloxyhydroxy-substituted alkyl), an acyloxyhydroxy-substituted alkyl) heterocycloalkyl, and a carbamylalkylaminoalkyl.

Preferred $R_{15}$ groups are carboxamido, a carboxamidoalkyl, a carboxamido(hydroxy-substituted) alkyl, a carboxamido(cyano-substituted alkyl), a carboxamido(carboxamido-substituted alkyl), a carboxamidoaralkyl, a carboxamido(hydroxyalkyl-substituted alkyl)amido, and a carboxamidoalkylaminoalkyl.

Thus, exemplary inhibitor compounds of the present invention include (4-phenylpyrimidin-2-yl)(2-(2-pyridyl)ethyl)amine, (4-phenylpyrimidin-2-yl)[2(2-pyridylamino)ethyl]amine, [2-(2-pyridylamino)ethyl](4-(3-pyridyl)pyrimidin-2-yl)amine, 4-{2-[(2-(2-pyridyl)ethyl)amino]pyrimidin-4-yl}benzenecarbonitrile, 4-{2-[(4-pyridylmethyl)amino]pyrimidin-4-yl)}benzamide, 4-{2-[(3-imidazol-5-ylethyl)amino]pyrimidin-4-yl}benzamide, 4-(2-{[2-(2-pyridylamino)ethyl]amino}pyrimidin-4-yl)benzenecarbonitrile,4-methyl-2-({2-[(5-nitro(2-pyridyl))amino]ethyl}amino)pyrimidine-5-carboxylic acid, 4-(2-{[(3-methylphenyl)methyl]amino}pyrimidin-4-yl)benzamide, 4(2-{[(4-aminophenyl)methyl]amino}pyrimidin-4-yl)benzamide, (5-ethyl4-phenylpyrimidin-2-yl)[2-(2-pyridylamino)ethyl]amine, 4-(2-{[(5-methylpyrazin-2-yl)methyl]amino}pyrimidin-4-yl)benzamide, 4-{2-[(3-phenoxypropyl)amino]pyrimidin-4-yl}phenol, 4-{2-[(3-imidazolylpropyl)amino]pyrimidin-4-yl}benzamide, [4-(3,4-difluorophenyl)pyrimidin-2-yl][2-(2-pyridylamino)ethyl]amine, 4-(2-{[(4-cyanophenyl)methyl]amino}pyrimidin-4-yl)benzamide, 4-{2-[(2-phenoxyethyl)amino]pyrimidin-4-yl}benzamide, 4-(2-{[(3-methoxyphenyl)methyl]amino}pyrimidin-4-yl)benzamide, 4-(2-{[(4-methoxyphenyl)methyl]amino}pyrimidin-4-yl)benzamide, 4-(2-{[2-(4-fluorophenyl)ethyl]amino}pyrimidin-4-yl)benzamide, [2-(2,5-dimethoxyphenyl)ethyl](4-(3-pyridyl)pyrimidin-2-yl)amine, [4-(4-nitrophenyl)pyrimidin-2-yl][2-(2-pyridylamino)ethyl]amine, {2-[(5-nitro(2-pyridyl))amino]ethyl}(4-pyrazin-2-ylpyrimdin-2-yl)amine, ethyl 4-(2-furyl)-2-[(2-(2-pyridyl)ethyl)amino]pyridine-5-carboxylate, 4-(2-{[(3-chlorophenyl)methyl]amino}pyrimidin-4-yl)benzamide, [4-(4-chlorophenyl)-5-methylpyrimidin-2-yl][2-(2-pyridylamino)ethyl]amine, 4-{2-[(3-benzimidazolylpropyl)amino]pyrimidin-4-yl}phenol, 4-{2-[(4-phenylbutyl)amino]pyrimidin-4-yl}benzamide, 4-(2-{[2-(3-methoxyphenyl)ethyl]amino}pyrimidin-4-yl)benzamide, 4-{2-[(3-phenoxypropyl)amino]pyrimidin-4-yl}benzamide, 4-(2-{[(3-nitrophenyl)methyl]amino}pyrimidin-4-yl)benzamnide, 4-[2-({2-[(5-nitro-2-pyridyl)amino]ethyl}amino)pyrimidin 4-yl]phenol, 3-[2-({2-[(5-nitro-2-pyridyl)amino]ethyl}amino)pyrimidin-4-yl]phenol, 4-2-{[2-(3-chlorophenyl)ethyl]amino}pyrimidin-4-yl)benzamide, 4-{2-[(naphthylmethyl)amino]pyrimidin-4-yl}benzamide, [5-(4-fluorophenyl)pyrimidin-2-yl]{2-[(5-nitro(2-pyridyl))amino]ethyl}amine, 4-(2-{[3-(4-chlorophenoxy)propyl]amino}pyrimidin-4-yl)phenol, [4-(4-imidazolylphenyl)pyrimidin-2-yl][2-2-(2-pyridylamino)ethyl]amine, 4-(2-{[3-2-aminobenzimidazolyl)propyl]amino}pyrimidin-4-yl)phenol, 4-(2-{[2-(2,5-dimethoxyphenyl)ethyl]amino}pyrimidin-4-yl) benzenecarbonitrile, [4-(2,4-dichlorophenyl)pyrimidin-2-yl][2-(2-pyridylamino)ethyl]amine, 3-[2-({2-[(5-nitro-2-pyridyl)amino]ethyl}amino)pyrimidin-4-yl]benzenecarbonitrile, 4-(2-{[3-(3-methylphenoxy)propyl]amino}pyrimidin4-yl)benzamide, 4-{2-[(2-(2H-benzo[3,4-d]1,3-dioxolen-5-yl)ethyl)amino]pyrimidin-4-yl}benzamide, 4-(2-{[(2-(4-nitrophenyl)ethyl]amino}pyrimidin-4-yl)benzamide, 4-(2-{[(2,6-dimethoxyphenyl)methyl]amino}pyrimidin-4-yl)benzamide, 4-(2-{[(3,4-dimethoxyphenyl)methyl]amino}pyrimidin-4-yl)benzanide, [2-({2-[(5-nitro(2-pyridyl))amino]ethyl}amino)pyrimidin-4-yl]benzylamine, ethyl 4-(4-fluorophenyl)-2-[(2-(2-pyridyl)ethyl)amino]pyrimidine-5-carboxylate, [4-2,4dimethyl(1,3-thiazol-5-yl))pyrimidin-2-yl]{2-[(5-nitro(2-pyridyl))amino]ethyl}amine, [4-(4-methyl-1-phenylpyrazol-3-yl)pyrimidine-2-yl][2-(2-pyridylamino)ethyl]amine, 4-[2-({[3(trifluoromethyl)phenyl]methyl}amino)pyrimidin-4-yl]benzamide, 4-[2-({[4-(trifluoromethyl)phenyl]methyl}amino)pyrimidin-4-yl]benzamide,4-(2-{[(3,5-dichlorophenyl)methyl]amino}pyrimidin-4-yl)benzamide,4-{2-[4-benzylpiperazinyl]pyrimidin-4-yl}benzamide, 4-(2-{[(2,4-dichlorophenyl)methyl]amino}pyrimidin-4-yl)benzamide, ethyl 4-(4-cyanophenyl)-2-[(2-(2-pyridyl)ethyl)amino] pyrimidine-5-carboxylate, [2-(2-pyridylamino)ethyl]{4-[4-(trifluoromethoxy)phenyl]pyrimidin-2-yl}amine, {6[(2-methoxyethyl)amino]-5-nitro(2-pyridyl)}{2-[(5-nitro(2-pyridyl))amino]ethyl}amine, 4-(2-{[3-(3-methoxyphenoxy)propyl]amino}pyrimidin-4-yl)benzamide, ethyl4-(4-methoxyphenyl)-2-[(2-(2-pyridyl)ethyl)amino]pyrimidine-5-carboxylate, [(3-methylphenyl)methyl][2-({2-[(5-nitro(2-pyridyl))amino]ethyl}amino)pyrimidin-4-yl]amine, 4-(2-

{[3-(4-phenylimidazolyl)propyl]amino}pyrimidin-4-yl) benzenecarbonitrile, 4-{(2-[(3-benzimidazolylpropyl) amino]pyrimidin-4yl}-2-chlorophenol, 4-[2-({3-[4-(2,4-dichlorophenyl)imidazolyl]propyl}amino)pyrimidin-4-yl] benzamide, 4-[2-({3-[4-(3-methoxyphenyl)imidazolyl] propyl}amino)pyrimidin-4-yl]benzamide, (3-benzimidazolylpropyl)[4-(4-imidazolylphenyl) pyrimidin-2-yl]amine, N-{4-[2({2-[(5-nitro-2-pyridyl) amino]ethyl}amino)pyrimidin-4-yl]phenyl}acetamide, 4-(2-{[3-(4-chlorophenoxy)propyl[amino}pyrimidin-4-yl) benzamide, 4-(2-{[(4-bromophenyl)methyl] amino}pyrimidin-4-yl)benzamide,4-[2-({[4-(4-fluorophenyl)phenyl]methyl}amino)pyrimidin-4-yl] benzamide, 4-(2-{[(3-bromophenyl)methyl] amino}pyrimidin-4-yl)benzamide, 6-{[2-({5-nitro-6-benzylamino]-2-pyridyl}amino)ethyl]amino}pyridine-3-carbonitrile, ethyl4-(4cyanophenyl)-2-{[2-(pyrimidin-2-ylamino)ethyl]amino}pyrimidine-5-carboxylate, 4-{2-[4-(2-methoxyphenyl)piperazinyl]pyrimidin-4-yl}benzamide, 4(2-{[2-(benzothiazol-2-ylamino)ethyl]amino}pyrimidin-4-yl)benzamide, ethyl 4-(3-nitrophenyl)-2-[(2-(2-pyridyl) ethyl)amino]pyrimidine-5-carboxylate, 6-methyl-2-({2-[(5-nitro(2-pyridyl))amino]ethyl}amino)-4-phenylpyrimidine-5-carboxylic acid, 4-{2-[(2,2-diphenylethyl)amino] pyrimidin-4-yl}benzamide, 4-(2-{[(3,4,5-trimethoxyphenyl)methyl]amino}pyrimidin-4-yl) benzamide, methyl 2-({2-[(5-nitro(2-pyridyl))amino] ethyl}amino)-4-(3-pyridyl)pyrimidine-5-carboxylate, 4-[2-({[3-(3-aminophenyl)phenyl]methyl}amino)pyrimidin-4-yl]benzamide, 4-[2({[4-(3-aminophenyl)phenyl] methyl}amino)pyrimidin-4-yl]benzamide, 4-{2-[(3-(2-naphthyloxy)propyl]amino]pyrimidin-4-yl}benzamide, 4({2-[(3-(6-quinolyloxy)propyl)amino]pyrimidin-4-yl}benzamide, [(3-chlorophenyl)methyl][2-({2-[(5-nitro(2-pyridyl))amino]ethyl}amino)pyrimidin-4-yl]amine, [(4-chlorophenyl)methyl][2-({2-[(5-nitro(2-pyridyl))amino] ethyl}amino)pyrimidin4-yl]amine, ethyl 4-(4cyanophenyl)-2-({[2-(3-methoxyphenyl)ethyl]amino}pyrimidine-5-carboxylate, ethyl 2-({2-[(5-amino-(2-pyridyl))amino] ethyl}amino)-4-(4cyanophenyl)pyrimidine-5-carboxylate, 4-8 5-nitro-2-({2-[(5-nitro(2-pyridyl))amino]ethyl}amino) pyrimidin-4-yl]benzoate,ethyl4-(benzenecarbonitrile, ethyl 4-[2-({2-[(5-nitro-2-pyridyl)amino]ethyl}amino)pyrimidin-4-yl]benzoate, ethyl 4-(3-nitrophenyl)-2-({[2-(2-pyridylamino)ethyl]amino}pyrimidine-5-carboxylate, N-benzyl(4-{2-[(2-(2-pyridyl)ethyl)amino]pyrimidin-4-yl}phenyl)carboxamide, {2-[(5-nitro(2-pyridyl))amino] ethyl}{5-nitro-6-[benzylamino](2-pyridyl)}amine, 4-(2-methoxyphenyl)-2-({2-[(5-nitro(2-pyridyl))amino] ethyl}amino)pyrimidine-5-carboxylic acid, 4-[2-({[3-(3-methoxyphenyl)phenyl]methyl}amino)pyrimidin-4-yl] benzamide, 4-[2-({2-[(5-nitro-2-pyridyl)amino] ethyl}amino)pyrimidin-4-yl]benzenesufonamide, 4-(2-{[3-(2,4-dichlorophenoxy)propyl]amino}pyrimidin-4-yl) benzamide, 4-(2-{[3-(3,4-dichlorophenoxy)propyl]amino }pyrimidin-4-yl) benzamide, 4-(2-{[3-(3-phenylphenoxy) propyl]amino}pyrimidin-4-yl)benzamide, 4-(2-{[(3-{3-[(methylamino)methyl]phenyl}phenyl)methyl] amino}pyrimidin-4-yl)benzamide, ethyl 4-(3-fluorophenyl)-2-({2-[(5-nitro(2-pyridyl))amino] ethyl}amino)pyrimidine-5-carboxylate, [4-phenyl-5-benzylpyrimidin-2-yl][2-(2-pyridylamino)ethyl]amine, 4-(2-{[3-(3-bromophenoxy)propyl]amino}pyrimidin-4-yl) benzamide, 4-[2-({2-[(5-nitro(2-pyridyl))amino] ethyl}amino)-5-phenylpyrimidin-4yl]phenol, 4-(2, 4dichlorophenyl)-2-({2-[(5-nitro(2-pyridyl))amino] ethyl}amino)pyrimidine-5-carbonitrile, 4-(3, 4dichlorophenyl)-2-({2-[(5-nitro(2-pyridyl))amino] ethyl}amino)pyrimidine-5-carbonitrile, 6-[(2-{[4-(4-cyanophenyl)-5-(ethoxycarbonyl)pyrimidin-2-yl] amino}ethyl)amino]pyridine-3-carboxylic acid, ethyl4-(3-cyanophenyl)-2-({2-[(5-nitro(2-pyridyl))amino] ethyl}amino)pyrimidine-5-carboxylate, [(3,5-dichlorophenyl)methyl][2-({2-[(5-nitro(2-pyridyl))amino] ethyl}amino)pyrimidin-4-yl]amine, [(2,4-dichlorophenyl) methyl][2-({2-[(5-nitro(2-pyridyl))amino]ethyl}amino) pyrimidin-4-yl]amine,ethyl 4-(4-carbamoylphenyl)-6-ethyl-2-{[2-(2-pyridylamino)ethyl]amino}pyrimidine-5-carboxylate, ethyl 4-(4-carbamoylphenyl)-6-ethyl-2-{[2-(pyrimidin-2-ylamino)ethyl]amino})pyrimidine-5-carboxylate, ethyl 4-(3,4-dimethylphenyl)-2-({2-[(5-nitro (2-pyridyl))amino]ethyl}amino)pyrimidine-5-carboxylate, N-(2-methoxyethyl){4-[2-({2-[(5-nitro(2-pyridyl))amino] ethyl})amino)pyrimidin-4-yl]phenyl}carboxamide, 4-{2-[({3-[3-(acetylamino)phenyl]phenyl}methyl)amino] pyrimidin-4-yl}benzamide, ethyl 4-(4-cyanophenyl)-2-{[2-(2-quinolylamino)ethyl]amino}pyrimidine-5-carboxylate, 4-[2-({[3,5-bis(trifluoromethyl)phenyl]methyl}amino) pyrimidin-4-yl]benzamide, ethyl 4-(2,4-difluorophenyl)2-({2-[(5-nitro(2-pyridyl))amino]ethyl}amino)pyrimidine-5-carboxylate, (4-{[(3-bromophenyl)methyl] amino}pyrimidin-2-yl){2-[(5-nitro(2-pyridyl))amino] ethyl}amine, 2-({2-[(6-amino-5-nitro(2-pyridyl))amino] ethyl}amino)-4-(3,4-dichlorophenyl)pyrimidine-5-carbonitrile,methyl 6-[(2-{[4-(4cyanophenyl)-5-(ethoxycarbonyl)pyrimidin-2-yl]amino}ethyl)amino] pyridine-3-carboxylate, 4-{2-[({3-[3-(trifluoromethyl) phenyl]phenyl}methyl)amino]pyrimidin-4-yl}benzamide, [4-(4-benzimidazolylpropyl)pyrimidin-2-yl]{2-[(5-nitro(2-pyridyl))amino]ethyl}amine,ethyl 2-({2-[(5-nitro(2-pyridyl))amino]ethyl}amino-4-(-3-nitrophenyl)pyrimidine-5-carboxylate, ethyl 4-naphthyl-2-({2-[(5-nitro(2-pyridyl)) amino]ethyl}amino)pyrimidine-5-carboxylate, ethyl 2-({2-[(5-nitro(2-pyridyl))amino]ethyl}amino)-4-(3quinolyl) pyrimidine-5-carboxylate, ethyl 4-(4-cyanophenyl)-2-[(2-{[5-(N-ethylcarbamoyl)(2-pyridyl)]amino}ethyl)amino] pyrimidine-5-carboxylate, benzyl{[4-{2-[(2-(2-pyridylamino)ethyl)amino}pyrimidin-4-yl)phenyl] sulfonyl}amine, ethyl 4-(4-cyanophenyl)-2-[(2-{[6-(methylamino)-5-nitro(2-pyridyl)]amino}ethyl)amino] pyrimidine-5-carboxylate, {4-[2-({2-[(5-nitro(2-pyridyl)) amino]ethyl}amino)pyrimidin4-yl]phenyl}-N-(oxolan-2-ylmethyl)carboxamide, N-(1-carbamoyl-2-phenylethyl)[4-methyl-2-({2-[(5-nitro(2-pyridyl))amino]ethyl}amino) pyrimidin-5-yl)]carboxamide,N-(1-carbamoyl-2-phenylethyl)(4-{2-[(2-(2-pyridyl)ethyl)amino]pyrimidin-4-yl}phenyl)carboxamide, ethyl 4-(3,4 dimethoxyphenyl)-2-((2-[(5-nitro(2-pyridyl))amino]ethyl}amino)pyrimidine-5-carboxylate, {4-[2({2-[(5-nitro(2-pyridyl))amino] ethyl}amino)pyrimidin-4-yl]phenyl}-N-benzylcarboxamide, {4-[2({2-[(5-nitro(2-pyridyl))amino] ethyl}amino)pyrimidin-4-yl]phenyl}-N-(3-pyridylmethyl) carboxamide, {4-[4-(4,5-dichloroimidazol-2-yl)phenyl] pyrimidin-2-yl}{2-[(5-nitro(2-pyridyl))amino]ethyl}amine, ethyl 4-(4-butoxyphenyl)-2-({2-[(5-nitro(2-pyridyl))amino] ethyl}amino)pyrimidine-5-carboxylate, ethyl 4-{[(2-chlorophenyl)methyl]amino}-2-({2-[(5-nitro(2-pyridyl)) amino]ethyl}amino)pyrimidine-5-carboxylate, 6-(2-fluorophenyl)-2-({2-[(5-nitro(2-pyridyl))amino] ethyl}amino)-4-phenylpyrimidine-5-carboxylc acid, {4-[2 ({2-[(5-nitro(2-pyridyl))amino]ethyl}amino)pyrimidin-4-yl]phenyl}-N-2-thienylmethyl)carboxamide, ethyl 2-({2-[(5-nitro(2-pyridyl))amino]ethyl}amino)-4-[3-(trifluoromethyl)phenyl]pyrimidine-5-carboxylate, ethyl 4-(3,4dichlorophenyl)-2-({2-[(5-nitro(2-pyridyl))amino]ethyl}amino)pyrimidine-5-carboxylate, ethyl 4-(3,5dichlorophenyl)-2-({2-[(5-nitro(2-pyridyl))amino]ethyl}amino)pyrimidine-5-carboxylate, {4-[2-({2-[(5-nitro(2-pyridyl))amino]ethyl}amino)pyrimidin-4-yl]phenyl}-N-(4-piperidylmethyl)carboxamide,(6-{[((2,4-dichlorophenyl)methyl]amino}-5-nitro(2-pyridyl)){2-[(5-nitro(2-pyridyl))amino]ethyl}amine, ethyl 4-(4-carbamoylphenyl)-6-ethyl-2-({2-[(3-nitro(2-pyridyl))amino[ethyl}amino)pyrimidine-5-carboxylate, ethyl 4-[4-(diethylamino)phenyl]-2-({2-[(5-nitro(2-pyridyl))amino]ethyl}amino)pyrimidine-5-carboxylate, {4-[2-({2-[(5-nitro(2-pyridyl))amino]ethyl}amino)pyrimidin-4-yl]phenyl}-N-(2-phenylethyl)carboxamide, N-[(3-methylphenyl)methyl]{4-[2-({2-[(5-nitro(2-pyridyl))amino]ethyl}amino)pyrimidin-4-yl]phenyl}carboxamide, 2-({2-[(5-nitro(2-pyridyl))amino]ethyl}amino)-4-(2,4,6-trichlorophenyl)pyrimidine-5-carboxylic acid, ethyl 2-({2-[(5-nitro(2-pyridyl))amino]ethyl}amino)-4-phenylphenyl)pyrimidine-5-carboxylate, {4-[2-({2-[(6amino-5-nitro(2-pyridyl))amino]ethyl}amino)pyrimidin-4-yl]phenyl}-N-benzylcarboxamide, N-[(5-methylpyrazin-2-yl)methyl]{4-2-({2-[(5-nitro(2-pyridyl))amino]ethyl}amino)pyrimidin4-yl]phenyl}carboxamide, N-[(3-fluorophenyl)methyl]{4-({2-[(5-nitro(2-pyridyl))amino]ethyl}amino)pyrimidin-4-yl]phenyl)carboxamide, ethyl 2-({2-[(5-nitro(2-pyridyl))amino]ethyl}amino)-4-(4-sulfamoylphenyl)pyrimidine-5-carboxylate, N-[(4-fluorophenyl)methyl]{4-[2-({2-[(5-nitro(2-pyridyl))amino]ethyl}amino)pyridin-4-yl]phenyl}carboxamide, [4-(2-{[([3-bromophenyl)methyl]amino}pyrimidin-4-yl)phenyl]-N-[(3-methylphenyl)methyl]carboxamide, ethyl 4-(5-bromo(3-pyridyl))-2-({2-[(5-nitro(2-pyridyl))amino]ethyl}amino)pyrimidine-5-carboxylate, N-(3-imidazolylpropyl){4-[2({2-[(5-nitro(2-pyridyl))amino]ethyl}amino)pyrimidin-4-yl]phenyl}carboxamide, tert-butyl 6-[(2-{[4-(4-cyanophenyl)-5-(ethoxycarbonyl)pyrimidin-2-yl]amino]ethyl)amino]pyridine-3-carboxylate, N-[(3-bromophenyl)methyl](4-{2-[(3-imidazolylpropyl)amino]pyrimidin-4-yl}phenyl)carboxamide, ethyl 4-[(2,4-dichlorophenyl)amino]-2-({2-[(5-nitro(2-pyridyl))amino]ethyl}amino)pyrimidine-5-carboxylate, ethyl 4-(4carbamoylphenyl)-6-ethyl-2-({3-[(5-nitro(2-pyridyl))amino]propyl}amino)pyrimidine-5carboxylate, {4-[2-({2-[(5-nitro (2-pyridyl))amino]ethyl}amino)pyrimidin-4-yl]phenyl}-N-(2-phenylcyclopropyl)carboxamide, N-[(4-methoxyphenyl)methyl]{4-[2({2-[(5-nitro(2-pyridyl))amino]ethyl}amino)pyrimidin-4-yl]phenyl}carboxamide, 2-({2-[(5-nitro(2-pyridyl))amino]ethyl}amino)-6-(4-nitrophenyl)-4-phenylpyrimidine-5-carboxylic acid, 2-({2-[(5-nitro(2-pyridyl))amino]ethyl}amino)-6-(4-nitrophenyl)-4-(4-pyridyl)pyrimidine-5-carboxylic acid, ethyl 4-4-carbamoylphenyl)-6-ethyl-2-[(2-{[5-(trifluoromethyl)(2-pyridyl)]amino}ethyl)amino]pyrimidine-5-carboxylate, ethyl 4-(4-cyanophenyl)-2-[(2-{[5-(morpholin-4-ylcarbonyl)(2-pyridyl)]amino}ethyl)amino]pyrimidine-5-carboxylate, N-[(3chlorophenyl)methyl]{4-[2-({2-[(5-nitro(2-pyridyl))amino]ethyl}amino)pyrimidin-4-yl]phenyl}carboxamide, N-[(3,4-difluorophenyl)methyl]{4-[2-({2-[(5-nitro(2-pyridyl))amino]ethyl}amino)pyrimidin-4-yl]phenyl}carboxamide, ethyl 4-[4-(4methylpiperazinyl)phenyl]-2-({2-[(5-nitro(2-pyridyl))amino]ethyl}amino)pyrimidine-5-carboxylate, 4-cyclohexyl-2-({2-[(5-nitro(2-pyridyl))amino]ethyl}amino-6-(4-nitrophenyl)pyrimidine-5-carboxylic acid, {4-[2-({2-[(5nitro(2-pyridyl))amino]ethyl}amino)pyrimidin-4-yl]phenyl}-N-[(3-nitrophenyl)methyl]carboxamide, ethyl 4-{[(3-bromophenyl)methyl]amino}-2-({2-[(5-nitro(2-pyridyl))amino]ethyl}amino)pyrimidine-5-carboxylate, N-[(3-bromophenyl)methyl][4-(2-{[2-(3-methoxyphenyl)ethyl]amino}pyrimidin-4-yl)phenyl]carboxamide, N-(naphthylmethyl){4-[2-({2-[(5-nitro(2-pyridyl))amino]ethyl}amino)pyrimidin-4-yl]phenyl}carboxamide, 4-(3-cyanophenyl)-2-({2-[5-nitro(2-pyridyl))amino]ethyl}amino)-6-(4-nitrophenyl)pyrimidine-5-carboxylic acid, N-[(3,4-dimethoxyphenyl)methyl]{4-[2-({2-[(5-nitro(2-pyridyl))amino]ethyl}amino)pyrimidin-4-yl]phenyl}carboxamide, N-[(2,3-dimethoxyphenyl)methyl]{4-[2-({2-[(5-nitro(2-pyridyl))amino]ethyl}amino)pyrimidin-4-yl]phenyl}carboxamide, 4-(4methoxyphenyl)-2-({2-[(5-nitro(2-pyridyl))amino]ethyl}amino)-6-(4-nitrophenyl)pyrimidine-5-carboxylic acid, N-[(3-bromophenyl)methyl]{4-[2-({2-[(6-methoxy(2-pyridyl))amino]ethyl}amino)pyrimidin-4-yl]phenyl}carboxamide, {4-[2-({2-[(5-nitro(2-pyridyl))amino]ethyl}amino)pyrimidin-4-yl]phenyl}-N-{[3-(trifluoromethyl)phenyl]methyl}carboxamide, N-[(3,5-dichlorophenyl)methyl]{4-[2-({2-[(5-nitro(2-pyridyl))amino]ethyl}amino)pyrimidin-4-yl]phenyl}carboxamide, N-[(3,4-dichlorophenyl)methyl]{4-[2-({2-[(5-nitro(2-pyridyl))amino]ethyl}amino)pyrimidin-4-yl]phenyl}carboxamide, ethyl 4-(4-cyanophenyl)-2-{[2-({5-nitro-6-[benzylamino](2-pyridyl)}amino)ethyl]amino}pyrimidine-carboxylate, ethyl 4-[3,5-bis(trifluoromethyl)phenyl]-2-({2-[(5-nitro(2-pyridyl))amino]ethyl}amino)pyrimidine-5-carboxylate, 4,6-bis(4-nitrophenyl)-2-({2-[(5-nitro(2-pyridyl))amino]ethyl}amino)pyrimidine-5-carboxylic acid, [4-(2-{[2-(2,5-dimethoxyphenyl)ethyl]amino}pyrimidin-4-yl)phenyl]-N-[(3-bromophenyl)methyl]carboxamide, 2-({2-[(5-nitro(2-pyridyl))amino]ethyl}amino)-4-(3-nitrophenyl)-6-(4-nitrophenyl)pyrimidine-5-carboxylic acid, N-[(3-bromophenyl)methyl]{4-[2-({2-[(4-nitrophenyl)amino]ethyl}amino)pyrimidin-4-yl]phenyl}carboxamide, N-[(3-bromophenyl)methyl]{4-[2-({2-[(5-nitro(2-pyridyl))amino]ethyl}amino)pyrimidin4-yl]phenyl}carboxamide, N-[(4bromophenyl)methyl]{4-[2-[(5-nitro(2-pyridyl))amino]ethyl)amino)pyrimidin-4-yl]phenyl}carboxamide, {4-[2-({2-[(5-nitro(2-pyridyl))amino]ethyl}amino)pyrimidin-4-yl]phenyl}-N-[(4-sulfamoylphenyl)methyl]carboxamide, N-[2-(2,4-dichlorophenyl)ethyl]{4-[2({2-[(5-nitro(2-pyridyl))amino]ethyl}amino)pyrimidin-4-yl]phenyl}carboxamide, N-[(3-bromophenyl)methyl][4-(2-{[2-(2quinolylamino)ethyl]amino}pyrimidin-4-yl)phenyl]carboxamide, 2-({2-[(5-nitro(2-pyridyl))amino]ethyl}amino)-6-(4-nitrophenyl)-4-(4-quinolyl)pyrimidine-5-carboxylic acid, N-(2,2-diphenylethyl){4-[2-({2-[(5-nitro(2-pyridyl))amino]ethyl}amino)pyrimidin-4-yl]phenyl}carboxamide, N-[(3-bromophenyl)methyl]{(4-[2-({3-[[(5-nitro(2-pyridyl))amino]propyl}amino)pyrimidin-4-yl]phenyl}carboxamide, {4-[2-({2-[(6-amino-5-nitro(2-pyridyl))amino]ethyl}amino)pyrimidin-4-yl]phenyl}-N-[(3-bromophenyl)methyl]carboxamide, 2-({2-[(5-nitro(2-pyridyl))amino]ethyl}amino6-(4-nitrophenyl)-4-[4-(trifluoromethyl)phenyl]pyrimidine-5-carboxylic acid, N-[(3-bromophenyl)methyl](4-{2-[(2-{[5-(trifluoromethyl)(2-pyridyl)]amino}ethyl)amino]pyrimidin-4-yl}phenyl)carboxamide, [(3-bromophenyl)methyl]({4-[2-({2-[(5-nitro(2-pyridyl))amino]ethyl}amino)pyrimidin-4-yl]phenyl}sulfonyl)amine, and N-[(3-iodophenyl)methyl]{4-[2-({2-[(5-nitro(2-pyridyl))amino]ethyl}amino)pyrimidin-4-yl]phenyl}carboxamide. These compounds exhibited an IC$_{50}$ of µM or less in the cell-free assay for GSK3 inhibitory activity described in Example 74, herein below.

Preferred inhibitor compounds of the present invention, which exhibit an IC$_{50}$ of 1 µM or less in a cell-free assay for GSK3 inhibitory activity (described in Example 74 herein below), are 4-{2-[(2-(2-pyridyl)ethyl)amino]pyrimidin-4-yl}benzamide, 4-{2-[(2-phenylpropyl)amino]pyrimidin-4-yl}benzamide, 4-(2-{[2-(2-pyridylamino)ethyl]amino}pyrimidin-4-yl)benzamide, 4-(2-{[2-(pyrimidin-2-ylamino)ethyl]amino}pyrimidin-4-yl)benzamide,(5-nitro4-phenylpyrimidin-2-yl)[2-(2-pyridylamino)ethyl]amine,4-(2-{[3-(4-nitroimidazolyl)propyl]amino}pyrimidin-4-yl)phenol,4-(4-(2-{[2-(2-methoxyphenyl)ethyl]amino}pyrimidin-4-yl)benzamide, 4-[2-({2-[(5-cyano-2-pyridyl)amino]ethyl}amino)pyrimidin4-yl]benzamide, 2-({2-[(5-nitro(2-pyridyl))amino]ethyl}amino)-4-phenylpyrimidine-5-carbonitrile, 4-[2-({2-[(6-methoxy-2-pyridyl)amino]ethyl}amino)pyrimidin-4-yl]benzamide, 4-(2-{[3-(4,5-dichloroimidazolyl)propyl]amino}pyrimidin-4-yl)phenol, 4-(2-{[3-(4-nitroimidazolyl)propyl]amino}pyrimidin-4-yl)benzamide, 4-({2-[(3-benzimidazolylpropyl)amino]pyrimidin-4-yl}benzamide, 4-[2-({2-[(4-amino-5cyanopyrimidin-2-yl)amino]ethyl}amino)pyrimidin-4-yl]benzamide, 4-{2-[(3-benzimidazolylpropyl)amino]pyrimidin-4-yl}-2-methoxyphenol, 4-(2-{[2-(2,5-dimethoxyphenyl)ethyl]amino}pyrimidin-4-yl)benzamide, 4-(2-{[2-(2,3-dimethoxyphenyl)ethyl]amino}pyrimidin-4-yl)benzamide, 4-(2-{[3-(4-methoxyphenoxy)propyl]amino}pyrimidin4-yl)benzamide, 4-[2({2-[(5-nitro-2-pyridyl)amino]ethyl}amino)pyrimidin-4-yl]benzamide, {2-[(5,-nitro(2-pyridyl))amino]ethyl}(5-nitro-4-phenylpyrimidin-2-yl)amine, 4-(2-{[2-(2quinolylamino)ethyl]amino}pyrimidin-4-yl)benzamide, 4-(4-cyanophenyl)-2-({2-[(5-nitro(2-pyridyl))amino]ethyl}amino)pyrimidine-5-carbonitrile, 4-(2-{[3-(4,5dichloroimidazolyl)propyl]amino}pyrimidin-4-yl)benzamide, 4-{2-[(2-{[5(aminothioxomethyl)-2-pyridyl]amino}ethyl)amino]pyrimidin-4-yl}benzamide, 4-[2-({3-[(5-nitro-2-pyridyl)amino]propyl}amino)pyrimidin-4-yl]benzamide, 4-(2-{[3-(4-phenylimidazolyl)propyl]amino}pyrimidin-4-yl)benzamide, 4-{2-[(3-naphthyloxypropyl)amino]pyrimidin-4-yl}benzamide, 4-(2-{[3-(5,6-dimethylbenzimidazolyl)propyl]amino}pyrimidin-4-yl)benzamide, [4-(4-imidazolylphenyl)pyrimidin-2-yl]{2-[(5-nitro(2-pyridyl))amino]ethyl}amine, 4-{2-[(2-{[5-(trifluoromethyl)-2-pyridyl]amino}ethyl)amino]pyrimidin-4-yl}benzamide, 4-(4-cyanophenyl)-2-({2-[(5-nitro(2-pyridyl))amino]ethyl}amino)pyrimidine-5-carboxamide, 4-(4-cyanophenyl)-2-({2-[(5-nitro(2-pyridyl))amino]ethyl}amino)pyrimidine-5-carboxylic acid, 2-({2-[(6-amino-5-nitro(2-pyridyl))amino]ethyl}amino)-4-(2,4-dichlorophenyl)pyrimidine-5-carboxylic acid, ethyl 2({2-[(5-nitro(2-pyridyl))amino]ethyl}amino)-4-(4-pyridyl)pyrimidine-5-carboxylate, ethyl 2-({2-[(5-cyano(2-pyridyl))amino[ethyl}amino)-4-cyanophenyl)pyrimidine-5-carboxylate, 4-[2-({3-[3-(trifluoromethyl)phenoxy]propyl}amino]pyrimidin-4-yl]benzamide, [4-4cyanophenyl)-2({2-[(5-nitro(2-pyridyl))amino]ethyl}amino)pyrimidin-5-yl]-N-methylcarboxamide, methyl 4-(4Cyanophenyl)-2({2-[(5-nitro(2-pyridyl))amino]ethyl}amino)pyrimidine-5-carboxylate, [4-(4-(4-morpholin4-ylphenyl)pyrimidin-2-yl]{2-[(5-nitro(2-pyridyl))amino]ethyl}amine, ethyl 4-(4-methylphenyl)-2-({2-[(5-nitro(2-pyridyl))amino]ethyl}amino)pyrimidine-5-carboxylate, {2-[(6-amino-5-nitro(2-pyridyl))amino]ethyl}{5-nitro-6-[benzylamino](2-pyridyl)}amine, 2-({2-[(5-nitro (2-pyridyl))amino]ethyl}amino)-4-(4-nitrophenyl)pyrimidine-5-carboxylic acid, ethyl 4-(4-fluorophenyl)-2-({2-(5-nitro(2-pyridyl))amino]ethyl}amino)pyrimidine-5-carboxylate, 4-[5-imidazolyl-2-({2-[(5-nitro(2-pyridyl))amino]ethyl}amino)pyrimidin-4-yl]benzenecarbonitrile, 4-[5-imidazol-2-yl-2-({2-[(5-nitro(2-pyridyl))amino]ethyl}amino)pyrimidin-4-yl]benzenecarbonitrile, ethyl 2-({2-[(4-amino-5cyanopyrimidin-2-yl)amino]ethyl}amino)-4-(4-cyanophenyl)pyrimidine-5-carboxylate, [4-(2,4dimethylphenyl)-5-imidazolylpyrimidin-2-yl](2-[(5-nitro(2-pyridyl))amino]ethyl}amine, 2-({2-[(6-amino-5-nitro(2-pyridyl)) amino]ethyl}amino)-4-(2,4-dichlorophenyl)pyrimidine-5-carbonitrile, ethyl 4-(4-cyanophenyl)-2-({2-[(4-nitrophenyl)amino]ethyl}amino)pyrimidine-5-carboxylate, [4-(4-cyanophenyl)-2-({2-[(5-nitro(2-pyridyl))amino]ethyl}amino)pyrimidin-5-yl]-N,N-dimethylcarboxamide, ethyl 4-(4-cyanophenyl)-2-({2-[(5-nitro(2-pyridyl))amino]ethyl}amino)pyrimidine-5-carboxylate, [4-(2,4-dichlorophenyl)5-ethylpyrimidin-2-yl]{2-[(5-nitro(2-pyridyl))amino]ethyl}amine, ethyl 4-(4-ethylphenyl)-2-({2-[(5-nitro(2-pyridyl))amino]ethyl}amino)pyrimidine-5-carboxylate, ethyl 4-(4-methoxyphenyl)-2-{2-[(5-nitro(2-pyridyl))amino]ethyl}amino)pyrimidine-5-carboxylate, 4-[5(methylsulfonyl)-2-({2-[(5nitro(2-pyridyl))amino]ethyl}amino)pyrimidin-4-yl]benzenecarbonitrile, 4-(2-{[3-(5,6-dichlorobenzimidazolyl) propyl]amino}pyrimidin-4-yl)benzamide, 4-[2-({2-[(6-amino-5-nitro(2-pyridyl))amino]ethyl}amino)-5-imidazolylpyrimidin-4-yl]benzenecarbonitrile, 4-[2-({2-[(6-amino-5-nitro(2-pyridyl))amino]ethyl}amino)-5-imidazol-2-ylpyrimidin-4-yl]benzenecarbonitrile, N-(cyanomethyl)[4-(4-cyanophenyl)-2-{2-[(5-nitro(2-pyridyl))amino]ethyl}amino)pyrimidin-5-yl]carboxamide, 4-[5-(3-methyl(1,2,4-oxadiazol-5-yl))-2-({2-[(5-nitro(2-pyridyl))amino]ethyl}amino)pyrimidin-4-yl]benzenecarbonitrile, ethyl 4-(4chlorophenyl)-2-({2-[(5-nitro(2-pyridyl))amino]ethyl}amino)pyrimidine-5-carboxylate, ethyl 4-(3,4-difluorophenyl)-2-({2-[5-nitro(2-pyridyl))amino]ethyl}amino)pyrimidine-5-carboxylate, N-(2-aminoethyl)[4-(4-cyanophenyl)-2-({5-nitro(2-pyridyl))amino]ethyl}amino)pyrimidin-5-yl]carboxamide, ethyl 4-(4cyanophenyl)-2-({2-[(4-methyl-5-nitro(2-pyridyl))amino]ethyl}amino)pyrimidine-5-carboxylate, ethyl 2-({2-[(6-amino-5-nitro(2-pyridyl))amino]ethyl}amino-4-(4-cyanophenyl)pyrimidine-5-carboxylate, [4-(4cyanophenyl)-2-({2-[(5-nitro(2-pyridyl))amino]ethyl}amino)pyrimidin-5-yl]-N-(2-hydroxyethyl)carboxamide, 2-hydroxyethyl 4-(4-cyanophenyl)-2-({2-[(5-nitro(2-pyridyl))amino]ethyl}amino)pyrimidine-5-carboxylate, ethyl 2-({2-[(4-amino-5-nitropyrimidin-2-yl)amino]ethyl}amino)-4-(4-cyanophenyl)pyrimidine-5-carboxylate, ethyl 4-[4-(methylethyl)phenyl]-2-({2-[(5-nitro(2-pyridyl))amino]ethyl}amino)pyrimidine-5-carboxylate, ethyl 4-[4-(dimethylamino)phenyl]-2-({2-[(5-nitro(2-pyridyl))amino]ethyl}amino)pyrimidine-5-carboxylate, ethyl 4-(2H-benzo[3,4-d]1,3dioxolen-5-yl)-2-({2-[(5-nitro(2-pyridyl))amino]ethyl}amino)pyrimidine-5carboxylate, ethyl 2-({2-[(5-nitro(2-pyridyl))amino]ethyl}amino)-4-(4-nitrophenyl)pyrimidine-5-carboxylate, ethyl 4-(4-methylthiophenyl)-2-({2-[(5-nitro(2-pyridyl))amino]ethyl}amino)pyrimidine-5-carboxylate, ethyl 4-(cyanophenyl)-2-[(2-{[5-(trifluoromethyl)(2-pyridyl)]amino}ethyl)amino]pyrimidine-5-carboxylate, ethyl 4-(2-naphthyl)-2-({2-[(5-nitro(2-pyridyl))amino]ethyl}amino)pyrimidine-5-carboxylate, N-butyl[4-(4cyanophenyl)-2-({2-[(5-nitro(2-pyridyl))amino]ethyl}amino)pyrimidin-5-yl]carboxamide, N-(tert-butyl)[4-(4-cyanophenyl)-2-({2-[(5-nitro(2-pyridyl))amino]ethyl}amino)pyrimidin-5-yl]carboxamide, ethyl 4-(4carbamoylphenyl)-2-({2-[(5-cyano(2-pyridyl))amino]ethyl}amino(-6-ethylpyrimidine-5-carboxylate,tert-butyl [4-(4-cyanophenyl)-2-({2-[(5-nitro(2-pyridyl))amino]ethyl}amino)pyrimidine-5-(carboxylate,N-(carbamoylmethyl)[4(4-cyanophenyl)-2-({2-[(5-nitro(2- pyridyl))amino]ethyl}amino)pyrimidin-5-yl]carboxamide, ethyl 4-(4-cyanophenyl)-6-ethyl-2-({2-[(5-nitro(2-pyridyl))amino]ethyl}amino)pyrimidine-5-carboxylate, butyl 4-(4-cyanophenyl)-2-({2-[(5-nitro(2-pyridyl))amino]ethyl}amino)pyrimidine-5-carboxylate, ethyl 4-{[(4-cyanophenyl)methyl]amino)-2-({2-[(5-nitro(2-pyridyl))amino]ethyl}amino)pyrimidine-5-carboxylate, ethyl 4-{[(3-cyanophenyl) methyl]amino}-2-({2-1(5-nitro(2-pyridyl))amino]ethyl}amino)pyrimidine-5-carboxylate, ethyl 4-[4tert-butyl)phenyl]-2-({2-[(5-nitro(2-pyridyl))amino]ethyl}amino)pyrimidine-5-5-carboxylate, 4-[2-({2-[(5-nitro(2-pyridyl))amino]ethyl}amino-5-[benzylamino]pyrimidin-4-yl]benzenecabonitrile, [4-(2,4-dichlorophenyl)-5-imidazolylpyrimidin-2-yl]{2-[(5-nitro(2-pyridyl))amino]ethyl}amine, [4(2,4-dichlorophenyl)-5-imidazol-2-ylpyrimidin-2-yl]{2-[(5-nitro(2-pyridyl))amino]ethyl}amine, 4-(4-cyanophenyl)-6-(3-furyl)-2-({2-[(5-nitro(2-pyridyl))amino]ethyl}amino)pyrimidine-5 carboxylic acid, 4-[2-({2-[(5-nitro(2-pyridyl))amino]ethyl}amino)-5-(piperazinylcarbonyl)pyrimidin-4-yl]benzenecarbonitrile, ethyl 4-(4-imidazolylphenyl)-2-({2-[(5-nitro(2-pyridyl))amino]ethyl}amino)pyrimidine-5-carboxylate, 4-[5-(morpholin-4-ylcarbonyl)-2-({2-[(5-nitro(2-pyridyl))amino]ethyl}amino)pyrimidin-4-yl]benzenecarbonitrile, ethyl 4-(4-2-furyl)phenyl]-2-({2-[(5-nitro(2-pyridyl))amino]ethyl}amino)pyrimidine-5-carboxylate, ethyl 2-({2-[(5-nitro(2-pyridyl))amino]ethyl}amino)-4-(4-(1,3-oxazol-5-yl)phenyl)pyrimidine-5-carboxylate, ethyl 2-({2-[(5-nitro(2-pyridyl))amino]ethyl}amino)-4-(4-(1,2,4-triazol-4-yl)phenyl)pyrimidine-5-carboxylate, N-[2-(dimethylamino)ethyl][4-(4cyanophenyl)-2-({2-[(5-nitro(2-pyridyl))amino]ethyl}amino)pyrimidin-5-yl]carboxamide, 2-(dimethylamino)ethyl 4-(4-cyanophenyl)-2-((2-[(5-nitro(2-pyridyl))amino]ethyl}amino)pyrimidine-5-carboxylate, ethyl 2-({2-[(5-nitro(2-pyridyl))amino]ethyl}amino)-4-[4-(trifluoromethyl)phenyl]pyrimidine-5-carboxylate, ethyl 4-(2,4-dichlorophenyl)-2-({2-[(5-nitro(2-pyridyl))amino]ethyl}amino)pyrimidine-5-carboxylate, ethyl 4-(4-(1H-1,2,3,4-tetraazol-5-yl)phenyl)-2-({2-[(5-nitro(2-pyridyl))amino]ethyl}amino)pyrimidine-5-carboxylate, ethyl 4-(4-carbamoylphenyl)-6-ethyl-2({2-[(5-nitro(2-pyridyl))amino]ethyl}amino)pyrimidine-5-carboxylate, 4-(4-cyanophenyl)-2-({2-[(5-nitro(2-pyridyl))amino]ethyl}amino)-6-phenylpyrimidine-5-carboxylic acid, {2-[(6amino-5-nitro(2-pyridyl))amino]ethyl}[4-(2,4-dichlorophenyl)-5-imidazolylpyrimidin-2-yl]amine, {2-[(6-amino-5-nitro(2-pyridyl))amino]ethyl}[4-(2,4dichlorophenyl))-5-imidazol-2-ylpyrimidin-2-yl]amine, ethyl 4-(4-bromophenyl)-2-({2-[(5-nitro(2-pyridyl))amino]ethyl}amino)pyrimidine-5carboxylate, ethyl 4-[methylsulfonyl)phenyl]-2-({2-[(5-nitro(2-pyridyl))amino]ethyl}amino)pyrimidine-5-carboxylate, ethyl 2-({2-[(6-amino-5-nitro(2-pyridyl))amino]ethyl}amino)-4-(4-(1,3-oxazol-5-yl)phenyl)pyrimidine-5-carboxylate, N-[2dimethylamino)ethyl][4-(4-cyanophenyl)-2-({2-[(5-nitro(2-pyridyl))amino]ethyl}amino)pyrimidin-5-yl]-N-methylcarboxamide, N-(1-carbamoyl-2-hydroxyethyl)[4-(4-cyanophenyl)-2-({2-[(5-nitro(2-pyridyl))amino]ethyl}amino) pyrimidin-5-yl]carboxamide, 3-(dimethylamino)propyl 4-(4-cyanophenyl)-2-({2-[(5-nitro(2-pyridyl))amino]ethyl}amino)pyrimidine-5-carboxylate, ethyl 2-({2-[(6-amino-5-nitro(2-pyridyl))amino]ethyl}amino)-4-(2,4dichlorophenyl)pyrimidine-5-carboxylate, 2-(dimethylamino)ethyl 2-({2-[(6amino-5-nitro(2-pyridyl))amino]ethyl}amino)-4-(4-cyanophenyl)pyrimidine-5-carboxylate, [2-(dimethylamino)ethoxy]-N-[4-(4-cyanophenyl)-2-({2-[(5-nitro(2-pyridyl))amino]ethyl}amino)pyridin-5-yl]carboxamide, ethyl 2-({2-[(5-nitro(2-pyridyl))amino]ethyl}amino)-4-[4(trifluoromethoxy)phenyl]pyrimidine-5-carboxylate, ethyl 4-(4-morpholin-4-ylphenyl)-2-({2-[(5-nitro(2-pyridyl))amino]ethyl}amino)pyrimidine-5-carboxylate, [4-(4-cyanophenyl)-2-({2-[(5-nitro(2-pyridyl))amino]ethyl}amino)pyrimidin-5-yl]-N-benzylcarboxamide, ethyl 4-(6morpholin-4-yl(3-pyridyl))-2-({2-[(5-nitro(2-pyridyl))amino]ethyl}amino)pyrimidine-5-carboxylate, [4-(4-cyanophenyl)-2-({2-[(5-nitro(2-pyridyl))amino]ethyl}amino)pyrimidin-5-yl]-N-(4pyridylmethyl)carboxamide, phenylmethyl 4-(4cyanophenyl)-2-({2-[(5-nitro(2-pyridyl))amino]ethyl}amino)pyrimidine-5-carboxylate, 4-(4-cyanophenyl)-6-(4-fluorophenyl)-2-({2-[(5-nitro(2-pyridyl))amino]ethyl}amino)pyrimidine-5-carboxylic acid, N-[(3-methoxyphenyl)methyl]{4-[2({2-[(5-nitro(2-pyridyl))amino)ethyl}amino]pyrimidin-4-yl]phenyl}carboxamide, 4-[5-{3-[2-(dimethylamino)ethyl](1,2,4-oxadiaxol-5-yl)}-2-({2-[(5-nitro(2-pyridyl))amino]ethyl}amino)pyrimidin-4-yl]benzenecarbonitrile, N-[(3-bromophenyl)methyl][4-(2-{[2-(pyrimidin-2-ylamino)ethyl]amino}pyrimidin-4-yl)phenyl]carboxamide, 4-(dimethylamino)butyl 4-4-cyanophenyl)-2-({2-[(5-nitro(2-pyridyl))amino]ethyl}amino)pyrimidine-5-carboxylate, 4,6-bis(4-cyanophenyl)-2-({2-[(5-nitro(2-pyridyl))amino]ethyl}amino)pyrimidine-5-carboxylic acid, ethyl 2-({2-[(6-amino-5-nitro(2-pyridyl))amino]ethyl}amino)-4-(4-morpholin-4-ylphenyl)pyrimidine-5carboxylate, 4-(3-hydroxyphenyl)-2-({2-[(5-nitro(2-pyridyl))amino]ethyl}amino)-6-(4-nitrophenyl)pyrimidine-5-carboxylic acid, 2-morpholin-4-ylethyl 4-(4-cyanophenyl)-2-({2-[(5-nitro(2-pyridyl))amino]ethyl}amino)pyrimidine-5-carboxylate, 4-(4-cyanophenyl)-2-({2-[(5-nitro(2-pyridyl))amino]ethyl}amino)-6-(4-nitrophenyl)pyrimidine-5carboxylic acid, 4-(4-cyanophenyl)-2({2-[(5-nitro(2-pyridyl))amino]ethyl}amino)6-(3-nitrophenyl)pyrimidine-5-carboxylic acid, N-[(3-bromophenyl)methyl]{4-[2({2-[(5-cyano(2-pyridyl))amino]ethyl}amino)pyrimidin-4-yl]phenyl}carboxamide, ethyl 4-(4-carbamoylphenyl)-2-({2-[(5-nitro(2-pyridyl))amino]ethyl}amino)-6-(4-pyridyl)pyrimidine-5carboxylate, 2-(dimethylamino)ethyl 2-({2-[(6-amino-5-nitro(2-pyridyl)amino]ethyl}amino)-4-(2,4-dichlorophenyl)pyrimidine-5-carboxylate,2-[bis(2-hydroxyethyl)amino]ethyl 4-(4cyanophenyl)-2-({2-[(5-nitro(2-pyridyl))amino]ethyl}amino)pyrimidine-5-carboxylate, {4-[2-({2-[(4-amino-5-cyanopyrimidin-2-yl)amino]ethyl}amino)pyrimidin-4-yl]phenyl}-N-[(3-bromophenyl)methyl]carboxamide, 4-(4-carboxyphenyl)-2-({2-[(5-nitro(2-pyridyl))amino]ethyl}amino)-6-(4-nitrophenyl)pyrimidine-5-carboxylic acid, 2-hydroxy-3-morpholin-4-ylpropyl 4-(4-cyanophenyl)-2-({(2-[(5-nitro(2-pyridyl))amino]ethyl}amino)pyrimidine-5-carboxylate, ethyl 4-(4cyanophenyl)-2-({2-[(5-nitro(2-pyridyl))amino]ethyl}amino)-6-(4nitrophenyl)pyrimidine-5-carboxylate, (2-{5-[2({2-[(6-amino-5-nitro(2-pyridyl))amino]ethyl}amino)-4-(2,4-dichlorophenyl)pyrimidin-5-yl](1,2,4-oxadiazol-3-yl)}ethyl)dimethylamine, and ethyl 4-(4carbamoylphenyl)-2-({2-[(5-nitro(2-pyridyl))amino]ethyl}amino)-4-(4-nitrophenyl)pyrimidine-5-carboxylate.

Compounds of the present invention can be readily synthesized using the methods described herein, or other methods, which are well known in the art For example, the synthesis of pyrimidines having a wide variety of substituents is comprehensibly reviewed in D. J. Brown, "The Pyrimidines," vol. 54, Wiley (1994), which is incorporated herein by reference. The compounds described herein were synthesized using both solution-phase and resin-based (i.e., solid-phase) techniques.

Compounds of the present invention of the type shown as pyrimidine product in FIG. 1 can be readily synthesized in solution by reaction of a carbonyl-containing derivative of $R_5$ or $R_{15}$ (or alternatively, a carbonyl-containing compound from which $R_5$ or $R_{15}$ can be derived) with N,N-dimethylformamide dimethyl acetal (DMFDMA). The intermediate enaminoketone that results is then reacted with a guanidine in the presence of an organic solvent and a suitable base such as sodium ethoxide, sodium methoxide, sodium hydroxide or cesium carbonate at various temperatures to give a pyrimidine. This method is generally.described in Menozzi et al., *J. Heterocyclic Chem.*, 24: 1669 (1987), P. Schenone et al, *J. Heterocyclic Chem.*, 27:295 (1990), R. Paul et al., *J. Med. Chem.* 36:2716 (1993) and J. Zimmermann et al., *Arch. Pharm.*, 329:371 (1996), all of which are incorporated herein by reference.

Carbonyl-containing starting reagents that are suitable for use in this reaction scheme include, for example, β-keto esters, alkyl aryl ketones, β-keto sulfones, α-nitro ketones, β-keto nitriles, desoxybenzoins, aryl heteroarylmethyl ketones, and the like. The carbonyl-containing starting reagents can either be purchased or synthesized using known methods.

For example, β-keto esters can be readily synthesized by reaction of an acid chloride or other activated carboxylic acid with potassium ethyl malonate in the presence of triethylamine in accordance with the method described in R. J. Clay et al., *Synthesis*, 1992:290 (1992), which is incorporated herein by reference. Alternatively, the desired β-keto ester can be synthesized by deprotonating an appropriate methyl ketone with a suitable base such as sodium hydride, followed by condensation with diethylcarbonate in accordance with the method described in Sircar et al., *J. Med. Chem.*, 28:1405 (1985), which is incorporated herein by reference.

Likewise, β-keto sulfones and α-nitro ketones can be prepared using known methods, such as those described in N. S. Simpkins, "Sulphones in Organic Synthesis," Pergamon (1993) (β-keto sulfones) and M. Jung et. al, *J. Org. Chem.*, 52:4570 (1987) (α-nitro ketones), both of which are incorporated herein by reference. β-keto nitriles can be readily prepared by reaction of an α-halo ketone with sodium or potassium cyanide.

When the substrate is a doubly activated carbonyl compound (e.g., α-keto ester, β-keto sulfone, β-keto nitrile, and the like) the first condensation is typically conducted with a small excess of DMFDMA in a solvent such as THF at 70–80° C. for several hours. This method is described in more detail in Example 25, herein below (i.e., "Solution Method A").

When a mono-activated substrate such as a methyl ketone is involved, DMFDMA is often used as the solvent at a higher temperature (90–100° C.) for a longer period of time (e.g., overnight). After completion of the condensation reaction, the solvent and excess DMFDMA are removed in vacuo. The resulting solid or oil is dissolved in an appropriate solvent and heated with an equimolar amount of the guanidine and base. This method is described in more detail in Example 60, herein below (i.e., "Solution Method B").

When $R_5$ (shown in FIG. 1) is an ester, alkaline or acidic hydrolysis of the resulting pyrimidine yields the corresponding carboxylic acid. This acid can then be further coupled to various alcohols or amines to provide a variety of ester or amide derivatives at position 5.

Guanidines employed in the synthesis of invention compounds can be purchased or, alternatively, synthesized by reacting the corresponding amine with a guanidino transfer reagent, such as, for example, benzotriazole carboxamidinium 4-methylbenzenesulfonate. This guanidino transfer reagent is described in A. R. Katritzky et al, 1995, *Synthetic Communications*, 25:1173 (1995), which is incorporated herein by reference. Thus, for example, benzotriazole carboxamidinium 4-methylbenzenesulfonate can be reacted in equimolar quantity with an amine and one equivalent of diisopropyl ethyl amine (DIEA) in acetonitrile at room temperature overnight to yield guanidinium 4-methylbenzenesulfonate upon addition of diethyl ether. Amines containing a nitrogen heterocyclic aryl can be prepared by nucleophilic substitution of a halo-substituted nitrogen heterocyclic aryl with an appropriate diamine, such as, for example, ethylenediamine or propylenediamine. These diamines are particularly suitable for use as reaction solvents at reaction temperatures in the range of about 25° C. to 125° C. The preparation of specialized amines is noted in the Examples provided herein Other known synthesis methods can be used to prepare compounds of the present invention. For example, 5-aryl 2-aminopyrimidine can be prepared by reacting a guanidine with a vinamidinium salt, in accordance with the method described in R. M. Wagner and C. Jutz, *Chem. Berichte*, 2975: (1971), which is incorporated herein by reference. This method is illustrated in Example 67, herein below (i.e.,"Solution Method C").

Similarly, 4-anilo-2-chloropyrimidine can be prepared by reacting aniline with 2,4-dichloropyrimidine. Likewise, an aniline can be treated with a 2,4-dichloropyrimidine to give the 4-anilo-2-chloropyrimidine. Further substitution with a second amine gives 2-amino4-anilinopyrimidine.

Figure 2:
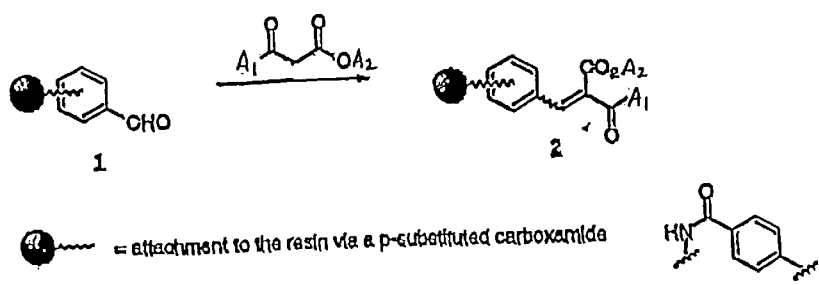
FIG. 2 illustrates the reaction scheme for the synthesis of compounds of the present invention in accordance with Resin Method A, described in Example 2.
Figure 2:
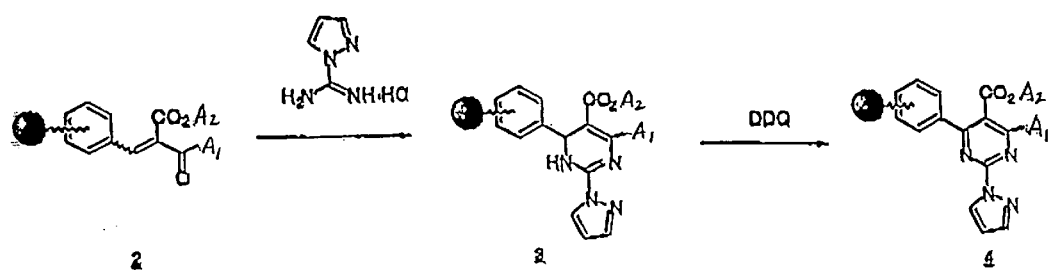
Figure 2:
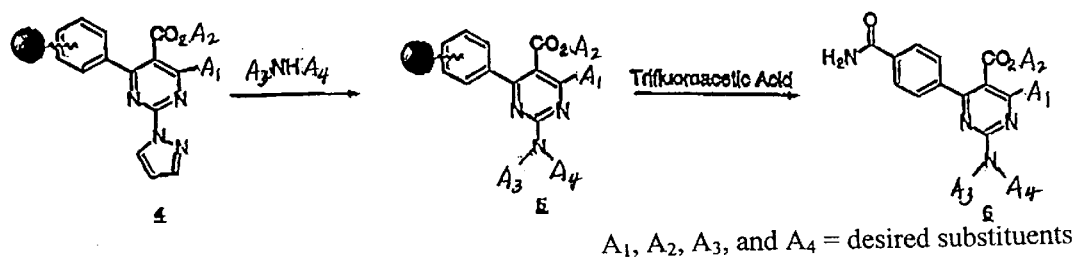

In addition to solution-phase synthesis methods, resin-based synthesis methods can also be used to synthesize compounds of the present invention. For example, FIG. 2 illustrates the synthesis of tetra-substituted pyrimidines which begins with the loading of an aromatic carboxylic acid aldehyde, in this case, 4-formyl benzoic acid, to the amino group of a suitable resin, such as, for example, Rink amide resin (Novabiochem, San Diego, Calif.) ("Resin Method A" which is described in more detail in Example 2). Knoevenagel condensation of a β-keto ester gives an unsaturated intermediate which can be condensed with 1-pyrazologuanidine hydrochloride in the presence of a suitable base (e.g., potassium carbonate). The intermediate dihydropyrimidine can then be oxidized to the resin bound pyrimidine with 2,3-dichloro,5,6-dicyano-1,4benzoquinone (DDQ) in benzene. Finally, substitution of the pyrazolo moiety by heating with an amine in 1-methylpyrrolidone (NMP) or other suitable solvent is followed by acidolytic cleavage to give the desired pyrimidine. This synthesis method can be used to generate pyrimidines with a substituent in the 4-position of the pyrimidine ring.

Figure 3:
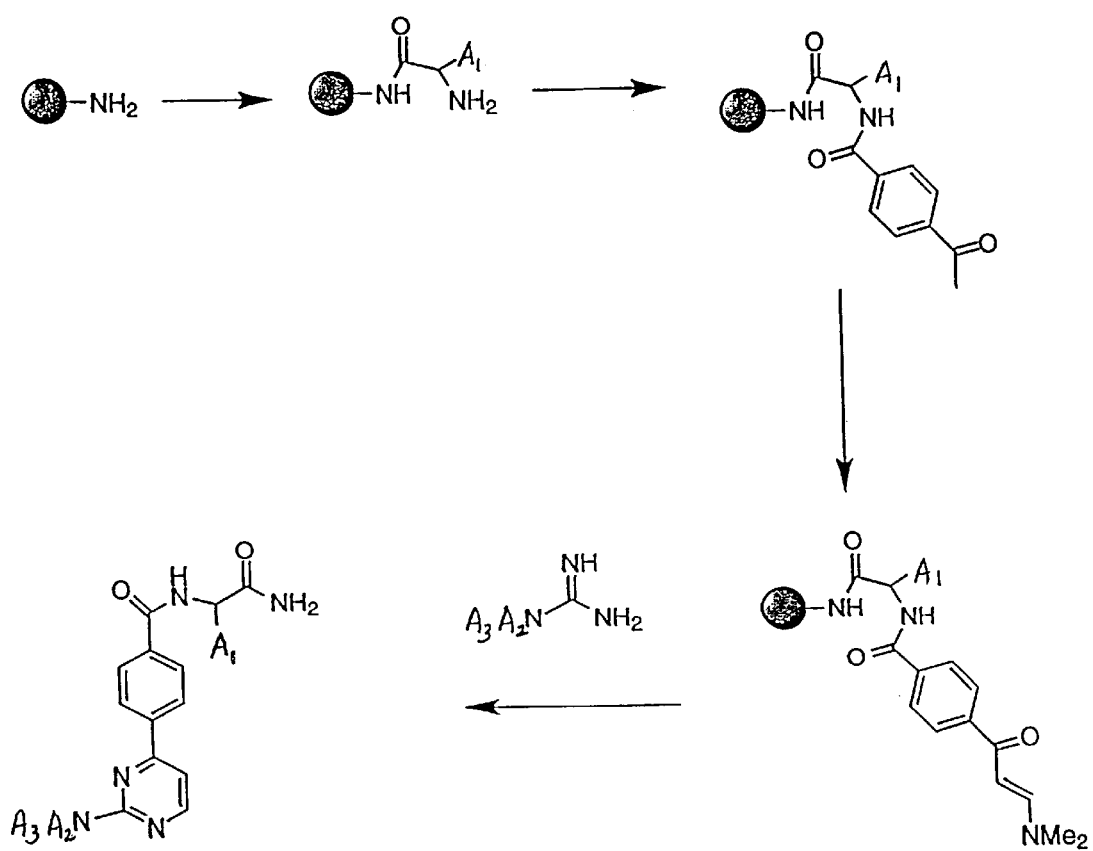
FIG. 3 illustrates the reaction scheme for the synthesis of compounds of the present invention in accordance with Resin Method B, described in Example 3.

Resin Method B, which is illustrated in FIG. 3, can be used to synthesize pyrimidines in which the 4-position is unsubstituted. A hydroxymethyl-resin, such as commercially available Sasrin resin (Bachem Biosciences, King of Prussia, Pennsylvania), is treated with triphenylphosphine dibromide in dichloromethaue to convert the hydroxymethyl group on the resin to a bromomethyl group, as generally described in K. Ngu et al., *Tetrahedron Letters*, 38:973 (1997), which is incorporated herein by reference. The bromine is then displaced by reaction with a primary amine in NMP (at room temperature or 70–80° C.). The amine is then coupled with the appropriate aromatic compound containing an acetyl group. The coupling can be carried out with PyBOP® (Novabiochem, San Diego, Calif.), and 4-methylmorpholine in NMP. Resin Method B is described in more detail in Example 3, herein below.

Resin Method B can also be used to incorporate an amino acid residue into the resulting pyrimidine. For example, amino resin can be coupled to a 9-fluorenyl-methoxycarbonyl (FMOC)-protected amino acid using standard peptide synthesis conditions and methods. Further coupling with 4-acetylbenzoic acid followed by reaction with N,N-dimethylformamide dimethyl acetal and cyclization with a guanidine produces a pyrimidine derivative having an amino acid residue incorporated within it.

Pyrimidines having e.g., a carboxamidophenyl group at position 6 and hydrogen at position 5 can be prepared from an amino (i.e., —NH$_2$)-containing resin such as Rink amide resin (Novabiochem, San Diego, Calif.). This method is describe in more detail in Example 10, herein below ("Resin Method C").

Compounds of the present invention can also be prepared according to Resin Method D, to produce a 2,4-diaminopyrimidine. Resin-bound amine is reacted with a 2,4-dichloropyrimidine to give a resin-bound 6-amino-2-chloropyrimidine. The resin-bound amine can be derived from any suitable primary amine, however, anilines generally are not suitable. Displacement with a second amine and cleavage gives a 2,4-diaminopyrimidine. For the second displacement, primary or secondary amines which may contain other functional groups such as unprotected hydroxy groups are suitable. The resulting dichloropyrimidine may be further substituted, for example, with an ester group at the 5-position. A 2,6-dichloropyrimidine can be used instead of 2,4-dichloropyrimidine to produce a 2,6-diaminopyridine. This scheme is described in more detail in Examples 17–19, herein below.

Resin Method E can be used to produce a 2,6diaminopyridine. The method is analogous to Resin Method D except that a 2,6-dichloropyrimidine is used as the electrophile and the final product is a 2,6diaminopyridine. Resin Method E is described in more detail in Examples 20–21, herein below.

Resin Method F can be used to synthesize S-amino substituted compounds of the present invention. Resin-bound amine is reacted with a halomethyl aryl ketone. The resulting resin-bound aminomethyl ketone is then treated with DMFDMA (neat) followed by cyclization with a guanidine to give the 2,5-diamino-6-arylpyrimidine. Resin Method F is described in more detail in Example 22, herein below.

Figure 4:
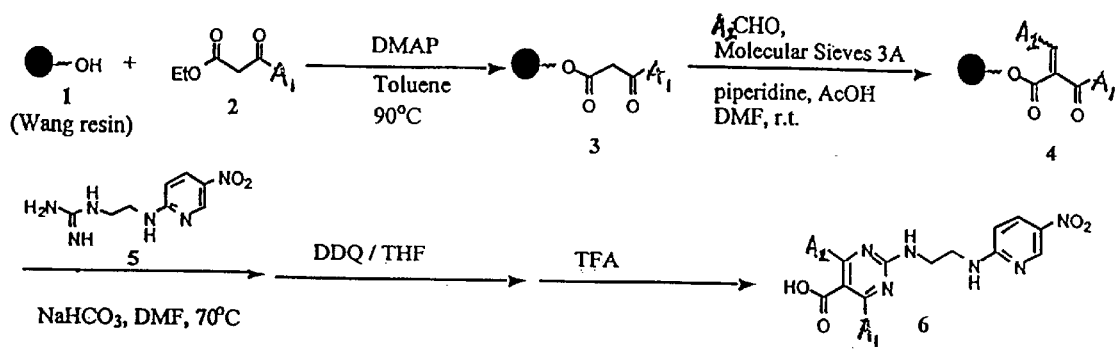
FIG. 4 illustrates the reaction scheme for the synthesis of compounds of the present invention in accordance with Resin Method G, described in Example 23.

Resin Method G, which is illustrated in FIG. 4 and described in more detail in Example 23, can be used to synthesize compounds of the present invention having a carboxyl group at the 5-position.

GSK3 inhibitor compounds of the present invention can be purified using known methods, such as, for example, chromatography, crystalization, and the like.

Compounds of the present invention typically exhibit inhibitory activity that is selective with respect to GSK3, as compared to at least one other type of kinase. As used herein, the term "selective" refers to a relatively greater potency for inhibition against GSK3, as compared to at least one other type of kinase. Preferably, GSK3 inhibitors of the present invention are selective with respect to GSK3, as compared to at least two other types of kinases. Kinase activity assays for kinases other than GSK3 are generally known See e.g., Havlicek et al., *J. Med. Chem.,* 40:408–12(1997), incorporated herein by reference. GSK3 selectivity can be quantitated according to the following: GSK3 selectivity= $IC_{50\ (other\ kinase)} \div IC_{50\ (GSK3)}$, where a GSK3 inhibitor is selective for GSK3 when $IC_{50\ (other\ kinase)} > IC_{50\ (GSK3)}$. Thus, an inhibitor that is selective for GSK3 exhibits a GSK3 selectivity of greater than 1-fold with respect to inhibition of a kinase other than GSK3. As used herein, the term "other kinase" refers to a kinase other than GSK3. Such selectivities are generally measured in the cell-free assay described in Example 74. A cell-free GSK3 kinase assay detects inhibitors that act by direct interaction with the polypeptide GSK3, while a cell-based GSK3 kinase assay may identify inhibitors that function either by direct interaction with GSK3 itself, or by interference with GSK3 expression or with post-translational processing required to produce mature active GSK3.

Typically, GSK3 inhibitors of the present invention exhibit a selectivity of at least about 2-fold (i.e., $IC_{50\ (other\ kinase)} \div IC_{50\ (GSK3)}$) for GSK3, as compared to another kinase and more typically they exhibit a selectivity of at least about 5-fold. Usually, GSK3 inhibitors of the present invention exhibit a selectivity for GSK3, as compared to at least one other kinase, of at least about 10-fold, desirably at least about 100-fold, and preferably, at least about 1000-fold.

GSK3 inhibitory activity can be readily detected using the assays described herein, as well as assays generally known to those of ordinary skill in the art. Exemplary methods for identifying specific inhibitors of GSK3 include both cell-free and cell-based GSK3 kinase assays;

In general, a cell-free GSK3 kinase assay can be readily carried out by: (1) incubating GSK3 (SEQ ID NO: 1) with a peptide substrate, radiolabeled ATP (such as, for example, $\gamma^{33}$P- or $\gamma^{32}$P-ATP, both available from Amersham, Arlington Heights, Ill.), magnesium ions, and optionally, one or more candidate inhibitors; (2) incubating the mixture for a period of time to allow incorporation of radiolabeled phosphate into the peptide substrate by GSK3 activity; (3) transferring all or a portion of the enzyme reaction mix to a separate vessel, typically a microtiter well that contains a uniform amount of a capture ligand that is capable of binding to an anchor ligand on the peptide substrate; (4) washing to remove unreacted radiolabeled ATP; then (5) quantifying the amount of $^{33}$P or $^{32}$P remaining in each well. This amount represents the amount of radiolabeled phosphate incorporated into the peptide substrate. Inhibition is observed as a reduction in the incorporation of radiolabeled phosphate into the peptide substrate.

The term "peptide substrate" refers herein to a peptide, a polypeptide or a synthetic peptide derivative that can be phosphorylated by GSK3 in the presence of an appropriate amount of ATP. Suitable peptide substrates may be based on portions of the sequences of various natural protein substrates of GSK3, and may also contain N-terminal or C-terminal modifications or extensions including spacer sequences and anchor ligands. Thus, the peptide substrate may reside within a larger polypeptide, or may be an isolated peptide designed for phosphorylation by GSK3.

For example, a peptide substrate can be designed based on a subsequence of the DNA binding protein CREB, such as the SGSG-linked CREB peptide, SGSGKRREILSRRPSYR (SEQ ID NO: 2). The term "CREB" peptide refers herein to a sequence within the CREB DNA binding protein described in Wang et al., *Anal. Biochem.,* 220:397402.(1994), incorporated herein by reference. In the assay reported by Wang et al., the C-terminal serine in the SXXXS motif (SEQ ID NO: 3) of the CREB peptide is enzymatically prephosphorylated by cAMP-dependent protein kinase (PKA), a step which is required to render the N-terminal serine in the motif phosphorylatable by GSK3. As an alternative, a modified CREB peptide substrate can be employed which has the same SXXXS motif(SEQ ID NO: 3) and which also contains an N-terminal anchor ligand, but which is synthesized with its C-terminal serine prephosphorylated (Chiron Technologies PTY Ltd., Clayton, Australia). Phosphorylation of the second serine in the SXXXS motif (SEQ ID NO: 3) during peptide synthesis eliminates the need to enzymatically phosphorylate that residue with PKA as a separate step, and incorporation of an anchor ligand facilitates capture of the peptide substrate after its reaction with GSK3.

Generally, a peptide substrate used for a kinase activity assay may contain one or more sites that are phosphorylatable by GSK3, and one or more other sites that are phosphorylatable by other kinases, but not by GSK3. Thus, these other sites can be prephosphorylated in order to create a motif that is phosphorylatable by GSK3. The term "prephosphorylated" refers herein to the phosphorylation of a substrate peptide with non-radiolabeled phosphate prior to conducting a kinase assay using that substrate peptide. Such prephosphorylation can conveniently be performed during synthesis of the peptide substrate. The SGSG-linked CREB peptide (SEQ ID NO: 2) can be linked to an anchor ligand, such as biotin, where the serine near the C terminus between P and Y is prephosphorylated. As used herein, the term "anchor ligand" refers to a ligand that can be attached to a peptide substrate to facilitate capture of the peptide substrate on a capture ligand, and which functions to hold the peptide substrate in place during wash steps, yet allows removal of unreacted radiolabeled ATP. An exemplary anchor ligand is biotin. The term "capture ligand" refers herein to a molecule which can bind an anchor ligand with high affinity, and which is attached to a solid structure. Examples of bound capture ligands include, for example, avidin- or streptavidin-coated microtiter wells or agarose beads. Beads bearing capture ligands can be flirter combined with a scintillant to provide a means for detecting captured radiolabeled substrate peptide, or scintillant can be added to the captured peptide in a later step.

The captured radiolabeled peptide substrate can be quantitated in a scintillation counter using known methods. The signal detected in the scintillation counter will be proportional to GSK3 activity if the en2yme reaction has been run under conditions where only a limited portion (e.g., less than 20%) of the peptide substrate is phosphorylated. If an inhibitor is present during the reaction, GSK3 activity will be reduced, and a smaller quantity of radiolabeled phosphate will thus be incorporated into the peptide substrate. Hence, a lower scintillation signal will be detected. Consequently, GS3 inhibitory activity will be detected as a reduction in scintillation signal, as compared to that observed in a negative control where no inhibitor is present during the reaction. This assay is described in more detail in Example 74, herein below.

A cell-based GSK3 kinase activity assay typically utilizes a cell that can express both GSK3 and a GSK3 substrate, such as, for example, a cell transformed with genes encoding GSK3 and its substrate, including regulatory control sequences for the expression of the genes. In carrying out the cell-based assay, the cell capable of expressing the genes is incubated in the presence of a compound of the present invention. The cell is lysed and the proportion of the substrate in the phosphorylated form is determined, e.g., by observing its mobility relative to the unphosphorylated form on SDS PAGE or by determining the amount of substrate that is recognized by an antibody specific for the phosphorylated form of the substrate. The amount of phosphorylation of the substrate is an indication of the inhibitory activity of the compound, i.e., inhibition is detected as a decrease in phosphorylation as compared to the assay conducted with no inhibitor present. GSK3 inhibitory activity detected in a cell-based assay may be due, for example, to inhibition of the expression of GSK3 or by inhibition of the kinase activity of GSK3.

Thus, cell-based assays can also be used to specifically assay for activities that are implicated by GSK3 inhibition, such as, for example, inhibition of tau protein phosphorylation, potentiation of insulin signaling, and the like. For example, to assess the capacity of a GSK3 inhibitor to inhibit Alzheimer's-like phosphorylation of microtubule-associated protein tau, cells may be co-transfected with human GSK3β (SEQ ID NO: 1) and human tau protein,. then incubated with one or more candidate inhibitors. Various mammalian cell lines and expression vectors can be used for this type of assay. For instance, COS cells may be transfected with both a human GSK3β expression plasmid according to the protocol described in Stambolic et al., 1996, *Current Biology* 6:1664–68, which is incorporated herein by reference, and an expression plasmid such as pSG5 that contains human tau protein coding sequence under an early SV40 promoter. The sequence of tau protein is provided in SEQ ID NO: 4. See also Goedert et al., *EMBO J.*, 8:393–399 (1989), which is incorporated herein by reference. Alzheimer's-like phosphorylation of tau can be readily detected with a specific antibody such as, for example, AT8, which is available from Polymedco Inc. (Cortlandt Manor, N.Y.) after lysing the cells. This assay is described in greater detail in Example 76, herein below.

Likewise, the ability of GSK3 inhibitor compounds to potentiate insulin signaling by activating glycogen synthase can be readily ascertained using a cell-based glycogen synthase activity assay. This assay employs cells that respond to insulin stimulation by increasing glycogen synthase activity, such as the CHO-HIRC cell line, which overexpresses wild-type insulin receptor (~100,000 binding sites/cell). The CHO-HIRC cell line can be generated as described in Moller et al., *J. Biol. Chem.*, 265:14979–14985 (1990) and Moller et al., *Mol. Endocrinol.*, 4:1183–1191 (1990), both of which are incorporated herein by reference. The assay can be carried out by incubating serum-starved CHO-HIRC cells in the presence of various concentrations of compounds of the present invention in the medium, followed by cell lysis at the end of the incubation period. Glycogen synthase activity can be detected in the lysate as described in Thomas et al., *Anal. Biochem.*, 25:486–499 (1968). Glycogen synthase activity is computed for each sample as a percentage of maximal glycogen synthase activity, as described in Thomas et al., supra and is plotted as a function of candidate GSK3 inhibitor concentration. The concentration of candidate GSK3 inhibitor that increased glycogen synthase activity to half of its maximal level (i.e., the $IC_{50}$) can be calculated by fitting a four parameter sigmoidal curve using routine curve fitting methods that are well known to those having ordinary skill in the art. This is described in more detail in Example 75, herein below.

GSK3 inhibitors can be readily screened for in vivo activity such as, for example, insulin potentiating activity, using methods that are well known to those having ordinary skill in the art. For example, candidate compounds having potential therapeutic activity in the treatment of NIDDM can be readily identified by detecting a capacity to induce insulin sensitization in animal models of type 2 diabetes. Specifically, the candidate compound can be dosed via several routes prior to administration of a glucose bolus in either diabetic mice (e.g. KK, db/db, ob/ob) or diabetic rats (e.g. Zucker Fa/Fa or GK). Following administration of the candidate compound and glucose, blood samples are removed at preselected time intervals and evaluated for serum glucose and insulin levels. Improved disposal of glucose in the absence of elevated secretion levels of endogenous insulin is indicative of insulin sensitization. A detailed description of this assay is provided in Example 77, herein below.

In accordance with another embodiment of the present invention, there is provided a composition comprising a pharmaceutically acceptable excipient and a GSK3-inhibitor compound of the present invention.

Suitable pharmaceutically acceptable excipients include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), incorporated herein by reference.

Pharmaceutical compositions containing GSK-3 inhibitor compounds of the present invention may be in any form suitable for the intended method of administration, including, for example, a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof.

In accordance with yet another embodiment, the present invention provides a method for inhibiting GSK3 activity in a subject, said method comprising administering to a subject an effective amount of a GSK3 inhibitor compound having the structure (I) or (II).

As used herein, the term "inhibition of GSK3 activity" and its various grammatical equivalents refers to a detectable suppression of GSK3 activity either as compared to a control or as compared to expected GSK3 activity. The term "control" refers herein to GSK3 activity exhibited by the subject in the absence of administration of compounds of the present invention. As used herein, the term "subject" refers to a GSK3 producing organism, such as, for example, a cell, cell culture, tissue culture, or a mammal, and the like, or alternatively, a test sample of GSK3 and a protein substrate of GSK3.

The term "effective amount" refers to the amount of invention compound sufficient to detectably inhibit GSK3 activity: (1) by any of the assays described herein or by any other GSK3 kinase activity assays known to those having ordinary skill in the art; or (2) by detecting an alleviation of symptoms in a subject afflicted with a GSK3-mediated disorder.

As used herein, the term "GSK3-mediated disorder" refers to any biological or medical disorder in which GSK3 activity is implicated. The condition or disorder may be caused by abnormal GSK3 activity or may be characterized by abnormal GSK3 activity. As used herein, the term "normal" refers to the GSK3 activity in a subject that has no such disorder, based on a clinical diagnosis. Thus, the term "GSK3-mediated disorder" refers herein to diseases such as, for example, non-insulin dependent diabetes mellitus (NIDDM), Alzheimer's disease, manic depression (i.e., bipolar disorder), and the like.

In accordance with a still further embodiment of the present invention, there is provided a method for treating a GSK3-mediated disorder, said method comprising:

(i) providing a therapeutically effective amount of GSK3 inhibitor compound, wherein said inhibitor has the structure (I) or (II); then (ii) administering said therapeutically effective amount of said GSK3 inhibitor compound to a subject afflicted with a GSK3-mediated disorder.

The term "treating" and its grammatical variations refer herein to the inducement of a reduction or alleviation of symptoms in a subject afflicted with a medical or biological disorder to, for example, halt the further progression of the disorder, or the prevention of the disorder. Thus, for example, treatment of NIDDM can result in abduction in serum glucose levels in the patient. Likewise, treatment of Alzheimer's disease can result in a reduction in rate of disease progression, detected, for example, by measuring a reduction in the rate of increase of dementia. The term "therapeutically effective amount" refers herein to an amount of GSK3 inhibitor sufficient to treat a GSK3-mediated disorder or to induce a detectable therapeutic or preventative effect.

The precise therapeutically effective amount for a subject will depend upon the subject's size and health, the nature and extent of the condition, and the specific GSK3-inhibitor (s) selected for administration, the mode and route of administration, the kind(s) of concurrent treatment, the effect desired, and the like, and will be less than a toxic dose. Thus, it is not useful to specify an exact effective amount in advance. However, the therapeutically effective amount for a given situation can be readily determined by routine experimentation and is within the skill and judgement of the ordinary clinician.

For purposes of the present invention, a therapeutically effective dose will be from about 20 mg/kg/day to about 2 mg/kg/day or from about 500 mg/kg/day to about 1.5 g/kg/day, optionally from about 100 mg/kg/day to about 1 g/kg/day or from about 125 mg/kg/day to about 500 mg/kg/day, or from about 150 mg/kg/day to about 300 mg/kg/day of GSK3 inhibitor of the present invention.

Compounds of the present invention can be administered in a variety of ways including both enteral and parenteral routes of administration. For example, suitable modes of administration include, for example, oral, subcutaneous, transdermal, transmucosal, iontophoretic, intravenous, transnasal, rectal, and the like.

The invention will now be described in greater detail by reference to the following non-limiting examples.

EXAMPLE 1

Characterization and Purification Methods

Compounds of the present invention were characterized by high performance liquid chromatography (HPLC) using a Waters Millenium chromatography system with a 2690

Separation Module (Milford, Mass.). The analytical columns were Alltima C-18 reversed phase, 4.6×250 mm from Alltech (Deerfield, Ill.). A gradient elution was used, typically starting with 5% acetonitrile/95% water and progressing to 100% acetonitrile over a period of 40 minutes. All solvents contained 0.1% trifluoroacetic acid (TFA). Compounds were detected by ultraviolet light (UV) absorption at either 220 or 254 nm. HPLC solvents were from Burdick and Jackson (Muskegan, Mich.), or Fisher Scientific (Pittsburg, Pa.). In some instances, purity was assessed by thin layer chromatography (TLC) using glass or plastic backed silica gel plates, such as, for example, Baker-Flex Silica Gel 1B2-F flexible sheets. TLC results were readily detected visually under ultraviolet light, or by employing well known iodine vapor and other various staining techniques.

Mass spectrometric analysis was performed on a Fisons VG Electrospray Mass Spectrometer. All masses are reported as those of the protonated parent ions.

Nuclear magnetic resonance (NMR) analysis was performed with a Varian 300 Mhz NMR (Palo Alto, Calif.). The spectral reference was either TMS or the known chemical shift of the solvent. Some compound samples were run at elevated temperatures (i.e. 75° C.) to promote increased sample solubility.

The purity of some of the invention compounds was assessed by elemental analysis (Desert Analytics, Tuscon, Ariz.)

Melting points were determined on a Laboratory Devices Mel-Temp apparatus (Holliston, Mass.).

Preparative separations were carried out using either a Flash 40 chromatography system and KP-Sil, 60A (Biotage, Charlottesville, Va.), a Chromatotron radial chromatography device (Harrison Research, Palo Alto, Calif.), or by HPLC using a C-18 reversed phase column. Typical solvents employed were dichloromethane, methanol, ethyl acetate and triethyl amine.

EXAMPLE 2

Solid Phase Synthesis of Pyrimidine Compounds (Resin Method A)

This reaction scheme is illustrated in FIG. 2.

Step A: Knoevenagel Condensation

A suspension of benzaldehyde-bound resin (1 g, 0.52 mmol) in 8 mls of 1:1 alcohol:dioxane was treated with 2.2 mole β-ketoester and 1.3 mmol an amine, e.g., piperidine. The reaction mixture was shaken for 20 hours at room temperature and the resin was then filtered and washed with 4×10 mls dichloromethane (DCM).

Step B: Cyclization and Oxidation to the Pyrimidine Nucleus

The product from Step A (100 mg, 0.052 mmol), shown as compound 2 in FIG. 2, was combined with 0.26 mmol of the pyrazole carboxamidine hydrochloride and 0.13 mmol NaHCO$_3$ in 1 ml N-methylpyrrolidinone. The reaction mixture was shaken at 70° C. for 24 hours. Following cooling, the reaction was washed successively with water, methanol, DMF, methylene chloride and ether, then dried. Cleavage of a small amount of resin indicated that the desired dihydropyrimidine, compound 3 in FIG. 2, was present in high yield.

The dried resin was then taken up in THF and 1.1 eq of dicyanodicloroquinone (DDQ) was added. The resulting slurry was stirred for 0.5 hours at which time the resin was washed with DMF, 10% Na$_2$HCO$_3$, H$_2$O, dimethylformamide (DMF), methanol (MeOH), methylene chloride and ether, then dried. Cleavage of a small amount of this resin with trifluoroacetic acid/methylene chloride indicated the presence of a pyrimidine in high yield, shown as compound 4 in FIG. 2.

Step C: Amine Displacement and Release from the Solid Support

A suspension of the pyrimidine shown as compound 4 in FIG. 2 (50 mg, 0.026 mmol) in 0.75 ml NMP was treated with 1 mmol of an amine and 0.26 mmol acetic acid. The reaction mixture was shaken at 80° C. for 24–48 hours. Following cooling, the resin was washed 4× each with methanol, DMF, and methylene chloride. The resin was then dried and a solution of 5% trifluoroacetic acid in methylene chloride was added. The resin was shaken for 2 hours, then filtered and washed 3× with methylene chloride. The combined filtrates were concentrated, taken up in 1:1 water/acetonitrile and lyophilized to dryness.

The following compounds of the present invention were prepared according to Resin Method A using the ketoester and amine identified in parentheses:

Ethyl 4-(4-carbamoylphenyl)-6-ethyl-2-({2-[(5-nitro(2-pyridyl))amino]ethyl}amino)pyrimidine-5-carboxylate (from ethyl 3-oxo-valerate and 2-(2-aminoethylamino)-5-nitropyridine (dehydration of this compound using trifluoroacetic anhydride yielded ethyl 4-(4-cyanophenyl)-6-ethyl-2-({2-[(5-nitro(2-pyridyl)amino]ethyl}amino)pyrimidine-5-carboxylate)

Ethyl 4-(4-carbamoylphenyl)-2-({2-[5-nitro(2-pyridyl))amino]ethyl}amino)-6-(4-pyridyl)pyrimidine-5-carboxylate (from ethyl 3-(4-pyridyl)-3-oxopropionate and 2-(2-aminoethylamino)-5-nitropyridine)

Ethyl 4-(4-carbamoylphenyl)-2-({2-[(5-nitro(2-pyridyl))amino]ethyl}amino)-6-(4-nitrophenyl)pyrimidine-5-carboxylate (from ethyl 3-(4-nitrophenyl)-3-oxoproprionate and 2-(2-aminoethylamino)-5-nitropyridine)

EXAMPLE 3

Solid Phase Synthesis of Pyrimidine Compounds (Resin Method B)

Step 1

Sasrin resin (Bachem Biosciences, 5.0 g, nominal substitution 1.02 mmol/g) was shaken with triphenylphosphine dibromide (2.3 g) in dry dichloromethane (60–70 ml) for 4 hours at room temperature. All solvents and glassware used to carry out this reaction were dry. The resin was washed well with dichloromethane.

Step 2

The resin from Step 1 was then reacted with a primary amine (0.5–1 M) in 1-methylpyrrolidone (NMP) at 70–80° C. for 3–5 hours to produce an aminomethyl resin, which was used immediately after preparation. The resin was then thoroughly washed with dimethylsulfoxide (DMSO) (or DMF) and dichloromethane, then dried in vacuo at room temperature.

Step 3

After drying, the resin was coupled overnight with 4-acetylbenzoic acid using benzotriazole-1-yl-oxy-tris-pyrollidino-phosphonium hexafluorophosphate (PyBop®, which is available from Novabiochem, San Diego, Calif.), 4-methylmorpholine and NMP in accordance with the method described in Example 10 (i.e., "Resin Method C")) (except that cleavage of the product from the resin was carried out under more strongly acidic conditions, i.e., typically 20–100% trifluoroacetic acid (TFA) in DCM (e.g., 60% TFA in DCM)).

Other types of resin having a pendant CH$_2$OH group can also be used in carrying out this method such as, for example, Wang resin (Novabiochem, San Diego, Calif.). It is also possible to load the primary amine onto a solid support by other methods such as, for example, reductive amination of a solid support containing an aldehyde.

Examples 4–9 describe the synthesis of compounds of the present invention pursuant to Resin Method B.

EXAMPLE 4

Synthesis of N-{(3-bromophenyl)methyl}{4-[2-({3-[(5-nitro(2-pyridyl)amino]propyl}amino)pyrimidin-4-yl]phenyl}carboxamide Step 1

A solution of 2-chloro-5-nitropyridiue (3.16 g, 20 mmol) in dry acetonitrile (40 ml) was added dropwise to a solution of 1,3-diaminopropane (5.0 ml) in acetonitrile (20 ml) at room temperature. After 7.5 hour, a yellow solid precipitated in the reaction mixture. The solvent was removed in vacuo and the residue was partitioned between 2.5 M aqueous sodium hydroxide and dichloromethane. The layers were separated and the aqueous portion was extracted 3× with dichloromethane. The combined organic layers were back-extracted with a saturated sodium chloride solution, then dried and concentrated in vacuo using a Buchi rotary evaporator Model R-124 to give (3-aminopropyl)(5-nitro(2-pyridyl))amine as a yellow solid (2.55 g). The amine (1.14 g, 6 mmol) was shaken with benzotriazole carboxamidinium 4-methylbenzenesulfonate (2.0 g, 6 mmol) and diisopropylethyl amine (DIEA) (1.05 ml, 6 mmol) in acetonitrile (10 ml) at room temperature over two days. Dilution with ether gave the amino-{3-[(5-nitro(2-pyridyl))amino]propyl}carboxamidinium 4-methylbenzenesulfonate as a solid.

Step 2

Sasrin resin (10 g) was shaken with triphenylphosphine dibromide (4.5 g) in dry dichloromethane (ca. 80 ml) at room temperature for 4 hours. The resin was washed well with dichloromethane and air-dried briefly. The air-dried resin was divided into 6 equal portions. One portion was heated at 70° C. for 4 hours with a solution of 3-bromobenzylamine (8 mmol) in NMP (12 ml). The resin was washed well with DMF and dichloromethane and dried overnight in vacuo at room temperature. The dried resin was then shaken with a solution of PyBop® (3.12 g, 6 mmol), 4-acetylbenzoic acid (1.0 g, 6 mmol), and 4-methylmorpholine (12 mmol) in NMP (12 ml) at room temperature overnight The resin was washed with DMF, DMSO and dichloromethane and briefly air-dried. The resin was then heated with N,N-dimethylformamide dimethylacetal (10 ml) at 95° C. for 9 hours. After cooling, the resin was washed with dichloromethane and dried in vacuo at room temperature. The resin (80 mg) was then reacted with 100 mg of the guanidine prepared in Step 1 plus cesium carbonate (160 mg) with NMP (2 ml) at 95° C. overnight, followed by cleavage with 60% TFA in dichloromethane to give N-{(3-bromophenyl)methyl}{(4-[2-({3-[(5-nitro(2-pyridyl)amino)propyl}amino)pyrimidin-4-yl]phenyl}carboxamide.

HPLC: 25.31 min (98% pure); MS: MH$^+$=562/564 (1 Br); $C_{26}H_{24}N_7BrO_3$=561/563 g/mol.

EXAMPLE 5

Synthesis of N-{(3-bromophenyl)methyl}{4-[2-({2-[(5-cyano(2-pyridyl)amino]ethyl}amino)pyrimidin-4-yl]phenyl}carboxamide Step 1

6-Chloronicotinitrile (2.0 g) was treated with ethylenediamine (5 ml). The mixture was then heated at 50° C. for 22 hours. Excess ethylenediamine was removed by rotary evaporation. The residue was partitioned between 2.5 M aqueous sodium hydroxide and dichloromethane. The aqueous layer was extracted 4× more with dichloromethane. The combined organic layers were washed with a saturated sodium chloride solution, dried and then concentrated in vacuo to give 6-[(2-aminoethyl)amino]pyridine-3-carbonitrile as an amber liquid which solidified upon standing. The amine (0.97 g, 6 mmol) was shaken overnight with benzotriazole carboxamidinium 4-methylbenzenesulfonate (2.0 g, 6 mmol) and DIEA (1.05 ml, 6 mmol) in acetonitrile (10 ml). Addition of ether gave amino{2-[(5-cyano(2-pyridyl)amino]ethyl}carboxamidinium 4-methylbenzenesulfonate as a white solid.

Step 2

The guanidine from Step 1 (120 mg) was reacted with the resin prepared as in Example 4, Step 2 (80 mg) in the presence of cesium carbonate (160 mg) in NMP (2 ml) at 90° C. overnight. Treatment of the resin with 60% TFA in dichloromethane gave the title compound.

HPLC: 23.70 min (98% purity)

MS: MH$^+$=528/530 (1 Br) $C_{26}H_{22}N_7BrO$=527/529 g/mole

EXAMPLE 6

Synthesis of N-[(3-methoxyphenyl)methyl]{4-[2-({2-[5-nitro(2-pyridyl)amino]ethyl}amino)pyrimidin-4-yl]phenyl}carboxamide Step 1

2-(2-aminoethylamino)-5-nitropyridine (Aldrich Chemical Co., Milwaukee, Wis.) (1.08 g, 6 mol) was shaken with benzotriazole carboxamidinium 4-methylbenzenesulfonate (2.0 gm, 6 mmol) and DIEA (1.05 ml, 6 mmol) in a mixture of acetonitrile (10 ml) and DMF (3 ml) at room temperature overnight. Addition of ether gave amino[2-[(5-nitro(2-pyridyl)amino]ethyl}carboxamidinium 4-methylbenzenesulfonate as light orange crystals.

Step 2

The Sasrin resin was prepared as described in Step 2 of Example 3. The resin (500 mg) was heated with a solution of 3-methoxybenzylamine (600 μl) in NMP (6 ml) at 70° C. for 4 hours. The resin was then washed with DMF and dichloromethane and then shaken with a solution of PyBop® (1.04 g, 2 mmol), 4-acetylbenzoic acid (0.33 g, 2 mmol), 4-methylmorpholine (4 mmol) in NMP (6 ml) at room temperature overnight. A small aliquot of the resin was treated with 20% TFA In dichloromethane to give the intermediate, (4-acetylphenyl)-N-[(3-methoxyphenyl) methyl]carboxamide (HPLC: 23.94 min (97%); MS; MH$^+$=284 (as required)). The resin was then heated at 95° C. for 7 hours in DMFDMA (5 ml).

After heating, the resin was washed with dichloromethane, then dried in vacuo. Dried resin (120 mg) was reacted with 120 mg of the guanidine prepared in Step 1 plus cesium carbonate (160 mg) in NMP (2 ml) overnight at 90° C. Cleavage with 20% TFA in dichloromethane gave the title compound.

HPLC: 22.32 min (85% pure)

MS: MH$^+$=500 $C_{26}H_{25}N_7O_4$=499 g/mole

EXAMPLE 7

Synthesis of 4-(2-{[3-(4-nitroimidazolyl)propyl]amino}pyrimidin-4-yl)phenol

Step 1

4-Nitroimidazole (5.0 g, 44 mol) in DMF:THF (1:1 (v/v), 40 ml) was treated at room temperature with 60% NaH (2.2 g). When hydrogen evolution had ceased, 3-bromopropylphthalimide (11.79 g, 44 mmol) was added, followed by heating at 70° C. overnight. The mixture was cooled, diluted with dichloromethane and carefully quenched with water. At this point the solid product precipitated out to give 2-[3-(4-nitroimidazolyl)propyl] isoindoline-1,3-dione as a white solid, 8.85 g. The solid was refluxed with methanol (60 ml) and anhydrous hydrazine (4 ml) overnight. The mixture was cooled to 4° C., then filtered. The filtrate was concentrated to dryness, then partitioned between dichloromethane and 2.5 M aqueous sodium hydroxide. The organic layer was washed with saturated sodium chloride solution, dried and concentrated in vacuo to give 3-(4-nitroimidazolyl)propylamine as an orange syrup, 2.24 g. The amine, 1.18 g was treated with benzotriazole carboxamidinium 4-methylbenzenesulfonate (2.2 g) and DIEA (1.5 ml) in acetonitrile (8 ml) with shaking at room temperature overnight. Addition of ether gave amino[3-(4-nitroimidazolyl)propyl]carboxamidinium 4-methylbenzenesulfonate as a beige solid.

Step 2

The Sasrin resin (prepared according to Example 3, Step 2) (2.5 g) was heated at 80° C. with 4-hydroxyacetophenone (700 mg) and cesium carbonate (600 mg) in NMP (10 ml) for 24 hours. The resin was then washed with DMF, water, DMF and dichloromethane and dried in vacuo. The dried resin was then heated overnight with DMFDMA (10 ml) at 105° C. The resin was cooled, filtered and washed well with dichloromethane and dried in vacuo. The dried resin (100 mg) was then treated with 100 mg of the guanidine prepared in Step 1,200 mg of cesium carbonate and 3 ml of NMP at 105° C. for 66 h. The resin was washed with DMSO, acetic acid, water, DMSO and dichloromethane, then shaken with 100% TFA for 1 h, and filtered. The filtrate was concentrated in vacuo and lyophilized to give the title compound.

HPLC: 16.85 min (75% purity)
MS: MH$^+$=341 C$_{16}$H$_{16}$N$_6$O$_3$=340 g/mol

EXAMPLE 8

Synthesis of 4-[2-({2-[(5-nitro(2-pyridyl))amino] ethyl}amino)-5-phenylpyrimidin-4-yl]phenol Bromomethyl sasrin resin (prepared according to Example 3, Step 2), 0.9 g, was heated with benzyl 4-hydroxyphenyl ketone (1.06 g, 5 mmol) and cesium carbonate (1.6 g) in NMP (8 ml) at 80° C. overnight. The resin was washed serially with DMF, water, DMF and dichloromethane and dried in vacuo. The dried resin was heated with DMFDMA (8 ml) at 100° C. overnight. After cooling the resin was filtered and washed well with dichloromethane, then dried in vacuo. The resin (75 mg) was then reacted with 100 mg of amino{2-[(5-nitro(2-pyridyl)) amino]ethyl}carboxamidinium 4-methylbenzenesulfonate and 200 mg of cesium carbonate in NMP (2 ml) at 104° C. for 64 hours. The resin was then washed with DMSO, acetic acid, water, DMSO and dichloromethane. The resin was shaken with 100% TFA at room temperature (1 h). The resin was filtered and the filtrate concentrated in vacuo, then lyophilized to give the title compound.

HPLC: 22.53 min (95% purity)
MS: MH$^+$=429 C$_{23}$H$_{20}$N$_6$O$_3$=428 g/mol

EXAMPLE 9

Synthesis of [(3-Bromophenyl)methyl]({4-[2-({2-[(5-nitro (2-pyridyl))amino]ethyl}amino)pyrimidine-4-yl] phenyl}sulfonyl)amine Step 1

Sasrin resin (500 mg) substituted with m-bromobenzrylamine (according to Step 1 of Example 3) was treated with 4-acetylbenzenesulfonyl chloride (1.1 g, 5 mmol) and DIEA 1.22 ml, 7 mmol) in dichloromethane (10 ml) with shaking at room temperature for 0.5 hours. Then 4-dimethylaminopyridine (122 mg, 1 mmol) was added, followed by shaking overnight at room temperature. The resin was washed well with DMF and dichloromethane, then heated with DMFDMA (10 mL) at 95° C. overnight. The resin was washed well with dichloromethane and dried in vacuo at room temperature.

Step 2

The resin prepared in Step 1 (70 mg) was treated with amino[2-[(5-nitro(2-pyridyl)amino]ethyl}carboxamidinium 4-methylbenzenesulfonate (100 mg) and cesium carbonate (160 mg) in NMP 2 ml) at 95° C. overnight. The resin was serially washed with DMSO, acetic acid, water, DMSO, dichloromethane and then treated with 60% TFA in dichloromethane at room temperature for 0.5 hours. The resin was filtered off and the filtrate was concentrated in vacuo and lyophilized to give the title compound.

HPLC: 26.62 min (100% purity)
MS: MH$^+$=584/586 C$_{24}$H$_{22}$N$_7$BrO$_4$S=583/585 g/mol (1 Br)

The following additional compounds were similarly synthesized according to Resin Method B by varying the guanidine used:

4-(2-{[2-(4-nitrophenyl)ethyl]amino}pyrimidin-4-yl) benzamide
4-{2-[(2-(2-pyridyl)ethyl)amino]pyrimidin4-yl}benzamide
4-{2-[(4-pyridylmethyl)amino]pyrimidin-4-yl}benzamide
4-[2-({2-[(5-nitro-2-pyridyl)amino]ethyl}amino)pyrimidin-4-yl]benzamide
4-(2-{[2-(pyrimidin-2-ylamino)ethyl]amino}pyrimidin-4-yl)benzamide
4-{2-[(3-imidazol-5-ylethyl)amino]pyrimidin-4-yl}benzamide
4-(2-{[2-(benzothiazol-2-ylamino)ethyl]amino}pyrimidin-4-yl)benzamide
4-{2-[(2-{[5-(trifluoromethyl)-2-pyridyl]amino}ethyl) amino]pyrimidin-4-yl}benzamide
4-[2-({2-[(5cyano-2-pyridyl)amino]ethyl}amino) pyrimidin-4-yl]benzamide
4-{2-[(2-{[5-aminothioxomethyl)-2-pyridyl]amino}ethyl) amino]pyrimidin-4-yl}benzamide
4-(2-{[(3-bromophenyl)methyl]amino}pyrimidin-4-yl) benzamide
4-[2-({[4-(4-fluorophenyl)phenyl]methyl}amino) pyrimidin-4-yl]benzamide
4-{2-[4-benzylpiperazinyl]pyrimidin-4-yl}benzamide
4-(2-{[(5-methylpyrazin-2-yl)methyl]amino}pyrimidin-4-yl)benzamide
4-{2-[(3-imidazolylpropyl)amino]pyrimidin-4-yl}benzamide
4-{2-[(2,2-diphenylethyl)amino]pyrimidin-4-yl}benzamide
4-[2-({[3-(trifluoromethyl)phenyl]methyl}amino) pyrimidin-4-yl]benzamide
4-(2-{[(3-nitrophenyl)methyl]amino}pyrimidin-4-yl) benzamide
4-{2-[(naphthylmethyl)amino]pyrimidin-4-yl}benzamide
4(2-{[(4-bromophenyl)methyl]amino}pyrimidin-4-yl) benzamide
4-(2-{[(3,5dichlorophenyl)methyl]amino}pyrimidin-4-yl) benzamide
4-(2-{[(3-methoxyphenyl)methyl]amino}pyrimidin-4-yl) benzamide
4-[2-({[3-(3-methoxyphenyl)phenyl]methyl}amino) pyrimidin-4-yl]benzamide
4-[2-({[3-(3-aminophenyl)phenyl]methyl}amino) pyrimidin-4-yl]benzamide
4-{2-[({3-[3-(acetylamino)phenyl]phenyl}methyl)amino] pyrimidin-4-yl}benzamide
4-[2-({[4-(3-aminophenyl)phenyl]methyl}amino) pyrimidin-4-yl]benzamide 4-(2-{[(3-chlorophenyl)methyl]amino}pyrimidin-4-yl)benzamide
4-(2-{[(2,4dichlorophenyl)methyl]amino}pyrimidin-4-yl)benzamide
4-(2-{[(3-methylphenyl)methyl]amino}pyrimidin-4-yl)benzamide
4-(2-{[(3,4-dimethoxyphenyl)methyl]amino}pyrimidin-4-yl)benzamide
4-[2-({[4-(trifluoromethyl)phenyl]methyl}amino)pyrimidin-4-yl]benzamide
4-(2-{[(4-methoxyphenyl)methyl]amino}pyrimidin-4-yl)benzamide
4-(2-{[(4-aminophenyl)methyl]amino}pyrimidin-4-yl)benzamide
4-[2-({[3,5-bis(trifluoromethyl)phenyl]methyl}amino)pyrimidin-4-yl]benzamide
4-{2-[4-(2-methoxyphenyl)piperazinyl]pyrimidin-4-yl}benzamide
4-{2-[({3-[3-trifluoromethyl)phenyl]phenyl}methyl)amino]pyrimidin-4-yl}benzamide
4-(2-{[2-(3-methoxyphenyl)ethyl]amino}pyrimidin-4-yl)benzamide
4-(2-{[2-(4-fluorophenyl)ethyl]amino}pyrimidin-4yl)benzamide
4-(2-{[(3,4,5-trimethoxyphenyl)methyl]amino}pyrimidin-4-yl)benzamide
{4-[2-({2-[(4-amino-5-cyanopyrimidin-2-yl)amino]ethyl}amino)pyrimidin-4-yl]phenyl}-N-[(3-bromophenyl)methyl]carboxamide
4-[2-({2-[(4-amino-5-cyanopyrimidin-2-yl)amino]ethyl}amino)pyrimidin-4-yl]benzamide
4-[2-({3-[(5-nitro-2-pyridyl)amino]propyl}amino)pyrimidin-4-yl]benzamide
4-(2-{[(4-cyanophenyl)methyl]amino}pyrimidin-4-yl)benzamide
4-{2-[(2-phenylpropyl)amino]pyrimidin-4-yl}benzamide
4-{2-[(2-phenoxyethyl)amino]pyrimidin-4-yl}benzamide
4-(2-{[2-(2,5-dimethoxyphenyl)ethyl]amino}pyrimidin-4-yl)benzamide
4-(2-{[(2,6dimethoxyphenyl)methyl]amino}pyrimidin-4-yl)benzamide
4-(2-{[2-(2-methoxyphenyl)ethyl]amino}pyrimidin-4-yl)benzamide
4-{2-[(4-phenylbutyl)amino]pyrimidin-4-yl}benzamide
4-{2-[(2-(2H-benzo[3,4-d]1,3-dioxolen-5-yl)ethyl)amino]pyrimidin-4-yl}benzamide
4-(2-{[2-(3-chlorophenyl)ethyl]amino}pyrimidin-4-yl)benzamide
4-(2-{[2-(2,3 dimethoxyphenyl)ethyl]amino}pyrimidin-4-yl)benzamide
4-{2-[(3-phenoxypropyl)amino]pyrimidin-4-yl}benzamide
4-(2-{[3-(4-chlorophenoxy)propyl]amino}pyrimidin-4-yl)benzamide
4-(2-{[3-(4-methoxyphenoxy)propyl]amino}pyrimidin-4-yl)benzamide
4-(2-{[3-(3-methoxyphenoxy)propyl]amino}pyrimidin-4-yl)benzamide
4-(2-{[3-(3-bromophenoxy)propyl]amino}pyrimidin-4-yl)benzamide
4-(2-{[3-(2,4dichlorophenoxy)propyl]amino}pyrimidin-4-yl)benzamide
4-[2-({3-[3-(trifluoromethyl)phenoxy]propyl}amino)pyrimidin-4-yl]benzamide
4-(2-{[3-(3-methylphenoxy)propyl]amino}pyrimidin-4-yl)benzamide
4-(2-{[3-(4-phenylimidazolyl)propyl]amino}pyrimidin-4-yl)benzamide
4-(2-{[3-(5,6dichlorobenzimidazolyl)propyl]amino}pyrimidin-4-yl)benzamide
4-(2-{[3-(3,4-dichlorophenoxy)propyl]amino}pyrimidin-4-yl)benzamide
4-(2-{[3-(5,6dimethylbenzimidazolyl)propyl]amino}pyrimidin-4-yl)benzamide
4-{2-[(3-(6-quinolyloxy)propyl)amino]pyrimidin-4-yl}benzamide
4-{2-[(3-naphthyloxypropyl)amino]pyrimidin-4-yl}benzamide
4-(2-{[3-(3-phenylphenoxy)propyl]amino}pyrimidin-4-yl)benzamide
4-(2-{[3-(4-nitroimidazolyl)propyl]amino}pyrimidin-4yl)benzamide
4-(2-{[3-(4,5dichloroimidazolyl)propyl]amino}pyrimidin-4-yl)benzamide
4-{2-[(3-benzimidazolylpropyl)amino]pyrimidin-4-yl}-2-chlorophenol
4-[2-({3-[4-(2,4-dichlorophenyl)imidazolyl]propyl}amino)pyrimidin-4yl]benzamide
4-[2-({3-[4-(3-methoxyphenyl)imidazolyl]propyl}amino)pyrimidin-4-yl]benzamide

EXAMPLE 10

Solid Phase Synthesis of Pyridine Compounds (Resin Method C)

Rink amide resin (Novabiochem, San Diego, Calif., nominally 0.46 mmol/g substitution) was deprotected with 20% v/v piperidine in DMF (ca. 60 ml, 0.5 hours, room temperature). The resin was washed thoroughly with DMF and dichloromethane, then treated with 4-acetylbenzoic acid (8 mmol), PyBOP® (8 mmol, Novabiochem), 4-methylmorpholine (12 mmol) and NMP (50 ml) for 8.5 hours at room temperature on a wrist shaker. The resin was washed with DMF and dichloromethane, air dried, and then divided into 3 portions. Each portion was treated with N,N-dimethylformamide dimethyl acetal (ca. 12 ml) with heating at 105° C. overnight (ca. 13 hours). The reactions were allowed to cool and the resin was washed with dichloromethane, then dried in vacuo at room temperature.

For the synthesis of pyrimidines, typically 100 mg of the above dried resin was mixed with 200–300 mg of anhydrous cesium carbonate, 80–200 mg (most usually 100 mg) of the appropriate guanidine as its tosylate salt and 2–3 ml of NMP. This mixture was heated at 90–105° C. for at least 12 hours. In many cases the reactions were allowed to proceed for about 65 hours at this temperature. The resin was cooled, filtered and washed with DMSO, glacial acetic acid, water, DMSO and finally dichloromethane. The product was removed by treatment of the resin with 95:5 V/V dichloromethane/TFA for 0.5–1 hours at room temperature. The resin was then filtered, washed with dichloromethane and the filtrates were concentrated on a rotary evaporator. An aliquot was withdrawn for HPLC analysis and the rest of the sample was lyophilized twice from a 1:1 acetonitrile:water solvent mixture, which usually gave the pyrimidine as a fluffy solid.

Examples 11–16 describe the synthesis of compounds of the present invention pursuant to Resin Method C.

EXAMPLE 11

Synthesis of 4-(2-{[2-(2-pyridylamino)ethyl]amino}pyrimidin-4-yl)benzamide 2-(2-Aminoethylamino)pyridine (prepared from 2-chloropyrimidine and ethylenediamine in accordance with the method described in T. Mega et al., 1988, *Bull. Chem. Soc. Japan* 61:4315, which is incorporated herein by reference) (6 mmol) was treated wit benzotriazole carboxamidinium 4-methylbenzenesulfonatesulfonate (2.0 g, 6 mmol) and DIEA (1.05 ml, 6 mmol) in anhydrous acetonitrile (10 ml) for 65 hours. Ether (ca. 10 ml) was then added to this mixture. After 8 hours the white solid amino[2-(2-pyridylamino)ethyl]carboxamidinium 4-methylbenzenesulfonate was filtered off and dried in vacuo. The resulting guanidine (200 mg) was reacted with 100 mg of resin (21 hours, 90° C.) according to the method described in Example 10 (Resin method C), to give the title compound.

HPLC: 11.20 min (97% pure)
MS: MH$^+$=335 C$_{18}$H$_{18}$N$_6$O=334 g/mol

EXAMPLE 12

Synthesis of 4-(2-{[2-(2-quinolylamino)ethyl]amino}pyrimidin-4-yl)benzamide

2-Chloroquinoline (7.0 g) was heated at 120° C. under argon with ethylenediamine (50 ml) for 6 hours. The excess ethylenediamine was removed by rotary evaporation (oil pump). The residue was taken up in 2.5 M aqueous sodium hydroxide and extracted 6 times with dichloromethane. The combined organic layers were washed with a small portion of saturated aqueous NaCl, dried over Na$_2$SO$_4$ and concentrated in vacuo. A portion of the viscous product, 0.55 g (3 mmol) was treated with benzotriazole carboxamidinium 4-methylbenzenesulfonate (1.0 g, 3 mmol), DIEA (0.78 mL 4.5 mmol) and acetonitrile (8 ml) with shaking at room temperature overnight. Precipitation with ether gave amino [2-(2-quinolylamino)ethyl]carboxamidinium 4-methylbenzenesulfonate. The resulting guanidine (200 mg) was reacted (21 hours, 90° C.) with 100 mg of resin according to the method described in Example 10 (i.e., Resin method C) to give the title compound.

HPLC: 12.04 min (95% pure)
MS: MH$^+$=385 C$_{22}$H$_{20}$N$_6$O=384 g/mol

EXAMPLE 13

Synthesis of 4-[2-({2-[6-methoxy-2-pyridyl)amino]ethyl}amino)pyrimidin-4-yl]benzamide 2-Chloro-6-methoxypyridine (5.0 g) was heated with ethylenediamine (30 ml) at 120° C. overnight. The excess ethylenediamine was removed by rotary evaporation. The residue was dissolved in a small volume of 2.5 M aqueous sodium hydroxide and extracted thoroughly with dichloromethane. The combined organic layers were washed with saturated aqueous sodium chloride, dried over sodium sulfate and concentrated in vacuo to give (2-aminoethyl)(6-methoxy(2-pyridyl)amine as an orange syrup. The amine (2.58 g) was treated with benzotriazole carboxamidinium 4-methylbenzenesulfonate (0.86 g) and 4DIEA (0.45 mmol) in acetonitrile (6 ml) and stirred overnight at room temperature. Trituration with ether gave the guanidine, amino-{2-[(6-methoxy(2-pyridyl))amino]ethyl} carboxamidinium 4-methylbenzenesulfonate as an oil. The oily guanidine (200 mg) was reacted with 100 mg of resin according to Resin Method C (90° C., overnight) to give the title compound.

HPLC: 11.84 min (85% purity)
MS: MH$^+$=365 C$_{19}$H$_{20}$N$_6$O$_2$=364 g/mol

EXAMPLE 14

Synthesis of 4-{2-[(3-Benzimidazolylpropyl)amino]pyrimidin-4-yl}benzamide

Benzimidazole (2.4 g, 20 mmol) in dry THF (40 ml) was treated at room temperature with 60% NaH in oil (0.96 g). After hydrogen evolution ceased, 3-bromopropylphthalimide (5.36 g, 20 mmol) was added and the mixture heated at 80° C. overnight. The reaction was cooled, diluted with dichloromethane and water and then extracted twice with 5% aqueous potassium carbonate solution. The organic layer was dried over sodium sulfate and concentrated in vacuo to give a beige solid, 4.1 g. The solid was dissolved in methanol (60 ml) and treated with anhydrous hydrazine (4.0 ml), followed by refluxing for 4 hours. The mixture was then cooled to 4° C. for several hours, then filtered. The filtrate was concentrated in vacuo. The residue was partitioned between dichloromethane and 2.5 M aqueous sodium hydroxide. The organic layer was washed with saturated sodium chloride solution, dried over sodium sulfate and concentrated in vacuo to give 3-benzimidazolylpropyl amine as a pale pink oil, 1.1 g. This amine (1.03 g, 6 mmol) was reacted with benzotriazole carboxamidinium 4-methylbenzenesulfonate (2.0 g, 6 mmol) and DIEA (1.39 ml) in acetonitrile (8 ml) overnight at room temperature to give amino(3-benzimidazolylpropyl) carboxamidinium 4-methylbenzenesulfonate which was obtained as a beige solid after repeated trituration with ether. The guanidine (100 mg) was reacted ) (65 hours, 105° C.) with 100 mg of resin in accordance with the method described in Example 10 (i.e., Resin Method C) to give the title compound.

HPLC: 12.12 min (95% purity)
MS: MH$^+$=373 C$_{21}$H$_{20}$N$_6$O=372 g/mol

EXAMPLE 15

Synthesis of 4-{2-[(3-(2-naphthyloxy)propyl)amino]pyrimidin-4-yl)benzamide

2-Naphthol (2.9 g, 20 mmol) in dry THF (40 ml) was treated with 60% NaH suspension (0.96 g) at room temperature. After hydrogen evolution ceased, 3-bromopropylphthalimide (5.36 g, 20 mmol) was added and the mixture was heated at 80° C. overnight. The reaction was cooled, diluted with ethyl acetate and water. The layers were separated and the aqueous layer extracted 3 times with ethyl acetate. The combined organic layers were then extracted 5 times with 5% aqueous potassium carbonate, dried over sodium sulfate and concentrated in vacuo. The crude product (observed as a single spot by TLC) was taken up in methanol (60 ml), treated with anhydrous hydrazine (4 ml) and refluxed for 3.5 hours. The mixture was cooled to 4° C. for several hours, then filtered. The filtrate was concentrated to dryness, then partitioned between dichloromethane and 2.5 M aqueous sodium hydroxide. The organic layer was washed with saturated sodium chloride solution, dried and concentrated in vacuo to give 3-(2-naphthyloxy)propyl amine as a beige solid, 1.14 g. The amine (1.14 g, 5.7 mmol) was treated with benzotriazole carboxamidinium 4-methylbenzenesulfonate (1.89.g, 5.7 mmol) and DIEA (1.39 ml) in a mixture of acetonitrile (8 ml) and DMF (2 ml) with shaking at room temperature overnight. Precipitation with ether gave amino(3-(2-naphthyloxy)propyl) carboxamidinium 4-methylbenzenesulfonate as a white crystalline solid. This guanidine (100 mg) was reacted (65 hours, 105° C.) with resin (100 mg) in accordance with the method described in Example 10 (i.e., Resin Method C) to give the title compound.

HPLC: 22.52 min (95% purity)
MS: MH$^+$=399 C$_{24}$H$_{22}$N$_4$O$_2$=398 g/mol

EXAMPLE 16

Synthesis of N-(1-carbamoyl-2-phenylethyl)(4-{2-{(2-(2-pyridyl)ethyl)amino]pyrimidin-4-yl}phenyl)carboxamide This Example provides a variation of Resin Method C in which the pyrimidine is linked to an α-amino acid residue.

Step 1

Rink amide resin (1.5 g) was deprotected with 20% piperidine in DMF (1×0.5 hours). The resin was washed well with DMF and thin treated with FMOC (L)-phenylalanine (5.0 mmol), 1-hydroxybenzotriazole (5.0 mmol) and diisopropylcarbodiimide (5.0 mmol) in DMF (10 ml) with shaking at room temperature for 2 hours. The resin was washed with DMF and then treated with 20% piperidine in DMF (1×30 min). The resin was washed well with DMF and then treated with PyBOP® (5 mmol), 4-methylmorpholine (8 mmol) and 4-acetylbenzoic acid (5 mmol) in NMP (10 ml). After 5 hours at room temperature, a negative ninhydrin test indicated completion of the reaction. The resin was washed with DMF and dichloromethane, air dried and then heated with DMFDMA at 110° C. overnight. The resin was then washed well with dichloromethane and dried in vacuo at room temperature.

Step 2

The resin prepared in Step 1 (150 mg) was treated with amino(2-(2-pyridyl)ethyl)carboxamidinium 4-methylbenzenesulfonate (200 mg) and cesium carbonate (160 mg) in NMP (2 ml) at 85° C. overnight. The resin was washed with DMF and dichloromethane and then treated with 5% TFA in dichloromethane. The resin was filtered off and the filtrate concentrated and lyophilized to give the title compound.

HPLC: 15.08 min (95% purity)

MS: MH$^+$=467 $C_{27}H_{26}N_6O_2$=466 g/mol

The following additional compounds were analogously synthesized according to Resin Method C by varying the guanidine used:

N-benzyl(4-{2-[(2-(2-pyridyl)ethyl)amino]pyrimidin-4-yl}phenyl)carboxamide benzyl{[4-(2-{[2-(2-pyridylamino)ethyl]amino}pyrimidin-4-yl)phenyl]sulfonyl}amine {4-[2({2-[(5-nitro(2-pyridyl))amino]ethyl}amino) pyrimidin-4-yl]phenyl}-N-benzylcarboxamide {4-[2-({2-[(6-amino-5-nitro(2-pyridyl))amino] ethyl}amino)pyrimidin-4-yl]phenyl}-N-benzylcarboxamide N-[(4-fluorophenyl)methyl]{4-[2-({2-[(5-nitro(2-pyridyl)) amino]ethyl}amino)pyrimidine-4-yl] phenyl}carboxamide N-[(3-bromophenyl)methyl]{4-[2-({2-[(5-nitro(2-pyridyl)) amino]ethyl}amino)pyrimidin-4-yl]phenyl}carboxamide N-(2-methoxyethyl){4-[2-({2-[(5-nitro(2-pyridyl))amino] ethyl}amino)pyrimidin-4-yl]phenyl}carboxamide N-(naphthylmethyl){4-[2-({2-[(5-nitro(2-pyridyl))amino] ethyl}amino)pyrimidin-4-yl]phenyl}carboxamide {4-[2-({2-[(5-nitro(2-pyridyl))amino]ethyl}amino) pyrimidin-4-yl]phenyl}-N-{[3-(trifluoromethyl)phenyl] methyl}carboxamide {4-[2-({2-[(5-nitro(2-pyridyl))amino]ethyl}amino) pyrimidin-4-yl]phenyl}-N-(2-phenylethyl)carboxamide N-[(4-methoxyphenyl)methyl]{4-[2-({2-[(5-nitro(2-pyridyl))amino]ethyl}amino)pyrimidin-4-yl] phenyl}carboxamide N-[(3-methoxyphenyl)methyl]{4-[2-({2-[(5-nitro (2pyridyl))amino]ethyl}amino)pyrimidin-4-yl] phenyl}carboxamide {4-[2-({2-[(5-nitro(2-pyridyl))amino]ethyl}amino) pyrimidin-4-yl]phenyl}-N-(oxolan-2-ylmethyl) carboxamide N-[(5-methylpyrazin-2-yl)methyl]{4-[2-({2-[(5-nitro(2-pyridyl))amino]ethyl}amino)pyrimidin-4-yl] phenyl}carboxamide N-(2,2-diphenylethyl){4-[2-({2-[(5-nitro(2-pyridyl))amino] ethyl}amino)pyrimidin-4-yl]phenyl}carboxamide {4-[2-({2-[(5-nitro(2-pyridyl))amino]ethyl}amino) pyrimidin-4-yl]phenyl}-N-(4-piperidylmethyl) carboxamide N-[2-(2,4-dichlorophenyl)ethyl]{4-[2-({2-[(5-nitro(2-pyridyl))amino]ethyl}amino)pyrimidin-4-yl] phenyl}carboxamide {4-[2-({2-[(5-nitro(2-pyridyl))amino]ethyl}amino) pyrimidin-4-yl]phenyl}-N-(3-pyridylmethyl) carboxamide N-(3-imidazolylpropyl){4-[2-({2-[(5-nitro(2-pyridyl)) amino]ethyl}amino)pyrimidin-4-yl]phenyl}carboxamide {4-[2-({2-[(5-nitro(2-pyridyl))amino]ethyl}amino) pyrimidin-4-yl]phenyl}-N-2-thienylmethyl)carboxamide {4-[2-({2-[(5-nitro(2-pyridyl)amino]ethyl}amino) pyrimidin-4-yl]phenyl}-N-[(3-nitrophenyl)methyl] carboxamide N-[(3-methylphenyl)methyl]{4-[2-({2-[(5-nitro(2-pyridyl)) amino]ethyl}amino)pyrimidin-4-yl]phenyl}carboxamide {4-[2-({2-[(5-nitro(2-pyridyl))amino]ethyl}amino) pyrimidin-4-yl]phenyl}-N-[(4-sulfamoylphenyl)methyl] carboxamide {4-[2-({2-[(6-amino-5-nitro(2-pyridyl))amino] ethyl}amino)pyrimidin-4-yl]phenyl}-N-[(3-bromophenyl)methyl]carboxamide N-[(3,5-dichlorophenyl)methyl]{4-[2-({2-[(5-nitro(2-pyridyl))amino]ethyl}amino)pyrimidin-4-yl] phenyl}carboxamide N-[(3,4-difluorophenyl)methyl]{4-[2-({2-[(5-nitro(2-pyridyl))amino]ethyl}amino)pyrimidin-4-yl] phenyl}carboxamide N-[(4-bromophenyl)methyl]{4-[2-({2-[(5-nitro(2-pyridyl)) amino]ethyl}amino)pyrimidin-4-yl]phenyl}carboxamide N-[(2,3-dimethoxyphenyl)methyl]{4-[2-({2-[(5-nitro(2-pyridyl))amino]ethyl}amino)pyrimidin-4-yl] phenyl}carboxamide N-[(3-fluorophenyl)methyl]{4-[2-({2-[(5-nitro(2-pyridyl)) amino]ethyl}amino)pyrimidin-4-yl]phenyl}carboxamide N-[(3-bromophenyl)methyl]{4-[2-({2-[(6-methoxy(2-pyridyl))amino]ethyl}amino)pyrimidin-4-yl] phenyl}carboxamide

[4-(2-{[(3-bromophenyl)methyl]amino}pyrimidin-4-yl) phenyl]-N-[(3-methylphenyl)methyl]carboxamide N-[(3-bromophenyl)methyl]{4-[2-({2-[(5-cyano(2-pyridyl))amino]ethyl}amino)pyrimidin-4-yl] phenyl}carboxamide 4-(2-{[(3-{3-[(methylamino)methyl]phenyl}phenyl) methyl]amino}pyrimidin-4-yl)benzamide N-[(3-bromophenyl)methyl](4-{2-[(3-imidazolylpropyl) amino]pyrimidin-4-yl}phenyl)carboxamide N-[(3-bromophenyl)methyl][4-(2-{[2-(2-quinolylamino) ethyl]amino}pyrimidin-4-yl)phenyl]carboxamide N-[(3-bromophenyl)methyl]{4-[2-({2-[(4-nitrophenyl) amino]ethyl}amino)pyrimidin-4-yl]phenyl}carboxamide N-[(3-bromophenyl)methyl](4-{2-[(2-{[5-(trifluoromethyl) (2-pyridyl)]amino}ethyl)amino]pyrimidin-4-yl}phenyl) carboxamide N-[(3-bromophenyl)methyl][4-(2-{[2-(pyrimidin-2-ylamino)ethyl]amino}pyrimidin-4-yl)phenyl] carboxamide N-[(3-chlorophenyl)methyl]{4-[2-({2-[(5-nitro(2-pyridyl)) amino]ethyl}amino)pyrimidin-4-yl]phenyl}carboxamide N-[(3,4-dimethoxyphenyl)methyl]{4-[2-({2-[(5-nitro(2-pyridyl))amino]ethyl}amino)pyrimidin-4-yl] phenyl}carboxamide N-[(3,4-dichlorophenyl)methyl]{4-[2-({2-[(5-nitro(2-pyridyl))amino]ethyl}amino)pyrimidin-4-yl] phenyl}carboxamide

[(3-bromophenyl)methyl]({4-[2-({2-[(5-nitro(2-pyridyl)) amino]ethyl}amino)pyrimidin-4-yl]phenyl}sulfonyl) amine N-[(3-iodophenyl)methyl]{4-[2-({2-[(5-nitro(2-pyridyl))amino]ethyl}amino)pyrimidin-4-yl]phenyl}carboxamide
[4-(2-{[2-(2,5-dimethoxyphenyl)ethyl]amino}pyrimidin-4-yl)phenyl]-N-[(3-bromophenyl)methyl]carboxamide
N-[(3-bromophenyl)methyl][4-(2-{[2-(3-methoxyphenyl)ethyl]amino}pyrimidin-4-yl)phenyl]carboxamide
{4-[2-({2-[(5-nitro(2-pyridyl))amino]ethyl}amino)pyrimidin-4-yl]phenyl}-N-(2-phenylcyclopropyl)carboxamide
3-[2-({2-[(5-nitro-2-pyridyl)amino]ethyl}amino)pyrimidin-4-yl]phenol
4-[2-({2-[(5-nitro-2-pyridyl)amino]ethyl}amino)pyrimidin-4-yl]phenol
4-{2-[(3-phenoxypropyl)amino]pyrimidin-4-yl}phenol
4-(2-{[3-(4-chlorophenoxy)propyl]amino}pyrimidin-4-yl)phenol
4-[2-({2-[(5-nitro(2-pyridyl))amino]ethyl}amino)-5-phenylpyrimidin-4-yl]phenol
4-{2-[(3-benzimidazolylpropyl)amino]pyrimidin-4-yl}phenol
4-{2-[(3-benzimidazolylpropyl)amino]pyrimidin-4-yl}-2-methoxyphenol
4-(2-{[3-(4-nitroimidazolyl)propyl]amino}pyrimidin-4-yl)phenol
4-(2-{[3-(2-aminobenzimidazolyl)propyl]amino}pyrimidin-4-yl)phenol
4-(2-{[3-(4,5-dichloroimnidazolyl)propyl]amino}pyrimidin-4-yl)phenol

EXAMPLE 17

Solid Phase Synthesis of Pyrimidine Compounds (Resin Method D)

A primary amine was loaded onto Sasrin resin as in Example 3 (i.e., Resin Method B). This amine resin was then heated with either 2,4-dichloropyrimidine or ethyl 2,4-dichloropyrimidine-5-carboxylate (200 mg of pyrimidine per 200 mg of amine resin) and cesium carbonate (250 mg) in NMP (3 ml) overnight. The resin was washed with the appropriate solvents (typically DMF or DMSO and dichloromethane) and then reacted with a second amine (e.g., a primary or secondary amine). Second amine displacement was typically conducted at a higher temperature in NMP, for example for 48 hours at 120–130° C. The resin was again washed and treated with 100% TFA for 0.5–1 hours to obtain the 2,4-diaminopyrimidine, which was frequently obtained as a solid after lyophilization from a mixture of acetonitrile and water.

Examples 18–19 describe the synthesis of compounds of the present invention pursuant to Resin Method D.

EXAMPLE 18

Synthesis of [(3-chlorophenyl)methyl][2-({2-[(5-nitro(2-pyridyl)amino]ethyl}amino)pyrimidin-4-yl]amine Bromomethyl Sasrin resin prepared as in Step 1 of Example 3, 0.9 g) was heated with 3-chlorobenzylamine (1 ml) in NMP (8 ml) at 80° C. for 1.5 hours, then overnight at room temperature. The resin was washed with DMF and dichloromethane and dried in vacuo. The dried resin (200 mg) was then heated with 2,4-dichloropyrimidine and 250 mg of cesium carbonate in NMP (3 ml) at 80° C. overnight. The resin was washed as before. One half of the resin was heated with 2-(2-aminoethylamino)-5-nitropyridine (180 mg, 1 mmol) in NMP (2 ml) at 125° C. for 66 hours. The resin was washed as before and then treated with 100% TFA for 0.5 hours. The resin was filtered off and the filtrate was concentrated in vacuo, then lyophilized from acetonitrile and water to give the title compound as a yellow solid.

HPLC: 23.46 min (82% purity)
MS: MH$^+$=400 C$_{18}$H$_{18}$ClN$_7$O$_2$=399 g/mol

EXAMPLE 19

Synthesis of Ethyl-4-{[(3-cyanophenyl)methyl]amino}-2-({2-[(5-nitro(2-pyridyl)amino]ethyl}amino)pyrimidine-5-carboxylate Bromomethyl Sasrin resin (prepared as in Step 1 of Example 3, 1.0 g) was reacted with 4-cyanobenzylamine (1.5 ml) in NMP (8 ml) at 80° C. for 4 hours. The resin was washed with DMF and dichloromethane and dried in vacuo at room temperature. The dried resin (400 mg) was then reacted with ethyl 2,4-dichloropyrimidine-5-carboxylate (prepared according to V. H. Smith and B. E. Christensen, *J. Organic Chem.*, 20: 829(1955), which is incorporated herein by reference) (400 mg) and cesium carbonate (400 mg) in NMP (4 ml) at 80° C. overnight. The resin was washed as before and dried. The dried resin (200 mg) was then heated with 2-(2-aminoethylamino)-5-nitropyridine (180 mg, 1 mmol) in NMP (2 ml) at 104° C. for 21 hours. The resin was washed with DMSO, glacial acetic acid, water, DMSO, dichloromethane and then treated with 100% TFA to obtain the title compound.

HPLC: 25.27 m (100% purity)
MS: MH$^+$=463 C$_{22}$H$_{22}$N$_8$O$_4$=462 g/mol

The following additional compounds were prepared according to Resin method D using the appropriate amine:
(4-{[(3-bromophenyl)methyl]amino}pyrimidin-2-yl){2-[(5-nitro(2-pyridyl))amino]ethyl}amine
[(2,4-dichlorophenyl)methyl][2-({2-[(5-nitro(2-pyridyl))amino]ethyl}amino)pyrimidin-4-yl]amine
[(3-methylphenyl)methyl][2-({2-[(5-nitro(2-pyridyl))amino]ethyl}amino)pyrimidin-4-yl]amine
[(3,5-dichlorophenyl)methyl][2-({2-[(5-nitro(2-pyridyl))amino]ethyl}amino)pyrimidin-4-yl]amine
Ethyl 4-{[(3-bromophenyl)methyl]amino}-2-({2-[(5-nitro(2-pyridyl))amino]ethyl}amino)pyrimidine-5-carboxylate
[2-({2-[(5-nitro(2-pyridyl))amino]ethyl}amino)pyrimidin-4-yl]benzylamine
[(4-chlorophenyl)methyl][2-({2-[(5-nitro(2-pyridyl))amino]ethyl}amino)pyrimidin-4-yl]amine
Ethyl 4-{[(2-chlorophenyl)methyl]amino}-2-({2-[(5-nitro(2-pyridyl))amino]ethyl}amino)pyrimidine-5-carboxylate
Ethyl 4-{[(4-cyanophenyl)methyl]amino}-2-({2-[(5-nitro(2-pyridyl))amino]ethyl}amino)pyrimidine-5-carboxylate

EXAMPLE 20

Solid Phase Synthesis of Pyridine Compounds (Resin Method E)

An amino resin (for example Sasrin resin loaded with a primary amine as described in Resin Methods B (Example 3) and D (Example 18)) was reacted with, e.g., 2,6-dichloro-3-nitropyrimidine and cesium carbonate in NMP at temperatures within the range of about 25–50° C. for a period within the range of from about 5 hours to about 24 hours. The resin was then washed with DMF and dichloromethane and heated with a primary amine in NMP at temperatures from 70–100° C. overnight. The resins were washed as described in Example 18, and the pyridine products obtained by treating the resin with 20–100% TFA for 0.5–1 hours (preferably with 80–100% TFA).

Example 21 describes the synthesis of compounds of the present invention pursuant to Resin Method E.

EXAMPLE 21

Synthesis of {2-[(6-amino-5-nitro(2-pyridyl)amino]ethyl}{5-nitro-6-[benzylamino](2-pyridyl)}amine Step 1: 2-Amino-6-chloro-3-nitropyridine (obtained from 2,6-dichloro-3-nitropyridine by the method of V. W. von Bebenberg, *Chemiker-Zeitung,* 103:387 (1979), which is incorporated herein by reference) (2.65 g) was treated at room temperature with ethylenediamine (5 ml). The temperature was gradually raised to 100° C. After 4 h the excess ethylenediamine was removed by rotary evaporation. The residue was partitioned between dichloromethane and 2.5 M aqueous sodium hydroxide. The aqueous layer was further extracted 3 times with dichloromethane. The combined organic layers were concentrated in vacuo to give (2-aminoethyl) (6-amino-5-nitro(2-pyridyl))amine as a canary yellow solid.

Step 2: Bromomethyl Sasrin resin, prepared according to Step 1 of Example 3, was heated with benzylamine (2 ml) in NMP (6 ml) at 70° C. for 4 hours. The resin was washed with DMF and dichloromethane and dried in vacuo. The dried resin (100 mg) was heated with 2,6-dichloro-3-nitropyridine (190 mg, 1 mmol) and cesium carbonate (100 mg) in NMP (2 ml) at 50° C. for 5.5 hours. The resin was then washed with water, DMF and dichloromethane. The resin was air dried and then heated with the amine from Step 1 (90 mg) in NMP (2 ml) at 95° C. overnight. The resin was washed with DMSO, acetic acid, water, DMSO, dichloromethane and then treated with 20% TFA to give the title compound.

HPLC: 28.47 min (87% purity)

NMR: (300 MHz, 7/1 acetonitrile-$d_3$/$D_2O$, 75° C.: 8.0 (2H, two overlapping d), 7.2–7.4 (5H, Ph), 5.9 (2H, 2d overlapping), 4.75 (s, 2H), 3.50–3.65 (m, 4H)

The following additional compounds were similarly prepared according to Resin Method E by varying the pyridine and primary amine:

{2-[(5-nitro(2-pyridyl))amino]ethyl}{5-nitro-6-[benzylamino](2-pyridyl)}amine
6-{[2-({5-nitro-6-[benzylamino]-2-pyridyl}amino)ethyl]amino}pyridine-3-carbonitrile
{6-[(2-methoxyethyl)amino]-5-nitro(2-pyridyl)}{2-[(5-nitro(2-pyridyl))amino]ethyl}amine
(6-{[(2,4-dichlorophenyl)methyl]amino}-5-nitro(2-pyridyl)){2-[(5-nitro(2-pyridyl))amino]ethyl}amine.

EXAMPLE 22

Synthesis of 4-[2-({2-[(5-nitro(2-pyridyl)amino]ethyl}amino)-5-[benzylamino]pyrimidin-4-yl]benzenecarbonitrile (Resin Method F)

Benzylamine was reacted with bromomethyl Sasrin resin to give a benzylamine substituted resin as in Step 1 of Example 3. This resin (150 mg) was shaken with 4-cyanophenacylbromide (130 mg), DMF (2 ml) and 2,6-lutidine (200 µl) at room temperature for 6.5 hours. The resin was washed with DMF and dichloromethane and briefly air dried. It was then heated with DMFDMA (3 ml) at 80° C. overnight. The resin was then washed with DMF and dichloromethane and dried in vacuo. The dried resin was heated with amino{2-[(5-nitro(2-pyridyl))amino]ethyl}carboxamidinium 4-methylbenzenesulfonate (120 mg) and cesium carbonate (160 mg) in NMP (2 ml) at 90° C. overnight. The resin was washed with DMF, water, DMF and dichloromethane and then treated with 95:5 TFA:water to give the title compound.

HPLC: 25.61 min (80% pure)

MS: $MH^+$=467 $C_{25}H_{22}N_8O_2$=466 g/mol

EXAMPLE 23

Solid Phase Synthesis of Pyrimidines ($C_5$= carboxyl)

(Resin Method G)

A mixture of polystyrene Wang resin (Novabiochem, 0.41 mmol/g, 2.2 g, 1.21 mmol), a β-ketoester (commercially avaiable from Aldrich or Lancaster Chemical, 36.3 mmol) and dimethylaminopyridine (DMAP, 12.1 mmol) in toluene (22 ml) was shaken for 16 hours at 90° C. The resin was filtered and washed with DCM, DMF, DCM, then dried.

A mixture of the dried resin (100 mg, 0.055 mmol), an aldehyde (0.55 mmol), piperidine (0.055 mmol), acetic acid (0.055 mmol) and 3A Molecular Sieves (Aldrich) in DMF (1.0 ml) was shaken for 16 hours at room temperature. The resin was filtered and washed with DMF and DCM, then dried.

To a mixture of the resulting resin (100 mg, 0.055 mmol) and $NaHCO_3$ (12 mg, 0.138 mmol) was added 0.4 M of the appropriate guanidine in DMF (1.0 ml, 0.4 mmol). The mixture was then shaken for 16 hours at 70° C. The resin was then filtered and washed with DMF, water, methanol, DMF, DCM, and dried.

This resin was treated with 0.1 M DDQ in THF (1.1 ml, 0.11 mmol) for 3 hours at room temperature. The resin was filtered and washed with DMF, saturated $NaHCO_3$ (aq), water, methanol, DMF, DCM, then dried. The resin was treated with 95% TFA/water for 1 hour at room temperature, then filtered and washed with DCM. The filtrate and washings were combined and evaporated. The residue was dissolved in acetonitrile/water (1:1) then lyophilized.

In all cases, the product pyrimidines were of purity >80% as determined by HPLC; MS and NMR analysis.

The following compounds were prepared according to Resin Method G using amino {2-[(5-nitro(2-pyridyl)amino]ethyl}carboxamidinium 4-toluene sulfonate as the guanidine source and the β-ketoester and aldehyde indicated in parentheses.

6-(2-Fluorophenyl)-2-({2-[5-nitro(2-pyridyl)amino]ethyl}amino)-4-phenylpyrimidine-5-carboxylic acid (ethyl 3-(4-fluorophenyl)-3-oxoproprionate and benzaldehyde)
2-({2-[5-Nitro(2-pyridyl)amino]ethyl}amino)-6-(4-nitrophenyl)-4-phenylpyridine-5-carboxylic acid (ethyl 3-(4-nitrophenyl)-3-oxoproprionate and benzaldehyde)
6-Methyl-2-({2-[(5-nitro(2-pyridyl)amino]ethyl}amino)-4-phenylpyrimidine-5-carboxylic acid(ethyl acetoacetate and benzaldehyde)
4,6-bis(4-Nitrophenyl)-2-({2-[5-nitro(2-pyridyl)amino]ethyl}amino)pyridine-5-carboxylic acid(ethyl 3-(4-nitrophenyl)-3-oxoproprionate and 4-nitrobenzaldehyde)
2-({2-[5-Nitro(2-pyridyl)amino]ethyl}amino)-6-(4-nitrophenyl)-4-(4-pyridyl)pyrimidine-5-carboxylic acid (ethyl 3-(4-nitrophenyl)-3-oxoproprionate and 4-pyridylcarboxaldehyde)
4-(4-Methoxyphenyl)-2-({2-[5-nitro(2-pyridyl)amino]ethyl}amino)-6-(4-nitrophenyl)pyrimidine-5-carboxylic acid(ethyl 3-(4-nitrophenyl)-3-oxoproprionate and 4-methoxybenzaldehyde)
4-(4-Cyanophenyl)-2-({2-[(5-nitro(2-pyridyl)amino]ethyl}amino)-6-(4-nitrophenyl)pyrimidine-5-carboxylic acid(ethyl 3-(4-nitrophenyl)-3-oxoproprionate and 4-cyanobenzaldehyde)
2-({2-[(5-Nitro(2-pyridyl))amino]ethyl}amino)-4-(4-nitrophenyl)pyrimidine-5-carboxylic acid(ethyl 3-(4-nitrophenyl)-3-oxoproprionate and formaldehyde)
4,6-bis(4-Cyanophenyl)-2-({2-[(5-nitro(2-pyridyl)amino]ethyl}amino)pyridine-5-carboxylic acid(ethyl 3-(4- cyanophenyl)-3-oxoproprionate and 4-cyanobenzaldehyde)
4-(4-Cyanophenyl)-2-({2-[(5-nitro(2-pyridyl)amino]ethyl}amino)-6-(3-nitrophenyl)pyrimidine-5-carboxylic acid(ethyl 3-(4-cyanophenyl)-3-oxoproprionate and 3-nitrobenzaldehyde)
4-(4-Cyanophenyl)-2-({2-[(5-nitro(2-pyridyl)amino]ethyl}amino)-6-phenylpyrimidine-5-carboxylic acid (ethyl 3-(4-cyanophenyl)-3-oxproprionate and benzaldehyde)
4-(3-Cyanophenyl)-2-({2-[(5-nitro(2-pyridyl)amino]ethyl}amino)-6-(4-nitrophenyl)pyrimidine-5-carboxylic acid(ethyl 3-(4-nitrophenyl)-3-oxoproprionate and 3-cyanobenzaldehyde)
4-(3-Hydroxyphenyl)-2-({2-(5-nitro(2-pyridyl)amino]ethyl}amino)-6-(4-nitrophenyl)pyrimidine-5-carboxylic acid(ethyl 3-(4-nitrophenyl)-3-oxoproprionate and 3-hydroxybenzaldehyde)
2-({2-[(5-Nitro(2-pyridyl))amino]ethyl}amino)-4-(3-nitrophenyl)-6-(4-nitrophenyl)pyrimidine-5-carboxylic acid(ethyl 3-(4-nitrophenyl)-3-oxoproprionate and 3-nitrobenzaldehyde)
2-({2-[(5-Nitro(2-pyridyl))amino]ethyl}amino)-6-(4-nitrophenyl)-4-(4-quinolyl)pyrimidine-5-carboxylic acid (ethyl 3-(4-nitrophenyl)-3-oxoproprionate and 4-quinolinecarboxaldehyde)
2-({2-[(5-Nitro(2-pyridyl))amino]ethyl}amino)-6-(4-nitrophenyl)-4-[4-(trifluoromethyl)phenyl]pyrimidine-5-carboxylic acid(ethyl 3-(4-nitrophenyl)-3-oxoproprionate and 4-trifluoromethylbenzaldehyde)
4-({4-Carboxyphenyl)-2-({2-[(5-nitro(2-pyridyl))amino]ethyl}amino)-6-(4-nitrophenyl)pyrimidine-5-carboxylic acid(ethyl 3-(4-nitrophenyl)-3-oxoproprionate and 4-carboxybenzaldehyde)
4-Cyclohexyl-2-({2-[(5-nitro(2-pyridyl))amino]ethyl}amino)-6-(4-nitrophenyl)pyrimidine-5-carboxylic acid(ethyl 3-(4-nitrophenyl)-3-oxoproprionate and cyclohexanecarboxaldehyde)
4-(4-Cyanophenyl)-6-(4-fluorophenyl)-2-({2-[(5-nitro(2-pyridyl)amino]ethyl}amino)pyrimidine-5-carboxylic acid(ethyl 3-(4-cyanophenyl)-3-oxoproprionate and 4-fluorophenylbenzaldehyde)
4-(4-Cyanophenyl)-6-(3-furyl)-2-({2-[(5-nitro(2-pyridyl)amino]ethyl}amino)pyrimidine-5-carboxylate(ethyl 3-(4-cyanophenyl)-3-oxoproprionate and 3-furylcarboxaldehyde)

EXAMPLE 24

Solid Phase Synthesis of Pyrimidines ($C_5$=carboxyl, $C_4$ or $C_6$=H)

(Resin Method G)

A suspension of resin (Novabiochem, San Diego, USA, 0.51 mmol/g, 100 mg, 0.055 mmol) in DMF-dimethylacetal (1 ml) was shaken for 17 hour at room temperature. The resin was filtered and washed with DCM and ether, then dried.

To a mixture of the resulting dried resin (100 mg, 0.055 mmol) and $NaHCO_3$ (12 mg, 0.138 mmol) was added 0.4 M solution of the appropriate guanidine in DMF (1.0 ml, 0.4 mmol). The mixture was shaken for 16 hours at 70° C. This resin was then filtered and washed successively with DMF, water, MeOH, DMF, DCM, and then dried. The resin was treated with 95% TFA/water for 1 hour at room temperature, then filtered and washed with DCM. The filtrate and washings were combined and evaporated. The residue was dissolved in acetonitrile:water (1:1 v/v) and lyophilized to give a pyrimidine.

The following compounds were prepared according to the above method using N-(3-nitropyridine-6-yl) aminoethylguanidine and the appropriate β-ketoester and aldehyde:
4-methyl-2-({2-[(5-nitro(2-pyridyl)amino]ethyl}amino) pyrimidine-5-carboxylic acid
2-({2-[(5-nitro(2-pyridyl)amino]ethyl}amino)-4-(4-nitrophenyl)pyrimidine-5-carboxylic acid
4-(4-cyanophenyl)-2-({2-[(5-nitro(2-pyridyl))amino]ethyl}amino)-6-(3-nitrophenyl)pyrimidine-5-carboxylic acid.

EXAMPLE 25

Solution Phase Synthesis
(Solution Method A)

A carbonyl-containing compound (e.g., β-keto esters, β-keto sulfones, β-keto nitriles, α-nitro ketones, and the like) was dissolved in a suitable organic solvent (usually THF) and treated with a slight excess (1.2–2 equivalents) of DMFDMA. The mixture was heated at 60–80° C. for 3–15 hours, most typically 3–5 hours. The reaction mixture was then cooled. When a done on a small scale (0.2–1 mmol) there was no attempt to remove the slight excess of DMFDMA present, rather the cooled mixture was directly added to a mixture of a guanidine (1 equivalent) and an appropriate base (for example, cesium carbonate or 1.2 equivalents of sodium ethoxide in 1 ml of ethanol).

The reaction was then heated at 70–80° C. for 12–24 h. At the conclusion of the reaction the vials were cooled, poured into dichloromethane or ethyl acetate and washed with saturated aqueous sodium bicarbonate solution. The organic layer was concentrated in vacuo and the product was precipitated or crystallized, usually by addition of water to acetonitrile or ethanol solutions of the product. In some cases chromatographic purification was performed, either by semi-preparative HPLC or by radial chromatography using silica gel plates on a Chromatotron (Harrison Research, Palo Alto, Calif.) eluting with mixtures of dichloromethane and methanol. Larger scale reactions were performed in round bottom flasks using typical organic chemistry apparatus.

Examples 31, 35–45, and 50–59 describe the synthesis of compounds of the present invention pursuant to Solution Method A.

EXAMPLE 26

Synthesis of Ethyl 4-(4-cyanophenyl)-2-}[2-(2-quinolylamino)ethyl]amino}pyrimidine-5-carboxylate Ethyl 3-(4-cyanophenyl)3-oxopropanoate (64 mg, 0.3 mmol) was heated with DMFDMA 50 μl) and dry THF (1 ml) at 70° C. for 3 hours. The cooled mixture was then added to a suspension of amino[2-(2-quinolylamino)ethyl] carboxamidinium 4-methylbenzenesulfonate (prepared according to Example 12), (120 mg, 0.3 mmol) in ethanol (2 ml) containing 0.35 mmol of sodium ethoxide. The reaction was then heated at 80° C. overnight and then concentrated in vacuo. The residue was taken up in dichloromethane and washed with saturated aqueous sodium bicarbonate. The organic layer was concentrated in vacuo. The residue was taken up in acetonitrile. Addition of water gave a precipitate which was filtered off and dried to give the title compound.
HPLC: 22.12 min (90% purity)
MS: $MH^+$=439 $C_{25}H_{22}N_6O_2$=438 g/mol

EXAMPLE 27

Synthesis of Ethyl 4-(6-morpholin-4-yl(3-pyridyl))-2-({2-[(5-nitro(2-pyridyl))amino]ethyl}amino)pyrimidine-5-carboxylate Step 1

Ethyl 6-chloronicotinate (5.0 g) and morpholine (10 ml) were mixed and then heated to 100° C. In less than 5 minutes at this temperature, a thick paste formed. Acetonitrile (15 ml) was added and heating was continued overnight at 90° C. The mixture was cooled, diluted with water and extracted with ethyl acetate. The organic layer was dried and concentrated in vacuo to give ethyl 6-morpholin-4-ylpyridine-3-carboxylate as a white solid. NMR (300 MHz, $CDCl_3$: 8.80 (s, 1H), 8.05 (d, 1H), 6.60 (d, 1H), 4.35 (q, 2H), 3.80 (m, 4H), 3.65 (m, 4H), 1.35 (t, 3H).

The solid was refluxed in a mixture of THF and aqueous potassium hydroxide for 2 hours. The THF was removed in vacuo and the aqueous layer was extracted with ethyl acetate. The aqueous layer was then acidified with acetic acid. A white solid precipitated out and was washed with water and dried to give 6-morpholin-4-ylpyridine-3-carboxylic acid. NMR(300 Mhz, $DMSO-d_6$) 8.65 (s, 1H), 7.95 (d, 1H), 6.85 (d, 1H), 3.70 (m, 4H), 3.60 (m, 4H)

Step 2

The acid described in Step 1 was converted to the β-keto ester as follows. The acid (5.6 g., 27 mmol) in dry THF (100 ml) was treated at room temperature with oxalyl chloride (40 mmol) followed by seven drops of DMF. The mixture was then refluxed for 2 hours. The solvent was removed in vacuo to give a yellow solid acid chloride. Potassium ethyl malonate (Aldrich Chemical Co., 9.2 g, 54 mmol) and anhydrous magnesium chloride (6.48 g) were mixed in dry acetonitrile (100 ml). Then triethylamine (6 ml) was added and the mixture stirred at room temperature for 4 hours. An additional 3 ml of triethylamine was added, followed by addition of the acid chloride dissolved in 50 ml of dry acetonitrile. The mixture stirred overnight at room temperature, then the solvent was removed in vacuo. The residue was treated with toluene (ca. 200 ml) and then sufficient 25% aqueous HCl was added to dissolve the residue entirely. The mixture was shaken and organic and aqueous layers separated. The toluene layer was washed with water. The combined aqueous layers were then washed twice with toluene. The organic layers were discarded. The pH of the aqueous layer was adjusted to pH 7 by addition of solid sodium carbonate. The aqueous layer was then extracted with toluene. Concentration of the toluene layer in vacuo gave ethyl 3-(6-morpholin-4-yl)(3-pyridyl)-3-oxopropanoate as a yellow solid.

Step 3

The β-keto ester from Step 2 (83 mg, 0.3 mmol) was heated with DMFDMA (50 μl) and dry THF (1 ml) at 70° C. for 3 hours. The cooled mixture was then added to a suspension of amino[2-[(5-nitro(2-pyridyl)amino]ethyl}carboxamidinium 4-methylbenzenesulfonate (120 mg, 0.3 mmol) in ethanol (2 ml) containing 0.35 mmol of sodium ethoxide. The reaction was then heated at 80° C. overnight and then concentrated in vacuo. The residue was dissolved in dichloromethane, then washed with saturated aqueous sodium bicarbonate. This organic layer was then concentrated in vacuo, then redissolved in acetonitrile. Addition of water gave a precipitate which was filtered off and dried to give the title compound.

HPLC: 18.77 min (98%)

MS: $MH^+$=495 $C_{23}H_{26}N_8O_5$=494 g/mol

EXAMPLE 28

Synthesis of Ethyl 2-({2-[(6-amino-5-nitro(2-pyridyl))amino]ethyl}amino)-4-(4-cyanophenyl)pyrimidine-5-carboxylate To a solution of ethyl 3-(4-cyanophenyl)-3-oxopropionate (63 mg, 0.3 mmol) in THF (1 ml) was added DMFDMA (50 μl). The solution was heated at 70° C. for 3 hours and then added to a mixture of amino[2-[(5-nitro(2-pyridyl)amino]ethyl}carboxamidinium 4-methylbenzenesulfonate (123 mg, 0.3 mmol), ethanol (1 ml) and 1.0 M sodium ethoxide (0.35 ml). This mixture was heated at 80° C. overnight. The reaction was cooled, diluted with dichloromethane and washed with aqueous sodium bicarbonate. The organic layer was concentrated in vacuo, the dissolved in acetonitrile. The product was precipitated with water to give the title compound.

HPLC: 25.21 min

MS: $MH^+$=449 $C_{21}H_{20}N_8O_4$=448 g/mol

NMR (DMSO-d6): 1.02 (t, 3H), 3.60 (m, 4H), 4.10 (q, 2H), 5.95 (d, 1H), 7.60 (d, 2H), 7.85 (d, 2H), 7.90 (d, 1H), 8.80 (s, 1H)

EXAMPLE 29

Synthesis of ethyl 2-({2-[(6-amino-5-nitro(2-pyridyl))amino]ethyl}amino)-4-(4-morpholin-4-ylphenyl)pyrimidin-5-carboxylate To a solution of ethyl 3-(4-morpholinophenyl)3-oxopropanoate (70 mg, 0.3 mmol) in THF (1 ml) was added DMFDMA (60 μl). The solution was heated at 70° C. for 3 hours, then added to a mixture of amino[2-(6-amino-5-nitro(2-pyridyl)amino]ethyl}carboxamidinium 4-methylbenzenesulfonate (123 mg, 0.3 mmol), ethanol (1 ml) and 1.0 M sodium ethoxide (0.35 ml). The mixture was heated at 80° C. overnight, then cooled, diluted with dichloromethane and washed with saturated aqueous sodium bicarbonate solution. The organic layer was concentrated in vacuo, dissolved in acetonitrile and the product precipitated with water to give the title compound.

HPLC: 22.37 min. (85% purity)

MS: $MH^+$=509 $C_{24}H_{28}N_8O_5$=508 g/mol

NMR ($DMSO-d_6$): 1.05 (t, 3H), 3.3 (m, 4H), 3.60 (m, 4H), 3.78 (m, 4H), 4.15 (q, 2H), 5.95 (d, 1H), 6.90 (d, 2H), 7.45 (d, 2H), 7.95 9d, 1H), 8.60 (s, 1H)

EXAMPLE 30

Synthesis of Ethyl 2-({2-[(6-amino-5-nitro(2-pyridyl)amino]ethyl}amino)-4-(2,4-dichlorophenyl)pyrimidine-5-carboxylate To a solution of ethyl 3-(2,4-dichlorophenyl)-3-oxopropionate (78 mg, 0.3 mmol) in THF (2 ml) was added DMFDMA (70 μl). The solution was heated 3 hours at 70° C., then cooled and added to a suspension of amino[2-(6-amino-5-nitro(2-pyridyl)amino]ethyl}carboxamidinium 4-methylbenzenesulfonate (123 mg, 0.3 mmol), dry ethanol, (1 ml) and 1.0 M sodium ethoxide (0.35 ml). This mixture was heated at 80° C. overnight. The mixture was cooled, diluted with dichloromethane and then extracted with saturated aqueous sodium bicarbonate. The organic layer was concentrated in vacuo and the residual oil was dissolved in acetonitrile. Addition of water gave the title compound as a yellow solid.

EXAMPLE 31

Synthesis of Ethyl 4-(4-cyanophenyl)-2-({2-[(5-nitro(2-pyridyl))amino]ethyl}amino)pyrimidine-5-carboxylate To a solution of ethyl 3-(4-cyanophenyl)-3-oxopropionate (65 mg, 0.3 mmol) in THF (1 ml) was added DMFDMA (50 μl). The solution was heated at 70° C. for 3 hours. The solution was then added to a mixture of amino[2-[(5-nitro(2-pyridyl)amino]ethyl}carboxamidinium 4-methylbenzenesulfonate (120 mg, 0.3 mmol), dry ethanol (1 ml) and 1.0 M sodium ethoxide (0.35 ml). The mixture was heated at 80° C. overnight. The mixture was cooled, diluted with dichloromethane and washed with saturated aqueous sodium bicarbonate. The organic layer was concentrated in vacuo, then dissolved in acetonitrile. The solid product was precipitated by addition of water to give the title compound.

HPLC: 28.05 min. (95% pure)

EXAMPLE 32
Synthesis of 2-((2-((5-nitro(2-pyridyl)amino)ethyl)amino)-4-(4-cyanophenyl)-pyrimidine-5-carboxylate To a suspension of 1.0 g (2.3 mmol) of ethyl 4-(4-cyanophenyl)-2-({2-[(5-nitro(2-pyridyl)amino]ethyl}amino)pyrimidine-5-carboxylate (prepared as described in Example 31) in 1:1 methanol/water was added 1.5 mmol of sodium hydroxide and the solution warmed to 60° C. for 45 minutes. During this time the reaction became homogenous. After cooling the mixture, the pH was adjusted to about 5.0 at which time the desired acid precipitated from solution. This solid was collected and dried to give 890 mg (2.2 mmol, 98% yield) of 2-((2-((5-nitro(2-pyridyl)amino)ethyl)amino)-4-cyanophenyl)-pyrimidine-5-carboxylate as a light yellow powder.

EXAMPLE 33
Synthesis of 2-(dimethylamino)ethyl 4-(4-cyanophenyl)-2-({2-[(5-nitro(2-pyridyl)amino]ethyl}amino)pyrimidine-5-carboxylate 2-((2-((5-nitro(2-pyridyl)amino)ethyl)amino)-4-(4-cyanophenyl)-pyrimidine-5-carboxylate (300 mg, 0.74 mmol) (prepared as described in Example 32) was suspended in 5 ml of 2-(dimethylamino)ethanol at room temperature. O-Benzotriazole-N,N,N',N'-tetramethyluronium-hexafluoro-phosphate (HBTU) (Advance Chem Tech, Louisville, Ky.) was then added in one portion and the mixture stirred for 18 hours at room temperature. The resulting clear solution was poured onto an ice water mixture and extracted thoroughly with ethyl acetate. The aqueous layer was back extracted with ethyl acetate 2x. The combined organic layers were then dried with sodium sulfate and concentrated in vacuo. HPLC and NMR analysis indicated that the desired compound, 2-(dimethylamino)ethyl 2-((2-((5-nitro(2-pyridyl)amino)ethyl)amino)-4-(4-cyanophenyl)pyrimidine-5-carboxylate, was formed in quantitative yield (>95%).

By substituting an alcohol or amine for the 2-(dimethylamino)ethanol indicated above, the following additional compounds of the present invention were similarly synthesized (the alcohol or amine employed is indicated in parentheses):

tert-Butyl 4-(4-cyanophenyl)-2-({2-[(5-nitro(2-pyridyl))amino]ethyl}amino)pyrimidine-5-carboxylate (tert-butyl alcohol)

Methyl 4-(4-cyanophenyl)-2-({2-[((5-nitro(2-pyridyl))amino]ethyl}amino)pyrimidine-5-carboxylate (methanol)

Butyl 4-(4-cyanophenyl)-2-({2-[(5-nitro(2-pyridyl))amino]ethyl}amino)pyrimidine-5-carboxylate (n-butanol)

Phenylmethyl 4-(4cyanophenyl)-2-({2-[(5-nitro(2-pyridyl))amino]ethyl}amino)pyrimidine-5-carboxylate (benzyl alcohol)

N-Butyl[4-(4-cyanophenyl)-2-({2-[(5-nitro(2-pyridyl)amino]ethyl}amino)pyrimidin-5-yl]carboxamide (n-butylamine)

[4-(4-Cyanophenyl)-2-({2-[(5-nitro(2-pyridyl))amino]ethyl}amino)pyrimidin-5-yl]-N-benzylcarboxamide (benzylamine)

[4-(4-Cyanophenyl)-2-({2-[(5-nitro(2-pyridyl))amino]ethyl}amino)pyrimidin-5-yl]-N,N-dimethylcarboxamide (dimethylamine)

N-(Cyanomethyl)[4-(4-cyanophenyl)-2-({2-[(5-nitro(2-pyridyl)amino]ethyl}amino)pyrimidin-5-yl]carboxamide (aminoacetonitrile)

N-(tert-Butyl)[4-(4-cyanophenyl)-2-({2-[(5-nitro(2-pyridyl)amino]ethyl}amino)pyrimidin-5-yl]carboxamide (t-butylamine)

N-[2-(Dimethylamino)ethyl][4-(4-cyanophenyl)-2-({2-[(5-nitro(2-pyridyl)amino]ethyl}amino)pyrimidin-5-yl]carboxamide 38564 (2-(dimethylamino)ethyl amine)

[4-(4-Cyanophenyl)-2-({2-[(5-nitro(2-pyridyl))amino]ethyl}amino)pyrimidin-5-yl]-N-(2-hydroxyethyl)carboxamide (2-aminoethanol)

4-[5-(Morpholin-4-ylcarbonyl)-2-({2-[(5-nitro(2-pyridyl))amino]ethyl}amino)pyrimidin-4-yl]benzenecarbonitrile (morpholine)

[4-(4-Cyanophenyl)-2-({2-[(5-nitro(2-pyridyl))amino]ethyl}amino)pyrimidin-5-yl]-N-methylcarboxamide (methylamine)

N-(2-Aminoethyl)[4-(4-cyanophenyl)-2-({2-[(5-nitro(2-pyridyl)amino]ethyl}amino)pyrimidin-5-yl]carboxamide (ethylenediamine)

4-[2-({2-[(5-nitro(2-pyridyl))amino]ethyl}amino)-5-(piperazinylcarbonyl)pyrimidin-4-yl]benzenecarbonitrile (piperazine)

4-(4-Cyanophenyl)-2-({2-[5-nitro(2-pyridyl)amino]ethyl}amino)pyrimidine-5-carboxamide (ammonia)

N-(Carbamoylmethyl)[4-(4-cyanophenyl)-2-({2-[(5-nitro(2-pyridyl))amino]ethyl}amino)pyrimidin-5-yl]carboxamide (glycinamide)

[4-(4-cyanophenyl)-2-({2-[(5-nitro(2-pyridyl))amino]ethyl}amino)pyrimidin-5-yl]-N-(4-pyridylmethyl)carboxamide ((4-pyridyl)methylamine)

2-Hydroxyethyl 4-(4-cyanophenyl)-2-({2-[(5-nitro(2-pyridyl))amino]ethyl}amino)pyrimidine-5-carboxylate (ethylene glycol)

N-(1-Carbamoyl-2-hydroxyethyl)[4-(4-cyanophenyl)-2-({2-[(5-nitro(2-pyridyl))amino]ethyl}amino)pyrimidin-5-yl]carboxamide (serinamide)

EXAMPLE 34
Synthesis of 4-[5-(3-methyl(1,2,4-oxadiazol-5-yl))-2-({2-[(5-nitro(2-pyridyl)amino]ethyl}amino)pyrimidin-4-yl]benzenecarbonitrile To a mixture of ethyl 4-(4-cyanophenyl)-2-({2-[(5-nitro(2-pyridyl))amino]ethyl}amino)pyrimidine-5-carboxylate (0.069 mmol, prepared as described in Example 31) and triethylamine (19.3 μl, 0.14 mmol) in THF (1 ml) was added isobutyl chloroformate (13.4 μl, 0.14 mmol). After stirring at room temperature overnight, the appropriate amidoximine (0.14 mmol) prepared according to C. D. Bedfore et al., *J. Med. Chem.* 20:2174–2183 (1986), which is incorporated herein by reference) was added and the mixture stirred at 70° C. for 6 hours. After stirring an additional 72 hours at room temperature, the reaction was filtered, the solid washed successively with methanol and water, and dried under vacuum to give the desired oxadiazole, 4-[5-(3-methyl(1,2, 4-oxadiazol-5-yl))-2-({2-[(5-nitro(2-pyridyl))amino]ethyl}amino)pyrimidin-4-yl]benzenecarbonitrile. The following additional compounds were prepared according to this method by using the appropriate amidoximine:

4-[5-{3-[2-(dimethylamino)ethyl](1,2,4-oxadiazol-5-yl)-2-({2-[(5-nitro(2-pyridyl))amino]ethyl}amino)pyrimidin-4-yl)

(2-{5-[2-({2-[(6-amino-5-nitro(2-pyridyl)amino]ethyl}amino)-4-(2,4-dichlorophenyl)pyrimidin-5-yl](1,2, 4-oxadiazol-3-yl)}ethyl)dimethylamine

EXAMPLE 35
Synthesis of Ethyl 4-(4-morpholin-4-ylphenyl)-2-({2-[(5-nitro(2-pyridyl))amino]ethyl}amino)pyrimidine-5-carboxylate To a solution of ethyl 3-(4-morpholinophenyl)3-oxopropionate (193 mg, 0.7 mmol) in THF (1 ml) was added DMFDMA(140 μl). The solution was heated at 70° C. for 3 hours. This solution was added to a mixture of amino[2-[(5-nitro(2-pyridyl)amino]ethyl}carboxamidinium 4-methylbenzenesulfonate (280 mg, 0.7 mmol), ethanol (1 ml) and 1.0 M sodium ethoxide (0.82 ml). The mixture was heated at 80° C. overnight. The cooled mixture was diluted with dichloromethane and extracted with saturated aqueous sodium bicarbonate. The organic layer was concentrated in vacuo, then dissolved in acetonitrile. The product was precipitated as an orange solid (126 mg) by addition of water to give the title compound.

HPLC 25.25 min (95% purity)

NMR (DMSO-d6): 1.15 (t, 3H), 3.20 (m, 4H), 3.60 (br, s, 4H), 3.78 (m, 4H), 4.05 (q, 2H), 6.59 (d, 1H), 6.95 (d, 2H), 7.40 (d, 2H), 8.0 (m, 1H), 8.60 (s, 1H), 8.90 (d, 1H)

MS: MH$^+$=494 $C_{24}H_{27}N_7O_5$=493 g/mol

EXAMPLE 36

Synthesis of Ethyl 4-((4-imidazolylphenyl)-2-({2-[(5-nitro(2-pyridyl))amino]ethyl}amino)pyrimidine-5-carboxylate To a solution of ethyl 3-[4-(imidazol-1-yl)phenyl]3-oxopropanoate (78 mg, 0.3 mmol) (prepared according to I. Sircar et al., *J. Med. Chem.*, 28:1405 (1985), which is incorporated herein by reference) in THF (1 ml) was added DMFDMA (50 μl). The solution was heated at 70° C. for 3 hours. The solution was then added to a mixture of amino [2-[(5-nitro(2-pyridyl)amino]ethyl}carboxamidinium 4-methylbenzenesulfonate (120 mg, 0.3 mmol), ethanol (1 ml) and 1.0 M sodium ethoxide (0.35 ml). The mixture was heated at 80° C. overnight, cooled, diluted with dichloromethane and washed with saturated aqueous sodium bicarbonate solution. The organic layer was concentrated in vacuo, redissolved in acetonitrile and then the product was precipitated by addition of water as a yellow solid to give the title compound.

HPLC: 18.50 min. (95% purity)

MS: MH$^+$=475 $C_{23}H_{22}N_8O_4$ =474 g/mol

NMR(DMSO-d6): 1.05 (t, 3H), 3.62 (br, s, 4H), 4.10 (q, 2H), 6.58 (d, 1H), 7.15 (s, 1H), 7.60 (d, 2H), 7.70 (d, 2H), 7.75 (s, 1H), 7.85 (br, s, 1H), 7.9–8.1 (m, 2H), 8.25 (s, 1H), 8.75 (s, 1H), 8.90 (s, 1H)

EXAMPLE 37

Synthesis of Ethyl 2-({2-[(5-nitro-(2-pyridyl))amino] ethyl}amino)-4-(4-(1,3-oxazol-5-yl)phenyl)pyrimidine-5-carboxylate Step 1

Methyl 4-formylbenzoate (Aldrich Chemical Co., St Louis, Mo.) (5.0 g, 30.5 mmol), anhydrous potassium carbonate (4.55 g, 33 mmol) and p-toluenesulfonylmethyl isocyanide (TOSMIC, Aldrich Chemical Co.) (6.83 g, 30.5 mmol) were refluxed in methanol (100 ml) for 3.5 hours. The mixture was then concentrated to dryness in vacuo. The residue was dissolved in ethyl acetate, washed twice with water, dried and concentrated in vacuo to give methyl 4-(1,3-oxazol-5-yl)benzoate as a beige solid (4.95 g). (NMR (300 MHz, CDCl$_3$: 8.10 (d, 2H), 7.98 (s, 1H), 7.75 (d, 2H), 7.48 (s, 1H), 3.94 (s, 3H)).

The above ester was heated at reflux for 2 hours in a mixture of 1 M aqueous potassium hydroxide and 50 ml THF. The THF was removed in vacuo and the solution cooled, then acidified with 50% HCl to give 4-(1,3-oxazol-5-yl)benzoic acid as a white solid. NMR (300 MHz, DMSO-d6; 8.52 (s, 1H), 8.05 (d, 2H), 7.82–7.9, m, 3H).

The dried acid above was refluxed in neat thionyl chloride until all the solid had dissolved. The thionyl chloride was removed by rotary evaporation (with hexane). The crude acid chloride was then dried in vacuo briefly. Meanwhile, potassium ethyl malonate (11.1 g, 65 mmol) and anhydrous magnesium chloride (7.7 g, 81 mmol) in dry acetonitrile (150 ml) were treated with triethylamine (5.15 ml, 37 mmol). The mixture was stirred for 3 hours at room temperature, then an additional 1 ml of triethylamine was added, followed by a solution of the acid chloride prepared above in dry acetonitrile (50 ml). The reaction was stirred overnight at room temperature. The mixture was concentrated to dryness in vacuo and then partitioned between toluene and 0.25 M aqueous HCl. The organic layer was washed with water, dried and concentrated to give crude ethyl 3-(4-(1,3-oxazol-5-yl)phenyl)-3-oxopropanoate. The crude product was purified by silica gel chromatography (hexanes/ethyl acetate).

Step 2

To a solution of ethyl 3-(4-(1,3-oxazol-5-yl)phenyl)-3-oxopropanoate (76 mg, 0.3 mmol) in THF (1 ml) was added DMFDMA (60 μl). The solution was heated at 70° C. for 3 hours. This solution was added to a mixture of amino[2-[(5-nitro(2-pyridyl)amino]ethyl}carboxamidinium 4-methylbenzenesulfonate (120 mg, 0.3 mmol), ethanol (1 ml) and 1.0 M sodium ethoxide (035 ml). The mixture was heated at 80° C. overnight, cooled, diluted with dichloromethane and washed with saturated sodium bicarbonate solution. The organic layer was concentrated in vacuo, redissolved in acetonitrile and the product precipitated with water to give the title compound as an orange solid.

HPLC: 26.75 min. (90% purity)

NMR (DMSO-d$_6$): 1.05 (t, 3H), 3.65 (br. s, 4H), 4.10 (q, 2H), 6.58 (d, 1H), 7.58 (d, 2H), 7.70 (s, 1H), 7.75 (d, 2H), 7.82 (br. s, 1H), 7.95–8.10 (m, 2H), 8.40 (s, 1H), 8.75 (s, 1H), 8.85 (s, 1H)

EXAMPLE 38

Synthesis of Ethyl 4-(4-(2-furyl)phenyl)-2-({2-[(5-nitro(2-pyridyl))amino]ethyl}amino)pyrimidine-5-carboxylate Step 1

Ethyl 4-iodobenzoate (2.76 g, 10 mmol) and 2-furylboronic acid (Frontier Scientific, 1.12 g, 10 mmol)) were mixed with bis (triphenylphosphine)palladium dichloride (100 mg) in 1,2-dimethoxyethane (20 ml) and 2 M aqueous sodium carbonate (20 ml). The mixture was bubbled with argon gas, then heated at 80° C. under argon overnight. The mixture was cooled, diluted with ethyl acetate, then washed with water. The organic layer was dried and concentrated in vacuo to give a crude solid ester. This material was taken up in a mixture of THF and 1 M aqueous potassium hydroxide and refluxed for 2.5 hours. The THF was removed by rotary evaporation and the aqueous layer acidified with acetic acid. Cooling to 4° C. resulted in the precipitation of 4-(2-furyl)benzoic acid as a brown solid (1.49 g) (NMR (300 MHz, DMSO-d6: 8.10 (d, 2H), 7.90 (m, 3H), 7.24 (d, 1H), 6.75 (dd, 1H)).

Step 2

The acid from Step 1 was converted to the acid chloride by refluxing in a mixture of oxalyl chloride (1.3 ml), THF (20 ml) and several drops of DMF. Small portions of oxalyl chloride were added until the reaction was homogeneous. Reflux continued for 0.5 hours, then the solvent was removed in vacuo to give the crude acid chloride. Meanwhile, potassium ethyl malonate (2.7 g) was reacted with anhydrous magnesium chloride (1.9 g) and triethylamine (2.21 ml) in dry acetonitrile (50 ml) at room temperature for 3 hours. Triethylamine (1 ml) was added, followed by addition of a solution of the acid chloride in acetonitrile. The mixture was then stirred overnight at room temperature, then concentrated to dryness. The residue was partitioned between toluene and 10% aqueous HCl. The organic layer was washed with 10% HCl and water, dried and was then concentrated to give crude ethyl 3-(4-(2-furyl) phenyl)-3-oxopropanoate as a solid.

Step 3

The β-keto ester prepared in Step 2 (76 mg, 0.3 mmol) was dissolved in dry THF (2 ml) and heated with DMFDMA (60 μl) at 70° C. for 4 hours. This solution was then added to a mixture of amino[2-[(5-nitro(2-pyridyl)amino] ethyl}carboxamidinium 4-methylbenzenesulfonate (120 mg, 0.3 mmol) and cesium carbonate (160 mg) and then heated at 80° C. overnight to give ethyl 4-(4-(2-furyl) phenyl)-2-({2-[(5-nitro(2-pyridyl))amino]ethyl}amino) pyrimidine-5-carboxylate.

HPLC: 32.05 min (80% purity)
MS: MH$^+$=476 C$_{24}$H$_{23}$N$_6$O$_5$=475 g/mol

EXAMPLE 39

Synthesis of Ethyl 4-(4-cyanophenyl)-2-({2-[(4-methyl-5-nitro(2-pyridyl))amino]ethyl}amino)pyrimidine-5-carboxylate Step 1

2-Chloro-4-methyl-5-nitropyrimidine (2.0 g, 11.5 mmol) in acetonitrile (10 ml) was added dropwise to ethylenediamine (2.5 ml) in acetonitrile (10 ml). The mixture was stirred overnight at room temperature. The solvent was removed by rotary evaporation and the residue was partitioned between dichloromethane and 2.5 M aqueous sodium hydroxide. The aqueous layer was further extracted 4 times with dichloromethane. The combined organic layers were washed with a saturated sodium chloride solution, dried and concentrated in vacuo to give (2-aminoethyl)(4-methyl-5-nitro(2-pyridyl))amine as an orange solid (1.74 g).

Step 2

The amine from Step 1 (1.2 g, 6 mmol) was shaken with benzotriazole carboxamidinium 4-methylbenzenesulfonate (2.0 g, 6 mmol) and DIEA (1.05 ml, 6 mmol) in dry acetonitrile (10 ml) at room temperature overnight. Addition of ether resulted in the precipitation of amino{2-[(4-methyl-5-nitro(2-pyridyl))amino]ethyl}carboxamidinium 4-methylbenzenesulfonate as a yellow solid.

Step 3

Ethyl 3-(4-cyanophenyl)-3-oxopropanoate (64 mg, 0.3 mmol) in THF (1 ml) and DMFDMA (0.3 mmol) was heated at 70° C. for 3 hours. The solution was added to a mixture of the guanidine from Step 2 (123 mg, 0.3 mmol), 1.0 M sodium ethoxide in ethanol (0.35 ml) and ethanol (1 ml). The mixture was then heated overnight at 80° C., cooled, diluted with dichloromethane, then washed with saturated sodium bicarbonate solution. The organic layer was concentrated in vacuo, redissolved in acetonitrile and the product precipitated with water.

HPLC: 27.63 min (85% pure)
MS: MH$^+$=448 C$_{22}$H$_{21}$N$_7$O$_4$=447 g/mol

EXAMPLE 40

Synthesis of 2-({2-[(5-nitro(2-pyridyl))amino] ethyl}amino)-4-phenylpyrimidine-5-carbonitrile 3-Oxo-3-phenylpropanenitrile (44 mg, 0.3 mmol) in THF (1 ml) and DMFDMA (50 μl) was heated at 70° C. for 3 hours. This solution was added to a mixture of amino[2-[(5-nitro(2-pyridyl)amino]ethyl}carboxamidinium 4-methylbenzenesulfonate (120 mg, 0.3 mmol), 1.0 M sodium ethoxide in ethanol (0.35 ml) and dry ethanol (1 ml) and heated at 80° C. overnight, then concentrated in vacuo. The residue was then taken up in dichloromethane and washed with a saturated aqueous sodium bicarbonate solution. The organic layer was concentrated in vacuo. The residue was taken up in acetonitrile. Addition of water gave a precipitate which was filtered off and dried to give the title compound.

HPLC: 13.87 min (95% pure)

EXAMPLE 41

Synthesis of {2-[(5-nitro(2-pyridyl))amino]ethyl}(5-nitro-4-phenylpyrimidin-2-yl)amine 2-Nitro-1-phenylethan-1-one (50 mg, 0.3 mMol) was heated in THF (1 ml) and DMFDMA (50 μl) for 3 h at 70° C. This solution was added to a mixture of amino[2-[(5-nitro(2-pyridyl)amino]ethyl}carboxamidinium 4-methylbenzenesulfonate (120 mg, 0.3 mmol), 1.0 M sodium ethoxide in ethanol (0.35 ml) and dry ethanol (1 ml), heated at 80° C. overnight, then concentrated in vacuo. The residue was taken up in dichloromethane and washed with saturated aqueous sodium bicarbonate. The organic layer was concentrated in vacuo. The residue was taken up in acetonitrile. Addition of water gave a precipitate which was filtered off and dried to give the title compound.

HPLC: 15.33 min (100% purity)
MS: MH$^+$=382 C$_{17}$H$_{15}$N$_7$O$_4$=381 g/mol

EXAMPLE 42

Synthesis of (5-Nitro-4-phenylpyrimidin-2-yl)[2-(2-pyridylamino)ethyl]amine

2-Nitro-1-phenylethan-1-one (50 mg, 0.3 mmol) was heated in THF (1 ml) and DMFDMA (50 μl) for 3 hours at 70° C. This solution was added to a mixture of amino[2-(2-pyridyl)amino)ethyl}carboxamidinium 4-methylbenzenesulfonate (105 mg, 0.3 mmol), 1.0 M sodium ethoxide in ethanol (0.35 ml) and dry ethanol (1 ml), heated at 80° C. overnight, then concentrated in vacuo. The residue was taken up in dichloromethane and washed with saturated aqueous sodium bicarbonate. The organic layer was concentrated in vacuo. The residue was taken up in acetonitrile. Addition of water gave a precipitate which was filtered off and dried to give the title compound.

HPLC: 19.66 min (100% purity)
MS: MH$^+$=337 C$_{17}$H$_{16}$N$_6$O$_2$=336 g/mol

EXAMPLE 43

Synthesis of Ethyl 4-(4-cyanophenyl)-2-[(2-{[5-trifluoromethyl)(2-pyridyl)]amino}ethyl)amino] pyrimidine-5-carboxylate Step 1

2-Chloro-5-(trifluoromethyl)pyrimidine (5.0 g) was heated with ethylenediamine (20 ml) at 120° C. overnight. The excess ethylenediamine was removed by rotary evaporation and the residue was partitioned between dichloromethane and 2.5 M aqueous sodium hydroxide. The aqueous layer was extracted 5 times further with dichloromethane. The combined organic layers were washed with a saturated aqueous sodium chloride solution, dried, then concentrated in vacuo to give (2-aminoethyl)[5-(trifluoromethyl)(2-pyridyl)]amine as an orange oil.

Step 2

The amine from Step 1 (1.1 g, 5.36 mmol) was treated with benzotriazole carboxamidinium 4-methylbenzenesulfonate (1.78 g, 5.36 mmol) and DIEA (0.93 ml, 5.36 mmol) in acetonitrile (6 ml) with shaking at room temperature overnight. Addition of ether gave amino (2-{[5-(trifluoromethyl)(2-pyridyl)]amino}ethyl) carboxamidinium 4-methylbenzenesulfonate as a white solid.

Step 3

Ethyl 3-(4-cyanophenyl)-3-oxopropanoate (64 mg, 0.3 mmol) was heated in THF (1 ml) with DMFDMA (50 μl) at 70° C. for 4 hours. This solution was added to a mixture of the guanidine from Step 2 (123 mg, 0.3 mmol), 1.0 M sodium ethoxide in ethanol (0.35 ml) and dry ethanol (1 ml). This mixture was heated at 80° C. overnight, then concentrated in vacuo. The residue was taken up in dichloromethane and washed with a saturated aqueous sodium bicarbonate solution. The organic layer was concentrated in vacuo. The residue was taken up in acetonitrile. Addition of water gave a precipitate which was filtered off and dried to give the title compound.

HPLC: 24.46 min (85% purity)
MS: MH$^+$=457 $C_{22}H_{19}N_6O_2F_3$=456 g/mol

EXAMPLE 44

Synthesis of [4-(2,4-dichlorophenyl)-5-imidazolylpyrimidin-2-yl]{2-[(5-nitro(2-pyridyl))amino]ethyl}amine Step 1

2,4-Dichlorophenacyl chloride (1.42 g, 6.4 mmol) and imidazole (1.18 g, 16 mmol) were heated in toluene (40 ml) at 75° C. for 2.25 hours. The mixture was concentrated to dryness in vacuo. The residue was dissolved in dichloromethane and washed with 5% aqueous potassium carbonate solution and water, dried and concentrated in vacuo. The crude product was purified by passage over a pad of silica gel, eluting with 5% methanol in dichloromethane to give 1-(2,4-dichlorophenyl)-2-imidazolylethan-1-one as an orange oil.

Step 2

The product of Step 1 (95 mg) was heated with DMFDMA (2 ml) at 105° C. for 9 hours. The solvent was removed in vacuo and the residue was dissolved in dry THF (2 ml) and added to a mixture of amino[2-[(5-nitro(2-pyridyl)amino]ethyl}carboxamidinium 4-methylbenzenesulfonate (100 mg, 0.3 mmol) and cesium carbonate (200 mg). The mixture was heated overnight at 80° C., then concentrated in vacuo. The residue was taken up in dichloromethane and washed with saturated aqueous sodium bicarbonate. The organic layer was concentrated in vacuo. The product was purified by radial chromatography on silica gel.

HPLC: 22.48 min (96% purity)
MS: MH$^+$=471–473 (cluster, 2 Cl) $C_{20}H_{16}Cl_2N_8O_2$=471 g/mol

EXAMPLE 45

4-[2-({2-[(6-amino-5-nitro(2-pyridyl))amino]ethyl}amino)-5-imidazolylpyrimidin-4-yl]benzenecarbonitrile Step 1

4-Cyanophenacyl bromide (0.72 g, 3.2 mmol) and imidazole (0.55 g, 8 mmol) were heated at 75° C. in toluene (20 ml) for 2.5 hours. The mixture was concentrated to dryness in vacuo. The residue was dissolved in dichloromethane and washed with a 5% aqueous potassium carbonate solution and water, dried and concentrated in vacuo to give a pink solid (0.35 g). This method is a variation of the one described in Sakurai et al., 1996, Chem. Pharm. Bull. 44:1510, which is incorporated herein by reference.

Step 2

1-(4-Cyanophenyl)-2-imidazolylethan-1-one (from Step 1, 63 mg, 0.3 mmol) was heated with DMFDMA (2 ml) at 105° C. for 9 hours. The solvent was removed in vacuo and the residue was dissolved in dry THF (2 ml) and added to a mixture of amino[2-[(6-amino-5-nitro(2-pyridyl))amino]ethyl}carboxamidinium 4-methylbenzenesulfonate (105 mg, 0.3 mmol) and cesium carbonate (200 mg). The mixture was heated overnight at 80° C., then concentrated in vacuo. The residue was taken up in dichloromethane and washed with a saturated aqueous sodium bicarbonate solution. The organic layer was concentrated in vacuo. The residue was crystallized from ethanol/water to give yellow needles.

HPLC: 17.68 min (100% purity)
MS: MH$^+$=443 $C_{21}H_{18}N_{10}O_2$=442 g/mol

EXAMPLE 46

Synthesis of [4-(2,4-dichlorophenyl)-5-imidazol-2-ylpyrimidin-2-yl]{2-[(5-nitro(2-pyridyl)amino]ethyl}amine A solution of 1-(2,4-dichlorophenyl)-2-imiazol-2-ylethan-1-one (prepared from the appropriate acid chloride and 2-methylimidazole according to the procedure described in Macco et al., J. Org. Chem., 20:252 (1985), which is incorporated herein by reference) and DMFDMA (10 ml/mmol of ketone) was stirred at reflux for 12 hours. After concentration of this solution, the resulting solid was redissolved in DMF (10 ml/mmol). $Cs_2CO_3$ (3 mmol) and (2-(5-nitro(2-pyridyl)amino]ethyl)carboxamidinium 4-methylbenzenesulfonate (1.5 mmol) were added, and the mixture stirred for 8 hours at 100° C. The mixture was cooled, filtered and the filtrate diluted with ethyl acetate and washed with saturated aqueous sodium bicarbonate. Concentration of the organic layers yielded [4-(2,4-dichlorophenyl)-5-imidazol-2-ylpyrimidin-2-yl]{2-[(5-nitro(2-pyridyl)amino]ethyl}amine.

EXAMPLE 47

Synthesis of [2-[(6-amino-5-nitro(2-pyridyl))amino]ethyl}[4-(2,4-dichlorophenyl)-5-imidazol-2-ylpyrimidin-2-yl]amine A solution of 1-(2,4-dichlorophenyl)-2-imiazol-2-ylethan-1-one (prepared from the appropriate acid chloride and 2-methylimidazole according to the procedure described in Macco et al., J. Org. Chem., 20.252 (1985), which is incorporated herein by reference) and DMFDMA (10 ml/mmol of ketone) was stirred at reflux for 12 hours. After concentration of this solution, the resulting solid was redissolved in DMF (10 ml/mmol). $Cs_2CO_3$ (3 mmol) and (2-(6-amino-5-nitro(2-pyridyl)amino)ethyl) carboxamidinium 4-methylbenzenesulfonate (1.5 mmol) were added, and the mixture stirred for 8 hours at 100° C. The mixture was cooled, filtered and the filtrate diluted with ethyl acetate and washed with saturated aqueous sodium bicarbonate. Concentration of the organic layers yielded [2-[(6-amino-5-nitro(2-pyridyl))amino]ethyl}[4-(2,4-dichlorophenyl)-5-imidazol-2-ylpyrimidin-2-yl]amine.

EXAMPLE 48

Synthesis of 4-[5-imidazol-2-yl-2-({2-[(5-nitro(2-pyridyl)amino]ethyl}amino)pyrimidin-4-yl]benzenecarbonitrile A solution of 4-(2-midazol-2-ylacetyl)benzenecarbonitrile (prepared from the appropriate acid chloride and 2-methylimidazole according to the procedure described in Macco et al., J. Org. Chem., 20:252 (1985) and DMFDMA (10 ml/mmol of ketone) was stirred at reflux for 12 hours. After concentration of this solution, the resulting solid was redissolved in DMF (10 ml/mmol). $Cs_2CO_3$ (3 mmol) and (2-(5-nitro(2-pyridyl)amino]ethyl) carboxamidinium 4-methylbenzenesulfonate (1.5 mmol) were added, and the mixture stirred for 8 hours at 100° C. The mixture was cooled, filtered and the filtrate diluted with ethyl acetate and washed with saturated aqueous sodium bicarbonate. Concentration of the organic layers yielded 4-[5-imidazol-2-yl-2-({2-[(5-nitro(2-pyridyl)amino]ethyl}amino)pyrimidin-4-yl]benzenecarbonitrile.

EXAMPLE 49

Synthesis of 4-[2-({2-[(6-amino-5-nitro(2-pyridyl))amino]ethyl}amino)-5-imidazol-2-ylpyrimidin-4-yl]benzenecarbonitrile A solution of 4-(2-midazol-2-ylacetyl)benzenecarbonitrile (prepared from the appropriate acid chloride and 2-methylimidazole according to the procedure described in Macco et al., *J. Org. Chem.*, 20:252 (1985) and DMFDMA (10 ml/mmol of ketone) was stirred at reflux for 12 hours. After concentration of this solution, the resulting solid was redissolved in DMF (10 ml/mmol). $Cs_2CO_3$ (3 mmol) and (2-(6-amino-5-nitro(2-pyridyl)amino)ethyl) carboxamidinium 4-methylbenzenesulfonate (1.5 mmol) were added, and the mixture stirred for 8 hours at 100° C. The mixture was cooled, filtered and the filtrate diluted with ethyl acetate and washed with saturated aqueous sodium bicarbonate. Concentration of the organic layers yielded 4-[2-({2-(6-amino-5-nitro(2-pyridyl))amino]ethyl}amino)-5-imidazol-2-ylpyrimidin-4-yl]benzenecarbonitrile.

EXAMPLE 50
Synthesis of Ethyl 2-({2-[(5-nitro(2-pyridyl))amino]ethyl}amino)-4-(4-pyridyl)pyrimidine-5-carboxylate This compound was prepared from ethyl 3-oxo-3-(4-pyridyl)propanoate and amino[2-[(5-nitro(2-pyridyl)amino]ethyl}carboxamidinium 4-methylbenzenesulfonate in accordance with Solution Method A.

HPLC: 17.78 min (90% purity)

NMR (300 MHz, 5/1 acetonitrile-$d_3$/$D_2O$): 8.85 (d, 1H), 8.82 (s, 1H), 8.80 (d, 2H), 8.01 (dd, 1H), 7.38 (d, 2H), 6.43 (d, 1H), 4.10 (q, 2H), 3.60–3.80 (m, 4H), 1.06 (t, 3H).

EXAMPLE 51
Synthesis of Ethyl 4-(3-nitrophenyl)-2-{[2-(2-pyridylamino)ethyl]amino}pyrimidine-5-carboxylate This compound was prepared from ethyl 3-oxo-3-(3-nitrophenyl)propanoate and amino[2-(2-pyridylamino)ethyl]carboxamidinium 4-methylbenzenesulfonate in accordance with Solution Method A.

HPLC: 21.25 min (90% purity)

MS: $MH^+$=409 $C_{20}H_{19}N_6O_4$=408 g/mol

EXAMPLE 52
Synthesis of Ethyl 2-({2-[(5-nitro(2-pyridyl))amino]ethyl}amino)-4-[4-(trifluoromethoxy)phenyl]pyrimidine-5-carboxylate This compound was prepared from ethyl 3-oxo-3-(4-trifluoromethoxyphenyl)propanoate and amino[2-[(5-nitro(2-pyridyl)amino]ethyl}carboxamidinium 4-methylbenzenesulfonate in accordance with Solution Method A.

HPLC: 22.50 min (91% purity)

MS: $MH^+$=493 $C_{21}H_{19}N_6O_5F_3$=472 g/mol

EXAMPLE 53
Synthesis of Ethyl 4-(3,4-difluorophenyl)-2-({2-[(5-nitro(2-pyridyl))amino]ethyl}amino)pyrimidine-5-carboxylate This compound was prepared from ethyl 3-oxo-3-(3,4-difluorophenyl)propanoate and amino[2-[(5-nitro(2-pyridyl)amino]ethyl}carboxamidinium 4-methylbenzenesulfonate in accordance with Solution Method A.

HPLC: 17.96 min (100% purity)

MS: $MH^+$=445 $C_{20}H_{18}N_6O_4F_2$=444 g/mol

EXAMPLE 54
Synthesis of ethyl 4-[4-(methylsulfonyl)phenyl]-2-({2-[(5-nitro(2-pyridyl))amino]ethyl}amino)pyrimidine-5-carboxylate This compound was make from ethyl 3-(4-methylsulfonylphenyl)-3-oxopropanoate and amino[2-[(5-nitro(2-pyridyl)amino]ethyl}carboxamidinium 4-methylbenzenesulfonate in accordance with Solution Method A.

HPLC: 11.21 min (100% purity)

MS: $MH^+$=487 $C_{21}H_{22}N_6O_6S$=486 g/mol

EXAMPLE 55
Synthesis of Ethyl 4-(4-methylthiophenyl)-2-({2-[(5-nitro(2-pyridyl))amino]ethyl}amino)pyrimidine-5-carboxylate This compound was prepared from ethyl 3-(4-methylthiophenyl)-3-oxopropanoate and amino[2-[(5-nitro(2-pyridyl)amino]ethyl}carboxamidinium 4-methylbenzenesulfonate in accordance with Solution Method A.

HPLC: 17.26 min (92% purity)

MS: $MH^+$=455 $C_{21}H_{22}N_6O_4S$=454 g/mol

EXAMPLE 56
Synthesis of Ethyl 4-[4-(dimethylamino)phenyl]-2-({2-[(5-nitro(2-pyridyl))amino]ethyl}amino)pyrimidine-5-carboxylate This compound was prepared from ethyl 3-(4-dimethylaminophenyl)-3-oxopropanoate and amino[2-[(5-nitro(2-pyridyl)amino]ethyl}carboxamidinium 4-methylbenzenesulfonate in accordance with Solution Method A.

HPLC: 9.0 min (90% purity)

MS: $MH^+$=452 $C_{22}H_{25}N_7O_4$=451 g/mol

EXAMPLE 57
Synthesis of Ethyl 2-({2-[(6-amino-5-nitro(2-pyridyl))amino]ethyl}amino)-4-(4-cyanophenyl)pyrimidine-5-carboxylate This compound was prepared from ethyl 3-(4-cyanophenyl)-3-oxopropanoate and amino{2-[(6-amino-5-nitro(2-pyridyl))amino]ethyl}carboxamidinium 4-methylbenzenesulfonate in accordance with Solution Method A.

HPLC: 25.21 min (83% purity)

MS: $MH^+$=449 $C_{21}H_{20}N_8O_4$=448 g/mol

EXAMPLE 58
Synthesis of Ethyl 4-(4-imidazolyphenyl)-2-({2-[(5-nitro(2-pyridyl))amino]ethyl}amino)pyrimidine-5-carboxylate This compound was prepared from ethyl 3-[4(1-imidazolyl)phenyl]-3-oxopropanoate and amino[2-[(5-nitro(2-pyridyl)amino]ethyl}carboxamidinium 4-methylbenzenesulfonate in accordance with Solution Method A.

HPLC: 18.50 min (91% purity)

MS: $MH^+$=475 $C_{23}H_{22}N_8O_4$=474 g/mol

EXAMPLE 59
Synthesis of Ethyl 4-(4-ethylphenyl)-2-({2-[(5-nitro(2-pyridyl))amino]ethyl}amino)pyrimidine-5-carboxylate This compound was prepared from ethyl 3-(4-ethylphenyl)-3-oxopropanoate and amino[2-[(5-nitro(2-pyridyl)amino]ethyl}carboxamidinium 4-methylbenzenesulfonate in accordance with Solution Method A.

HPLC: 32.45 min (95% purity)

MS: $MH^+$=437 $C_{22}H_{24}N_6O_4$=436 g/mol

The following additional compounds were prepared according to Solution Method A using the appropriate carbonyl containing compound and guanidine.

Ethyl 4-(2-furyl)-2-[(2-(2-pyridyl)ethyl)amino]pyrimidine-5-carboxylate

Ethyl 4-(3-nitrophenyl)-2-[(2-(2-pyridyl)ethyl)amino]pyrimidine-5-carboxylate

Ethyl 4-(4-fluorophenyl)-2-[(2-(2-pyridyl)ethyl)amino]pyrimidine-5-carboxylate

Ethyl 4-(4-methoxyphenyl)-2-[(2-(2-pyridyl)ethyl)amino]pyrimidine-5-carboxylate
Ethyl 4-(4-cyanophenyl)-2-[(2-(2-pyridyl)ethyl)amino]pyrimidine-5-carboxylate
2-({2-[(5-nitro(2-pyridyl))amino]ethyl}amino)-4-(4-nitrophenyl)pyrimidine-5-carboxylic acid
Ethyl 4-(4fluorophenyl)-2-({2-[(5-nitro(2-pyridyl))amino]ethyl}amino)pyrmidine-5-carboxylate
Ethyl 2-({2-[(5-nitro(2-pyridyl))amino]ethyl}amino)-4-(3-quinolyl)pyrimidine-5-carboxylate
Ethyl 2-({2-[(5-nitro(2-pyridyl))amino]ethyl}amino)-4-(3-nitrophenyl)pyrimidine-5-carboxylate
Methyl 2-({2-[(5-nitro(2-pyridyl))amino]ethyl}amino)-4-(3-pyridyl)pyrmidine-5-carboxylate
Ethyl 2-({2-[(5-nitro(2-pyridyl))amino]ethyl}amino)-4-(4-nitrophenyl)pyrimidine-5-carboxylate
Ethyl 4-[3,5-bis(trifluoromethyl)phenyl]-2-({2-[(5-nitro(2-pyridyl))amino]ethyl}amino)pyrimidine-5-carboxylate
Ethyl 2-({2-[(5-nitro(2-pyridyl))amino]ethyl}amino)-4-[4-(trifluoromethyl)phenyl]pyrimidine-5-carboxylate
Ethyl 2-({2-[(5-nitro(2-pyridyl))amino]ethyl}amino)-4-[3-(trifluoromethyl)phenyl]pyrimidine-5-carboxylate
Ethyl 4-(5-bromo(3-pyridyl))-2-({2-[(5-nitro(2-pyridyl)amino]ethyl}amino)pyrimidine-5-carboxylate
Ethyl 4-(2,4-difluorophenyl)-2-({2-[(5-nitro(2-pyridyl)amino]ethyl}amino)pyrimidine-5-carboxylate
Ethyl 4-(2,4-dichlorophenyl)-2-({2-[(5-nitro(2-pyridyl))amino]ethyl}amino)pyrimidine-5-carboxylate
Ethyl 4-(4-cyanophenyl)-2-{[2-(pyrimidin-2-ylamino)ethyl]amino}pyrimidine-5-carboxylate
Ethyl 4-(4-methoxyphenyl)-2-({2-[(5-nitro(2-pyridyl))amino]ethyl}amino)pyrimidine-5-carboxylate
Ethyl 4-(3-cyanophenyl)-2-({2-[(5-nitro(2-pyridyl))amino]ethyl}amino)pyrimidine-5-carboxylate
Ethyl 4-(4-cyanophenyl)-2-({2-[(4-nitrophenyl)amino]ethyl}amino)pyrimidine-5-carboxylate
Ethyl 4-(3-fluorophenyl)-2-({2-[(5-nitro(2-pyridyl))amino]ethyl}amino)pyrimidine-5-carboxylate
Ethyl 4-(3,5-dichlorophenyl)-2-({2-[(5-nitro(2-pyridyl))amino]ethyl}amino)pyrimidine-5-carboxylate
4-[5-(methylsulfonyl)-2-({2-[(5-nitro(2-pyridyl))amino]ethyl}amino)pyrimidin-4-yl]benzenecarbonitrile
Ethyl 2-({2-[(5-nitro(2-pyridyl))amino]ethyl}amino)-4-(4-sulfanoylphenyl)pyrimidine-5-carboxylate
Ethyl 4-(4-chlorophenyl)-2-({2-[(5-nitro(2-pyridyl))amino]ethyl}amino)pyrimidine-5-carboxylate
Ethyl 4-(4-bromophenyl)-2-({2-[(5-nitro(2-pyridyl))amino]ethyl}amino)pyrimidine-5-carboxylate
Ethyl 4-naphthyl-2-({2-[(5-nitro(2-pyridyl))amino]ethyl}amino)pyrimidine-5-carboxylate
Ethyl 2-({2-[(5-nitro(2-pyridyl))amino]ethyl}amino)-4-(4-phenylphenyl)pyrimidine-5-carboxylate
Ethyl 4-(2H-benzo[3,4-d]1,3-dioxolen-5-yl)-2-({2-[(5-nitro(2-pyridyl))amino]ethyl}amino)pyrimidine-5-carboxylate
Ethyl 4-(4-butoxyphenyl)-2-({2-[(5-nitro(2-pyridyl))amino]ethyl}amino)pyrimidine-5-carboxylate
6-[(2-{[4-(4-cyanophenyl)-5-(ethoxycarbonyl)pyrimidin-2-yl]amino}ethyl)amino]pyridine-3-carboxylic acid
tert-Butyl 4-(4-cyanophenyl)-2-({2-[(5-nitro(2-pyridyl))amino]ethyl}amino)pyrimidine-5-carboxylate
tert-Butyl 6-[(2-{[4-(4-cyanophenyl)-5-(ethoxycarbonyl)pyrimidin-2-yl]amino}ethyl)amino]pyrimidine-3-carboxylate
Methyl 4-(4-cyanophenyl)-2-({2-[(5-nitro(2-pyridyl))amino]ethyl}amino)pyrimidine-5-carboxylate
Methyl 6-[(2-{[4-(4-cyanophenyl)-5-(ethoxycarbonyl)pyrimidin-2-yl]amino}ethyl)amino]pyridine-3-carboxylate
Ethyl 4-(4-cyanophenyl)-2-[(2-{[5-(morpholin-4-ylcarbonyl)(2-pyridyl)]amino}ethyl)amino]pyrimidine-5-carboxylate
Ethyl 4-(4-cyanophenyl)-2-[(2-{[5-(N-ethylcarbamoyl)(2-pyridyl)]amino}ethyl)amino]pyrimidine-5-carboxylate
4-[5-nitro-2-({-2-[(5-nitro(2-pyridyl))amino]ethyl}amino)pyrimidin-4-yl]benzenecarbonitrile
Ethyl 4-(4-cyanophenyl)-2-{[2-({5-nitro-6-[benzylamino](2-pyridyl)}amino)ethyl]amino}pyrimidine-5-carboxylate
Ethyl 4-[4-(4-methylpiperazinyl)phenyl]-2-({2-[(5-nitro(2-pyridyl))amino]ethyl}amino)pyrimidine-5-carboxylate
Ethyl 2-({2-[(5-cyano(2-pyridyl))amino]ethyl}amino)-4-(4-cyanophenyl)pyrimidine-5-carboxylate
Ethyl 4-(4-cyanophenyl)-2-[(2-{[6-(methylamino)-5-nitro(2-pyridyl)]amino}ethyl)amino]pyrimidine-5-carboxylate
Ethyl 2-({2-[(5-nitro(2-pyridyl))amino]ethyl}amino)-4-(4-(1,3-oxazol-5-yl)phenyl)pyrimidine-5-carboxylate
Ethyl 2-({2-[(4-amino-5-nitropyrimidin-2-yl)amino]ethyl}amino)-4-(4-cyanophenyl)pyrimidine-5-carboxylate
Ethyl 2-({2-[(6-amino-5-nitro(2-pyridyl))amino]ethyl}amino)-4-(4-(1,3-oxazol-5-yl)phenyl)pyrimidine-5-carboxylate
Ethyl 4-[4-(methylethyl)phenyl]-2-({2-[(5-nitro(2-pyridyl))amino]ethyl}amino)pyrimidine-5-carboxylate
Ethyl 4-[4-(tert-butyl)phenyl]-2-({2-[(5-nitro(2-pyridyl))amino]ethyl}amino)pyrimidine-5-carboxylate
Ethyl 4-(3,4-dichlorophenyl)-2-({2-[(5-nitro(2-pyridyl))amino]ethyl}amino)pyrimidine-5-carboxylate
Ethyl 4-(3,4-dimethoxyphenyl)-2-({2-[(5-nitro(2-pyridyl))amino]ethyl}amino)pyrimidine-5-carboxylate
Ethyl 4-[4-(diethylamino)phenyl]-2-({2-[(5-nitro(2-pyridyl))amino]ethyl}amino)pyrimidine-5-carboxylate
2-({2-[(5-nitro(2-pyridyl))amino]ethyl}amino)-4-(2,4,6-trichlorophenyl)pyrimidine-5-carboxylic acid
Ethyl 4-(4-methylphenyl)-2-({2-[(5-nitro(2-pyridyl))amino]ethyl}amino)pyrimidine-5-carboxylate
Ethyl 4-(2-naphthyl)-2-({2-[(5-nitro(2-pyridyl))amino]ethyl}amino)pyrimidine-5-carboxylate
Ethyl 4-(3,4-dimethylphenyl)-2-({2-[(5-nitro(2-pyridyl))amino]ethyl}amino)pyrimidine-5-carboxylate
Ethyl 2-({2-[(4-amino-5-cyanopyrimidin-2-yl)amino]ethyl}amino)-4-(4-cyanophenyl)pyrimidine-5-carboxylate
4-(2-methoxyphenyl)-2-({2-[(5-nitro(2-pyridyl))amino]ethyl}amino)pyrimidine-5-carboxylic acid
Ethyl 4-(4-cyanophenyl)-2-{[2-(3-methoxyphenyl)ethyl]amino}pyrimidine-5-carboxylate
2-({2-[(6-amino-5-nitro(2-pyridyl))amino]ethyl}amino)-4-(3,4-dichlorophenyl)pyrimidine-5-carbonitrile
4-(3,4-dichlorophenyl)-2-({2-[(5-nitro(2-pyridyl))amino]ethyl}amino)pyrimidine-5-carbonitrile
Ethyl 2-({2-[(5-nitro(2-pyridyl))amino]ethyl}amino)-4-(4-(1,2,4-triazol-4-yl)phenyl)pyrimidine-5-carboxylate
2-({2-[(6-amino-5-nitro(2-pyridyl))amino]ethyl}amino)-4-(2,4-dichlorophenyl)pyrimidine-5-carbonitrile
4-(2,4-dichlorophenyl)-2-({2-[(5-nitro(2-pyridyl))amino]ethyl}amino)pyrimidine-5-carbonitrile
2-({2-[(6-amino-5-nitro(2-pyridyl))amino]ethyl}amino)-4-(2,4-dichlorophenyl)pyrimidine-5-carboxylic acid
Ethyl 2-({2-[(5-amino(2-pyridyl))amino]ethyl}amino)-4-(4-cyanophenyl)pyrimidine-5-carboxylate

EXAMPLE 60

Solution Phase Synthesis
(Solution Method B)

A ketone with a $CH_2$ or $CH_3$ group adjacent to the carbonyl group was heated in neat N,N-dimethylformamide dimethyl acetal (DMFDMA) at 90–110° C. for 5 to 24 hours, usually 8 to 14 hours. The excess DMFDMA was then removed by rotary evaporation to give the intermediate enaminoketone as an oil or solid. This intermediate could be crystallized if desired, but was usually used in crude form in the next reaction step. The enaminoketone was dissolved in an appropriate solvent such as THF, ethanol, isopropanol or for syntheses where a higher reaction temperature was desired, in NMP (ca. 1–2 ml of solvent for 0.3–1 mmol of starting ketone).

This solution was then added to a mixture of a guanidine (1 equivalent) and a suitable base such as sodium ethoxide (freshly prepared), cesium carbonate or powdered sodium hydroxide. The usual combinations were cesium carbonate in THF or sodium ethoxide in ethanol or sodium hydroxide in isopropanol or cesium carbonate in NMP, although other base and/or solvent combinations can be used. The reaction was then heated at 80–125° C. (depending on the boiling point of the solvent) for 12 to 66 hours.

Small scale (i.e., 0.2–1 mmol) reactions were conducted in screw cap vials. The vials were placed into predrilled thermostated aluminum blocks (Digi-Block, Laboratory Devices, Holliston, Mass.) and shaken on a gyrotary shaker (Lab-Line Model G-2). After completion of the reaction, the vials were cooled, and their contents poured into dichloromethane or ethyl acetate, then washed with saturated aqueous sodium bicarbonate solution. The organic layer was concentrated in vacuo and the product was precipitated or crystallized, usually by addition of water to acetonitrile or ethanol solutions of the product. In some cases chromatographic purification was performed, either by semi-preparative HPLC or by radial chromatography using silica gel plates on a Chromatotron (Harrison Research, Palo Alto, Calif.) eluting with mixtures of dichloromethane and methanol. Larger scale reactions were performed in round bottom flasks using typical organic chemistry apparatus.

Examples 61–66 describe the synthesis of compounds prepared pursuant to Solution Method B.

EXAMPLE 61

Synthesis of [2-(2-pyridylamino)ethyl](4-(3-pyridyl)pyrimidin-2-yl)amine

3-Acetylpyrimidine (0.5 mmol) was heated with DMFDMA (300 μl) at 90° C. for 8.5 hours. The solvent was removed by rotary evaporation. The residue was dissolved in isopropanol (2 ml) and added to 170 mg (0.5 mmol) of amino[2-(2-pyridylamino)ethyl]carboxamidinium 4-methylbenzenesulfonate and powdered sodium hydroxide (70 mg). The mixture was heated at 85° C. overnight, then concentrated in vacuo. The residue was taken up in dichloromethane and washed with a saturated aqueous sodium bicarbonate solution. The organic layer was concentrated in vacuo. The residue was taken up in acetonitrile. Addition of water gave a precipitate which was filtered off and dried to give the title compound.

HPLC: 9.9 min (100% purity)

NMR (300 Mhz, 5/1 acetonitrile-$d_3$/$D_2O$, 75° C.): 9.20 (s, 1H), 8.65 (d, 1H), 8.2–8.4 (m, 2H), 7.94 (d, 1H), 7.50 (dd, 1H), 7.38 (t, 1H), 7.10 (d, 1H), 6.50 (m, 2H), 3.70 (t, 2H), 3.50 (t, 2H)

EXAMPLE 62

Synthesis of (5-Ethyl-4-phenylpyrimid-2-yl)[2-(2-pyridylamino)ethyl]amine

Butyrophenone (0.5 mmol) was heated with DMFDMA (300 μl) at 90° C. for 8.5 hours. The solvent was removed by rotary evaporation. The residue was dissolved in isopropanol (2 ml) and added to 170 mg (0.5 mmol) of amino[2-(2-pyridylamino)ethyl]carboxamidinium 4-methylbenzenesulfonate and powdered sodium hydroxide (70 mg). The mixture was heated at 90° C. overnight, then concentrated in vacuo. The residue was taken up in dichloromethane and washed with saturated aqueous sodium bicarbonate. The organic layer was concentrated in vacuo. The residue was taken up in acetonitrile. Addition of water gave a precipitate which was filtered off and dried to give the title compound.

HPLC: 17.46 min (98% purity)

MS: $MH^+$=320 $C_{18}H_{21}N_5$=319 g/mol

EXAMPLE 63

Synthesis of [2-(2,5-dimethoxyphenyl)ethyl](4-(3-pyridyl)pyrimidin-2-yl)amine

Step 1

2,5-Dimethoxyphenethylamine (1.08 g, 6 mmol) was shaken with benzotriazole carboxamidinium 4-methylbenzenesulfonate (2.0 g, 6 mmol) and DIEA (1.05 ml, 6 mmol) in dry acetonitrile (10 ml) at room temperature overnight. Addition of ether resulted in the precipitation of amino[2-(2,5-dimethoxyphenyl)ethyl]carboxamidinium 4-methylbenzenesulfonate as a white solid.

Step 2

3-Acetylpyrimidine (37 mg, 0.3 mmol) was heated at 100° C. in DMFDMA (1 ml) for 8 hours. The solvent was removed by rotary evaporation and the residue was dissolved in dry THF (2 ml) and added to a mixture of cesium carbonate (160 mg) and 120 mg (0.3 mmol) of the guanidine prepared in Step 1. The mixture was then heated at 80° C. overnight, then concentrated in vacuo. The residue was then taken up in dichloromethane and washed with a saturated aqueous sodium bicarbonate solution. The organic layer was concentrated in vacuo. The residue was taken up in ethanol (2 ml). Addition of water gave a precipitate which was filtered off and dried to give the title compound.

HPLC: 18.03 min (100% purity)

MS: $MH^+$=337 $C_{19}H_{20}N_4O_2$=336 g/mol

EXAMPLE 64

Synthesis of [4-(4-Morpholin-4-ylphenyl)pyrimidin-2-yl]{2-[(5-nitro(2-pyridyl))amino]ethyl}amine 4-Morpholinoacetophenone (0.633 g, 2.5 mmol) was heated at 100° C. in 4 ml of DMFDMA for 9 hours. The mixture was concentrated to a viscous oil by rotary evaporation. The oil was redissolved in isopropanol (10 ml) and treated with amino[2-[(5-nitro(2-pyridyl)amino]ethyl}carboxamidinium 4-methylbenzenesulfonate (1.0 g, 2.5 mmol) and powdered sodium hydroxide (200 mg). This mixture was heated at 80° C. overnight. The cooled mixture was diluted with dichloromethane and washed with saturated aqueous sodium bicarbonate solution. The organic layer was concentrated in vacuo, the dissolved in acetonitrile. The product was precipitated by addition of water. The brown solid was recrystalized from isopropanol to give the title compound.

M.P. 223–225° C. (with decomposition)

Elemental Analysis; $C_{21}H_{23}N_7O_3$. 0.7 $H_2O$ requires C 58.10 H 5.66 N 22.59 found C 58.02 H 5.30 N 22.39

HPLC: 20.85 min (100% purity)

MS: $MH^+$=422 g/mol (FW=421)

NMR (DMSO-$d_6$): 3.30 (m, 4H), 3.60 (m, 4H), 3.75 (m, 4H), 6.58 (d, 1H), 6.95 (m, 3H), 8.00 (d, 2H), 8.10 (d, 1H), 8.25 (d, 1H), 8.90 (s, 1H)

EXAMPLE 65

Synthesis of [4-(2,4-dichlorophenyl)-5-ethylpyrimid-2-yl]{2-[(5-nitro(2-pyridyl))amino]ethyl}amine Step 1

A mixture of 2,4-dichlorobenzoyl chloride (4.5 g) and copper (I) iodide (200 mg) in dry THF (30 ml) was cooled to −20° C. under argon. Then a solution of n-propyl magnesium chloride (2 M in ether, 11.0 ml) was added dropwise. Ten minutes after addition was complete, the cooling bath was removed and the mixture stirred for 1 hour. Water was carefully added, followed by extraction with toluene. The toluene layer was washed with dilute HCl, water, saturated sodium bicarbonate solution, dried and concentrated in vacuo to give 1-(2,4-dichlorophenyl)butan-1-one (4.0 g).

Step 2

The ketone from Step 1 (108 mg, 0.5 mmol) was heated at 95° C. overnight with DMFDMA (1.5 ml). The solvent was removed in vacuo and the residue was dissolved in dry ethanol (2 ml) and added to a mixture of amino[2-[(5-nitro(2-pyridyl)amino]ethyl}carboxamidinium 4-methylbenzenesulfonate (200 mg), 1.0 M sodium ethoxide (0.6 ml) and dry ethanol (2 ml). This mixture was heated at 85° C. overnight, then concentrated in vacuo, redissolved in dichloromethane and washed with saturated sodium bicarbonate solution. The organic layer was concentrated in vacuo. The residue was purified by chromatography on silica gel using 10% methanol in dichloromethane to give an oily product. Lyophilization from acetonitrile/water gave the title compound as a solid.

HPLC: 29.56 (85% purity)

MS: MH$^+$=433 $C_{19}H_{18}N_6Cl_2O_2$=432 g/mol

EXAMPLE 66

Synthesis of [4-(4-imidazolylphenyl)pyrimidin-2-yl]{2-[(5-nitro(2-pyridyl))amino]ethyl}amine 4-(1-Imidazolyl)acetophenone (57 mg, 0.3 mmol) was heated with DMFDMA (1 ml) for 8 hours at 105° C. The solvent was removed in vacuo and the residue was dissolved in dry THF (2 ml) and added to a mixture of amino[2-[(5-nitro(2-pyridyl)amino]ethyl}carboxamidinium 4-methylbenzenesulfonate (120 mg, 0.3 mmol) and cesium carbonate (200 mg) and heated overnight at 80° C., then concentrated in vacuo, redissolved in dichloromethane and washed with a saturated sodium bicarbonate solution. The organic layer was concentrated in vacuo. The residue was purified by crystallization to give the title compound.

HPLC: 15.17 min (100% purity)

NMR (300 Mhz, DMSO-d$_6$): 8.90 (s, 1H), 8.38 (d, 1H), 8.30 (s, 1H), 8.22 (d, 2H), 8.05 (d, 1H), 7.75 (d, 2H), 7.20 (s, 1H), 7.15 (d, 1H), 6.58 (d, 1H), 3.60 (m, 4H).

The following additional compounds were similarly prepared according to Solution Method B by varying the ketone and guanidine used:

(4-phenylpyrimidin-2-yl)(2-(2-pyridyl)ethyl)amine
4-(2-{[2-(2-pyridylamino)ethyl]amino}pyrimidin-4-yl)benzenecarbonitrile
(4-phenylpyrimidin-2-yl)[2-(2-pyridylamino)ethyl]amine
4-{2-[(2-(2-pyridyl)ethyl)amino]pyrimidin-4-yl}benzenecarbonitrile
[4-(4-nitrophenyl)pyrimidin-2-yl][2-(2-pyridylamino)ethyl]amine
[4-(4-imidazolylphenyl)pyrimidin-2-yl][2-(2-pyridylamino)ethyl]amine
[4-(3,4-difluorophenyl)pyrimidin-2-yl][2-(2-pyridylamino)ethyl]amine
[2-(2-pyridylamino)ethyl]{4-[4-(trifluoromethoxy)phenyl]pyrimidin-2-yl}amine
[4-(2,4-dichlorophenyl)pyrimidin-2-yl][2-(2-pyridylamino)ethyl]amine
[4-(4-chlorophenyl)-5-methylpyrimidin-2-yl][2-(2-pyridylamino)ethyl]amine
[4-(4-methyl-1-phenylpyrazol-3-yl)pyrimidin-2-yl][2-(2-pyridylamino)ethyl]amine
3-[2-({2-[(5-nitro-2-pyridyl)amino]ethyl}amino)pyrimidin-4-yl]benzenecarbonitrile
[4-(2,4-dimethyl(1,3-thiazol-5-yl))pyrimidin-2-yl]{2-[(5-nitro(2-pyridyl))amino]ethyl}amine
{2-[(5-nitro(2-pyridyl))amino]ethyl}(4-pyrazin-2-ylpyrimidin-2-yl)amine
[4-phenyl-5-benzylpyrimidin-2-yl][2-(2-pyridylamino)ethyl]amine
4-[2-({2-[(5-nitro-2-pyridyl)amino]ethyl}amino)pyrimidin-4-yl]benzenesulfonamide
{4-[4-(4,5-dichloroimidazol-2-yl)phenyl]pyrimidin-2-yl}{2-[(5-nitro(2-pyridyl))amino]ethyl}amine
4(2-{[2-(2,5-dimethoxyphenyl)ethyl]amino}pyrimidin-4-yl)benzenecarbonitrile
[2-(2,5-dimethoxyphenyl)ethyl](4-(3-pyridyl)pyrimidin-2-yl)amine
[4-(4-benzimidazolylphenyl)pyrimidin-2-yl]{2-[(5-nitro(2-pyridyl))amino]ethyl}amine
4-[5-imidazolyl-2-({2-[(5-nitro(2-pyridyl))amino]ethyl}amino)pyrimidin-4-yl]benzenecarbonitrile
4-[2-({2-[(6-amino-5-nitro(2-pyridyl))amino]ethyl}amino)-5-imidazolylpyrimidin-4-yl]benzenecarbonitrile
[4-(2,4-dichlorophenyl)-5-imidazolylpyrimidin-2-yl]{2-[(5-nitro(2-pyridyl))amino]ethyl}amine
{2-[(6-amino-5-nitro(2-pyridyl))amino]ethyl}[4-(2,4-dichlorophenyl)-5-imidazolylpyrimidin-2-yl]amine
[4-(2,4-dimethylphenyl)-5-imidazolylpyrimidin-2-yl]{2-[(5-nitro(2-pyridyl))amino]ethyl}amine
ethyl 4-[2-({2-[(5-nitro-2-pyridyl)amino]ethyl}amino)pyrimidin-4-yl]benzoate
4-(2-{[3-(4-phenylimidazolyl)propyl]amino}pyrimidin-4-yl)benzenecarbonitrile
(3-benzimidazolylpropyl)[4-imidazolylphenyl)pyrimidin-2-yl]amine
N-{4-[2-({2-[(5-nitro-2-pyridyl)amino]ethyl}amino)pyrimidin-4-yl]phenyl}acetamide

EXAMPLE 67

Synthesis of [5-(4-(Fluorophenyl)pyrimidin-2-yl]{2-[(5-nitro(2-pyridyl))amino]ethyl}amine
(Solution Method C)

Step 1

Dry DMF (22 ml) was cooled to 0° C. under argon. Phosphorous oxychloride (9.2 g) was added dropwise to the cooled DMF. The mixture was removed from the cooling bath and stirring continued for 1 hour. Then, 4-fluorophenylacetic acid (3.08 g, 20 mmol) was added as a solid and the mixture was heated at 85° C. for 6 hours. After the mixture was cooled to room temperature it was poured onto approximately 100 g of ice with stirring. A solution of sodium perchlorate monohydrate (3.66 g) in water (10 ml) was added. The precipitated solid was filtered, washed with water and dried in vacuo to give [(2-E,Z)-3-(dimethylamino)-2-(4-fluorophenyl)prop-2-enylidene]dimethylammonium perchlorate. This procedure is described in Church et al., *J. Org. Chem.*, 60:3750 (1995), which is incorporated herein by reference.

Step 2

The vinylogous amidinium salt obtained in Step 1 (100 mg, 0.3 mmol) was treated with dry ethanol (2 ml) and amino{2-[(5-nitro(2-pyridyl)amino]ethyl}carboxamidinium 4-methylbenzenesulfonate (180 mg, 0.45 mmol). Then, 0.45 ml of a 1.0 M solution of sodium ethoxide in ethanol was added and the mixture was shaken 0.5 hours at room temperature. Another 0.3 ml of sodium ethoxide solution was added, followed by heating at 70° C. for 2 hours. The solvent was removed in vacuo. The residue was partitioned between dichloromethane and water. The organic layer was dried and concentrated in vacuo, then the resulting residue was dissolved in acetonitrile. Addition of water to the residue/acetonitrile mixture caused the title compound to precipitate as an orange solid.

HPLC: 18.49 min (80% purity)

NMR(300 MHz, DMSO-$d_6$): 8.90 (d, 1H), 8.60 (s, 2H), 8.12 (dd, 1H), 7.65 (m, 2H), 7.24 (m, 2H), 6.60 (d, 1H), 3.58 (m, 4H)

EXAMPLE 68

Synthesis of Ethyl 4-[(2,4-dichlorophenyl)amino]-2-({2-[(5-nitro(2-pyridyl)amino]ethyl}amino)pyrimidine-5-carboxylate
(Solution Method D)
Step 1

Ethyl 2,4-dichloropyrimidine-5-carboxylate (0.49 g, 2 mmol) and 2,4-dichloroaniline (0.33 g, 2 mmol) and DIEA (0.35 ml, 2 mmol) in acetonitrile (6 ml) were heated at 80° C. for 36 hours. The mixture was cooled and the crystalline product, ethyl 4-[(2,4-dichlorophenyl)amino]-2-chloropyrimidine-5-carboxylate, 0.54 g was filtered off.

NMR (300 MHz,CDCl$_3$): 8.90 (s, 1H), 8.44 (d, 1H), 7.45 (d, 1H), 7.32 (dd, 1H), 4.45 (q, 2H), 1.45 (t, 3H)].
Step 2

The pyrimidine from Step 1 (69 mg, 0.2 mmol) was heated with DIEA (100 μL), and (2-aminoethyl)(5-nitro(2-pyridyl))amine (36 mg, 0.2 mmol) in NMP (3 ml) at 105° C. for 14 hours. The reaction was cooled, poured into water and extracted with ethyl acetate. The organic layer was separated, washed with water, dried, then concentrated in vacuo. The crude product was purified by radial chromatography on silica gel, followed by crystallization from a mixture of acetonitrile, methanol and water to give colorless crystals.

HPLC: 30.32 min (>95% purity)

MS: MH$^+$=492–494 (cluster) $C_{20}H_{19}N_7O_4Cl_2$=492 g/mol

EXAMPLE 69

Synthesis of tert-Butyl 6-[(2-{[4-(4-cyanophenyl)-5-ethoxycarbonyl)pyrimidin-2-yl]amino}ethyl)amino]pyridine-3-carboxylate
Step 1

6-Chloro-pyridine-3-carboxylic acid (5.6 g, 36 mmol) was treated with 1,1'-carbonyldiimidazole (6.93 g, 42 mmol) in DMF (40 ml) at 40° C. for 1 hour. Then, t-butanol (9.5 ml, 0.11 mol) and 1,8-Diazabicyclo[5.4.0]undec-7-ene (DBU) (5.38 ml, 36 mmol) were added and heating continued overnight. The mixture was cooled to room temperature and diluted with ether (300 ml). The mixture was extracted once with water. The aqueous layer was back-extracted twice with dichloromethane. The combined organic layers were washed with a saturated aqueous citric acid solution, dried and concentrated in vacuo to give a cream colored solid (7.07 g) (NMR (300 MHz, CDCl$_3$): 8.92 (d, 1H), 8.20 (dd, 1H), 7.40 (d, 1H), 1.60 (s, 9H)).

The tert-butyl 6-chloropyridine-3-carboxylate was heated with ethylenediamine (20 mL) at 80° C. overnight. The solvent was removed in vacuo. The residue was partitioned between dichloromethane and 2.5 M aqueous sodium hydroxide solution. The aqueous layer was extracted a further three times with dichloromethane. The combined organic layers were washed with water, dried and concentrated in vacuo to give tert-butyl 6-[(2-aminoethyl)amino]pyridine-3-carboxylate. NMR (300 MHz, CDCl$_3$): 8.70 (s, 1H), 7.95 (d, 1H), 6.40 (d, 1H), 3.42 (m, 2H), 2.96 (m, 2H), 1.70 (s, 9H)

Step 2 t-Butyl 6-[(2-aminoethyl)amino]pyridine-3-carboxylate (1.42 g, 6 mmol), benzotriazole carboxamidinium 4-methylbenzenesulfonate (2.0 g, 6 mmol) and DIEA (1.05 ml, 6 mmol) were shaken in a mixture of dry acetonitrile (10 ml) and DMF (2 ml) overnight. Ether was added, followed by cooling 4 days at 40° C. The solid was filtered off and dried in vacuo to give tert-butyl 6-{[(2-(amidinoammonium)ethyl]amino}pyridine-3-carboxylate 4-methylbenzenesulfonate (1.87 g). NMR (300 MHz, DMSO-$d_6$): 8.55 (br s, 1H), 7.80 (d, 1H), 7.55 (d, 2H), 7.10 (d, 2H), 6.50 (d, 1H), 3.50 (m, 2H), 3.30 (m, 2H), 2.30 (s, 3H), 1.52 (s, 9H).

Step 3

Ethyl 3-(4-cyanophenyl)-3-oxopropanoate (217 mg, 1.0 mmol) was heated with DMFDMA (200 μl) in dry THF (2 ml) at 70° C. for 5.5 hours. To the cooled solution was added tert-butyl 6-{[(2-(amidinoammonium)ethyl]amino}pyridine-3-carboxylate 4-methylbenzenesulfonate (451 mg, 1.0 mmol) along with dry ethanol (4 ml) and 1.0 M sodium ethoxide in ethanol (1.2 ml). The mixture was heated at 80° C. overnight. The solvents were removed in vacuo. The residue was partitioned between dichloromethane and the saturated aqueous sodium bicarbonate solution. The organic layer was concentrated in vacuo. The residue was dissolved in acetonitrile. Addition of water gave the title compound as a solid (230 mg).

HPLC: 25.90 min (80% purity)

MS: MH$^+$=489 $C_{26}H_{28}N_6O_4$=488 g/mol

EXAMPLE 70

Synthesis of 6-[(2-{[4-cyanophenyl)-5-ethoxycarbonyl)pyrimidin-2-yl]amino}ethyl)amino]pyridine-3-carboxylic Acid tert-Butyl 6-[(2-{[4-(4-cyanophenyl)-5-ethoxycarbonyl)pyrimidin-2-yl]amino}ethyl)amino]pyridine-3-carboxylate (prepared in Example 62, 220 mg) was shaken with 100% TFA for 1 hour at room temperature. The TFA was removed in vacuo. The residue was dissolved in acetonitrile and water was added. No precipitate formed. Several drops of concentrated ammonium hydroxide were added. Then glacial acetic acid was added dropwise until white solid formed. The mixture was then filtered to give the title compound as a white solid (180 mg, after drying).

MS: MH$^+$=433 $C_{22}H_{20}N_6O_4$=432 g/mol

NMR (300 MHZ, DMSO-$d_6$): 8.80 (s, 1H), 8.58 (s, 1H), 7.85 (d, 2H), 7.80 (m, 1H), 7.60 (d, 2H), 6.50 (d, 1H), 4.05 (q, 2H), 3.55 (m, 4H), 1.05 (t, 3H).

EXAMPLE 71

Synthesis of Methyl 6-[(2-{[4-(4-cyanophenyl)-5-ethoxycarbonyl)pyrimidin-2-yl]amino}ethyl)amino]pyridine-3-carboxylate
Step 1

6-[(2-{[4-(4-cyanophenyl)-5-ethoxycarbonyl)pyrimidin-2-yl]amino}ethyl)amino]pyridine-3-carboxylic acid (prepared in Example 70, 120 mg) was dissolved in thionyl chloride (3 ml) and then warmed at 50° C. for 0.5 hours. The solvent was removed in vacuo to give crude ethyl 2-({2-[(5-(chlorocarbonyl)(2-pyridyl))amino]ethyl}amino)-4-(4-cyanophenyl)pyrimidine-5-carboxylate. This compound was dissolved in dry dichloromethane (4 ml).
Step 2

The acid chloride solution prepared in Step 1 (1.0 ml) was treated with dry methanol (1 ml). After standing approximately 1 hour at room temperature, the solvent was removed in vacuo to give the title compound.

HPLC: 20.90 min (95% purity)

MS: MH$^+$=447 $C_{23}H_{22}N_6O_4$=446 g/mol

EXAMPLE 72

Synthesis of Ethyl 4-(4-cyanophenyl)-2-[(2-{[5-(morpholin-4-ylcarbonyl)(2-pyridyl)]amino}ethyl)amino]pyrimidine-5-carboxylate The solution of ethyl 2-({2-[(5-(chlorocarbonyl)(2-pyridyl))amino]ethyl}amino)-4-(4-cyanophenyl)pyrimidine-5-carboxylate in dichloromethane prepared in Step 1 of Example 71 (1.0 ml) was treated at room temperature with a solution of morpholine (150 µL) in dichloromethane (1 ml). After 1 hour the solvent was removed in vacuo to give the title compound.

HPLC: 19.63 min (96% purity)
MS: $MH^+$=502 $C_{26}H_{27}N_7O_4$=501 g/mol.

EXAMPLE 73

Synthesis of Ethyl 4-(4-cyanophenyl-2-{[2-({5-nitro-6[benzylamino](2-pyridyl)}amino)ethyl]amino}pyrimidine-5-carboxylate Step 1

6-Chloro-3-nitro(2-pyridyl))benzylamine was prepared in accordance with the method described in von Bebenberg, *Chemiker-Zeitung*, 103:387 (1979), which is incorporated herein by reference. This amine (1.8 g) was heated with ethylenediamine (5 ml) in acetonitrile (15 ml) at 100° C. for 3.5 hours. The solvent was removed in vacuo and the residue was partitioned between dichloromethane and 2.5 M aqueous sodium hydroxide solution. The aqueous layer was extracted 3× further with dichloromethane. The combined organic layers were washed with a satured sodium chloride solution, dried and concentrated in vacuo to give a yellow solid. NMR (300 MHz, $CDCl_3$): 8.10 (d, 1H), 7.2–7.4 (m, 5H), 5.80 (s, 1H), 4.80 (AB q, 2H), 3.42 (m, 2H), 2.85 (m, 2H).

Step 2

The amine from Step 1 (1.31 g) was treated with benzotriazole carboxamidinium 4-methylbenzenesulfonate (1.52 g) and DIEA (800 µl) in acetonitrile (15 ml) at room temperature overnight. The mixture was diluted with ether, then filtered to give the guanidine, amino [2-({5-nitro-6-[benzylamino](2-pyridyl)}amino)ethyl]carboxamidinium 4-methylbenzenesulfonate, as a yellow solid. NMR (300 MHz, DMSO-$d_6$): 8.02 (d, 1H), 7.72 (d, 2H), 7.30–7.40 (m, 5H), 7.10 (d, 2H), 6.00 (d, 1H), 4.78 (AB q, 2H), 3.50 (m, 2H), 3.30 (m, 2H), 2.25 (s, 3H).

Step 3

Ethyl 3-(4-cyanophenyl)-3-oxopropanoate (65 mg, 0.3 mmol) was heated with DMFDMA (60 µL) in THF (1 ml) at 70° C. for 3 h. This solution was then added to a mixture of the guanidine prepared in Step 2 (150 mg, 0.3 mmol), dry ethanol (1 ml) and 1.0 M sodium ethoxide in ethanol (0.35 ml) and heated at 80° C. overnight. The solvents were removed in vacuo. The residue was partitioned between dichloromethane and saturated aqueous sodium bicarbonate solution. The organic layer was concentrated in vacuo. The residue was dissolved in acetonitrile. Addition of water gave the title compound as a yellow solid.

HPLC: 34.06 min (98% purity)
MS: $MH_+$=539 $C_{28}H_{26}N_8O_4$=538 g/mol

EXAMPLE 74

Screening for GSK3 Inhibitory Activity Using a Cell-Free Assay

Pyrimidine and pyridine compounds of the present invention were dissolved in DMSO, then tested for inhibition of human GSK3β (SEQ ID NO: 1) (the nucleotide sequence for human GSK3β appears in GenBank under Accession No. L33801). Expression of GSK3β is described, for example, in Hughes et al., *Eur. J. Biochem.*, 203:305–11 (1992), which is incorporated herein by reference.

An aliquot of 300 µl of substrate buffer (30 mM tris-HCl, 10 mM $MgCl_2$, 2 mM DTT, 3 µg/ml GSK3β (SEQ ID NO: 1) and 0.5 µM-biotinylated prephosphorylated SGSG-linked CREB peptide (Chiron Technologies PTY Ltd., Clayton, Australia) (SEQ ID NO: 2) was dispensed into wells of a 96 well polypropylene microtiter plate. 3.5 µl/well of DMSO containing varying concentrations of each compound to be assayed or staurosporine (a known kinase inhibitor used as a positive control, or a negative control (i.e., DMSO only), was added and mixed thoroughly. The reactions were then initiated by adding 50 µl/well of 1 µM unlabeled ATP and 1–2×$10^7$ cpm $\gamma^{33}$P-labeled ATP, and the reaction was allowed to proceed for about three hours at room temperature.

While the reaction was proceeding, streptavidin-coated Labsystems "Combiplate 8" capture plates (Labsystems, Helsinki, Finland) were blocked by incubating them with 300 µl/well of PBS containing 1% bovine serum albumin for at least one hour at room temperature. The blocking solution was then removed by aspiration, and the capture plates were filled with 100 µl/well of stopping reagent (50 µM ATP/20 mM EDTA).

When the three hour enzyme reaction was finished, triplicate 100 µl aliquots of each reaction mix were transferred to three wells containing stopping solution, one well on each of the three capture plates, and the well contents were mixed well. After one hour at room temperature, the wells of the capture plates were emptied by aspiration and washed five times using PBS and a 12 channel Corning 430474 ELISA plate washer. Finally, 200 µl of Microscint-20 scintillation fluid was added to each well of the plate. The plates were coated with plate sealers, then left on a shaker for 30 minutes. Each capture plate was counted in a Packard TopCount scintillation counter (Meridian, Conn.) and the results were plotted as a function of compound concentration.

Compounds of the present invention were then screened for inhibitory activity against GSK3 according to this assay. The following compounds exhibited $IC_{50}$s of 10 µM or less with respect to GSK3 in this cell-free assay: (4-phenylpyrimidin-2-yl)(2-(2-pyridyl)ethyl)amine, (4-phenylpyrimidin-2-yl)[2-(2-pyridylamino)ethyl]amine, [2-(2-pyridylamino)ethyl](4-(3-pyridyl)pyrimidin-2-yl)amine, 4-{2-[(2-(2-pyridyl)ethyl)amino]pyrimidin-4-yl}benzenecarbonitrile, 4-{2-[(4-pyridylmethyl)amino]pyrimidin-4-yl}benzamide, 4-{2-[(3-imidazol-5-ylethyl)amino]pyrimidin-4-yl}benzamide, 4-(2-{[2-(2-pyridylamino)ethyl]amino}pyrimidin-4-yl)benzenecarbonitrile,4-methyl-2-({2-[(5-nitro(2-pyridyl))amino]ethyl}amino)pyrimidine-5-carboxylic acid, 4-(2-{[(3-methylphenyl)methyl]amino}pyrimidin-4-yl)benzamide, 4-(2-{[(4-aminophenyl)methyl]amino}pyrimidin-4-yl)benzamide, (5-ethyl-4-phenylpyrimidin-2-yl)[2-(2-pyridylamino)ethyl]amine, 4-(2-{[(5-methylpyrazin-2-yl)methyl]amino}pyrimidin-4-yl)benzamide, 4-{2-[(3-phenoxypropyl)amino]pyrimidin-4-yl}phenol, 4-{2-[(3-imidazolylpropyl)amino]pyrimidin-4-yl}benzamide, [4-(3,4-difluorophenyl)pyrimidin-2-yl][2-(2-pyridylamino)ethyl]amine, 4-(2-{[(4-cyanophenyl)methyl]amino}pyrimidin-4-yl)benzamide,4-{2-[(2-phenoxyethyl)amino]pyrimidin-4-yl}benzamide, 4-(2-{[(3-methoxyphenyl)methyl]amino}pyrimidin-4-yl)benzamide, 4-(2-{[(4-methoxyphenyl)methyl]amino}pyrimidin-4-yl)benzamide, 4-(2-{[2-(4-fluorophenyl)ethyl]

amino}pyrimidin-4-yl)benzamide, [2-(2,5-dimethoxyphenyl)ethyl](4-(3-pyridyl)pyrimidin-2-yl)amine, [4-(4-nitrophenyl)pyrimidin-2-yl][2-(2-pyridylamino)ethyl]amine, {2-[(5-nitro(2-pyridyl))amino]ethyl}(4-pyrazin-2-ylpyrimidin-2-yl)amine, ethyl 4-(2-furyl)-2-[(2-(2-pyridyl)ethyl)amino]pyrimidine-5-carboxylate, 4-(2-{[(3-chlorophenyl)methyl]amino}pyrimidin-4-yl)benzamide, [4-(4-chlorophenyl)-5-methylpyrimidin-2-yl][2-(2-pyridylamino)ethyl]amine, 4-{2-[(3-benzimidazolylpropyl)amino]pyrimidin-4-yl}phenol, 4-{2-[(4-phenylbutyl)amino]pyrimidin-4-yl}benzamide, 4-{2-[(2-(3-methoxyphenyl)ethyl)amino}pyrimidin-4-yl)benzamide, 4-{2-[(3-phenoxypropyl)amino]pyrimidin-4-yl}benzamide, 4-(2-{[(3-nitrophenyl)methyl]amino}pyrimidin-4-yl)benzamide, 4-[2-({2-[(5-nitro-2-pyridyl)amino]ethyl}amino)pyrimidin-4-yl]phenol, 3-[2-({2-[(5-nitro-2-pyridyl)amino]ethyl}amino)pyrimidin yl]phenol, 4-(2-{[2-(3-chlorophenyl)ethyl]amino}pyrimidin-4-yl)benzamide, 4-{2-[(naphthylmethyl)amino]pyrimidin-4-yl}benzamide, [5-(4-fluorophenyl)pyrimidin-2-yl]{2-[(5-nitro(2-pyridyl))amino]ethyl}amine, 4-(2-{[3-(4chlorophenoxy)propyl]amino}pyrimidin-4-yl)phenol, [4-(4-imidazolylphenyl)pyrimidin-2-yl][2-(2-pyridylamino)ethyl]amine, 4-(2-{[3-(2-aminobenzimidazolyl)propyl]amino}pyrimidin-4-yl)phenol, 4-(2-{[2-(2,5-dimethoxyphenyl)ethyl]amino}pyrimidin-4-yl)benzenecarbonitrile, [4-(2,4-dichlorophenyl)pyrimidin-2-yl][2-(2-pyridylamino)ethyl]amine, 3-[2-({2-[(5-nitro-2-pyridyl)amino]ethyl}amino)pyrimidin-4-yl]benzenecarbonitrile, 4-(2-{[3-(3-methylphenoxy)propyl]amino}pyrimidin-4-yl)benzamide, 4-{2-[(2-(2H-benzo[3,4-d]1,3-dioxolen-5-yl)ethyl)amino]pyrimidin-4-yl}benzamide, 4-(2-{(2-(4-nitrophenyl)ethyl]amino}pyrimidin-4-yl)benzamide, 4-({2-{[(2,6-dimethoxyphenyl)methyl]amino}pyrimidin-4-yl)benzamide, 4-(2-{[(3,4-dimethoxyphenyl)methyl]amino}pyrimidin-4-yl)benzamide, [2-({2-[(5-nitro(2-pyridyl))amino]ethyl}amino)pyrimidin-4-yl]benzylamine, ethyl 4-(4-fluorophenyl)-2-[(2-(2-pyridyl)ethyl)amino]pyrimidine-5-carboxylate, [4-(2,4-dimethyl(1,3-thiazol-5-yl))pyrimidin-2-yl]{2-[(5-nitro(2-pyridyl))amino]ethyl}amine, [4-(4-methyl-1-phenylpyrazol-3-yl)pyrimidin-2-yl][2-(2-pyridylamino)ethyl]amine, 4-[2-({[3-(trifluoromethyl)phenyl]methyl}amino)pyrimidin-4-yl]benzamide, 4-[2-({[4-(trifluoromethyl)phenyl]methyl}amino)pyrimidin-4-yl]benzamide, 4-(2-{[(3,5-dichlorophenyl)methyl]amino}pyrimidin-4-yl)benzamide, 4-{2-[4-benzylpiperazinyl]pyrimidin4-yl}benzamide, 4-(2-{[(2,4-dichlorophenyl)methyl]amino}pyrimidin-4-yl)benzamide, ethyl 4-(4-cyanophenyl)-2-[(2-(2-pyridyl)ethyl)amino]pyrimidine-5-carboxylate, [2-(2-pyridylamino)ethyl]{4-[4-(trifluoromethoxy)phenyl]pyrimidin-2-yl}amine, {6(2-methoxyethyl)amino]-5-nitro(2-pyridyl)}{2-[(5-nitro(2-pyridyl))amino]ethyl}amine, 4-(2-{[3-(3-methoxyphenoxy)propyl]amino}pyrimidin-4-yl)benzamide, ethyl 4-(4-methoxyphenyl)-2-[(2-(2-pyridyl)ethyl)amino]pyrimidine-5-carboxylate, [(3-methylphenyl)methyl][2-({2-[(5-nitro(2-pyridyl)}amino]ethyl}amino)pyrimidin-4-yl]amine, 4-(2-{[3-(4-phenylimidazolyl)propyl]amino}pyrimidin-4-yl)benzenecarbonitrile, 4-{2-[(3-benzimidazolylpropyl)amino]pyrimidin-4-yl}-2-chlorophenol, 4-[2-({3-[4-(2,4-dichlorophenyl)imidazolyl]propyl}amino)pyrimidin-4-yl]benzamide, 4-[2-({3-[4-(3-methoxyphenyl)imidazolyl]propyl}amino)pyrimidin-4-yl]benzamide, (3-benzimidazolylpropyl)[4-(4-imidazolylphenyl)pyrimidin-2-yl]amine, N-{4-[2-({2-[(5-nitro-2-pyridyl)amino]ethyl}amino)pyrimidin-4-yl]phenyl}acetamide, 4-(2-{[3-(4-chlorophenoxy)propyl]amino}pyrimidin-4-yl)benzamide, 4-(2-{[(4-bromophenyl)methyl]amino}pyrimidin-4-yl)benzamide, 4-[2-({[4-(4-fluorophenyl)phenyl]methyl}amino)pyrimidin-4-yl]benzamide, 4-(2-{[(3-bromophenyl)methyl]amino}pyrimidin-4-yl)benzamide, 6-{[2-({5-nitro-6-[benzylamino]-2-pyridyl}amino)ethyl]amino}pyridine-3-carbonitrile, ethyl 4-(4-cyanophenyl)-2-{[2-(pyrimidin-2-ylamino)ethyl]amino}pyrimidine-5-carboxylate, 4-{2-[4-(2-methoxyphenyl)piperazinyl]pyrimidin-4-yl}benzamide, 4-(2-{[2-benzothiazol-2-ylamino)ethyl]amino}pyrimidin-4-yl)benzamide, ethyl 4-(3-nitrophenyl)-2-[(2-(2-pyridyl)ethyl)amino]pyrimidine-5-carboxylate, 6-methyl-2-({2-[(5-nitro(2-pyridyl))amino]ethyl}amino)-4-phenylpyrimidine-5-carboxylic acid, 4-{2-[(2,2-diphenylethyl)amino]pyrimidin-4-yl}benzamide, 4-(2-{[(3,4,5-trimethoxyphenyl)methyl]amino}pyrimidin-4-yl)benzamide, methyl 2-({2-[(5-nitro(2-pyridyl))amino]ethyl}amino)-4-(3-pyridyl)pyrimidine-5-carboxylate, 4-[2-({[3-(3-aminophenyl)phenyl]methyl}amino)pyrimidin-4-yl]benzamide, 4-[2-({[4-(3-aminophenyl)phenyl]methyl}amino)pyrimidin-4-yl]benzamide, 4-{2-[(3-(2-naphthyloxy)propyl)amino]pyrimidin-4-yl}benzamide, 4-{2-[(3-(6-quinolyloxy)propyl)amino]pyrimidin-4-yl}benzamide, [(3-chlorophenyl)methyl][2-({2-[(5-nitro(2-pyridyl))amino]ethyl}amino)pyrimidin-4-yl]amine, [(4-chlorophenyl)methyl][2-({2-[(5-nitro(2-pyridyl))amino]ethyl}amino)pyrimidin-4-yl]amine, ethyl 4-(4-cyanophenyl)-2-{[2-(3-methoxyphenyl)ethyl]amino}pyrimidine-5-carboxylate, ethyl 2-({2-[(5-amino(2-pyridyl))amino]ethyl}amino)-4-(4-cyanophenyl)pyrimidine-5-carboxylate, 4-[5-nitro-2-({2-[(5-nitro(2-pyridyl))amino]ethyl}amino)pyrimidin-4-yl]benzenecarbonitrile, ethyl 4-[2-({2-[(5-nitro-2-pyridyl)amino]ethyl}amino)pyrimidin-4-yl]benzoate, ethyl 4-(3-nitrophenyl)-2-{[2-(2-pyridylamino)ethyl]amino}pyrimidine-5-carboxylate, N-benzyl(4-{2-[(2-(2-pyridyl)ethyl)amino]pyrimidin-4-yl}phenyl)carboxamide, {2-[(5-nitro(2-pyridyl))amino]ethyl}{5-nitro-6-[benzylamino](2-pyridyl)}amine, 4-(2-methoxyphenyl)-2-({2-[(5-nitro(2-pyridyl))amino]ethyl}amino)pyrimidine-5-carboxylic acid, 4-[2-({[3-(3-methoxyphenyl)phenyl]methyl}amino)pyrimidin-4-yl]benzamide, 4-[2-({2-[(5-nitro-2-pyridyl)amino]ethyl}amino)pyrimidin-4-yl]benzenesulfonamide, 4-(2-{[3-(2,4-dichlorophenoxy)propyl]amino}pyrimidin-4-yl)benzamide, 4-(2-{[3-(3,4-dichlorophenoxy)propyl]amino}pyrimidin-4-yl)benzamide, 4-(2-{[3-(3-phenylphenoxy)propyl]amino}pyrimidin-4-yl)benzamide, 4-(2-{[(3-{3-[(methylamino)methyl]phenyl}phenyl)methyl]amino}pyrimidin-4-yl)benzamide, ethyl 4-(3-fluorophenyl)-2-({2-[(5-nitro(2-pyridyl))amino]ethyl}amino)pyrimidine-5-carboxylate, [4-phenyl-5-benzylpyrimidin-2-yl][2-(2-pyridylamino)ethyl]amine, 4-(2-{[3-(3-bromophenoxy)propyl]amino}pyrimidin-4-yl)benzamide, 4-[2-({2-[(5-nitro(2-pyridyl))amino]ethyl}amino)-5-phenylpyrimidin-4-yl]phenol, 4-(2,4-dichlorophenyl)-2-({2-[(5-nitro(2-pyridyl))amino]ethyl}amino)pyrimidine-5-carbonitrile, 4-(3,4-dichlorophenyl)-2-({2-[(5-nitro(2-pyridyl))amino]ethyl}amino)pyrimidine-5-carbonitrile, 6-[(2-{[4-(4-cyanophenyl)-5-(ethoxycarbonyl)pyrimidin-2-yl]amino}ethyl)amino]pyridine-3-carboxylic acid, ethyl 4-(3-cyanophenyl)-2-({2-[(5-nitro(2-pyridyl))amino]ethyl}amino)pyrimidine-5-carboxylate, [(3,5-dichlorophenyl)methyl][2-({2-[(5-nitro(2-pyridyl))amino]ethyl}amino)pyrimidin-4-yl]amine, [(2,4-dichlorophenyl)methyl][2-({2-[(5-nitro(2-pyridyl))amino]ethyl}amino pyrimidin-4-yl]amine, ethyl 4-(4-carbamoylphenyl)-6-ethyl-2-{[2-(2-pyridylamino)ethyl]amino}pyrimidine-5-carboxylate, ethyl 4-(4-carbamoylphenyl)-6-ethyl-2-{[2-(pyrimidin-2-ylamino)ethyl]amino}pyrimidine-5-carboxylate, ethyl 4-(3,4-dimethylphenyl)-2-({2-[(5-nitro(2-pyridyl))amino]ethyl}amino)pyrimidine-5-carboxylate, N-(2-methoxyethyl){4-[2-({2-[(5-nitro(2-pyridyl))amino]ethyl}amino)pyrimidin-4-yl]phenyl}carboxamide, 4-{2-[({3-[3-(acetylamino)phenyl]phenyl}methyl)amino]pyrimidin-4-yl}benzamide, ethyl 4-(4-cyanophenyl)-2-{[2-(2-quinolylamino)ethyl]amino}pyrimidine-5-carboxylate, 4-[2-({[3,5-bis(trifluoromethyl)phenyl]methyl}amino)pyrimidin-4-yl]benzamide, ethyl 4-(2,4-difluorophenyl)-2-({2-[(5-nitro(2-pyridyl))amino]ethyl}amino)pyrimidine-5-carboxylate, (4-{[(3-bromophenyl)methyl]amino}pyrimidin-2-yl){2-[(5-nitro(2-pyridyl))amino]ethyl}amine, 2-({2-[(6-amino-5-nitro(2-pyridyl))amino]ethyl}amino)-4-(3,4-dichlorophenyl)pyrimidine-5-carbonitrile,methyl 6-[(2-{[4-(4-cyanophenyl)-5-(ethoxycarbonyl)pyrimidin-2-yl]amino}ethyl)amino]pyridine-3-carboxylate, 4-{2-[({3-[3-(trifluoromethyl)phenyl]phenyl}methyl)amino]pyrimidin-4-yl}benzamide, [4-(4-benzimidazolylphenyl)pyrimidin-2-yl]{2-[(5-nitro(2-pyridyl))amino]ethyl}amine,ethyl 2-({2-[(5-nitro(2-pyridyl))amino]ethyl}amino)-4-(3-nitrophenyl)pyrimidine-5-carboxylate, ethyl 4-naphthyl-2-({2-[(5-nitro(2-pyridyl))amino]ethyl}amino)pyrimidine-5-carboxylate, ethyl 2-({2-[(5-nitro(2-pyridyl))amino]ethyl}amino)-4-(3-quinolyl)pyrimidine-5-carboxylate, ethyl 4-(4-cyanophenyl)-2-[(2-{[5-(N-ethylcarbamoyl)(2-pyridyl)]amino}ethyl)amino]pyrimidine-5-carboxylate, benzyl{[4-(2-{[2-(2-pyridylamino)ethyl]amino}pyrimidin-4-yl)phenyl]sulfonyl}amine, ethyl 4-(4-cyanophenyl)-2-[(2-{[6-(methylamino)-5-nitro(2-pyridyl)]amino}ethyl)amino]pyrimidine-5-carboxylate, {4-[2-({2[(5-nitro(2-pyridyl))amino]ethyl}amino)pyrimidin-4-yl]phenyl}-N-(oxolan-2-ylmethyl)carboxamide, N-(1-carbamoyl-2-phenylethyl)[4-methyl-2-({2-[(5-nitro(2-pyridyl))amino]ethyl}amino)pyrimidin-5-yl]carboxamide, N-(1-carbamoyl-2-phenylethyl)(4-{2-[(2-(2-pyridyl)ethyl)amino]pyrimidin-4-yl}phenyl)carboxamide, ethyl 4-(3,4-dimethoxyphenyl)-2-({2-[(5-nitro(2-pyridyl))amino]ethyl}amino)pyrimidine-5-carboxylate, {4-[2-({2-[(5-nitro(2-pyridyl))amino]ethyl}amino)pyrimidin-4-yl]phenyl}-N-benzylcarboxamide, {4-[2-({2-[(5-nitro(2-pyridyl))amino]ethyl}amino)pyrimidin-4-yl]phenyl}-N-(3-pyridylmethyl)carboxamide, {4-[4-(4,5-dichloroimidazol-2-yl)phenyl]pyrimidin-2-yl}{2-[(5-nitro(2-pyridyl))amino]ethyl}amine, ethyl 4-(4-butoxyphenyl)-2-({2-[(5-nitro(2-pyridyl))amino]ethyl}amino)pyrimidine-5-carboxylate, ethyl 4-{[(2-chlorophenyl)methyl]amino}-2-({2-[(5-nitro(2-pyridyl))amino]ethyl}amino)pyrimidine-5-carboxylate, 6-(2-fluorophenyl)-2-({2-[(5-nitro(2-pyridyl))amino]ethyl}amino)-4-phenylpyrimidine-5-carboxylic acid, {4-[2-({2-[(5-nitro(2-pyridyl))amino]ethyl}amino)pyrimidin-4-yl]phenyl}-N-(2-thienylmethyl)carboxamide, ethyl 2-({2-[(5-nitro(2-pyridyl))amino]ethyl}amino)-4-[3-(trifluoromethyl)phenyl]pyrimidine-5-carboxylate, ethyl 4-(3,4-dichlorophenyl)-2-({2-[(5-nitro(2-pyridyl))amino]ethyl}amino)pyrimidine-5-carboxylate, ethyl 4-(3,5-dichlorophenyl)-2-({2-[(5-nitro(2-pyridyl))amino]ethyl}amino)pyrimidine-5-carboxylate, {4-[2-({2-[(5-nitro(2-pyridyl))amino]ethyl}amino)pyrimidin-4-yl]phenyl}-N-(4-piperidylmethyl)carboxamide, (6-{[(2,4-dichlorophenyl)methyl]amino}-5-nitro(2-pyridyl)){2-[(5-nitro(2-pyridyl))amino]ethyl}amine, ethyl 4-(4-carbamoylphenyl)-6-ethyl-2-({2-[(3-nitro(2-pyridyl))amino]ethyl}amino)pyrimidine-5-carboxylate, ethyl 4-[4-(diethylamino)phenyl]-2-({2-[(5-nitro(2-pyridyl))amino]ethyl}amino)pyrimidine-5-carboxylate, {4-[2-({2-[(5-nitro(2-pyridyl))amino]ethyl}amino)pyrimidin-4-yl]phenyl}-N-(2-phenylethyl)carboxamide, N-[(3-methylphenyl)methyl]{4-[2-({2-[(5-nitro(2-pyridyl))amino]ethyl}amino)pyrimidin-4-yl]phenyl}carboxamide, 2-({2-[(5-nitro(2-pyridyl))amino]ethyl}amino)-4-(2,4,6-trichlorophenyl)pyrimidine-5-carboxylic acid, ethyl 2-({2-[(5-nitro(2-pyridyl))amino]ethyl}amino)-4-(4-phenylphenyl)pyrimidine-5-carboxylate, {4-[2-({2-[(6-amino-5-nitro(2-pyridyl))amino]ethyl}amino)pyrimidin-4-yl]phenyl}-N-benzylcarboxamide, N-[(5-methylpyrazin-2-yl)methyl]{4-[2-({2-[(5-nitro(2-pyridyl))amino]ethyl}amino)pyrimidin-4-yl]phenyl}carboxamide, N-[(3-fluorophenyl)methyl]{4-[2-({2-[(5-nitro(2-pyridyl))amino]ethyl}amino)pyrimidin-4-yl]phenyl}carboxamide, ethyl 2-({2-[(5-nitro(2-pyridyl))amino]ethyl}amino)-4-(4-sulfamoylphenyl)pyrimidine-5-carboxylate, N-[(4-fluorophenyl)methyl]{4-[2-({2-[(5-nitro(2-pyridyl))amino]ethyl}amino)pyrimidin-4-yl]phenyl}carboxamide, [4-(2-{[(3-bromophenyl)methyl]amino}pyrimidin-4-yl)phenyl]-N-[(3-methylphenyl)methyl]carboxamide, ethyl 4-(5-bromo(3-pyridyl))-2-({2-[(5-nitro(2-pyridyl))amino]ethyl}amino)pyrimidine-5-carboxylate, N-(3-imidazolylpropyl){4-[2-({2-[(5-nitro(2-pyridyl))amino]ethyl}amino)pyrimidin-4-yl]phenyl}carboxamide, tert-butyl 6-[(2-{[4-(4-cyanophenyl)-5-(ethoxycarbonyl)pyrimidin-2-yl]amino}ethyl)amino]pyridine-3-carboxylate, N-[(3-bromophenyl)methyl](4-{2-[(3-imidazolylpropyl)amino]pyrimidin-4-yl}phenyl)carboxamide, ethyl 4-(2,4-dichlorophenyl)amino]-2-({2-[(5-nitro(2-pyridyl))amino]ethyl}amino)pyrimidine-5-carboxylate, ethyl 4-(4-carbamoylphenyl)-6-ethyl-2-({3-[(5-nitro(2-pyridyl))amino]propyl}amino)pyrimidine-5-carboxylate, {4-[2-({2-[(5-nitro(2-pyridyl))amino]ethyl}amino)pyrimidin-4-yl]phenyl}-N-(2-Phenylcyclopropyl)carboxamide, N-[(4-methoxyphenyl)methyl]{4-[2-({2-[(5-nitro(2-pyridyl))amino]ethyl}amino)pyrimidin-4-yl]phenyl}carboxamide, 2-({2-[(5-nitro(2-pyridyl))amino]ethyl}amino)-6-(4-nitrophenyl)-4-phenylpyrimidine-5-carboxylic acid, 2-({2-[(5-nitro(2-pyridyl))amino]ethyl}amino)-6-(4-nitrophenyl)-4-(4-pyridyl)pyrimidine-5-carboxylic acid, ethyl 4-(4-carbamoylphenyl)-6-ethyl-2-[(2-{[5-(trifluoromethyl)(2-pyridyl)]amino}ethyl)amino]pyrimidine-5-carboxylate, ethyl 4-(4-cyanophenyl)-2-[(2-{[5-(morpholin-4-ylcarbonyl)(2-pyridyl)]amino}ethyl)amino]pyrimidine-5-carboxylate, N-[(3-chlorophenyl)methyl]{4-[2-({2-[(5-nitro(2-pyridyl))amino]ethyl}amino)pyrimidin-4-yl]phenyl}carboxamide, N-[(3,4-difluorophenyl)methyl]{4-[2-({2-[(5-nitro(2-pyridyl))amino]ethyl}amino)pyrimidin-4-yl]phenyl}carboxamide, ethyl 4-[4-(4-methylpiperazinyl)phenyl]-2-({2-[(5-nitro(2-pyridyl))amino]ethyl}amino)pyrimidine-5-carboxylate, 4-cyclohexyl-2-({2-[(5-nitro(2-pyridyl))amino]ethyl}amino)-6-(4-nitrophenyl)pyrimidine-5-carboxylic acid, {4-[2-({2-[(5-nitro(2-pyridyl))amino]ethyl}amino)pyrimidin-4-yl]phenyl}-N-[(3-nitrophenyl)methyl]carboxamide, ethyl 4-{[(3-bromophenyl)methyl]amino}-2-({2-[(5-nitro(2-pyridyl))amino]ethyl}amino)pyrimidine-5-carboxylate, N-[(3-bromophenyl)methyl][4-(2-{[2-(3-methoxyphenyl)ethyl]amino}pyrimidin-4-yl)phenyl]carboxamide, N-(naphthylmethyl){4-[2-({2-[(5-nitro(2-pyridyl))amino]ethyl}amino)pyrimidin-4-yl]phenyl}carboxamide, 4-(3-cyanophenyl)-2-({2-[(5-nitro(2-pyridyl))amino]ethyl}amino)-6-(4-nitrophenyl)pyrimidine-5-carboxylic acid, N-[(3,4-dimethoxyphenyl)methyl]{4-[2-({2-[(5-nitro(2-pyridyl))amino]ethyl}amino)pyrimidin-4- yl]phenyl}carboxamide, N-[(2,3-dimethoxyphenyl)methyl]{4-[2-({2-[(5-nitro(2-pyridyl))amino]ethyl}amino)pyrimidin-4-yl]phenyl}carboxamide, 4-(4-methoxyphenyl)-2-({2-[(5-nitro(2-pyridyl))amino]ethyl}amino)-6-(4-nitrophenyl)pyrimidine-5-carboxylic acid, N-[(3-bromophenyl)methyl]{4-[2-({2-[(6-methoxy(2-pyridyl))amino]ethyl}amino)pyrimidin-4-yl]phenyl}carboxamide, {4-[2-({2-[(5-nitro(2-pyridyl))amino]ethyl}amino)pyrimidin-4-yl]phenyl}-N-{[3-(trifluoromethyl)phenyl]methyl}carboxamide, N-[(3,5-dichlorophenyl)methyl]{4-[2-({2-[(5-nitro(2-pyridyl))amino]ethyl}amino)pyrimidin-4-yl]phenyl}carboxamide, N-[(3,4-dichlorophenyl)methyl]{4-[2-({2-[(5-nitro(2-pyridyl))amino]ethyl}amino)pyrimidin-4-yl]phenyl}carboxamide, ethyl 4-(4-cyanophenyl)-2-{[2-({5-nitro-6-[benzylamino](2-pyridyl)}amino)ethyl]amino}pyrimidine-5-carboxylate, ethyl 4-[3,5-bis(trifluoromethyl)phenyl]-2-({2-[(5-nitro(2-pyridyl))amino]ethyl}amino)pyrimidine-5-carboxylate, 4,6-bis(4-nitrophenyl)-2-({2-[(5-nitro(2-pyridyl))amino]ethyl}amino)pyrimidine-5-carboxylic acid, [4-(2-{[2-(2,5-dimethoxyphenyl)ethyl]amino}pyrimidin-4-yl)phenyl]-N-[(3-bromophenyl)methyl]carboxamide, 2-({2-[(5-nitro(2-pyridyl))amino]ethyl}amino)-4-(3-nitrophenyl)-6-(4-nitrophenyl)pyrimidine-5-carboxylic acid, N-[(3-bromophenyl)methyl]{4-[2-({2-[(4-nitrophenyl)amino]ethyl}amino)pyrimidin-4-yl]phenyl}carboxamide, N-[(3-bromophenyl)methyl]{4-[2-({2-[(5-nitro(2-pyridyl))amino]ethyl}amino)pyrimidin-4-yl]phenyl}carboxamide, N-[(4-bromophenyl)methyl]{4-[2-({2-[(5-nitro(2-pyridyl))amino]ethyl}amino)pyrimidin-4-yl]phenyl}carboxamide, {4-[2-({2-[(5-nitro(-2-pyridyl))amino]ethyl}amino)pyrimidin-4-yl]phenyl}-N-[(4-sulfamoylphenyl)methyl]carboxamide, N-[2-(2,4-dichlorophenyl)ethyl]{4-[2-({2-[(5-nitro(2-pyridyl))amino]ethyl}amino)pyrimidin-4-yl]phenyl}carboxamide, N-[(3-bromophenyl)methyl][4-(2-{[2-(2-quinolylamino)ethyl]amino}pyrimidin-4-yl)phenyl]carboxamide, 2-({2-[(5-nitro(2-pyridyl))amino]ethyl}amino)-6-(4-nitrophenyl)-4-(4-quinolyl)pyrimidine-5-carboxylic acid, N-(2,2-diphenylmethyl){4-[2-({2-[(5-nitro(2-pyridyl))amino]ethyl}amino)pyrimidin-4-yl]phenyl}carboxamide, N-[(3-bromophenyl)methyl]{4-[2-({3-[(5-nitro(2-pyridyl))amino]propyl}amino)pyrimidin-4-yl]phenyl}carboxamide, {4-[2-({2-[(6-amino-5-nitro(2-pyridyl))amino]ethyl}amino)pyrimidin-4-yl]phenyl}-N-[(3-bromophenyl)methyl]carboxamide, 2-({2-[(5-nitro(2-pyridyl))amino]ethyl}amino)-6-(4-nitrophenyl)-4-[4-(trifluoromethyl)phenyl]pyrimidine-5-carboxylic acid, N-[(3-bromophenyl)methyl](4-{2-[(2-{[5trifluoromethyl](2-pyridyl)]amino}ethyl)amino]pyrimidin-4-yl}phenyl)carboxamide, [(3-bromophenyl)methyl]({4-[2-({2-[(5-nitro(2-pyridyl))amino]ethyl}amino)pyrimidin-4-yl]phenyl}sulfonyl)amine, and N-[(3-iodophenyl)methyl]{4-[2-({2-[(5-nitro(2-pyridyl))amino]ethyl}amino)pyrimidin-4-yl]phenyl}carboxamide.

The following compounds exhibited $IC_{50}$s of 1 µM or less with respect to GSK3 in this cell-free assay: 4-{2-[(2-(2-pyridyl)ethyl)amino]pyrimidin-4-yl}benzamide, 4-{2-[(2-phenylpropyl)amino]pyrimidin-4-yl}benzamide, 4-(2-{[2-]2-pyridylamino)ethyl]amino}pyrimidin-4-yl)benzamide, 4-(2-{[2-(pyrimidin-2-ylamino)ethyl]amino}pyrimidin-4-yl)benzamide, (5-nitro-4-phenylpyrimidin-2-yl)[2-(2-pyridylamino)ethyl]amine, 4-(2-{[3-(4-nitroimidazolyl)propyl]amino}pyrimidin-4-yl)phenol, 4-(2-{[2-(2-methoxyphenyl)ethyl]amino}pyrimidin-4-yl)benzamide, 4-[2-({2-[(5-cyano-2-pyridyl)amino]ethyl}amino)pyrimidin-4-yl]benzamide, 2-({2-[(5-nitro(2-pyridyl))amino]ethyl}amino)-4-phenylpyrimidine-5-carbonitrile, 4-[2({2-[(6-methoxy-2-pyridyl)amino]ethyl}amino)pyrimidin-4-yl]benzamide, 4-(2-{[3-(4,5-dichloroimidazolyl)propyl]amino}pyrimidin-4-yl)phenol, 4-(2-{[3-(4-nitroimidazolyl)propyl]amino}pyrimidin-4-yl)benzamide, 4-{2-[(3-benzimidazolylpropyl)amino]pyrimidin-4-yl}benzamide, 4-[2-({2-[(4-amino-5-cyanopyrimidin-2-yl)amino]ethyl}amino)pyrimidin-4-yl]benzamide, 4-{2-[(3-benzimidazolylpropyl)amino]pyrimidin-4-yl}-2-methoxyphenol, 4-(2-{[2-(2,5-dimethoxyphenyl)ethyl]amino}pyrimidin-4-yl)benzamide, 4-(2-{[2-(2,3-dimethoxyphenyl)ethyl]amino}pyrimidin-4-yl)benzamide, 4-(2-{[3-(4-methoxyphenoxy)propyl]amino}pyrimidin-4-yl)benzamide, 4-[2-({2-[(5-nitro-2-pyridyl)amino]ethyl}amino)pyrimidin-4-yl]benzamide, {2-[(5-nitro(2-pyridyl))amino]ethyl}(5-nitro4-phenylpyrimidin-2-yl)amine, 4-(2-{[2-(2-quinolylamino)ethyl]amino}pyrimidin-4-yl)benzamide, 4-(4-cyanophenyl)-2-({2-[(5-nitro(2-pyridyl))amino]ethyl}amino)pyrimidine-5-carbonitrile, 4-(2-{[3-(4,5-dichloroimidazolyl)propyl]amino}pyrimidin-4-yl)benzamide, 4-{2-{(2-{[5-amiothioxomethyl]-2-pyridyl}amino)ethyl)amino]pyrimidin-4-yl}benzamide, 4-[2-({3-[(5-nitro-2-pyridyl)amino]propyl}amino)pyrimidin-4-yl]benzamide, 4-(2-{[3-(4-phenylimidazolyl)propyl]amino}pyrimidin-4-yl)benzamide, 4-{2-[(3-naphthyloxypropyl)amino]pyrimidin-4-yl}benzamide, 4-(2-{[3-(5,6-dimethylbenzimidazolyl)propyl]amino}pyrimidin-4-yl)benzamide, [4-(4-imidazolylphenyl)pyrimidin-2-yl]{2-[(5-nitro(2 pyridly))amino]ethyl}amine, 4-{2-[(2-{[5-(trifluoromethyl)-2-pyridyl]amino}ethyl)amino]pyrimidin-4-yl}benzamide, 4-(4-cyanophenyl)-2-({2-[(5-nitro(2-pyridyl))amino]ethyl}amino)pyrimidine-5-carboxamide, 4-(4cyanophenyl)-2-({2-[(5-nitro(2-pyridyl))amino]ethyl}amino)pyrimidine-5-carboxylic acid, 2-({2-[(6-amino-5-nitro(2-pyridyl))amino]ethyl}amino)-4-(2,4-dichlorophenyl)pyrimidine-5-carboxylic acid, ethyl 2-({2-[(5-nitro(2-pyridyl))amino]ethyl}amino)-4-(4-pyridyl)pyrimidine-5-carboxylate, ethyl 2-({2-[(5-cyano(2-pyridyl))amino]ethyl}amino)-4-(4-cyanophenyl)pyrimidine-5-carboxylate, 4-[2-({3-[3-(trifluoromethyl)phenoxy]propyl}amino)pyrimidin-4-yl]benzamide, [4-4-cyanophenyl)-2-({2-[(5-nitro(2-pyridyl))amino]ethyl}amino)pyrimidin-5-yl]-N-methylcarboxamide, methyl 4-(4-cyanophenyl)-2-({2-[(5-nitro(2-pyridyl))amino]ethyl}amino)pyrimidine-5-carboxylate, [4-(4-morpholin-4-ylphenyl)pyrimidin-2-yl]{2-[(5-nitro(2-pyridyl))amino]ethyl}amine, ethyl 4-(4-methylphenyl)-2-({2-[(5-nitro(2-pyridyl))amino]ethyl}amino)pyrimidine-5-carboxylate, {2-[(6-amino-5-nitro(2-pyridyl))amino]ethyl}{5-nitro-6-[benzylamino](2-pyridyl)}amine, 2-({2-[(5-nitro(2-pyridyl))amino]ethyl}amino)-4-(4-nitrophenyl)pyrimidine-5-carboxylic acid, ethyl 4-(4-fluorophenyl)-2-({2-[(5-nitro(2-pyridyl))amino]ethyl}amino)pyrimidine-5-carboxylate, 4-[5-imidazolyl-2-({2-[(5-nitro(2-pyridyl))amino]ethyl}amino)pyrimidin-4-yl]benzenecarbonitrile, 4-[5-imidazol-2-yl-2-({2-[(5-nitro(2-pyridyl))amino]ethyl}amino)pyrimidin-4-yl]benzenecarbonitrile, ethyl 2-({2-[(4-amino-5-cyanopyrimidin-2-yl)amino]ethyl}amino)-4-(4-cyanophenyl)pyrimidine-5-carboxylate, [4-(2,4-dimethylphenyl)-5-imidazolylpyrimidin-2-yl]{2-[(5-nitro(2-pyridyl))amino]ethyl}amine, 2-({2-[(6-amino-5-nitro(2-pyridyl))amino]ethyl}amino)-4-(2,4-dichlorophenyl)pyrimidine-5-carbonitrile, ethyl 4-(4-cyanophenyl)-2-({2-[(4-nitrophenyl)amino]ethyl}amino)pyrimidine-5-carboxylate, [4-(4-cyanophenyl)-2-({2-[(5-nitro(2-pyridyl))amino]ethyl}amino)pyrimidin-5-yl]-N,N-dimethylcarboxamide, ethyl 4-(4-cyanophenyl)-2-({2-[(5- nitro(2-pyridyl))amino]ethyl}amino)pyrimidine-5-carboxylate, [4-(2,4-dichlorophenyl)-5-ethylpyrimidin-2-yl]{2-[(5-nitro(2-pyridyl))amino]ethyl}amine, ethyl 4-(4-ethylphenyl)-2-({2-[(5-nitro(2-pyridyl))amino]ethyl}amino)pyrimidine-5-carboxylate, ethyl 4-(4-methoxyphenyl)-2-({2-[(5-nitro(2-pyridyl))amino]ethyl}amino)pyrimidine-5carboxylate, 4-[5-(methylsulfonyl)-2-({2-[(5-nitro(2-pyridyl))amino]ethyl}amino)pyrimidin-4-yl]benzenecarbonitrile, 4-(2-{[3-(5,6-dichlorobenzimidazolyl)propyl]amino}pyrimidin-4-yl)benzamide, 4-[2-({2-[(6-amino-5-nitro(2-pyridyl))amino]ethyl}amino)-5-imidazolylpyrimidin-4-yl]benzenecarbonitrile, 4-({2-[2-[(6-amino-5-nitro(2-pyridyl))amino]ethyl}amino)-5-imidazol-2-ylpyrimidin-4-yl]benzenecarbonitrile, N-(cyanomethyl)[4-(4-cyanophenyl)-2-({2-[(5-nitro(2-pyridyl))amino]ethyl}amino)pyrimidin-5-yl]carboxamide, 4-[5-(3-methyl(1,2,4-oxadiazol-5-yl))-2-({2-[(5-nitro(2-pyridyl))amino]ethyl}amino)pyrimidin-4-yl]benzenecarbonitrile, ethyl 4-(4chlorophenyl)-2-({2-[(5-nitro(2-pyridyl))amino]ethyl}amino)pyrimidine-5-carboxylate, ethyl 4-(3,4-difluorophenyl)-2-({2-[(5-nitro(2-pyridyl))amino]ethyl}amino)pyrimidine-5carboxylate, N-(2-aminoethyl)[4-(4-cyanophenyl)-2-({2-[(5-nitro(2-pyridyl))amino]ethyl}amino)pyrimidin -5-yl]carboxamide, ethyl 4-(4-cyanophenyl)-2-({2-[(4-methyl-5-nitro(2-pyridyl))amino]ethyl}amino)pyrimidine-5-carboxylate, ethyl 2-({2-[(6-amino-5-nitro(2-pyridyl))amino]ethyl}amino)-4-(4-cyanophenyl)pyrimidine-5-carboxylate, [4-(4-cyanophenyl) -2-({2-[(5-nitro(2-pyridyl))amino]ethyl}amino)pyrimidin-5-yl]-N-(2-hydroxyethyl)carboxamide, 2-hydroxyethyl 4-(4-cyanophenyl)-2-({2-[(5-nitro(2-pyridyl))amino]ethyl}amino)pyrimidine-5-carboxylate, ethyl 2-({2-[(4-amino-5-nitropyrimidin-2-yl)amino]ethyl}amino)-4-(4-cyanophenyl)pyrimidine-5-carboxylate, ethyl 4-[4-(methylethyl)phenyl]-2-({2-[(5-nitro(2-pyridyl))amino]ethyl}amino)pyrimidine-5-carboxylate, ethyl 4-[4-(dimethylamino)phenyl]-2-({2-[(5-nitro(2-pyridyl))amino]ethyl}amino)pyrimidine-5-carboxylate, ethyl 4-(2H-benzo[3,4-d]1,3-dioxolen-5-yl)-2-({2-[(5-nitro(2-pyridyl))amino]ethyl}amino)pyrimidine-5-carboxylate, ethyl 2-({2-[(5-nitro(2-pyridyl))amino]ethyl}amino)-4-(4-nitrophenyl)pyrimidine-5-carboxylate, ethyl 4-(4-methylthiophenyl)-2-({2-[(5-nitro(2-pyridyl))amino]ethyl}amino)pyrimidine-5-carboxylate, ethyl 4-(4-cyanophenyl)-2-[(2-{[5-(trifluoromethyl)(2-pyridyl)]amino}ethyl)amino]pyrimidine-5-carboxylate, ethyl 4-(2-naphthyl)-2-({2-[(5-nitro(2-pyridyl))amino]ethyl}amino)pyrimidine-5-carboxylate, N-butyl[4-(4-cyanophenyl)-2-({2-[(5-nitro(2-pyridyl))amino]ethyl}amino)pyrimidin-5-yl]carboxamide, N-(tert-butyl)[4-(4-cyanophenol)-2-({2-[(5-nitro(2-yridyl)amino]ethyl}amino)pyrimidin-5-yl]carboxamide, ethyl 4-(4-carbamoylphenyl)-2-({2-[(5-cyano(2-pyridyl))amino]ethyl}amino)-6-ethylpyrimidine-5-carboxylate, tert-butyl 4-(4-cyanophenyl)-2-({2-[(5-nitro(2-pyridyl))amino]ethyl}amino)pyrimidine-5-carboxylate, N-(carbamoylmethyl)[4-(4-cyanophenyl)-2-({2-[(5-nitro(2-pyridyl))amino]ethyl}amino)pyrimidin-5-yl]carboxamide, ethyl 4-(4-cyanophenyl)-6-ethyl-2-({2-[(5-nitro(2-pyridyl))amino]ethyl}amino)pyrimidine-5-carboxylate, butyl 4-(4-cyanophenyl)-2-({2-[(5-nitro(2-pyridyl))amino]ethyl}amino)pyrimidine-5-carboxylate, ethyl 4-{[(4-cyanophenyl)methyl]amino}-2-({2-[(5-nitro(2-pyridyl))amino]ethyl}amino)pyrimidine-5-carboxylate, ethyl 4-{[(3-cyanophenyl)methyl]amino}-2-({2-[(5-nitro(2-pyridyl))amino]ethyl}amino)pyrimidine-5-carboxylate, ethyl 4-[4-(tert-butyl)phenyl]-2-({2-[(5-nitro(2-pyridyl))amino]ethyl}amino)pyrimidine-5-carboxylate, 4-[2-({2-[(5-nitro(2-pyridyl))amino]ethyl}amino)-5-[benzylamino]pyrimidin-4-yl]benzenecarbonitrile, [4-(2,4-dichlorophenyl)-5-imidazolylpyrimidin-2-yl]{2-[(5-nitro(2-pyridyl))amino]ethyl}amine, [4-(2,4-dichlorophenyl)-5-imidazol-2-ylpyrimidin-2-yl]{2-[(5-nitro(2-pyridyl))amino]ethyl}amine, 4-(4-cyanophenyl)-6-(3-furyl)-2-({2-[(5-nitro(2-pyridyl))amino]ethyl}amino)pyrimidine-5-carboxylic acid, 4-[2-({2-[(5-nitro(2-pyridyl))amino]ethyl}amino)-5-(piperazinylcarbonyl)pyrimidin-4-yl]benzenecarbonitrile, ethyl 4-(4-imidazolylphenyl)-2-({2-[(5-nitro(2-pyridyl))amino]ethyl}amino)pyrimidine-5-carboxylate, 4-[5-(morpholin-4-ylcarbonyl)-2-({2-[(5-nitro(2-pyridyl))amino]ethyl}amino)pyrimidin-4-yl]benzenecarbonitrile, ethyl 4-(4-(2-furyl)phenyl)-2-({2-[(5-nitro(2-pyridyl))amino]ethyl}amino)pyrimidine-5-carboxylate, ethyl 2-({2-[(5-nitro(2-pyridyl))amino]ethyl}amino)-4-(4-(1,3-oxazol-5-yl)phenyl)pyrimidine-5-carboxylate, ethyl 2-({2-[(5-nitro(2-pyridyl))amino]ethyl}amino)-4-(4-(1,2,4-triazol-4-yl)phenyl)pyrimidine-5-carboxylate, N-[2-(dimethylamino)ethyl][4-(4-cyanophenyl)-2-({2-[({5-nitro(2-pyridyl))amino]ethyl}amino)pyrimidin-5-yl]carboxamide, 2-(dimethylamino)ethyl 4-(4-cyanophenyl)-2-({2-[(5-nitro(2-pyridyl))amino]ethyl}amino)pyrimidine-5-carboxylate, ethyl 2-({2-[(5-nitro(2-pyridyl))amino]ethyl}amino)-4-[4-trifluoromethyl)phenyl]pyrimidine-5-carboxylate, ethyl 4-(2,4-dichlorophenyl)-2-({2-[(5-nitro(2-pyridyl))amino]ethyl}amino)pyrimidine-5-carboxylate, ethyl 4-(4-(1H-1,2,3,4-tetraazol-5-yl)phenyl)-2-({2-[(5-nitro(2-pyridyl))amino]ethyl}amino)pyrimidine-5-carboxylate, ethyl 4-(4-carbamoylphenyl)-6-ethyl-2-({2-[(5-nitro(2-pyridyl))amino]ethyl}amino)pyrimidine-5-carboxylate, 4-(4-cyanophenyl)-2-({2-[(5-nitro(2-pyridyl))amino]ethyl}amino)-6-phenylpyrimidine-5-carboxylic acid, {2-[(6-amino-5-nitro(2-pyridyl))amino]ethyl}[4-(2,4-dichlorophenyl)-5-imidazolylpyrimidin-2-yl]amine, {2-[(6-amino-5-nitro(2-pyridyl))amino]ethyl][4-(2,4-dichlorophenyl)-5-imidazol-2-ylpyrimidin-2-yl]amine, ethyl 4-(4-bromophenyl)-2-({2-[(5-nitro(2-pyridyl))amino]ethyl}amino)pyrimidine-5-carboxylate, ethyl 4-[4-(methylsulfonyl)phenyl]-2-({2-[(5-nitro(2-pyridyl))amino]ethyl}amino)pyrimidine-5-carboxylate, ethyl 2-({2-[(6-amino-5-nitro(2-pyridyl))amino]ethyl}amino)-4-(4-(1,3-oxazol-5-yl)phenyl)pyrimidine-5-carboxylate, N-[2-(dimethylamino)ethyl][4-(4-cyanophenyl)-2-({2-[(5-nitro(2-pyridyl))amino]ethyl}amino)pyrimidin-5-yl]-N-methylcarboxamide, N-(1carbamoyl-2-hydroxyethyl)[4-(4-cyanophenyl)-2-({2-[(5-nitro(2-pyridyl))amino]ethyl}amino)pyrimidin-5-yl]carboxamide, 3-(dimethylamino)propyl 4-(4-cyanophenyl)-2-({2-[(5-nitro(2-pyridyl))amino]ethyl}amino)pyrimidine-5-carboxylate, ethyl 2-({2-[(6-amino-5-nitro(2-pyridyl))amino]ethyl}amino)-4-(2,4-dichlorophenyl)pyrimidine-5-carboxylate, 2-(dimethylamino)ethyl 2-({2-[(6-amino-5-nitro(2-pyridyl))amino]ethyl}amino)-4-(4-cyanophenyl)pyrimidine-5-carboxylate, [2-(dimethylamino)ethoxy]-N-[4-(4-cyanophenyl)-2-({2-[(5-nitro(2-pyridyl))amino]ethyl}amino)pyrimidin-5-yl]carboxamide, ethyl 2-({2-[(5-nitro(2-pyridyl))amino]ethyl}amino)-4-[4-(trifluoromethoxy)phenyl]pyrimidine-5-carboxylate, ethyl 4-(4-morpholin-4-ylphenyl)-2-({2-[(5-nitro(2-pyridyl))amino]ethyl}amino)pyrimidine-5-carboxylate, [4-(4-cyanophenyl)-2-({2-[(5-nitro(2-pyridyl))amino]ethyl}amino)pyrimidin-5-yl]-N-benzylcarboxamide, ethyl 4-(6-morpholin-4-yl(3-pyridyl))-2-({2-[(5-nitro(2-pyridyl))amino]ethyl}amino)pyrimidine-5-carboxylate, [4-(4-cyanophenyl)-2-({2-[(5-nitro(2-pyridyl))amino]ethyl}amino)pyrimidin-5-yl]-N-(4-pyridylmethyl)

carboxamide, phenylmethyl 4-(4-cyanophenyl)-2-({2-[(5-nitro(2-pyridyl))amino]ethyl}amino)pyrimidine-5-carboxylate, 4-(4-cyanophenyl)-6-(4-fluorophenyl)-2-({2-[(5-nitro(2-pyridyl))amino]ethyl}amino)pyrimidine-5-carboxylic acid, N-[(3-methoxyphenyl)methyl]{4-[2-({2-[(5-nitro(2-pyridyl))amino]ethyl}amino)pyrimidin-4-yl]phenyl}carboxamide, 4-[5-{3-[2-(dimethylamino)ethyl](1,2,4-oxadiazol-5-yl)}-2-({2-[(5-nitro(2-pyridyl))amino]ethyl}amino)pyrimidin-4-yl]benzenecarbonitrile, N-[(3-bromophenyl)methyl][4-(2-([2-(pyrimidin-2-ylamino)ethyl]amino}pyrimidin-4-yl)phenyl]carboxamide, 4-(dimethylamino)butyl 4-(4-cyanophenyl)-2-({2-[(5-nitro(2-pyridyl))amino]ethyl}amino)pyrimidine-5-carboxylate, 4,6-bis(4-cyanophenyl)-2-({2-[(5-nitro(2-pyridyl))amino]ethyl}amino)pyrimidine-5-carboxylic acid, ethyl 2-({2-[(6-amino-5-nitro(2-pyridyl))amino]ethyl}amino)-4-(4-morpholin-4-ylphenyl)pyrimidine-5-carboxylate, 4-(3-hydroxyphenyl)-2-({2-[(5-nitro(2-pyridyl))amino]ethyl}amino)-6-(4-nitrophenyl)pyrimidine-5-carboxylic acid, 2-morpholin-4-ylmethyl 4-(4-cyanophenyl)-2-({2-[(5-nitro(2-pyridyl))amino]ethyl}amino)pyrimidine-5-carboxylate, 4-(4-cyanophenyl)-2-({2-[(5-nitro(2-pyridyl))amino]ethyl}amino)-6-(4-nitrophenyl)pyrimidine-5-carboxylic acid, 4-(4-cyanophenyl)-2-({2-[(5-nitro(2-pyridyl))amino]ethyl}amino)-6-(3-nitrophenyl)pyrimidine-5-carboxylic acid, N-[(3-bromophenyl)methyl]{4-[2-({2-[(5-cyano(2-pyridyl))amino]ethyl}amino)pyrimidin-4-yl]phenyl}carboxamide, ethyl 4-(4-carbamoylphenyl)-2-({2-[(5-nitro(2-pyridyl))amino]ethyl}amino)-6-(4-pyridyl)pyrimidine-5-carboxylate, 2-(dimethylamino)ethyl 2-({2-[(6-amino-5-nitro(2-pyridyl))amino]ethyl}amino)-4-(2,4-dichlorophenyl)pyrimidine-5-carboxylate, 2-[bis(2-hydroxyethyl)amino]ethyl 4-(4-cyanophenyl)-2-({2-[(5-nitro(2-pyridyl))amino]ethyl}amino)pyrimidine-5-carboxylate, {4-[2-({2-[(4-amino-5-cyanopyrimidin-2-yl)amino]ethyl}amino)pyrimidin-4-yl]phenyl}-N-[(3-bromophenyl)methyl]carboxamide, 4-(4-carboxyphenyl)-2-({2-[(5-nitro(2-pyridyl))amino]ethyl}amino)-6-(4-nitrophenyl)pyrimidine-5-carboxylic acid, 2-hydroxy-3-morpholin-4-ylpropyl 4-(4-cyanophenyl)-2-({2-[(5-nitro(2-pyridyl))amino]ethyl}amino)pyrimidine-5-carboxylate, ethyl 4-(4-cyanophenyl)-2-({2-[(5-nitro(2-pyridyl))amino]ethyl}amino)-6-(4-nitrophenyl)pyrimidine-5-carboxylate, (2-{5-[2-({2-[(6-amino-5-nitro(2-pyridyl))amino]ethyl}amino)-4-(2,4-dichlorophenyl)pyrimidin-5-yl](1,2,4-oxadiazol-3-yl)}ethyl)dimethylamine, and ethyl 4-(4-carbamoylphenyl)-2-({2-[(5-nitro(2-pyridyl))amino]ethyl}amino)-6-(4-nitrophenyl)pyrimidine-5-carboxylate.

Accordingly, these results demonstrate that compounds of the present invention exhibit inhibitory activity against GSK3.

EXAMPLE 75

Screening for GSK3 Inhibitory Activity Using a Cell-Based Glycogen Synthase Assay CHO-HIRC cells are maintained in 10 cm tissue culture plates in Ham's F12 medium/10% dialysed fetal bovine serum. Cells from a confluent 10 cm plate are harvested and divided into the 6 wells of a Corning 6-well tissue culture plate to a final volume of 2 ml of medium. The cells are left to grow at 37° C. for 24 hours. The cells are then washed three times in Ham's F12 medium containing no fetal bovine serum, and finally the cells are left for a further 24 hours at 37° C. in 2 ml of the serum-free medium.

At the end of this time, 20 µl of compound dissolved in DMSO is added to each well and incubated at 37° C. After 20 minutes the medium is removed and the cells are washed once in PBS at room temperature and then rapidly frozen in the plates in liquid nitrogen. Cells are then thawed on ice in the presence of 140 µl of lysis buffer (50 mM Tris pH 7.8; 1 mM EDTA, 100 mM NaF, 25 ng/ml leupeptin, 1 mM DTT, 1 mM PMSF) per well. Cells are scraped from the plates and frozen in Eppendorf tubes on dry ice. Lysates are then thawed and refrozen on dry ice.

After rethawing, lysates are spun at 14,000 g for 15 minutes. The supernatants are then removed and stored on ice. Each supernatant (45 µl) is added to 45 µl of reaction buffer (65 mM Tris pH 7.8; 26 mM EDTA, 32.5 mM KF, 9.3 mM UDP-glucose; 11 mg/ml glycogen; 500 nCi/ml $^{14}$C-UDP-glucose) and a further 45 µl is added to 45 µl reaction buffer/20 mM glucose-6-phosphate. Reactions are incubated at 30° C. for 30 minutes and then spotted onto a 2 cm square 31ET chromatograph paper (Whatman). Filter papers are washed twice for 20 minutes in 66% ethanol, rinsed briefly in acetone and dried for 1 hour at room temperature.

Filters are added to 5 ml of liquid scintillant and counted in a liquid scintillation counter. The percentage of the total glycogen synthase that is active in any lysate is expressed as 100×(cpm minus glucose-6-phosphate)/(cpm plus glucose-6-phosphate). Such values are determined in duplicate for 5 different concentrations of compound and for DMSO alone, and the values are then plotted against the logarithm of the concentration. The concentration of compound which stimulates glycogen synthase activity to 50% of the maximal level is determined by fitting a sigmoidal curve to the plotted data.

EXAMPLE 76

Screening for Inhibition of Tau Protein Phosphorylation

A. Transient Transfection of COS Cells with GSK3 Expression Plasmid and Tau Expression Plasmid Construction COS cells are maintained in T25 tissue culture flasks in high glucose MEM medium/5% fetal bovine serum. Cells from a confluent T25 flask are harvested and 80,000 cells/well are seeded into Corning 6-well tissue culture plates in a final volume of 2 ml/well of medium. The cells are left to grow at 37° C. for 48 hours. The cells are then washed twice in Opti-MEM containing no fetal bovine serum, and finally the cells are left in 1 ml of Opti-MEM.

Polynucleotide encoding tau protein (SEQ ID NO: 4) is subcloned into plasmid pSG5 under an early SV40 promotor to generate a tau expression plasmid. The cloning of cDNA encoding tau protein is generally described in Goedert et al., *EMBO Journal*, 8(2):393–399 (1989), which is incorporated herein by reference. A GSK3 expression plasmid is prepared by subcloning polynucleotide encoding GSK3β (SEQ ID NO: 1) into pCG, which is an ApEVRF derivative described in Giese et al., *Genes & Development*, 9:995–1008 (1995) and Matthias et al., *Nucleic Acid Research*, 17:6418 (1989), both of which are incorporated herein by reference.

The following solutions are prepared in 1.5 ml Eppendorf tubes: Solution A: for each transfection, 2 µg of DNA (tau expression plasmid) and 0.7 µg of DNA (GSK3 expression plasmid) are diluted into 100 µl of Opti-MEM (Gibco BRL); Solution B: for each transfection, 8 µl of Lipofectamine reagent is diluted into 100 µl of Opti-MEM. The two solutions are combined, mixed gently, and incubated at room temperature for 45 minutes to allow DNA-liposome complexes to form. For each transfection, 0.8 ml of Opti-MEM is added to the tube containing the complexes. The diluted solution is mixed gently and overlaid onto the rinsed cells.

The cells are incubated with the complexed DNA/Lipofectamine for 6 hours at 37° C. in a $CO_2$ incubator. Following incubation, 1 ml of growth medium (high glucose MEM) with 20% FBS is added to each well and incubated at 37° C. overnight. The medium is replaced with fresh, complete medium at 18 hours following the start of transfection, and the cells are left to grow at 37 ° C. for another 48 hours.

B. Tau Phosphorylation Inhibition Assay

Two hours before harvesting, 2 µl of test compound (GSK3 inhibitor) dissolved in DMSO is added to each well and incubated at 37° C. After 2 hours the medium is removed and the cells are rapidly frozen on the plates on dry ice and stored at −70° C. Cells are thawed on ice in the presence of 200 µl of lysing buffer (1% Tritone® X-100, 20 mM Tris pH 7.5, 137 mM NaCl, 15% glycerol, 25 µg/mL leupeptin, 1 µg mL pepstatin-A, 1 µM PMSF, 21 µg/ml aprotinin, 50 mM NaF, 50 mM β-glycerophosphate, 15 mM sodium pyrophosphate, 1 mM sodium orthovanadate). The contents of each well are centrifuged at 14,000 g, 4° C. for 5 minutes and the supernatants transferred to clean tubes. At this point the lysates may be stored at −20° C.

C. ELISA to Detect Phosphorylated Tau in Cell Lysates

Immulon 4 strips (Dynatech) are coated with monoclonal anti-phosphorylated tau (AT8, Polymedco, Inc.) at 5 µg/ml in PBS containing Ca++ and, Mg++, 100 µl/well. After overnight incubation at 4° C., the strips are washed twice with washing buffer (PBS containing 0.05% Tween® 20) and blocked with PBS containing 1% BSA, 5% normal mouse serum and 0.05% Tween® 20 at room temperature for 1 hour. The strips are washed 5 times with washing buffer. Lysate(100 µl) diluted 1:10 in PBS containing 1% BSA, 0.1% $NaN_3$ is added into each well and incubated at room temperature for 1 hour. After washing, 100 µl of 0.5 µg/ml biotinylated monoclonal anti-(non-phosphorylated) tau (HT7, Polymedco, Inc.) in PBS-BSA is added into each well. Strips are washed 5 times and HRP-conjugated streptavidin is added, incubated at room temperature for 30 minutes and washed extensively with washing buffer. TMB substrate (Pierce) is used for color development and the reaction is stopped by adding an equal volume of 0.8 M sulfuric acid. Strips are read on an ELISA plate reader using a 450 nm filter. The concentration of compound that inhibits tau phosphorylation to 50% of the maximal level (i.e., $IC_{50}$) is determined by fitting a sigmoidal curve to the plotted data.

EXAMPLE 77

Evaluation of Insulin Sensitization in Diabetic Rodents (The Glucose Tolerance Test)

Candidate drugs for potential use in the treatment of NIDDM can be tested for insulin sensitization in animal models of type 2 diabetes. Test compound can be dosed via several routes prior to administration of a glucose bolus in either diabetic mice (e.g. db/db, ob/ob) or diabetic rats (e.g. Zucker Fa/Fa or GK). Following drug and glucose administration, blood samples are removed at various times and evaluated for glucose and insulin levels. Improved disposal of glucose without the requirement for increased secretion of endogenous insulin is considered an indication of insulin sensitization. Consequently, drugs improving glucose tolerance in these diabetic rodents may have potential use in human NIDDM.

Specifically, 8–12 week-old animals obtained from standard supply companies such as Charles River or Jackson Labs are fasted for either 6–8 hours (mice) or 16–20 hours (rats). Test drug is administered (via a a route of administration such as, for example, oral, subcutaneous, intravenous, and the like) and, at a preselected time point following drug dosing, the rodents are given an injection of glucose intraperitoneally at a dose of 1.3 g/kg. Venous blood is sampled from the tail (via a small snip) or from an indwelling catheter at 15 to 30 minute intervals just before the glucose injections (e.g. 15 minutes prior) and for 2–4 hours following the glucose dose. The freshly-collected blood samples can be analyzed for serum glucose levels using a ONE-TOUCH® glucose monitor (LifeScan, Milpitas, Calif.) or a Beckman Glucose Analyzer (Beckman Coulter Inc., Fullerton, Calif.). Insulin levels can be determined by radioimmunoassay from plasma samples.using, for example, an insulin RIA kit (Linco Research Inc., St. Charles, Miss.).

While the invention has been described in detail with reference to certain preferred embodiments thereof, it will be understood that modifications and variations are within the spirit and scope of that which is described and claimed.

---

That which is claimed is:

1. A compound having the structure:

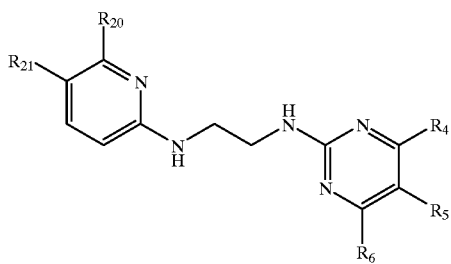

(I)

wherein:

R₄ and R₆ are each independently selected from the group consisting of hydrogen, a halo, and R₇,
  wherein R₇ is a monovalent radical selected from the group consisting of a lower alkyl, a cycloalkyl, an aryl, an aminoalkyl, an aminoaralkyl, an aminocycloalkylaryl, an arylcarboxamidocycloalkylaralkyl, an arylcarboxamidocycloalkylaryl, an arylcarboxarnidoalkylcycloalkyl, an arylcarboxamidoaryl, an arylcarboxamidoalkyl, an arylcarboxamidoaralkyl, an arylcarboxamidoalkoxyalkyl, an aminoalkoxyalkyl, and an arylsulfonamidoaralkyl, and
  wherein R₇ is optionally substituted;

R₅ is selected from the group consisting of hydrogen, carboxyl, nitro, amino, cyano, an optionally substituted lower alkyl, an optionally substituted aryl, an optionally substituted aralkyl, an optionally substituted aminoalkyl, an optionally substituted aminoaryl, an optionally substituted aminoaralkyl, an optionally substituted aminoalkoxyalkyl, an optionally substituted arylaminoalkyl, an optionally substituted arylaminoaryl, an optionally substituted arylaminoaralkyl, an optionally substituted arylalkylamino, an optionally substituted arylalkylaminoalkyl, an optionally substituted arylalkylaminoaralkyl, an optionally substituted carboxcycloamido, an optionally substituted acyloxyalkyl, an optionally substituted acyloxyaryl, an optionally substituted acyloxyaralkyl, an optionally substituted acyloxyalkylcycloalkyl, an optionally substituted acyloxyalkylaminoalkyl, and an optionally substituted sulfonylalkyl, an optionally substituted carbamylalkyl, an optionally substituted carbamylaryl, an optionally substituted carbamylaralkyl, an optionally substituted carbamylalkylamino, an optionally substituted carbamylalkylaminoalkyl, an optionally substituted carbamylalkylaminoaryl, and an optionally substituted carbamylalkylaminoaralkyl;
  wherein, no more than two of R₄, R₅, and R₆ are hydrogen;

R₂₀ and R₂₁ are selected independently from the group consisting of hydrogen, nitro, amino, cyano, halo, thioamido, sulfonamido, carboxyl, formyl, loweralkyl, haloloweralkyl, aminoloweralkyl, cyanoloweralkyl, loweralkoxy, haloloweralkoxy, loweralkoxyalkyl, loweralkylaminoloweralkoxy, alkylthio, aryl, and aralkyl;

and salts thereof.

2. A compound of claim 1, wherein at least one of R4 and R6 is selected from the group consisting of optionally substituted aryl and optionally substituted heteroaryl.

3. A compound of claim 2, wherein at least one of R₄ and R₆ is phenyl substituted optionally from the group consisting of nitro, amino, cyano, halo, thioamido, carboxyl, hydroxy, and optionally substituted loweralkyl, loweralkoxy, loweralkoxyalkyl, haloloweralkyl, haloloweralkoxy, aminoalkyl, alkylamino, alkylthio, alkylcarbonylamino, aralkylcarbonylamino, heteroaralkylcarbonylamino, arylcarbonylamino, heteroarylcarbonylamino aminocarbonyl, loweralkylaminocarbonyl, aminoaralkyl, loweralkylaminoalkyl aryl, heteroaryl, cycloheteroalkyl, aralkyl, alkylcarbonyloxy, arylcarbonyloxy, aralkylcarbonyloxy, arylcarbonyloxyalkyl, alkylcarbonyloxyalkyl, heteroarylcarbonyloxyalkyl, aralkycarbonyloxyalkyl, and heteroaralkcarbonyloxyalkyl.

4. A compound of claim 1, wherein R₅ is optionally substituted aryl.

5. A compound of claim 4, wherein $R_5$ is optionally substituted heteroaryl.

6. A compound of claim 1 have the structure:

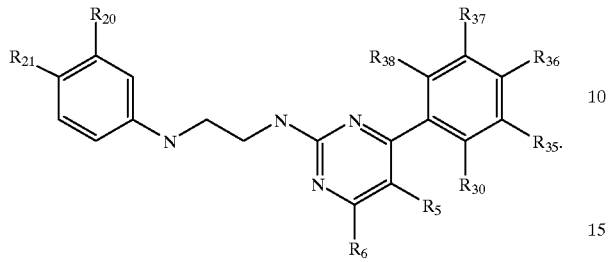

wherein:

$R_{34}$–$R_{38}$ are selected independently from the group consisting of hydrogen, nitro, amino, cyano, halo, thioamido, carboxyl, hydroxy, and optionally substituted loweralkyl, loweralkoxy, loweralkoxyalkyl, haloloweralkyl, haloloweralkoxy, aminoalkyl, alkylamino, alkylthio, alkylcarbonylamino, aralkylcarbonylamino, heteroaralkylcarbonylamino, arylcarbonylamino, heteroarylcarbonylamino, aminocarbonyl, loweralkylaminocarbonyl, aminoaralkyl, loweralkylaminoalkyl, aryl, heteroaryl, cycloheteroalkyl, aralkyl, alkylcarbonyloxy, arylcarbonyloxy, aralkylcarbonyloxy, arylcarbonyloxyalkyl, alkyloxycarbonylalkyl, heteroarylcarbonyloxyalkyl, aralkylcarbonyloxyalkyl, heteroaralkylcarbonyloxyalkyl, and the pharmaceutically acceptable salts thereof.

7. A compound of claim 6, wherein at least one of $R_{30}$ and $R_{31}$ is selected from the group consisting of nitro, amino, cyano, trifluoromethyl and loweralkoxy.

8. A compound of claim 6, wherein $R_{32}$ is selected from the group consisting of hydrogen and substituted and unsubstituted carbocyclic aryl and heteroaryl.

9. A compound of claim 6, wherein $R_{34}$–$R_{38}$, taken together with the phenyl ring to which they are attached, form a moiety selected from the group consisting of dichlorophenyl, difluorophenyl, trifluoromethylphenyl, chlorofluorophenyl, bromochlorophenyl, ethylphenyl, methylchlorophenyl, imidazolylphenyl, cyanophenyl, morpholinophenyl and cyanochlorophenyl.

10. A compound of claim 8, wherein $R_{33}$ is heteroaryl.

11. A compound of claim 9, wherein $R_{33}$ is selected from the group consisting of substituted or unsubstituted pyridyl, pyrimidinyl, pyrrolidinyl, thiazolyl, indolyl, imidazolyl, oxadiazolyl, tetrazolyl, pyrazinyl, triazolyl, thienyl, furanyl, quinolinyl, pyrrolylpyridyl, benzothiazolyl, benzopyridyl, benzotriazolyl, and benzimidazolyl.

12. A method for inhibiting GSK3 activity, said method comprising:
  (i) providing an effective amount of a GSK3 inhibitor having the structure:

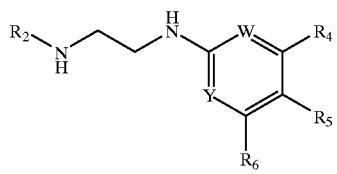

wherein:
W and Y are each nitrogen;
$R_2$ is an optionally substituted aryl;
$R_4$ and $R_6$ are each independently selected from the group consisting of hydrogen, a halo, and $R_7$,
  wherein $R_7$ is a monovalent radical selected from the group consisting of a lower alkyl, a cycloalkyl, an aryl, an aminoalkyl, an aminoaralkyl, an aminocycloalkylaryl, an arylcarboxamidocycloalkylaralkyl, an arylcarboxamidocycloalkylaryl, an arylcarboxamidoalkylcycloalkyl, an arylcarboxamidoaryl, an arylcarboxamidoalkyl, an arylcarboxamidoaralkyl, an arylcarboxamidoalkoxyalkyl, an aminoalkoxyalkyl, and an arylsulfonamidoaralkyl, and
  wherein $R_7$ is optionally substituted;
$R_5$ is selected from the group consisting of hydrogen, carboxyl, nitro, amino, cyano, an optionally substituted lower alkyl, an optionally substituted aryl, an optionally substituted aralkyl, an optionally substituted aminoalkyl, an optionally substituted aminoaryl, an optionally substituted aminoaralkyl, an optionally substituted aminoalkoxyalkyl, an optionally substituted arylaminoalkyl, an optionally substituted arylaminoaryl, an optionally substituted arylaminoaralkyl, an optionally substituted arylalkylamino, all optionally substituted arylalkylaminoalkyl, an optionally substituted arylalkylaminoaralkyl, an optionally substituted carboxcycloamido, an optionally substituted acyloxyalkyl, an optionally substituted acyloxyaryl, an optionally substituted acyloxyaralkyl, an optionally substituted acyloxyalkylcycloalkyl, an optionally substituted acyloxyalkylaminoalkyl, and an optionally substituted sulfonylalkyl, an optionally substituted carbamylalkyl, an optionally substituted carbamylaryl, an optionally substituted carbamylaralkyl, an optionally substituted carbamylalkylamino, an optionally substituted carbamylalkylaminoalkyl, an optionally substituted carbamylalkylaminoaryl, and an optionally substituted carbamylalkylaminoaralkyl;
wherein, no more than two of $R_4$, $R_5$, and $R_6$ are hydrogen;
and salts thereof; and
  (ii) administering said effective amount of said GSK3 inhibitor compound to a subject.

13. A method for treating a GSK3-mediated disorder in a subject, said method comprising:
  (i) providing a therapeutically effective amount of the GSK3 inhibitor compound of claim 1, then
  (ii) administering to a subject said therapeutically effective amount of said GSK3 inhibitor compound, wherein said subject is afflicted with a GSK3-mediated disorder.

* * * * *